US006958329B2

(12) United States Patent
Olson

(10) Patent No.: US 6,958,329 B2
(45) Date of Patent: Oct. 25, 2005

(54) LACTAMS SUBSTITUTED BY CYCLIC SUCCINATES AS INHIBITORS OF A-β PROTEIN PRODUCTION

(75) Inventor: Richard E. Olson, Wilmington, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 10/287,099

(22) Filed: Nov. 4, 2002

(65) Prior Publication Data

US 2003/0119815 A1 Jun. 26, 2003

Related U.S. Application Data

(62) Division of application No. 09/871,840, filed on Jun. 1, 2001, now Pat. No. 6,509,333.
(60) Provisional application No. 60/208,536, filed on Jun. 1, 2000.

(51) Int. Cl.$^7$ .................... C07D 491/00; C07D 409/00; C07D 403/00; C07D 223/12; A61K 31/55
(52) U.S. Cl. .......................... 514/212.03; 514/212.04; 514/212.07; 514/212.08; 540/522; 540/523; 540/524; 540/525; 540/527
(58) Field of Search ................ 540/522, 523, 540/524, 525, 527; 514/212.03, 212.04, 212.07, 212.08

(56) References Cited

U.S. PATENT DOCUMENTS

| | | | |
|---|---|---|---|
| 5,283,241 A | 2/1994 | Bochis et al. ................ 514/183 |
| 5,532,359 A | 7/1996 | Marsters et al. ............ 540/522 |
| 5,550,126 A | 8/1996 | Horwell et al. .......... 514/237.5 |
| 5,578,629 A | 11/1996 | Ciccarone et al. .......... 514/347 |
| 5,595,990 A | 1/1997 | Baldwin et al. ............ 514/221 |
| 5,602,145 A | 2/1997 | Samanen .................... 514/309 |
| 5,618,812 A | 4/1997 | Pineiro et al. ............. 514/221 |
| 5,672,596 A | 9/1997 | Wyvratt et al. ............. 514/183 |
| 5,710,153 A | 1/1998 | Ohmoto et al. .......... 514/236.5 |
| 5,710,171 A | 1/1998 | Dinsmore et al. .......... 514/396 |
| 5,756,528 A | 5/1998 | Anthony et al. ............ 514/399 |
| 5,763,437 A | 6/1998 | Sato et al. .................. 514/221 |
| 5,852,010 A | 12/1998 | Graham et al. ............. 514/221 |
| 5,856,326 A | 1/1999 | Anthony et al. ............ 514/254 |
| 5,859,012 A | 1/1999 | Dinsmore et al. .......... 514/252 |
| 5,869,682 A | 2/1999 | DeSolms .................. 548/335.5 |
| 5,872,105 A | 2/1999 | DeSolms .................... 514/320 |
| 5,885,995 A | 3/1999 | Dinsmore ................... 514/252 |
| 5,891,889 A | 4/1999 | Anthony et al. ............ 514/326 |
| 5,905,077 A | 5/1999 | Jungheim et al. ........ 514/222.2 |
| 5,919,705 A | 7/1999 | Dinsmore et al. .......... 514/266 |
| 5,936,089 A | 8/1999 | Carpino ..................... 546/113 |
| 5,965,578 A | 10/1999 | Ciccarone et al. .......... 514/326 |

FOREIGN PATENT DOCUMENTS

EP 0842944 5/1990

| | | |
|---|---|---|
| EP | 041802 | 4/1991 |
| EP | 0434360 | 6/1991 |
| WO | WO 9033100 | 10/1990 |
| WO | WO 9217460 | 10/1992 |
| WO | WO 9403437 | 2/1994 |
| WO | WO 9405634 | 3/1994 |
| WO | WO 9414776 | 7/1994 |
| WO | WO 9509633 | 4/1995 |
| WO | WO 9822441 | 5/1996 |
| WO | WO 9617833 | 6/1996 |
| WO | WO 9618602 | 6/1996 |
| WO | WO 9620918 | 7/1996 |
| WO | WO 9841510 | 9/1996 |
| WO | WO 9639137 | 12/1996 |
| WO | WO 9719053 | 5/1997 |
| WO | WO 9727852 | 8/1997 |
| WO | WO 9736877 | 10/1997 |
| WO | WO 9736900 | 10/1997 |
| WO | WO 9738664 | 10/1997 |
| WO | WO 9745412 | 12/1997 |
| WO | WO 9822493 | 3/1998 |
| WO | WO 9816523 | 4/1998 |
| WO | WO 9910951 | 4/1998 |
| WO | WO 9822430 | 5/1998 |
| WO | WO 9822433 | 5/1998 |
| WO | WO 9827053 | 6/1998 |
| WO | WO 9020260 | 7/1998 |
| WO | WO 9828980 | 7/1998 |
| WO | WO 9897079 | 8/1998 |

(Continued)

OTHER PUBLICATIONS

Dinowai.I; J. Clinical Invest., 108, Nov. 2001, 1243–1246.
Selkoe; J. Alzheimer's Disease, 3, 2001, P. 75–81.
Tanzi and Parson, "Decoding Darkness, The Search for the Genetic Causes Of Alzheimer's Disease", Perseus Publishing, 2000, pp. XVII–XVIII.
Olson et al, Current Opinion in Drug Discovery and Development, 4, 2001, pp. 390–401.

Primary Examiner—Bruck Kifle
(74) Attorney, Agent, or Firm—Pillsbury Winthrop LLP

(57) ABSTRACT

This invention relates to novel lactams having the Formula (I):

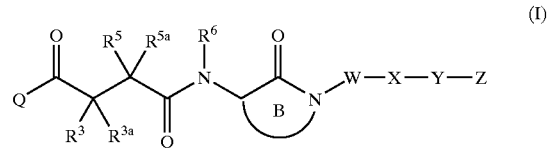

to their pharmaceutical compositions and to their methods of use. These novel compounds inhibit the processing of amyloid precursor protein and, more specifically, inhibit the production of Aβ-peptide, thereby acting to prevent the formation of neurological deposits of amyloid protein. More particularly, the present invention relates to the treatment of neurological disorders related to β-amyloid production such as Alzheimer's disease and Down's Syndrome.

72 Claims, No Drawings

FOREIGN PATENT DOCUMENTS

| | | |
|---|---|---|
| WO | WO 9844797 | 10/1998 |
| WO | WO 9858915 | 12/1998 |
| WO | WO 9900654 | 1/1999 |
| WO | WO 9903826 | 1/1999 |
| WO | WO 9907730 | 2/1999 |
| WO | WO 9907731 | 2/1999 |
| WO | WO 9917777 | 4/1999 |
| WO | WO 9919305 | 4/1999 |
| WO | WO 9932453 | 7/1999 |
| WO | WO 9961219 | 12/1999 |
| WO | WO 9966934 | 12/1999 |
| WO | WO 9967220 | 12/1999 |
| WO | WO 9967221 | 12/1999 |
| WO | WO 0007995 | 2/2000 |
| WO | WO 0028331 | 5/2000 |
| WO | WO 0038618 | 7/2000 |
| WO | WO 0160826 | 8/2001 |

LACTAMS SUBSTITUTED BY CYCLIC SUCCINATES AS INHIBITORS OF A-β PROTEIN PRODUCTION

FIELD OF THE INVENTION

This invention relates to novel lactams substituted by cyclic succinates having drug and bio-affecting properties, their pharmaceutical compositions and methods of use. These novel compounds inhibit the processing of amyloid precursor protein and, more specifically, inhibit the production of Aβ-peptide, thereby acting to prevent the formation of neurological deposits of amyloid protein. More particularly, the present invention relates to the treatment of neurological disorders related to β-amyloid production such as Alzheimer's disease and Down's Syndrome.

BACKGROUND OF THE INVENTION

Alzheimer's disease (AD) is a degenerative brain disorder characterized clinically by progressive loss of memory, temporal and local orientation, cognition, reasoning, judgment and emotionally stability. AD is a common cause of progressive dementia in humans and is one of the major causes of death in the United States. AD has been observed in all races and ethnic groups worldwide, and is a major present and future health problem. No treatment that effectively prevents AD or reverses the clinical symptoms and underlying pathophysiology is currently available (for review see Dennis J. Selkoe; Cell Biology of the amyloid (beta)-protein precursor and the mechanism of Alzheimer's disease, Annu Rev Cell Biol, 1994, 10: 373–403).

Histopathological examination of brain tissue derived upon autopsy or from neurosurgical specimens in effected individuals revealed the occurrence of amyloid plaques and neurofibrillar tangles in the cerebral cortex of such patients. Similar alterations were observed in patients with Trisomy 21 (Down's syndrome), and hereditary cerebral hemorrhage with amyloidosis of the Dutch-type. Neurofibrillar tangles are nonmembrane-bound bundles of abnormal proteinaceous filaments and biochemical and immunochemical studies led to the conclusion that their principle protein subunit is an altered phosphorylated form of the tau protein (reviewed in Selkoe, 1994).

Biochemical and immunological studies revealed that the dominant proteinaceous component of the amyloid plaque is an approximately 4.2 kilodalton (kD) protein of about 39 to 43 amino acids. This protein was designated Aβ, β-amyloid peptide, and sometimes β/A4; referred to herein as Aβ. In addition to its deposition in amyloid plaques, Aβ is also found in the walls of meningeal and parenchymal arterioles, small arteries, capillaries, and sometimes, venules. Aβ was first purified and a partial amino acid reported in 1984 (Glenner and Wong, Biochem. Biophys. Res. Commun. 120: 885–890). The isolation and sequence data for the first 28 amino acids are described in U.S. Pat. No. 4,666,829.

Compelling evidence accumulated during the last decade revealed that Aβ is an internal polypeptide derived from a type 1 integral membrane protein, termed β amyloid precursor protein (APP). β APP is normally produced by many cells both in vivo and in cultured cells, derived from various animals and humans. Aβ is derived from cleavage of β APP by as yet unknown enzyme (protease) system(s), collectively termed secretases.

The existence of at least four proteolytic activities has been postulated. They include β secretase(s), generating the N-terminus of Aβ, α secretase(s) cleaving around the 16/17 peptide bond in Aβ, and γ secretases, generating C-terminal Aβ fragments ending at position 38, 39, 40, 42, and 43 or generating C-terminal extended precursors which are subsequently truncated to the above polypeptides.

Several lines of evidence suggest that abnormal accumulation of Aβ plays a key role in the pathogenesis of AD. Firstly, Aβ is the major protein found in amyloid plaques. Secondly, Aβ is neurotoxic and may be causally related to neuronal death observed in AD patients. Thirdly, missense DNA mutations at position 717 in the 770 isoform of β APP can be found in effected members but not unaffected members of several families with a genetically determined (familiar) form of AD. In addition, several other β APP mutations have been described in familiar forms of AD. Fourthly, similar neuropathological changes have been observed in transgenic animals overexpressing mutant forms of human β APP. Fifthly, individuals with Down's syndrome have an increased gene dosage of β APP and develop early-onset AD. Taken together, these observations strongly suggest that Aβ depositions may be causally related to the AD.

It is hypothesized that inhibiting the production of Aβ will prevent and reduce neurological degeneration, by controlling the formation of amyloid plaques, reducing neurotoxicity and, generally, mediating the pathology associated with Aβ production. One method of treatment methods would therefore be based on drugs that inhibit the formation of Aβ in vivo.

Methods of treatment could target the formation of Aβ through the enzymes involved in the proteolytic processing of β amyloid precursor protein. Compounds that inhibit β or γ secretase activity, either directly or indirectly, could control the production of Aβ. Advantageously, compounds that specifically target γ secretases, could control the production of Aβ. Such inhibition of β or γ secretases could thereby reduce production of Aβ, which, thereby, could reduce or prevent the neurological disorders associated with Aβ protein.

PCT publication number WO 96/29313 discloses the general formula:

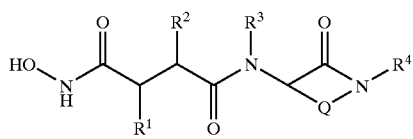

covering metalloprotease inhibiting compounds useful for the treatment of diseases associated with excess and/or unwanted matrix metalloprotease activity, particularly collagenase and or stromelysin activity.

Compounds of general formula:

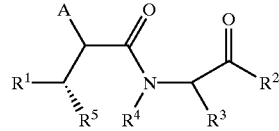

are disclosed in PCT publication number WO 95/22966 relating to matrix metalloprotease inhibitors. The compounds of the invention are useful for the treatment of conditions associated with the destruction of cartilage, including corneal ulceration, osteoporosis, periodontitis and cancer.

European Patent Application number EP 0652009A1 relates to the general formula:

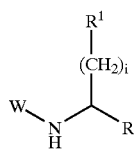

and discloses compounds that are protease inhibitors that inhibit Aβ production.

U.S. Pat. No. 5,703,129 discloses the general formula:

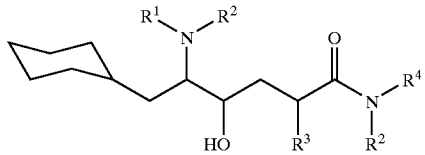

which covers 5-amino-6-cyclohexyl-4-hydroxy-hexanamide derivatives that inhibit Aβ production and are useful in the treatment of Alzheimer's disease.

Copending, commonly assigned U.S. patent application Ser. No. 09/370089 filed Aug. 7, 1999 (equivalent to international application PCT US99/17717) discloses lactams of general formula:

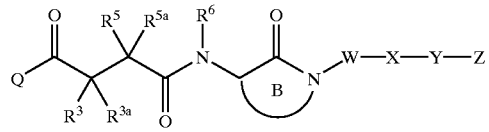

wherein the lactam ring B is substituted by succinamide and a carbocyclic, aryl, or heteroaryl group. These compounds inhibit the processing of amyloid precursor protein and, more specifically, inhibit the production of Aβ-peptide, thereby acting to prevent the formation of neurological deposits of amyloid protein.

None of the above references teaches or suggests the compounds of the present invention which are described in detail below.

SUMMARY OF THE INVENTION

One object of the present invention is to provide novel compounds which are useful as inhibitors of the production of Aβ protein or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating degenerative neurological disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of Formula (I):

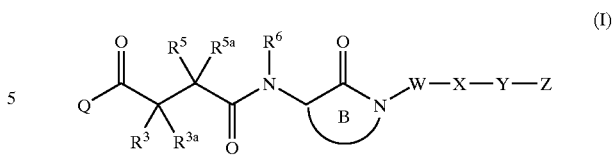

or pharmaceutically acceptable salt or prodrug forms thereof, wherein $R^3$ and $R^{3a}$ are combined to form a carbocyclic or heterocyclic ring, $R^5, R^{5a}, R^6, Q, B, W, X, Y,$ and Z are defined below, are effective inhibitors of the production of Aβ.

DETAILED DESCRIPTION OF PREFERRED EMBODIMENTS

Thus, in a first embodiment, the present invention provides a novel compound of Formula (I):

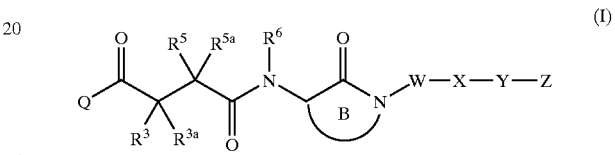

or a pharmaceutically acceptable salt or prodrug thereof, wherein:

Q is $-NR^1R^2$;

$R^1$ is H, $C_1-C_4$ alkyl, phenyl, benzyl, $C_3-C_6$ cycloalkyl, or ($C_3-C_6$ cycloalkyl)methyl-;

$R^2$ is H, $C_1-C_4$ alkyl, OH, $C_1-C_4$ alkoxy, phenyl, benzyl, $C_3-C_6$ cycloalkyl, or ($C_3-C_6$ cycloalkyl)methyl-;

$R^3$ and $R^{3a}$ may be combined to form a 3–8 membered carbocyclic moiety;

wherein said 3–8 membered carbocyclic moiety is saturated or partially unsaturated;

wherein said 3–8 membered carbocyclic moiety may optionally contain a heteroatom selected from $-O-$, $-S-$, $-S(=O)-$, $-S(=O)_2-$, $-N=$, $-NH-$, and $-N(R^{20})-$, and wherein said 3–8 membered carbocyclic moiety is substituted with 0–4 $R^4$;

additionally, two $R^4$ substituents on adjacent atoms may be combined to form a benzo fused radical; wherein said benzo fused radical is substituted with 0–4 $R^{23}$;

additionally, two $R^4$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{23}$;

additionally, two $R^4$ substituents on the same or adjacent carbon atoms may be combined to form a $C_3-C_6$ carbocycle substituted with 0–3 $R^{23}$;

alternatively, $R^3$ is H; $C_1-C_6$ alkyl substituted with 0–3 $R^4$; $C_2-C_6$ alkenyl substituted with 0–3 $R^4$; or $C_2-C_6$ alkynyl substituted with 0–3 $R^4$; and $R^{3a}$ is H, $C_1-C_6$ alkyl, or $C_2-C_6$ alkenyl;

$R^4$, at each occurrence, is independently selected from H, OH, Cl, F, Br, I, CN, $NO_2$, $CF_3$, acetyl, $SCH_3$, $S(=O)CH_3$, $S(=O)_2CH_3$, $NR^{15}R^{16}$, $OR^{14a}$, $C_1-C_4$ alkyl, $C_2-C_6$ alkenyl, alkynyl, $C_1-C_4$ alkoxy, $C_1-C_4$ haloalkyl, $C_1-C_4$ haloalkoxy, and $C_1-C_4$ haloalkyl-S—, $C_3-C_6$ carbocycle, aryl, and a 5 to 6 membered heterocycle containing 1 to 4 heteroatoms selected from nitrogen, oxygen, and sulphur;

$R^5$ is H, $C_1$–$C_6$ alkoxy;
  $C_1$–$C_6$ alkyl substituted with 0–3 $R^{5b}$;
  $C_2$–$C_6$ alkenyl substituted with 0–3 $R^{5b}$;
  $C_2$–$C_6$ alkynyl substituted with 0–3 $R^{5b}$;
  $C_3$–$C_{10}$ carbocycle substituted with 0–3 $R^{5c}$;
  $C_6$–$C_{10}$ aryl substituted with 0–3 $R^{5c}$; or
  5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5a}$ is H, $C_1$–$C_4$ alkyl, or $C_2$–$C_4$ alkenyl;
$R^{5b}$, at each occurrence, is independently selected from:
  H, $C_1$–$C_6$ alkyl, $CF_3$, $OR^{14}$, Cl, F, Br, I, =O, CN, $NO_2$, $NR^{15}R^{16}$;
  $C_3$–$C_{10}$ carbocycle substituted with 0–3 $R^{5c}$;
  $C_6$–$C_{10}$ aryl substituted with 0–3 $R^{5c}$; or
  5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;
alternatively, $R^5$ and $R^{5a}$ may be combined to form a 3–8 membered carbocyclic moiety;
  wherein said 3–8 membered carbocyclic moiety is saturated or partially unsaturated;
  wherein said 3–8 membered carbocyclic moiety may optionally contain a heteroatom selected from —O—, —S—, —S(=O)—, —S(=O)$_2$—, —N=, —NH—, and —N($R^{20}$)—, and
  wherein said 3–8 membered carbocyclic moiety is substituted with 0–4 $R^{5c}$;
provided at least:
  1) $R^3$ and $R^{3a}$ are combined to form a 3–8 membered carbocyclic moiety; or
  2) $R^5$ and $R^{5a}$ are combined to form a 3–8 membered carbocyclic moiety; or
  3) $R^3$ and $R^{3a}$ are combined to form a 3–8 membered carbocyclic moiety and $R^5$ and $R^{5a}$ are combined to form a 3–8 membered carbocyclic moiety;
$R^6$ is H;
  $C_1$–$C_6$ alkyl substituted with 0–3 $R^{6a}$;
  $C_3$–$C_{10}$ carbocycle substituted with 0–3 $R^{6b}$; or
  $C_6$–$C_{10}$ aryl substituted with 0–3 $R^{6b}$;
$R^{6a}$, at each occurrence, is independently selected from H, $C_1$–$C_6$ alkyl, $OR^{14}$, Cl, F, Br, I, =O, CN, $NO_2$, $NR^{15}R^{16}$, aryl or $CF_3$;
$R^{6b}$, at each occurrence, is independently selected from H, OH, Cl, F, Br, I, CN, $NO_2$, $NR^{15}R^{16}$, $CF_3$, $C_1$–$C_6$ alkyl, $C_1$–$C_4$ alkoxy, $C_1$–$C_4$ haloalkyl, and $C_1$–$C_4$ haloalkoxy;
Ring B is a 6, 7, or 8 membered lactam,
  wherein the lactam is saturated, partially saturated or unsaturated;
  wherein each additional lactam carbon is substituted with 0–2 $R^{11}$; and,
  optionally, the lactam contains an additional heteroatom selected from —O—, —S—, —S(=O)—, —S(=O)$_2$—, —N=, —NH—, and —N($R^{10}$)—;
additionally, two $R^{11}$ substituents on adjacent atoms may be combined to form a benzo fused radical; wherein said benzo fused radical is substituted with 0–4 $R^{13}$;
additionally, two $R^{11}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{13}$;
additionally, two $R^{11}$ substituents on the same or adjacent carbon atoms may be combined to form a $C_3$–$C_6$ carbocycle substituted with 0–3 $R^{13}$;
$R^{10}$ is H, $C(=O)R^{17}$, $C(=O)OR^{17}$, $C(=O)NR^{18}R^{19}$, $S(=O)_2NR^{18}R^{19}$, $S(=O)_2R^{17}$;
  $C_1$–$C_6$ alkyl optionally substituted with 0–3 $R^{10a}$;
  $C_6$–$C_{10}$ aryl substituted with 0–4 $R^{10b}$;
  $C_3$–$C_{10}$ carbocycle substituted with 0–3 $R^{10b}$; or
  5 to 10 membered heterocycle containing 1 to 4 heteroatoms selected from nitrogen, oxygen, and sulphur, wherein said 5 to 10 membered heterocycle is substituted with 0–3 $R^{10b}$;
$R^{10a}$, at each occurrence, is independently selected from H, $C_1$–$C_6$ alkyl, $OR^{14}$, Cl, F, Br, I, =O, CN, $NO_2$, $NR^{15}R^{16}$, $CF_3$, aryl substituted with 0–4 $R^{10b}$; or a 5–6 membered heterocycle substituted with 0–4 $R^{10b}$;
$R^{10b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;
$R^{11}$, at each occurrence, is independently selected from H, $C_1$–$C_4$ alkoxy, Cl, F, Br, I, =O, CN, $NO_2$, $NR^{18}R^{19}$, $C(=O)R^{17}$, $C(=O)OR^{17}$, $C(=O)NR^{18}R^{19}$, $S(=O)_2NR^{18}R^{19}$, $CF_3$;
  $C_1$–$C_6$ alkyl optionally substituted with 0–3 $R^{11a}$;
  $C_6$–$C_{10}$ aryl substituted with 0–3 $R^{11b}$;
  $C_3$–$C_{10}$ carbocycle substituted with 0–3 $R^{11b}$; or
  5 to 10 membered heterocycle containing 1 to 4 heteroatoms selected from nitrogen, oxygen, and sulphur, wherein said 5 to 10 membered heterocycle is substituted with 0–3 $R^{11b}$;
$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$;
  phenyl substituted with 0–3 $R^{11b}$;
  $C_3$–$C_6$ cycloalkyl substituted with 0–3 $R^{11b}$; and
  5 to 6 membered heterocycle containing 1 to 4 heteroatoms selected from nitrogen, oxygen, and sulphur, wherein said 5 to 6 membered heterocycle is substituted with 0–3 $R^{11b}$;
$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;
W is a bond or —$(CR^8R^{8a})_p$—;
p is 0, 1, 2, 3, or 4;
$R^8$ and $R^{8a}$, at each occurrence, are independently selected from H, F, $C_1$–$C_4$ alkyl, $C_2$–$C_4$ alkenyl, $C_2$–$C_4$ alkynyl and $C_3$–$C_8$ cycloalkyl;
X is a bond;
  $C_6$–$C_{10}$ aryl substituted with 0–3 $R^{Xb}$;
  $C_3$–$C_{10}$ carbocycle substituted with 0–3 $R^{Xb}$; or
  =to 10 membered heterocycle substituted with 0–2 $R^{Xb}$;
$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ halothioalkoxy;

Y is a bond or —$(CR^9R^{9a})_t$—V—$(CR^9R^{9a})_u$—;
t is 0, 1, or 2;
u is 0, 1, or 2;
$R^9$ and $R^{9a}$, at each occurrence, are independently selected from H, F, $C_1$–$C_6$ alkyl or $C_3$–$C_8$ cycloalkyl;
V is a bond, —C(=O)—, —O—, —S—, —S(=O)—, —S(=O)$_2$—, —N($R^{19}$)—, —C(=O)$NR^{19b}$—, $NR^{19b}$C(=O)—, —$NR^{19b}$S(=O)$_2$—, —S(=O)$_2NR^{19b}$—, —$NR^{19b}$S(=O)—, —S(=O)$NR^{19b}$—, —C(=O)O—, or —OC(=O)—;
Z is H;
  $C_1$–$C_8$ alkyl substituted with 0–3 $R^{12a}$;
  $C_2$–$C_6$ alkenyl substituted with 0–3 $R^{12a}$;
  $C_2$–$C_6$ alkynyl substituted with 0–3 $R^{12a}$;
  $C_6$–$C_{10}$ aryl substituted with 0–4 $R^{12b}$;
  $C_3$–$C_{10}$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;
$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl—S—, $C_6$–$C_{10}$ aryl substituted with 0–4 $R^{12b}$;
  $C_3$–$C_{10}$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;
$R^{12b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_3$–$C_6$ cycloalkyl, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S, and aryl substituted with 0–3 $R^{12c}$;
$R^{12c}$, at each occurrence, is independently selected from H, methyl, ethyl, propyl, methoxy, ethoxy, amino, hydroxy, Cl, F, Br, I, $CF_3$, $SCH_3$, S(O)$CH_3$, $SO_2CH_3$, —N($CH_3$)$_2$, N($CH_3$)H, CN, $NO_2$, $OCF_3$, C(=O)$CH_3$, $CO_2$H, $CO_2CH_3$, and $C_1$–$C_3$ haloalkyl;
$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;
$R^{14}$ is H, phenyl, benzyl, $C_1$–$C_6$ alkyl, $C_2$–$C_6$ alkoxyalkyl, or $C_3$–$C_6$ cycloalkyl;
$R^{14a}$ is H, phenyl, benzyl, or $C_1$–$C_4$ alkyl;
$R^{15}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;
$R^{16}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;
$R^{17}$ is H, $C_1$–$C_6$ alkyl, $C_2$–$C_6$ alkoxyalkyl, aryl substituted by 0–4 $R^{17a}$; or —$CH_2$-aryl substituted by 0–4 $R^{17a}$;
$R^{17a}$ is H, methyl, ethyl, propyl, butyl, methoxy, ethoxy, propoxy, butoxy, —OH, F, Cl, Br, I, $CF_3$, $OCF_3$, $SCH_3$, S(O)$CH_3$, $SO_2CH_3$, —$NH_2$, —N($CH_3$)$_2$, or $C_1$–$C_4$ haloalkyl;
$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;
$R^{19}$, at each occurrence, is independently selected from H, OH, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;
additionally, $R^{18}$ and $R^{19}$, when substituents on the same atom, may be combined to form a 3 to 6 membered heterocyclic ring;

$R^{19b}$, at each occurrence, is independently is H or $C_1$–$C_4$ alkyl;
$R^{20}$ is H, C(=O)$R^{17}$, C(=O)$OR^{17}$, C(=O)$NR^{18}R^{19}$, S(=O)$_2NR^{18}R^{19}$, S(=O)$_2R^{17}$;
  $C_1$–$C_6$ alkyl optionally substituted with 0–3 $R^{20a}$; or
  $C_6$–$C_{10}$ aryl substituted with 0–4 $R^{20b}$;
$R^{20a}$, at each occurrence, is independently selected from H, $C_1$–$C_4$ alkyl, $OR^{14}$, Cl, F, Br, I, =O, CN, $NO_2$, $NR^{15}R^{16}$, $CF_3$, or aryl substituted with 0–4 $R^{20b}$;
$R^{20b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_4$ alkyl, $C_1$–$C_4$ alkoxy, $C_1$–$C_4$ haloalkyl, $C_1$–$C_4$ haloalkoxy, and $C_1$–$C_4$ haloalkyl-S—;
$R^{23}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$.

[2] In a preferred embodiment the present invention provides for a compound of Formula (II):

$$\text{H}_2\text{N}\underset{R^3\ R^{3a}}{\overset{O}{\underset{\|}{C}}}\overset{R^5\ R^{5a}}{\underset{}{C}}\overset{R^6}{\underset{\|}{N}}\overset{O}{\underset{B}{C}}\text{N}-\text{W}-\text{X}-\text{Y}-\text{Z} \qquad (II)$$

or a pharmaceutically acceptable salt or prodrug thereof, wherein:
$R^3$ and $R^{3a}$ may be combined to form a 3–8 membered carbocyclic moiety;
  wherein said 3–8 membered carbocyclic moiety is saturated or partially unsaturated; and
$R^5$ and $R^{5a}$ may be combined to form a 3–8 membered carbocyclic moiety;
  wherein said 3–8 membered carbocyclic moiety is saturated or partially unsaturated;
provided at least:
1) $R^3$ and $R^{3a}$ are combined to form a 3–8 membered carbocyclic moiety; or
2) $R^5$ and $R^{5a}$ are combined to form a 3–8 membered carbocyclic moiety; or
3) $R^3$ and $R^{3a}$ are combined to form a 3–8 membered carbocyclic moiety and $R^5$ and $R^{5a}$ are combined to form a 3–8 membered carbocyclic moiety.

[3] In a preferred embodiment the present invention provides for a compound of Formula (II) wherein:
$R^3$ and $R^{3a}$ may be combined to form a 3–8 membered carbocyclic moiety selected from cyclopropyl, cyclobutyl, cyclopentyl, cyclopentenyl, cyclohexyl, and cyclohexenyl;
alternatively, $R^3$ and $R^{3a}$ are independently selected from the group H, $C_1$–$C_6$ alkyl, $C_2$–$C_6$ alkenyl, and $C_2$–$C_6$ alkynyl;
$R^5$ is H;
  $C_1$–$C_4$ alkyl substituted with 0–1 $R^{5b}$;
  $C_2$–$C_4$ alkenyl substituted with 0–1 $R^{5b}$;
  $C_2$–$C_4$ alkynyl substituted with 0–1 $R^{5b}$;
$R^{5a}$ is H, $C_1$–$C_4$ alkyl, or $C_2$–$C_4$ alkenyl;
$R^{5b}$ is selected from:
  H, methyl, ethyl, propyl, butyl, $CF_3$, Cl, F, $NR^{15}R^{16}$, cyclopropyl, cyclobutyl, cyclopentyl, and cyclohexyl;
alternatively, $R^5$ and $R^{5a}$ may be combined to form a 3–8 membered carbocyclic moiety selected from cyclopropyl, cyclobutyl, cyclopentyl, cyclopentenyl, cyclohexyl, and cyclohexenyl;

provided at least:
1) $R^3$ and $R^{3a}$ are combined to form a 3–8 membered carbocyclic moiety; or
2) $R^5$ and $R^{5a}$ are combined to form a 3–8 membered carbocyclic moiety; or
3) $R^3$ and $R^{3a}$ are combined to form a 3–8 membered carbocyclic moiety and $R^5$ and $R^{5a}$ are combined to form a 3–8 membered carbocyclic moiety;

Ring B is a 7 membered lactam,
wherein the lactam is saturated, partially saturated or unsaturated;
wherein each additional lactam carbon is substituted with 0–2 $R^{11}$; and,
optionally, the lactam contains an additional heteroatom selected from —O—, —S—, —S(=O)—, —S(=O)$_2$—, —N=, —NH—, and —N($R^{10}$)—;
additionally, two $R^{11}$ substituents on adjacent atoms may be combined to form a benzo fused radical; wherein said benzo fused radical is substituted with 0–4 $R^{13}$;
additionally, two $R^{11}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{13}$;
additionally, two $R^{11}$ substituents on the same or adjacent carbon atoms may be combined to form a $C_3$–$C_6$ carbocycle substituted with 0–3 $R^{13}$.

[4] In a preferred embodiment the present invention provides for a compound of Formula (I):

or a pharmaceutically acceptable salt or prodrug thereof, wherein:

Q is —NR$^1$R$^2$;

$R^1$ is H, methyl, ethyl, propyl, butyl, phenyl, benzyl, cyclopropyl, cyclobutyl, cyclopentyl, cyclohexyl, cyclopropylmethyl, cyclobutylmethyl, cyclopentylmethyl, or cyclohexylmethyl;

$R^2$ is H, methyl, ethyl, propyl, butyl, OH, methoxy, ethoxy, propoxy, phenyl, benzyl, cyclopropyl, cyclobutyl, cyclopentyl, cyclohexyl, cyclopropylmethyl, cyclobutylmethyl, cyclopentylmethyl, or cyclohexylmethyl;

$R^3$ and $R^{3a}$ are combined to form a 3–8 membered carbocyclic moiety;
wherein said 3–8 membered carbocyclic moiety is saturated or partially unsaturated;
wherein said 3–8 membered carbocyclic moiety may optionally contain a heteroatom selected from —O—, —S—, —S(=O)—, —S(=O)$_2$—, —N=, —NH—, and —N($R^{20}$)—, and
wherein said 3–8 membered carbocyclic moiety is substituted with 0–4 $R^4$;
additionally, two $R^4$ substituents on adjacent atoms may be combined to form a benzo fused radical; wherein said benzo fused radical is substituted with 0–4 $R^{23}$;
additionally, two $R^4$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{23}$;
additionally, two $R^4$ substituents on the same or adjacent carbon atoms may be combined to form a $C_3$–$C_6$ carbocycle substituted with 0–3 $R^{23}$;

$R^4$, at each occurrence, is independently selected from H, OH, Cl, F, Br, I, CN, NO$_2$, CF$_3$, acetyl, SCH$_3$, S(=O)CH$_3$, S(=O)$_2$CH$_3$, NR$^{15}$R$^{16}$, OR$^{14a}$, $C_1$–$C_4$ alkyl, $C_2$–$C_6$ alkenyl, alkynyl, $C_1$–$C_4$ alkoxy, $C_1$–$C_4$ haloalkyl, $C_1$–$C_4$ haloalkoxy, and $C_1$–$C_4$ haloalkyl-S—, $C_3$–$C_6$ carbocycle, aryl, and a
5 to 6 membered heterocycle containing 1 to 4 heteroatoms selected from nitrogen, oxygen, and sulphur;

$R^5$ is H, $C_1$–$C_6$ alkoxy;
$C_1$–$C_6$ alkyl substituted with 0–3 $R^{5b}$;
$C_2$–$C_6$ alkenyl substituted with 0–3 $R^{5b}$;
$C_2$–$C_6$ alkynyl substituted with 0–3 $R^{5b}$;
$C_3$–$C_{10}$ carbocycle substituted with 0–3 $R^{5c}$;
$C_6$–$C_{10}$ aryl substituted with 0–3 $R^5c$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5a}$ is H, $C_1$–$C_4$ alkyl, or $C_2$–$C_4$ alkenyl;

$R^{5b}$, at each occurrence, is independently selected from:
H, $C_1$–$C_6$ alkyl, CF$_3$, OR$^{14}$, Cl, F, Br, I, =O, CN, NO$_2$, NR$^{15}$R$^{16}$;
$C_3$–$C_{10}$ carbocycle substituted with 0–3 $R^{5c}$;
$C_6$–$C_{10}$ aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, NO$_2$, NR$^{15}$R$^{16}$, CF$_3$, acetyl, SCH$_3$, S(=O) CH$_3$, S(=O)$_2$CH$_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^6$ is H;
$C_1$–$C_6$ alkyl substituted with 0–3 $R^{6a}$;
$C_3$–$C_{10}$ carbocycle substituted with 0–3 $R^{6b}$; or
$C_6$–$C_{10}$ aryl substituted with 0–3 $R^{6b}$;

$R^{6a}$, at each occurrence, is independently selected from H, $C_1$–$C_6$ alkyl, OR$^{14}$, Cl, F, Br, I, =O, CN, NO$_2$, NR$^{15}$R$^{16}$, aryl or CF$_3$;

$R^{6b}$, at each occurrence, is independently selected from H, OH, Cl, F, Br, I, CN, NO$_2$, NR$^{15}$R$^{16}$, CF$_3$, $C_1$–$C_6$ alkyl, $C_1$–$C_4$ alkoxy, $C_1$–$C_4$ haloalkyl, and $C_1$–$C_4$ haloalkoxy;

Ring B is a 7 membered lactam,
wherein the lactam is saturated, partially saturated or unsaturated;
wherein each additional lactam carbon is substituted with 0–2 $R^{11}$; and,
optionally, the lactam contains an additional heteroatom selected from —O—, —S—, —S(=O)—, —S(=O)$_2$—, —N=, —NH—, and —N($R^{10}$)—;
additionally, two $R^{11}$ substituents on adjacent atoms may be combined to form a benzo fused radical; wherein said benzo fused radical is substituted with 0–4 $R^{13}$;
additionally, two $R^{11}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{13}$;

additionally, two $R^{11}$ substituents on the same or adjacent carbon atoms may be combined to form a $C_3$–$C_6$ carbocycle substituted with 0–3 $R^{13}$;

$R^{10}$ is H, $C(=O)R^{17}$, $C(=O)OR^{17}$, $C(=O)NR^{18}R^{19}$, $S(=O)_2NR^{18}R^{19}$, $S(=O)_2R^{17}$;

$C_1$–$C_6$ alkyl optionally substituted with 0–3 $R^{10b}$;

$C_6$–$C_{10}$ aryl substituted with 0–4 $R^{10b}$;

$C_3$–$C_{10}$ carbocycle substituted with 0–3 $R^{10b}$; or 5 to 10 membered heterocycle containing 1 to 4 heteroatoms selected from nitrogen, oxygen, and sulphur, wherein said 5 to 10 membered heterocycle is substituted with 0–3 $R^{10b}$;

$R^{10a}$, at each occurrence, is independently selected from H, $C_1$–$C_6$ alkyl, $OR^{14}$, Cl, F, Br, I, =O, CN, $NO_2$, $NR^{15}R^{16}$, $CF_3$, aryl substituted with 0–4 $R^{10b}$; or a 5–6 membered heterocycle substituted with 0–4 $R^{10b}$;

$R^{10b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{11}$, at each occurrence, is independently selected from H, $C_1$–$C_4$ alkoxy, Cl, F, Br, I, =O, CN, $NO_2$, $NR^{18}R^{19}$, $C(=O)R^{17}$, $C(=O)OR^{17}$, $C(=O)NR^{18}R^{19}$, $S(=O)_2NR^{18}R^{19}$, $CF_3$;

$C_1$–$C_6$ alkyl optionally substituted with 0–3 $R^{11b}$;

$C_6$–$C_{10}$ aryl substituted with 0–3 $R^{11b}$;

$C_3$–$C_{10}$ carbocycle substituted with 0–3 $R^{11b}$; or 5 to 10 membered heterocycle containing 1 to 4 heteroatoms selected from nitrogen, oxygen, and sulphur, wherein said 5 to 10 membered heterocycle is substituted with 0–3 $R^{11}$b;

$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$;

phenyl substituted with 0–3 $R^{11b}$;

$C_3$–$C_6$ cycloalkyl substituted with 0–3 $R^{11b}$; and 5 to 6 membered heterocycle containing 1 to 4 heteroatoms selected from nitrogen, oxygen, and sulphur, wherein said 5 to 6 membered heterocycle is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$alkoxy, $C_1$–$C_4$ haloalkyl, $C_1$–$C_4$ haloalkoxy, and $C_1$–$C_4$ haloalkyl-S—;

W is a bond or —$(CR^8R^{8a})_p$—;

p is 0, 1, 2, 3, or 4;

$R^8$ and $R^{8a}$, at each occurrence, are independently selected from H, F, $C_1$–$C_4$ alkyl, $C_2$–$C_4$ alkenyl, $C_2$–$C_4$ alkynyl and $C_3$–$C_8$ cycloalkyl;

X is a bond;

$C_6$–$C_{10}$ aryl substituted with 0–3 $R^{Xb}$;

$C_3$–$C_{10}$ carbocycle substituted with 0–3 $R^{Xb}$; or 5 to 10 membered heterocycle substituted with 0–2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ halothioalkoxy;

Y is a bond or —$(CR^9R^{9a})_t$—V—$(CR^9R^{9a})_u$—;

t is 0, 1, or 2;

u is 0, 1, or 2;

$R^9$ and $R^{9a}$, at each occurrence, are independently selected from H, F, $C_1$–$C_6$ alkyl or $C_3$–$C_8$ cycloalkyl;

V is a bond, —C(=O)—, —O—, —S—, —S(=O)—, —S(=O)_2—, —N(R^{19})—, —C(=O)NR^{19b}—, —NR^{19b}C(=O)—, —NR^{19b}S(=O)_2—, —S(=O)_2NR^{19b}—, —NR^{19b}S(=O)—, —S(=O)NR^{19b}—, —C(=O)O—, or —OC(=O)—;

Z is H;

$C_1$–$C_8$ alkyl substituted with 0–3 $R^{12a}$;

$C_2$–$C_6$ alkenyl substituted with 0–3 $R^{12a}$;

$C_2$–$C_6$ alkynyl substituted with 0–3 $R^{12a}$;

$C_6$–$C_{10}$ aryl substituted with 0–4 $R^{12b}$;

$C_3$–$C_{10}$ carbocycle substituted with 0–4 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from H, OH, Cl, F, Br, I, CN, $NO_2$, $NR^{15}R^{16}$, —C(=O)NR^{15}R^{16}, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, $C_6$–$C_{10}$ aryl substituted with 0–4 $R^{12b}$;

$C_3$–$C_{10}$ carbocycle substituted with 0–4 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_3$–$C_6$ cycloalkyl, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S, and aryl substituted with 0–3 $R^{12c}$;

$R^{12c}$, at each occurrence, is independently selected from H, methyl, ethyl, propyl, methoxy, ethoxy, amino, hydroxy, Cl, F, Br, I, $CF_3$, $SCH_3$, $S(O)CH_3$, $SO_2CH_3$, —N(CH_3)_2, $N(CH_3)H$, CN, $NO_2$, $OCF_3$, $C(=O)CH_3$, $CO_2H$, $CO_2CH_3$, and $C_1$–$C_3$ haloalkyl;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)_2—;

$R^{16}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)_2—;

$R^{17}$ is H, $C_1$–$C_6$ alkyl, $C_2$–$C_6$ alkoxyalkyl, aryl substituted by 0–4 $R^{17a}$, or —CH_2-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —NH_2, —N(CH_3)_2, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)_2—;

$R^{19}$, at each occurrence, is independently selected from H, OH, $C_1$–$C_6$ alkyl, phenyl, benzyl, phenethyl, ($C_1$–$C_6$ alkyl)-C(=O)—, and ($C_1$–$C_6$ alkyl)-S(=O)_2—;

additionally, $R^{18}$ and $R^{19}$, when substituents on the same atom, may be combined to form a 3 to 6 membered heterocyclic ring;

$R^{19b}$, at each occurrence, is independently is H or $C_1$–$C_4$ alkyl;

$R^{20}$ is H, $C(=O)R^{17}$, $C(=O)OR^{17}$, $C(=O)NR^{18}R^{19}$, $S(=O)_2NR^{18}R^{19}$, $S(=O)_2R^{17}$;
   $C_1$–$C_6$ alkyl optionally substituted with 0–3 $R^{20a}$; or
   $C_6$–$C_{10}$ aryl substituted with 0–4 $R^{20b}$;
$R^{20a}$, at each occurrence, is independently selected from H, $C_1$–$C_4$ alkyl, $OR^{14}$, Cl, F, Br, I, =O, CN, $NO_2$, $NR^{15}R^{16}$, $CF_3$, or aryl substituted with 0–4 $R^{20b}$;
$R^{20b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_4$ alkyl, $C_1$–$C_4$ alkoxy, $C_1$–$C_4$ haloalkyl, $C_1$–$C_4$ haloalkoxy, and $C_1$–$C_4$ haloalkyl-S—;
$R^{23}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$.

[5] In another preferred embodiment the present invention provides for a compound of Formula (Ia):

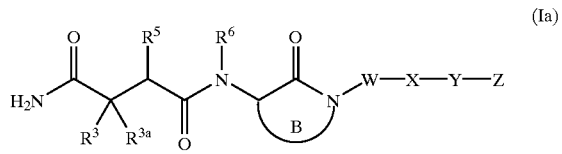

(Ia)

or a pharmaceutically acceptable salt or prodrug thereof, wherein:
$R^3$ and $R^{3a}$ are combined to form a 3–8 membered carbocyclic moiety;
   wherein said 3–8 membered carbocyclic moiety is saturated or partially unsaturated;
   wherein said 3–8 membered carbocyclic moiety is substituted with 0–4 $R^4$;
additionally, two $R^4$ substituents on adjacent atoms may be combined to form a benzo fused radical; wherein said benzo fused radical is substituted with 0–4 $R^{23}$;
additionally, two $R^4$ substituents on adjacent atoms may be combined to form a 5 to 6 membered heteroaryl fused radical, wherein said 5 to 6 membered heteroaryl fused radical comprises 1 or 2 heteroatoms selected from N, O, and; wherein said 5 to 6 membered heteroaryl fused radical is substituted with 0–3 $R^{23}$;
additionally, two $R^4$ substituents on the same or adjacent carbon atoms may be combined to form a $C_3$–$C_6$ carbocycle substituted with 0–3 $R^{23}$;
$R^4$, at each occurrence, is independently selected from H, OH, Cl, F, Br, I, CN, $NO_2$, $CF_3$, acetyl, $SCH_3$, $S(=O)CH_3$, $S(=O)_2CH_3$, $NR^{15}R^{16}$, $OR^{14a}$, $C_1$–$C_4$ alkyl, $C_2$–$C_6$ alkenyl, alkynyl, $C_1$–$C_4$ alkoxy, $C_1$–$C_4$ haloalkyl, $C_1$–$C_4$ haloalkoxy, and $C_1$–$C_4$ haloalkyl-S—, $C_3$–$C_6$ carbocycle, aryl, and a
   5 to 6 membered heterocycle containing 1 to 4 heteroatoms selected from nitrogen, oxygen, and sulphur; and
$R^5$ is H, $C_1$–$C_4$ alkoxy;
   $C_1$–$C_6$ alkyl substituted with 0–3 $R^{5b}$;
   $C_2$–$C_6$ alkenyl substituted with 0–3 $R^{5b}$;
   $C_2$–$C_6$ alkynyl substituted with 0–3 $R^{5b}$;
   $C_3$–$C_{10}$ carbocycle substituted with 0–3 $R^{5c}$;
   $C_6$–$C_{10}$ aryl substituted with 0–3 $R^{5c}$; or
   5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5b}$, at each occurrence, is independently selected from:
   H, $C_1$–$C_6$ alkyl, $CF_3$, $OR^{14}$, Cl, F, Br, I, =O, CN, $NO_2$, $NR^{15}R^{16}$;
   $C_3$–$C_{10}$ carbocycle substituted with 0–3 $R^{5c}$;
   $C_6$–$C_{10}$ aryl substituted with 0–3 $R^{5c}$; or
   5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;
$R^6$ is H, methyl, or ethyl;
Ring B is selected from:

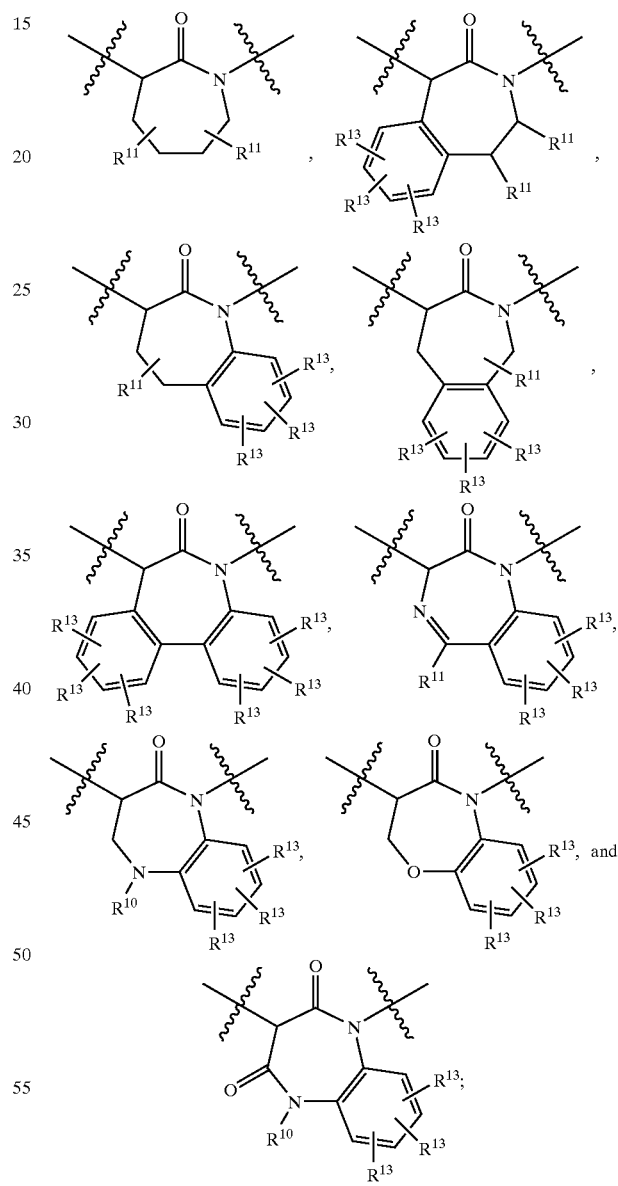

$R^{10}$ is H, $C(=O)R^{17}$, $C(=O)OR^{17}$, $C(=O)NR^{18}R^{19}$, $S(=O)_2NR^{18}R^{19}$, $S(=O)_2R^{17}$;
   $C_1$–$C_6$ alkyl optionally substituted with 0–3 $R^{10a}$;
   $C_6$–$C_{10}$ aryl substituted with 0–4 $R^{10b}$;
   $C_3$–$C_{10}$ carbocycle substituted with 0–3 $R^{10b}$; or
   5 to 10 membered heterocycle containing 1 to 4 heteroatoms selected from nitrogen, oxygen, and sulphur, wherein said 5 to 10 membered heterocycle is substituted with 0–3 $R^{10b}$;

$R^{10a}$, at each occurrence, is independently selected from H, $C_1$–$C_6$ alkyl, $OR^{14}$, Cl, F, Br, I, =O, CN, $NO_2$, $NR^{15}R^{16}$, $CF_3$, aryl substituted with 0–4 $R^{10b}$; or a 5–6 membered heterocycle substituted with 0–4 $R^{10b}$;

$R^{10b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{11}$, at each occurrence, is independently selected from H, $C_1$–$C_4$ alkoxy, Cl, F, Br, I, =O, CN, $NO_2$, $NR^{18}R^{19}$, $C(=O)R^{17}$, $C(=O)OR^{17}$, $C(=O)NR^{18}R^{19}$, $S(=O)_2NR^{18}R^{19}$, $CF_3$;

$C_1$–$C_6$ alkyl optionally substituted with 0–3 $R^{11b}$;

$C_6$–$C_{10}$ aryl substituted with 0–3 $R^{11b}$;

$C_3$–$C_{10}$ carbocycle substituted with 0–3 $R^{11b}$; or 5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$;

phenyl substituted with 0–3 $R^{11b}$;

$C_3$–$C_6$ cycloalkyl substituted with 0–3 $R^{11b}$; and 5 to 6 membered heterocycle containing 1 to 4 heteroatoms selected from nitrogen, oxygen, and sulphur, wherein said 5 to 6 membered heterocycle is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

W is a bond or —$(CH_2)_p$—;

is 1 or 2;

X is a bond;

phenyl substituted with 0–2 $R^{Xb}$;

$C_3$–$C_6$ carbocycle substituted with 0–2 $R^{Xb}$; or 5 to 6 membered heterocycle substituted with 0–2 $R^{Xb}$;

$R_{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_3$ haloalkyl, $C_1$–$C_3$ haloalkoxy, and $C_1$–$C_3$ halothioalkoxy;

Y is a bond, —C(=O)—, —O—, —S—, —S(=O)—, —$S(=O)_2$—, —$N(R^{19})$—, —$C(=O)NR^{19b}$—, —$NR^{19b}C(=O)$—, —$NR^{19b}S(=O)_2$—, —$S(=O)_2NR^{19b}$—, —$NR^{19b}S(=O)$—, —$S(=O)NR^{19b}$—, —C(=O)O—, or —OC(=O)—;

Z is H;

$C_1$–$C_8$ alkyl substituted with 0–3 $R^{12a}$;

$C_2$–$C_6$ alkenyl substituted with 0–3 $R^{12a}$;

$C_2$–$C_6$ alkynyl substituted with 0–3 $R^{12a}$;

$C_6$–$C_{10}$ aryl substituted with 0–4 $R^{12b}$;

$C_3$–$C_{10}$ carbocycle substituted with 0–4 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from H, OH, Cl, F, Br, I, CN, $NO_2$, $NR^{15}R^{16}$, —$C(=O)NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, $C_6$–$C_{10}$ aryl substituted with 0–4 $R^{12b}$;

$C_3$–$C_{10}$ carbocycle substituted with 0–4 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_3$–$C_6$ cycloalkyl, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S, and aryl substituted with 0–3 $R^{12c}$;

$R^{12c}$ at each occurrence, is independently selected from H, methyl, ethyl, propyl, methoxy, ethoxy, amino, hydroxy, Cl, F, Br, I, $CF_3$, $SCH_3$, $S(O)CH_3$, $SO_2CH_3$, —$N(CH_3)_2$, $N(CH_3)H$, CN, $NO_2$, $OCF_3$, $C(=O)CH_3$, $CO_2H$, $CO_2CH_3$, and $C_1$–$C_3$ haloalkyl;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_6$ alkyl)-$C(=O)$—, and ($C_1$–$C_6$ alkyl)-$S(=O)_2$—;

$R^{16}$, at each occurrence, is independently selected from H, $C_1$–$C_6$ alkyl, benzyl, phenethyl, ($C_1$–$C_6$ alkyl)-$C(=O)$—, and (Cl–$C_6$ alkyl)-$S(=O)_2$—;

$R^{17}$ is H, $C_1$–$C_6$ alkyl, $C_2$–$C_6$ alkoxyalkyl, aryl substituted by 0–4 $R^{17a}$; —$CH_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NR_2$, —$N(CH_3)_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)-$C(=O)$—, and ($C_1$–$C_6$ alkyl)-$S(=O)_2$—;

$R^{19}$, at each occurrence, is independently selected from H, OH, methyl, ethyl, propyl, butyl, phenyl, benzyl, phenethyl;

additionally, $R^{18}$ and $R^{19}$, when substituents on the same atom, may be combined to form a 3 to 6 membered heterocyclic ring selected from pyrrolyl, imidazolyl, imidazolidinyl, pyrrolidinyl, piperidinyl, piperazinyl, and morpholinyl;

$R^{19b}$, at each occurrence, is independently is H or $C_1$–$C_4$ alkyl; and $R^{23}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$.

[6] In another preferred embodiment the present invention provides for a compound of Formula (Ib):

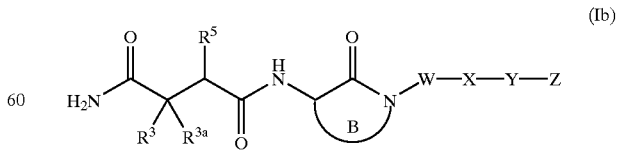

or a pharmaceutically acceptable salt or prodrug thereof, wherein:

$R^3$ and $R^{3a}$ are combined to form a 3–8 membered carbocyclic moiety;

wherein said 3–8 membered carbocyclic moiety is saturated or partially unsaturated;
wherein said 3–8 membered carbocyclic moiety is substituted with 0–4 $R^4$;
additionally, two $R^4$ substituents on adjacent atoms may be combined to form a benzo fused radical; wherein said benzo fused radical is substituted with 0–4 $R^{23}$;
additionally, two $R^4$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{23}$;
additionally, two $R^4$ substituents on the same or adjacent carbon atoms may be combined to form a $C_3$–$C_6$ carbocycle substituted with 0–3 $R^{23}$;
$R^4$, at each occurrence, is independently selected from H, OH, Cl, F, Br, I, CN, $NO_2$, $CF_3$, acetyl, $SCH_3$, S(=O)$CH_3$, S(=O)$_2CH_3$, $NR^{15}R^{16}$, $OR^{14}a$, $C_1$–$C_4$ alkyl, $C_2$–$C_6$ alkenyl, alkynyl, $C_1$–$C_4$ alkoxy, $C_1$–$C_4$ haloalkyl, $C_1$–$C_4$ haloalkoxy, and $C_1$–$C_4$ haloalkyl-S—, $C_3$–$C_6$ carbocycle, aryl, and a
5 to 6 membered heterocycle containing 1 to 4 heteroatoms selected from nitrogen, oxygen, and sulphur; and
$R^5$ is H;
$C_1$–$C_6$ alkyl substituted with 0–3 $R^{5b}$;
$C_2$–$C_6$ alkenyl substituted with 0–3 $R^{5b}$;
$C_2$–$C_6$ alkynyl substituted with 0–3 $R^{5b}$;
$C_3$–$C_{10}$ carbocycle substituted with 0–3 $R^{5c}$;
$C_6$–$C_{10}$ aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5b}$, at each occurrence, is independently selected from:
H, $C_1$–$C_6$ alkyl, $CF_3$, $OR^{14}$, Cl, F, Br, I, =O, CN, $NO_2$, $NR^{15}R^{16}$;
$C_3$–$C_{10}$ carbocycle substituted with 0–3 $R^{5c}$;
$C_6$–$C_{10}$ aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5c}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;
Ring B is selected from:

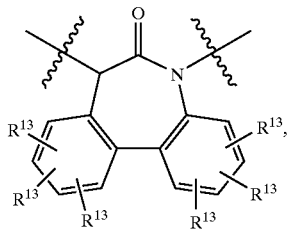
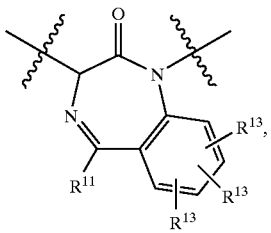
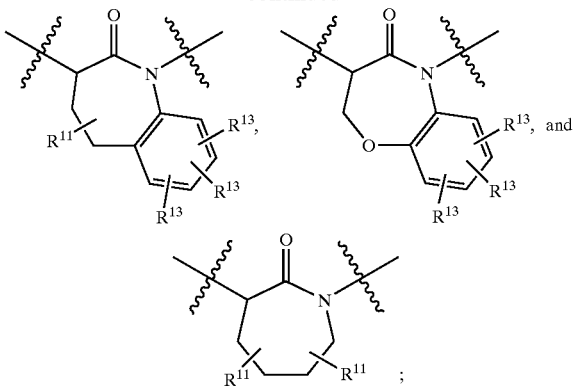

$R^{11}$, at each occurrence, is independently selected from H, $C_1$–$C_4$ alkoxy, Cl, F, Br, I, =I, CN, $NO_2$, $NR^{18}R^{19}$, C(=O)$R^{17}$, C(=O)$OR^{17}$, C(=O)$NR^{18}R^{19}$, S(=O)$_2$ $NR^{18}R^{19}$, $CF_3$;
$C_1$–$C_6$ alkyl optionally substituted with 0–3 $R^{11a}$;
$C_6$–$C_{10}$ aryl substituted with 0–3 $R^{11b}$;
$C_3$–$C_{10}$ carbocycle substituted with 0–3 $R^{11b}$; or
5 to 10 membered heterocycle containing 1 to 4 heteroatoms selected from nitrogen, oxygen, and sulphur, wherein said 5 to 10 membered heterocycle is substituted with 0–3 $R^{11b}$;
$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$;
phenyl substituted with 0–3 $R^{11b}$;
$C_3$–$C_6$ cycloalkyl substituted with 0–3 $R^{11b}$; and
5 to 6 membered heterocycle containing 1 to 4 heteroatoms selected from nitrogen, oxygen, and sulphur, wherein said 5 to 6 membered heterocycle is substituted with 0–3 $R^{11b}$;
$R^{11b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;
W is a bond;
X is a bond;
Y is a bond;
Z is H;
$C_1$–$C_8$ alkyl substituted with 0–3 $R^{12a}$;
$C_2$–$C_6$ alkenyl substituted with 0–3 $R^{12a}$;
$C_2$–$C_6$ alkynyl substituted with 0–3 $R^{12a}$;
$C_6$–$C_{10}$ aryl substituted with 0–4 $R^{12b}$;
$C_3$–$C_{10}$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;
$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, $C_6$–$C_{10}$ aryl substituted with 0–4 $R^{12b}$;
$C_3$–$C_{10}$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{16}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{17}$ is H, $C_1$–$C_6$ alkyl, $C_2$–$C_6$ alkoxyalkyl, aryl substituted by 0–4 $R^{17a}$, or —$CH_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(CH_3)_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

$R^{19}$, at each occurrence, is independently selected from H, OH, methyl, ethyl, propyl, butyl, phenyl, benzyl, phenethyl; and $R^{23}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$.

[7] In another preferred embodiment the present invention provides for a compound of Formula (Ib):

$R^3$ and $R^{3a}$ are combined to form a 3–8 membered carbocyclic moiety;
wherein said 3–8 membered carbocyclic moiety is saturated or partially unsaturated;
wherein said 3–8 membered carbocyclic moiety is substituted with 0–3 $R^4$;

$R^4$, at each occurrence, is independently selected from H, OH, Cl, F, Br, I, CN, $NO_2$, $CF_3$, acetyl, $SCH_3$, $S(=O)CH_3$, $S(=O)_2CH_3$, $NR^{15}R^{16}$, $OR^{14a}$, $C_1$–$C_4$ alkyl, $C_2$–$C_4$ alkenyl, $C_2$–$C_4$ alkynyl, $C_1$–$C_4$ alkoxy, $C_1$–$C_4$ haloalkyl, $C_1$–$C_4$ haloalkoxy, and $C_1$–$C_4$ haloalkyl-S—;

$R^5$ is H;
$C_1$–$C_6$ alkyl substituted with 0–3 $R^{5b}$;
$C_2$–$C_6$ alkenyl substituted with 0–3 $R^{5b}$;
$C_2$–$C_6$ alkynyl substituted with 0–3 $R^{5b}$;
$C_3$–$C_{10}$ carbocycle substituted with 0–3 $R^{5c}$;
$C_6$–$C_{10}$ aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5b}$, at each occurrence, is independently selected from: H, $C_1$–$C_6$ alkyl, $CF_3$, $OR^{14}$, Cl, F, Br, I, =O, CN, $NO_2$, $NR^{15}R^{16}$;
$C_3$–$C_{10}$ carbocycle substituted with 0–3 $R^{5c}$;
$C_6$–$C_{10}$ aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, and $C_1$–$C_4$ haloalkoxy;

Ring B is selected from:

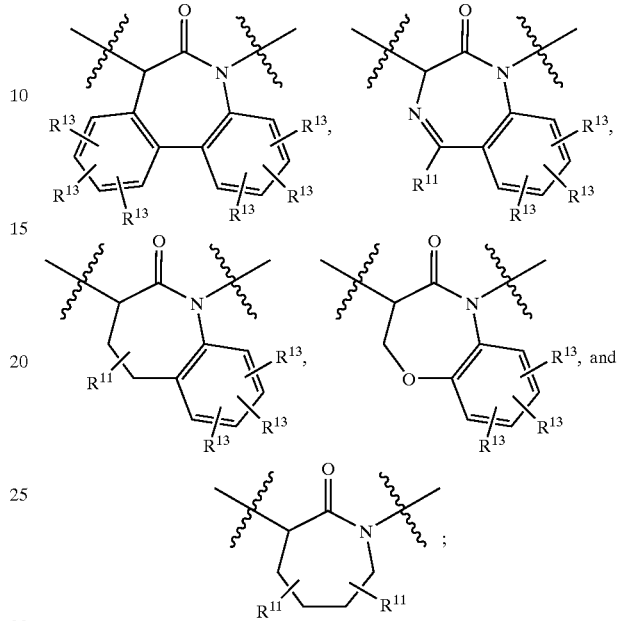

$R^{11}$, at each occurrence, is independently selected from H, =O, $NR^{18}NR^{19}$, $CF_3$;
$C_1$–$C_4$ alkyl optionally substituted with 0–1 $R^{11a}$;
phenyl substituted with 0–3 $R^{11b}$;
$C_3$–$C_7$ carbocycle substituted with 0–3 $R^{11b}$; and
5 to 7 membered heterocycle containing 1 to 4 heteroatoms selected from nitrogen, oxygen, and sulphur, wherein said 5 to 7 membered heterocycle is substituted with 0–3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11a}$, at each occurrence, is independently selected from H, $C_1$–$C_4$ alkyl, $OR^{14}$, F, Cl, =O, $NR^{15}R^{16}$, $CF_3$, or phenyl substituted with 0–3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;

W is a bond;
X is a bond;
Y is a bond;
Z is H;
$C_1$–$C_8$ alkyl substituted with 0–3 $R^{12a}$;
$C_2$–$C_6$ alkenyl substituted with 0–3 $R^{12a}$; or
$C_2$–$C_6$ alkynyl substituted with 0–3 $R^{12a}$;

$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, $C_6$–$C_{10}$ aryl substituted with 0–4 $R^{12b}$;
$C_3$–$C_{10}$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$; and wherein said 5 to 10 membered heterocycle is selected from pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_4$ alkyl)-C(=O)—, and ($C_1$–$C_4$ alkyl)-S(=O)$_2$—;

$R^{16}$, at each occurrence, is independently selected from H, $C_1$–$C_6$ alkyl, benzyl, phenethyl, ($C_1$–$C_4$ alkyl)-C(=O)—, and ($C_1$–$C_4$ alkyl)-S(=O)$_2$—;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—; and $R^{19}$, at each occurrence, is independently selected from H, OH, methyl, ethyl, propyl, butyl, phenyl, benzyl, and phenethyl.

[8] In another preferred embodiment the present invention provides for a compound of Formula (Ib):

$R^3$ and $R^{3a}$ are combined to form a 3–6 membered carbocyclic moiety;
  wherein said 3–6 membered carbocyclic moiety is saturated or partially unsaturated;
  wherein said 3–6 membered carbocyclic moiety is substituted with 0–2 $R^4$;

$R^4$, at each occurrence, is independently selected from H, OH, Cl, F, Br, I, CN, $NO_2$, $CF_3$, acetyl, $SCH_3$, methyl, ethyl, methoxy, ethoxy, allyl, —$OCF_3$, and —$SCF_3$;

$R^5$ is H;
  $C_1$–$C_4$ alkyl substituted with 0–3 $R^{5b}$;
  $C_2$–$C_4$ alkenyl substituted with 0–3 $R^{5b}$; or
  $C_2$–$C_4$ alkynyl substituted with 0–3 $R^{5b}$;

$R^{5b}$, at each occurrence, is independently selected from:
  H, methyl, ethyl, propyl, butyl, $CF_3$, $OR^{14}$, Cl, F, Br, I, =O;
  $C_3$–$C_6$ carbocycle substituted with 0–3 $R^{5c}$;
  phenyl substituted with 0–3 $R^{5c}$; or
  5 to 6 membered heterocycle containing 1 to 4 heteroatoms selected from nitrogen, oxygen, and sulphur, wherein said 5 to 6 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

Ring B is selected from:

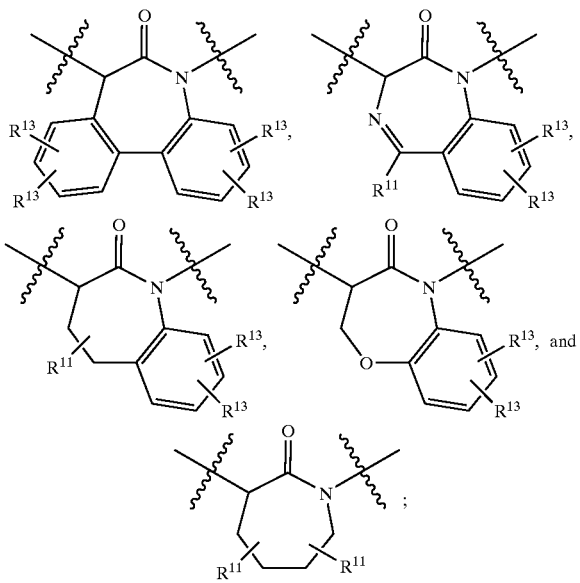

$R^{11}$, at each occurrence, is independently selected from H, =O, $NR^{18}R^{19}$, $CF_3$;
  $C_1$–$C_4$ alkyl optionally substituted with 0–1 $R^{11a}$;
  phenyl substituted with 0–3 $R^{11b}$;
  $C_3$–$C_7$ carbocycle substituted with 0–3 $R^{11b}$; and
  5 to 7 membered heterocycle containing 1 to 4 heteroatoms selected from nitrogen, oxygen, and sulphur, wherein said 5 to 7 membered heterocycle is substituted with 0–3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11a}$, at each occurrence, is independently selected from H, methyl, ethyl, propyl, butyl, methoxy, ethoxy, propoxy, phenoxy, F, Cl, =O, $NR^{15}R^{16}$, $CF_3$, or phenyl substituted with 0–3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;

W is a bond;
X is a bond;
Y is a bond;
Z is H;
  $C_1$–$C_4$ alkyl substituted with 0–3 $R^{12a}$;
  $C_2$–$C_4$ alkenyl substituted with 0–3 $R^{12a}$; or
  $C_2$–$C_4$ alkynyl substituted with 0–3 $R^{12a}$;

$R^{12a}$, at each occurrence, is independently selected from H, OH, Cl, F, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_4$ alkyl, or $C_2$–$C_4$ alkoxyalkyl;

$R^{15}$, at each occurrence, is independently selected from H, $C_1$–$C_4$ alkyl, and benzyl;

$R^{16}$, at each occurrence, is independently selected from H, methyl, ethyl, propyl, butyl, benzyl, phenethyl, methyl- C(=O)—, ethyl-C(=O)—, methyl-S(=O)$_2$—, and ethyl-S(=O)$_2$—;

$R^{18}$, at each occurrence, is independently selected from H, methyl, ethyl, propyl, butyl, phenyl, benzyl, and phenethyl; and $R^{19}$, at each occurrence, is independently selected from H, methyl, ethyl, propyl, and butyl.

[9] In another preferred embodiment the present invention provides for a compound of Formula (Ib):

$R^3$ and $R^{3a}$ are combined to form a 3–6 membered carbocyclic moiety selected from cyclopropyl, cyclobutyl, cyclopentyl, cyclopentenyl, cyclohexyl, and cyclohexenyl; wherein said 3–6 membered carbocyclic moiety is substituted with 0–1 $R^4$;

$R^4$ is selected from H, OH, Cl, F, CN, CF$_3$, methyl, ethyl, methoxy, ethoxy, allyl, and —OCF$_3$;

$R^5$ is C$_1$–C$_4$ alkyl substituted with 0–1 $R^{5b}$;
C$_2$–C$_4$ alkenyl substituted with 0–1 $R^{5b}$;
C$_2$–C$_4$ alkynyl substituted with 0–1 $R^{5b}$;

$R^{5b}$, at each occurrence, is independently selected from:
H, methyl, ethyl, propyl, butyl, CF$_3$, OR$^{14}$, =O;
C$_3$–C$_6$ carbocycle substituted with 0–2 $R^{5c}$;
phenyl substituted with 0–3 $R^{5c}$; or
5 to 6 membered heterocycle containing 1 to 4 heteroatoms selected from nitrogen, oxygen, and sulphur, wherein said 5 to 6 membered heterocycle is substituted with 0–3 $R^{5c}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{5c}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, methyl, ethyl, propyl, butyl, methoxy, ethoxy, propoxy, C$_1$–C$_2$ haloalkyl, and C$_1$–C$_2$ haloalkoxy;

Ring B is selected from:

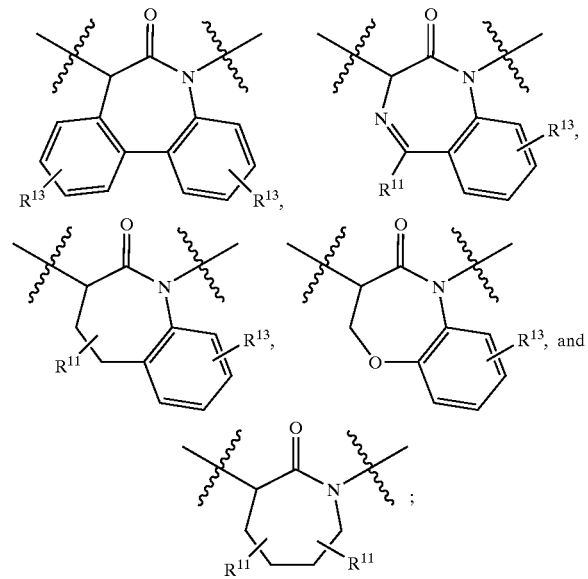

$R^{11}$, at each occurrence, is independently selected from H, =O, NR$^{18}$R$^{19}$;
C$_1$–C$_4$ alkyl optionally substituted with 0–1 $R^{11a}$;
phenyl substituted with 0–3 $R^{11b}$;
cyclohexyl substituted with 0–3 $R^{11b}$;
cycloheptyl substituted with 0–3 $R^{11b}$;

5 to 7 membered heterocycle containing 1 to 4 heteroatoms selected from nitrogen, oxygen, and sulphur, wherein said 5 to 7 membered heterocycle is substituted with 0–3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11a}$, at each occurrence, is independently selected from H, methyl, ethyl, propyl, methoxy, ethoxy, propoxy, phenoxy, F, Cl, =O, NR$^{15}$R$^{16}$, CF$_3$, or phenyl substituted with 0–3 $R^{11b}$;

$R^{11b}$, at each occurrence, is independently selected from H, OH, Cl, F, NR$^{15}$R$^{16}$, CF$_3$, methyl, ethyl, propyl, butyl, methoxy, ethoxy, propoxy, C$_1$–C$_2$ haloalkyl, and C$_1$–C$_2$ haloalkoxy;

W is a bond;
X is a bond;
Y is a bond;
Z is H;

C$_1$–C$_4$ alkyl substituted with 0–1 $R^{12a}$;
C$_2$–C$_4$ alkenyl substituted with 0–1 $R^{12a}$; or
C$_2$–C$_4$ alkynyl substituted with 0–1 $R^{12a}$;

$R^{12a}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, methyl, ethyl, propyl, butyl, methoxy, ethoxy, propoxy, C$_1$–C$_2$ haloalkyl, and C$_1$–C$_2$ haloalkoxy;

$R^{13}$, at each occurrence, is independently selected from H, OH, methyl, ethyl, propyl, butyl, methoxy, ethoxy, Cl, F, Br, CN, NR$^{15}$R$^{16}$, and CF$_3$;

$R^{14}$ is H, phenyl, benzyl, methyl, ethyl, propyl, or butyl;
$R^{15}$, at each occurrence, is independently selected from H, methyl, ethyl, propyl, and butyl;
$R^{16}$, at each occurrence, is independently selected from H, methyl, ethyl, propyl, butyl, benzyl, and phenethyl;
$R^{18}$, at each occurrence, is independently selected from H, methyl, ethyl, propyl, butyl, phenyl, benzyl, and phenethyl; and
$R^{19}$, at each occurrence, is independently selected from H, methyl, ethyl, propyl, and butyl.

[10] In another preferred embodiment the present invention provides for a compound of Formula (Ib):

$R^3$ and $R^{3a}$ are combined to form cyclobutyl, cyclopentyl, cyclopentenyl, or cyclohexyl;

$R^5$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$, —CH$_2$C(CH$_3$)$_3$, —CH$_2$CH$_2$CH$_2$CH$_2$CH$_3$, —CH(CH$_3$)CH$_2$CH$_2$CH$_3$, —CH$_2$CH(CH$_3$)CH$_2$CH$_3$, —CH$_2$CH$_2$CH(CH$_3$)$_2$, —CH(CH$_2$CH$_3$)$_2$, —CF$_3$, —CH$_2$CF$_3$, —CH$_2$CH$_2$CF$_3$, —CH$_2$CH$_2$CH$_2$CF$_3$, —CH$_2$CH$_2$CH$_2$CH$_2$CF$_3$, —CH=CH$_2$, —CH$_2$CH=CH$_2$, —CH=CHCH$_3$, cis-CH$_2$CH=CH(CH$_3$), trans-CH$_2$CH=CH(CH$_3$), trans-CH$_2$CH=CH(C$_6$H$_5$), —CH$_2$CH=C(CH$_3$)$_2$, cis-CH$_2$CH=CHCH$_2$CH$_3$, trans-CH$_2$CH=CHCH$_2$CH$_3$, cis-CH$_2$CH$_2$CH=CH(CH$_3$), trans-CH$_2$CH$_2$CH=CH(CH$_3$), trans-CH$_2$CH=CHCH$_2$(C$_6$H$_5$), —C≡CH, —CH$_2$C≡CH, —CH$_2$C≡C(CH$_3$), —CH$_2$C≡C(C$_6$H$_5$)—CH$_2$CH$_2$C≡CH, —CH$_2$CH$_2$C≡C(CH$_3$), —CH$_2$CH$_2$C≡C(C$_6$H$_5$)—CH$_2$CH$_2$CH$_2$C≡CH, —CH$_2$CH$_2$CH$_2$C≡C(CH$_3$), —CH$_2$CH$_2$CH$_2$C≡C(C$_6$H$_5$)cyclopropyl-CH$_2$—, cyclobutyl-CH$_2$—, cyclopentyl-CH$_2$—, cyclohexyl-CH$_2$—, (2-CH$_3$-cyclopropyl)CH$_2$—, (3-CH$_3$-cyclobutyl)CH$_2$—, cyclopropyl-CH$_2$CH$_2$—, cyclobutyl-CH$_2$CH$_2$—, cyclopentyl-CH$_2$CH$_2$—, cyclohexyl-CH$_2$CH$_2$—, (2-CH$_3$-cyclopropyl)CH$_2$CH$_2$—, (3-CH$_3$-cyclobutyl)

CH₂CH₂—, phenyl-CH₂—, (2-F-phenyl)CH₂—, (3-F-phenyl)CH₂—, (4-F-phenyl)CH₂—, furanyl-CH₂—, thienyl-CH₂—, pyridyl-CH₂—, 1-imidazolyl-CH₂—, oxazolyl-CH₂—, isoxazolyl-CH₂—, phenyl-CH₂CH₂—, (2-F-phenyl)CH₂CH₂—, (3-F-phenyl)CH₂CH₂—, (4-F-phenyl)CH₂CH₂—, furanyl-CH₂CH₂—, thienyl-CH₂CH₂—, pyridyl-CH₂CH₂—, 1-imidazolyl-CH₂CH₂—, oxazolyl-CH₂CH₂—, isoxazolyl-CH₂CH₂—, W is a bond;
X is a bond;
Y is a bond;
Z is methyl, ethyl, i-propyl, n-propyl, n-butyl, i-butyl, s-butyl, t-butyl, or allyl;
$R^{11}$, at each occurrence, is independently selected from H, =O, methyl, ethyl, phenyl, benzyl, phenethyl, 4-F-phenyl, (4-F-phenyl)CH₂—, (4-F-phenyl)CH₂CH₂—, 3-F-phenyl, (3-F-phenyl)CH₂—, (3-F-phenyl)CH₂CH₂—, 2-F-phenyl, (2-F-phenyl)CH₂—, (2-F-phenyl)CH₂CH₂—, 4-Cl-phenyl, (4-Cl-phenyl)CH₂—, (4-Cl-phenyl)CH₂CH₂—, 3-Cl-phenyl, (3-Cl-phenyl)CH₂—, (3-Cl-phenyl)CH₂CH₂—, 4-CH₃-phenyl, (4-CH₃-phenyl)CH₂—, (4-CH₃-phenyl)CH₂CH₂—, 3-CH₃-phenyl, (3-CH₃-phenyl)CH₂—, (3-CH₃-phenyl)CH₂CH₂—, 4-CF₃-phenyl, (4-CF₃-phenyl)CH₂—, (4-CF₃-phenyl)CH₂CH₂—, pyrid-2-yl, pyrid-3-yl, pyrid-4-yl, cyclohexyl, cycloheptyl, piperidinyl, or homopiperidinyl; and
$R^{13}$, at each occurrence, is independently selected from H, F, Cl, OH, —CH₃, —CH₂CH₃, —OCH₃, or —CF₃.

[11] In another preferred embodiment the present invention provides for a compound of Formula (Ib):
$R^3$ and $R^{3a}$ are combined to form cyclobutyl, cyclopentyl, cyclopentenyl, or cyclohexyl;
$R^5$ is —CH₃, —CH₂CH₃, —CH₂CH₂CH₃, —CH(CH₃)₂, —CH₂CH₂CH₂CH₃, —CH(CH₃)CH₂CH₃, —CH₂CH(CH₃)₂, —CH₂C(CH₃)₃, —CH₂CH₂CH₂CH₂CH₃, —CH(CH₃)CH₂CH₂CH₃, —CH₂CH(CH₃)CH₂CH₃, —CH₂CH₂CH(CH₃)₂, —CH(CH₂CH₃)₂, cyclopropyl-CH₂—, cyclobutyl-CH₂—, (2-CH₃-cyclopropyl)CH₂—, or (3-CH₃-cyclobutyl)CH₂—;
W is a bond;
X is a bond;
Y is a bond;
Z is methyl, ethyl, i-propyl, n-propyl, n-butyl, i-butyl, s-butyl, t-butyl, or allyl;
$R^{11}$, at each occurrence, is independently selected from H, =O, methyl, ethyl, phenyl, benzyl, phenethyl, 4-F-phenyl, (4-F-phenyl)CH₂—, (4-F-phenyl)CH₂CH₂—, 3-F-phenyl, (3-F-phenyl)CH₂—, (3-F-phenyl)CH₂CH₂—, 2-F-phenyl, (2-F-phenyl)CH₂—, (2-F-phenyl)CH₂CH₂—, 4-Cl-phenyl, (4-Cl-phenyl)CH₂—, (4-Cl-phenyl)CH₂CH₂—, 3-Cl-phenyl, (3-Cl-phenyl)CH₂—, (3-Cl-phenyl)CH₂CH₂—, 4-CH₃-phenyl, (4-CH₃-phenyl)CH₂—, (4-CH₃-phenyl)CH₂CH₂—, 3-CH₃-phenyl, (3-CH₃-phenyl)CH₂—, (3-CH₃-phenyl)CH₂CH₂—, 4-CF₃-phenyl, (4-CF₃-phenyl)CH₂—, (4-CF₃-phenyl)CH₂CH₂—, pyrid-2-yl, pyrid-3-yl, pyrid-4-yl, cyclohexyl, cycloheptyl, piperidinyl, or homopiperidinyl; and
$R^{13}$, at each occurrence, is independently selected from H, F, Cl, OH, —CH₃, —CH₂CH₃, —OCH₃, or —CF₃.

[12] In another preferred embodiment the present invention provides for a compound of Formula (Ib):

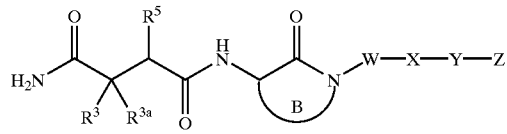

(Ib)

or a pharmaceutically acceptable salt or prodrug thereof, wherein:
$R^3$ and $R^{3a}$ are combined to form a 3–8 membered carbocyclic moiety;
    wherein said 3–8 membered carbocyclic moiety is saturated or partially unsaturated;
    wherein said 3–8 membered carbocyclic moiety is substituted with 0–3 $R^4$;
$R^4$, at each occurrence, is independently selected from H, OH, Cl, F, Br, I, CN, NO₂, CF₃, acetyl, SCH₃, S(=O)CH₃, S(=O)₂CH₃, $NR^{15}R^{16}$, $OR^{14a}$, $C_1$–$C_4$ alkyl, $C_2$–$C_4$ alkenyl, $C_2$–$C_4$ alkynyl, $C_1$–$C_4$ alkoxy, $C_1$–$C_4$ haloalkyl, $C_1$–$C_4$ haloalkoxy, and $C_1$–$C_4$ haloalkyl-S—;
$R^5$ is H;
    $C_1$–$C_6$ alkyl substituted with 0–3 $R^{5b}$;
    $C_2$–$C_6$ alkenyl substituted with 0–3 $R^{5b}$;
    $C_2$–$C_6$ alkynyl substituted with 0–3 $R^{5b}$;
    $C_3$–$C_{10}$ carbocycle substituted with 0–3 $R^{5c}$;
    $C_6$–$C_{10}$ aryl substituted with 0–3 $R^{5c}$; or
    5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5b}$, at each occurrence, is independently selected from:
    H, $C_1$–$C_6$ alkyl, CF₃, $OR^{14}$, Cl, F, Br, I, =O, CN, NO₂, $NR^{15}R^{16}$;
    $C_3$–$C_{10}$ carbocycle substituted with 0–3 $R^{5c}$;
    $C_6$–$C_{10}$ aryl substituted with 0–3 $R^{5c}$; or
    5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5c}$, at each occurrence, is independently selected from H, OH, Cl, F, Br, I, CN, NO₂, $NR^{15}R^{16}$, CF₃, acetyl, SCH₃, S(=O)CH₃, S(=O)₂CH₃, $C_1$–$C_6$ alkyl, $C_1$–$C_4$ alkoxy, $C_1$–$C_4$ haloalkyl, and $C_1$–$C_4$ haloalkoxy;
Ring B is selected from:

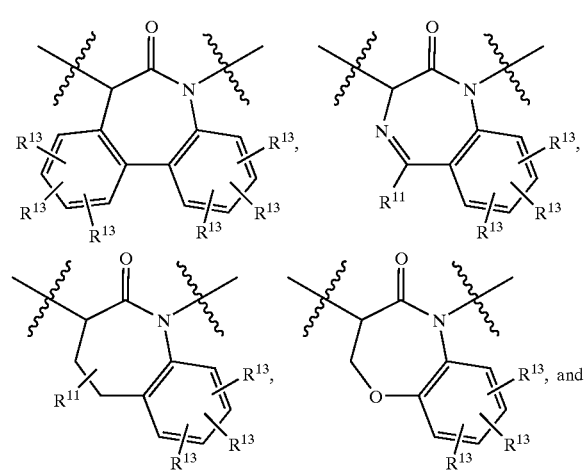

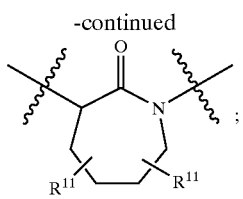

$R^{11}$, at each occurrence, is independently selected from H, =O, $NR^{18}R^{19}$, $CF_3$;

$C_1$–$C_4$ alkyl optionally substituted with 0–1 $R^{11a}$;

phenyl substituted with 0–3 $R^{11b}$;

$C_3$–$C_7$ carbocycle substituted with 0–3 $R^{11b}$; and 5 to 7 membered heterocycle containing 1 to 4 heteroatoms selected from nitrogen, oxygen, and sulphur, wherein said 5 to 7 membered heterocycle is substituted with 0–3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11a}$, at each occurrence, is independently selected from H, $C_1$–$C_4$ alkyl, $OR^{14}$, F, Cl, =O, $NR^{15}R^{16}$, $CF_3$, or phenyl substituted with 0–3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;

W is a bond, —$CH_2$—, —$CH_2CH_2$—;

X is a bond;

phenyl substituted with 0–2 $R^{Xb}$;

$C_3$–$C_6$ cycloalkyl substituted with 0–2 $R^{Xb}$; or 5 to 6 membered heterocycle substituted with 0–2 $R^{Xb}$;

$R^{Xb}$, at each occurrence, is independently selected from H, OH, Cl, F, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

Y is a bond, —C(=O)—, —O—, —S—, —S(=O)—, —S(=O)$_2$—, —N ($R^{19}$)—, —C(=O)$NR^{19b}$—, —$NR^{19b}$C(=O)—, —$NR^{19b}$S(=O)$_2$—, —S(=O)$_2NR^{19b}$—, —$NR^{19b}$S(=O)—, —S(=O)$NR^{19b}$—, —C(=O)O—, or —OC(=O)—;

Z is $C_1$–$C_3$ alkyl substituted with 1–2 $R^{12a}$;

$C_6$–$C_{10}$ aryl substituted with 0–4 $R^{12b}$;

$C_3$–$C_{10}$ carbocycle substituted with 0–3 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from $C_6$–$C_{10}$ aryl substituted with 0–4 $R^{12b}$;

$C_3$–$C_{10}$ carbocycle substituted with 0–4 $R^{12b}$; and 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_4$ alkyl)-C(=O)—, and ($C_1$–$C_4$ alkyl)-S(=O)$_2$—;

$R^{16}$, at each occurrence, is independently selected from H, OH, $C_1$–$C_6$ alkyl, benzyl, phenethyl, ($C_1$–$C_4$ alkyl)-C(=O)—, and ($C_1$–$C_4$ alkyl)-S(=O)$_2$—;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

$R^{19}$, at each occurrence, is independently selected from H, OH, methyl, ethyl, propyl, butyl, phenyl, benzyl, and phenethyl; and $R^{19b}$, at each occurrence, is independently selected from H, methyl, ethyl, propyl, butyl, phenyl, benzyl, and phenethyl.

[13] In another preferred embodiment the present invention provides for a compound of Formula (Ib) wherein:

$R^3$ and $R^{3a}$ are combined to form a 3–6 membered carbocyclic moiety;

wherein said 3–6 membered carbocyclic moiety is saturated or partially unsaturated;

wherein said 3–6 membered carbocyclic moiety is substituted with 0–2 $R^4$;

$R^4$, at each occurrence, is independently selected from H, OH, Cl, F, Br, I, CN, $NO_2$, $CF_3$, acetyl, $SCH_3$, methyl, ethyl, methoxy, ethoxy, allyl, —$OCF_3$, and —$SCF_3$;

$R^5$ is H;

$C_1$–$C_4$ alkyl substituted with 0–3 $R^{5b}$;

$C_2$–$C_4$ alkenyl substituted with 0–3 $R^{5b}$; or $C_2$–$C_4$ alkynyl substituted with 0–3 $R^{5b}$;

$R^{5b}$, at each occurrence, is independently selected from:

H, methyl, ethyl, propyl, butyl, $CF_3$, $OR^{14}$, Cl, F, Br, I, =O;

$C_3$–$C_6$ carbocycle substituted with 0–3 $R^{5c}$;

phenyl substituted with 0–3 $R^{5c}$; or 5 to 6 membered heterocycle containing 1 to 4 heteroatoms selected from nitrogen, oxygen, and sulphur, wherein said 5 to 6 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

Ring B is selected from:

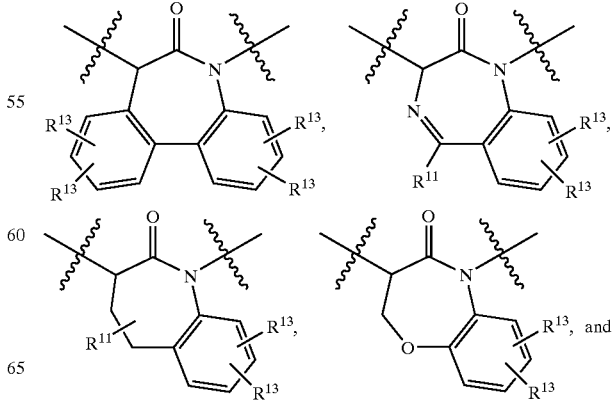

-continued

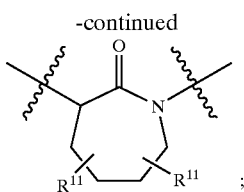

$R^{11}$, at each occurrence, is independently selected from H, =O, $NR^{18}R^{19}$, $CF_3$;
$C_1$–$C_4$ alkyl optionally substituted with 0–1 $R^{11a}$;
phenyl substituted with 0–3 $R^{11b}$;
$C_3$–$C_7$ carbocycle substituted with 0–3 $R^{11b}$; and
5 to 7 membered heterocycle containing 1 to 4 heteroatoms selected from nitrogen, oxygen, and sulphur, wherein said 5 to 7 membered heterocycle is substituted with 0–3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;
$R^{11a}$, at each occurrence, is independently selected from H, methyl, ethyl, propyl, butyl, methoxy, ethoxy, propoxy, phenoxy, F, Cl, =O, $NR^{15}R^{16}$, $CF_3$, or phenyl substituted with 0–3 $R^{11b}$;
$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;
W is a bond, —$CH_2$—, —$CH_2CH_2$—;
X is a bond;
phenyl substituted with 0–1 $R^{Xb}$;
$C_3$–$C_6$ cycloalkyl substituted with 0–1 $R^{Xb}$; or
5 to 6 membered heterocycle substituted with 0–1 $R^{Xb}$;
$R^{Xb}$ is selected from H, OH, Cl, F, $NR^{15}R^{16}$, $CF_3$, acetyl, $SCH_3$, $S(=O)CH_3$, $S(=O)_2CH_3$, methyl, ethyl, propyl, methoxy, ethoxy, propoxy, and —$OCF_3$;
Y is a bond, —C(=O)—, —O—, —S—, —S(=O)—, —S(=O)$_2$—, —NH—, —N($CH_3$)—, or —N($CH_2CH_3$)—;
Z is $C_1$–$C_2$ alkyl substituted with 1–2 $R^{12a}$;
$C_6$–$C_{10}$ aryl substituted with 0–4 $R^{12b}$;
$C_3$–$C_{10}$ carbocycle substituted with 0–3 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;
$R^{12a}$, at each occurrence, is independently selected from $C_6$–$C_{10}$ aryl substituted with 0–4 $R^{12b}$;
$C_3$–$C_{10}$ carbocycle substituted with 0–4 $R^{12b}$; and
5 to 10 membered heterocycle containing 1 to 4 heteroatoms selected from nitrogen, oxygen, and sulphur, wherein said
5 to 10 membered heterocycle is substituted with 0–3 $R^{12b}$;
$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;
$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;
$R^{14}$ is H, phenyl, benzyl, $C_1$–$C_4$ alkyl, or $C_2$–$C_4$ alkoxyalkyl;
$R^{15}$, at each occurrence, is independently selected from H, $C_1$–$C_4$ alkyl, and benzyl;
$R^{16}$, at each occurrence, is independently selected from H, OH, methyl, ethyl, propyl, butyl, benzyl, phenethyl, methyl-C(=O)—, ethyl-C(=O)—, methyl-S(=O)$_2$—, and ethyl-S(=O)$_2$—;
$R^{18}$, at each occurrence, is independently selected from H, methyl, ethyl, propyl, butyl, phenyl, benzyl, and phenethyl; and
$R^{19}$, at each occurrence, is independently selected from H, methyl, ethyl, propyl, and butyl.

[14] In another preferred embodiment the present invention provides for a compound of Formula (Ib) wherein:
$R^3$ and $R^{3a}$ are combined to form a 3–6 membered carbocyclic moiety selected from cyclopropyl, cyclobutyl, cyclopentyl, cyclopentenyl, cyclohexyl, and cyclohexenyl; wherein said 3–6 membered carbocyclic moiety is substituted with 0–1 $R^4$;
$R^4$ is selected from H, OH, Cl, F, CN, $CF_3$, methyl, ethyl, methoxy, ethoxy, allyl, and —$OCF_3$;
$R^5$ is $C_1$–$C_4$ alkyl substituted with 0–1 $R^{5b}$;
$C_2$–$C_4$ alkenyl substituted with 0–1 $R^{5b}$;
$C_2$–$C_4$ alkynyl substituted with 0–1 $R^{5b}$;
$R^{5b}$, at each occurrence, is independently selected from:
H, methyl, ethyl, propyl, butyl, $CF_3$, $OR^{14}$, =O;
$C_3$–$C_6$ carbocycle substituted with 0–2 $R^{5c}$;
phenyl substituted with 0–3 $R^{5c}$; or
5 to 6 membered heterocycle containing 1 to 4 heteroatoms selected from nitrogen, oxygen, and sulphur, wherein said 5 to 6 membered heterocycle is substituted with 0–3 $R^{5c}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;
$R^{5c}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy;
Ring B is selected from:

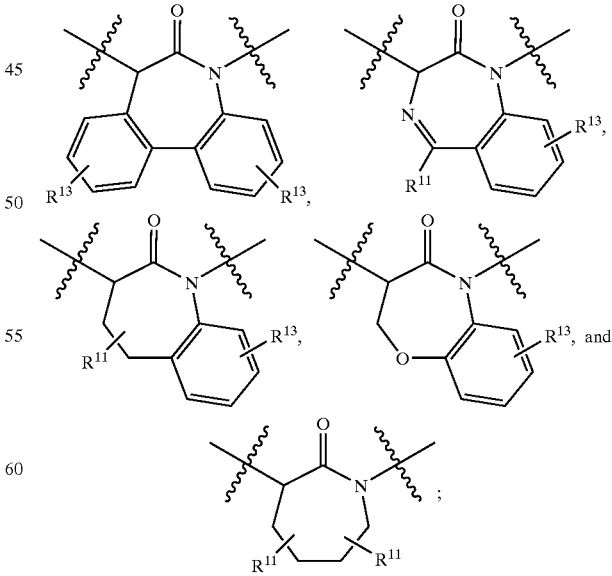

$R^{11}$, at each occurrence, is independently selected from H, =O, $NR^{18}R^{19}$;

$C_1$–$C_4$ alkyl optionally substituted with 0–1 $R^{11a}$;
phenyl substituted with 0–3 $R^{11b}$;
cyclohexyl substituted with 0–3 $R^{11b}$;
cycloheptyl substituted with 0–3 $R^{11b}$;
5 to 7 membered heterocycle containing 1 to 4 heteroatoms selected from nitrogen, oxygen, and sulphur, wherein said 5 to 7 membered heterocycle is substituted with 0–3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11a}$, at each occurrence, is independently selected from H, methyl, ethyl, propyl, methoxy, ethoxy, propoxy, phenoxy, F, Cl, =O, $NR^{15}R^{16}$, $CF_3$, or phenyl substituted with 0–3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;

W is a bond or —$CH_2$—;

X is a bond;
phenyl substituted with 0–1 $R^{Xb}$;
$C_3$–$C_6$ cycloalkyl substituted with 0–1 $R^{Xb}$; or
5 to 6 membered heterocycle substituted with 0–1 $R^{Xb}$;

$R^{Xb}$ is selected from H, OH, Cl, F, $NR^{15}R^{16}$, $CF_3$, acetyl, methyl, ethyl, methoxy, ethoxy, and —$OCF_3$;

Y is a bond, —C(=O)—, —O—, —S—, —S(=O)—, —S(=O)$_2$—, —NH—, —N(CH$_3$)—, or —N(CH$_2$CH$_3$)—;

Z is $C_1$–$C_2$ alkyl substituted with 1–2 $R^{12a}$;
$C_6$–$C_{10}$ aryl substituted with 0–4 $R^{12b}$;
$C_3$–$C_{10}$ carbocycle substituted with 0–3 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from $C_6$–$C_{10}$ aryl substituted with 0–4 $R^{12b}$;
$C_3$–$C_{10}$ carbocycle substituted with 0–4 $R^{12b}$; and
5 to 10 membered heterocycle containing 1 to 4 heteroatoms selected from nitrogen, oxygen, and sulphur, wherein said 5 to 10 membered heterocycle is substituted with 0–3 $R^{12b}$; and wherein said 5 to 10 membered heterocycle is selected from pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl;

$R^{12b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, and —$OCF_3$;

$R^{13}$, at each occurrence, is independently selected from H, OH, methyl, ethyl, propyl, butyl, methoxy, ethoxy, Cl, F, Br, CN, $NR^{15}R^{16}$, and $CF_3$;

$R^{14}$ is H, phenyl, benzyl, methyl, ethyl, propyl, or butyl;

$R^{15}$, at each occurrence, is independently selected from H, methyl, ethyl, propyl, and butyl;

$R^{16}$, at each occurrence, is independently selected from H, OH, methyl, ethyl, propyl, butyl, benzyl, and phenethyl;

$R^{18}$, at each occurrence, is independently selected from H, methyl, ethyl, propyl, butyl, phenyl, benzyl, and phenethyl; and $R^{19}$, at each occurrence, is independently selected from H, methyl, ethyl, propyl, and butyl.

[15] In another preferred embodiment the present invention provides for a compound of Formula (Ib) wherein:

$R^3$ and $R^{3a}$ are combined to form cyclobutyl, cyclopentyl, cyclopentenyl, or cyclohexyl;

$R^5$ is —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$CH_2C(CH_3)_3$, —$CH_2CH_2CH_2CH_2CH_3$, —$CH(CH_3)CH_2CH_2CH_3$, —$CH_2CH(CH_3)CH_2CH_3$, —$CH_2CH_2CH(CH_3)_2$, —$CH(CH_2CH_3)_2$, cyclopropyl-$CH_2$—, cyclobutyl-$CH_2$—, (2-$CH_3$-cyclopropyl)$CH_2$—, or (3-$CH_3$-cyclobutyl)$CH_2$—;

W is a bond or —$CH_2$—;

X is a bond;

Y is a bond, —C(=O)—, —O—, —S—, —S(=O)—, —S(=O)$_2$—, —NH—, or —N(CH$_3$)—,

Z is phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-$CF_3O$-phenyl, 3-$CF_3O$-phenyl, 4-$CF_3O$-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, cyclopropyl, cyclobutyl, cyclopentyl, cyclohexyl, morpholino, N-piperinyl, phenyl-$CH_2$—, (2-F-phenyl)$CH_2$—, (3-F-phenyl)$CH_2$—, (4-F-phenyl)$CH_2$—, (2-Cl-phenyl)$CH_2$—, (3-Cl-phenyl)$CH_2$, (4-Cl-phenyl)$CH_2$—, (2,3-diF-phenyl)$CH_2$—, (2,4-diF-phenyl)$CH_2$—, (2,5-diF-phenyl)$CH_2$—, (2,6-diF-phenyl)$CH_2$—, (3,4-diF-phenyl)$CH_2$—, (3,5-diF-phenyl)$CH_2$—, (2,3-diCl-phenyl)$CH_2$—, (2,4-diCl-phenyl)$CH_2$—, (2,5-diCl-phenyl)$CH_2$—, (2,6-diCl-phenyl)$CH_2$—, (3,4-diCl-phenyl)$CH_2$—, (3,5-diCl-phenyl)$CH_2$—, (3-F-4-Cl-phenyl)$CH_2$—, (3-F-5-Cl-phenyl)$CH_2$—, (3-Cl-4-F-phenyl)$CH_2$—, (2-MeO-phenyl)$CH_2$—, (3-MeO-phenyl)$CH_2$—, (4-MeO-phenyl)$CH_2$—, (2-Me-phenyl)$CH_2$—, (3-Me-phenyl)$CH_2$—, (4-Me-phenyl)$CH_2$—, (2-MeS-phenyl)$CH_2$—, (3-MeS-phenyl)$CH_2$—, 4-MeS-phenyl)

CH$_2$—, (2-CF$_3$O-phenyl)CH$_2$—, (3-CF$_3$O-phenyl)CH$_2$—, (4-CF$_3$O-phenyl)CH$_2$—, (furanyl)CH$_2$—, (thienyl)CH$_2$—, (pyridyl)CH$_2$—, (2-Me-pyridyl)CH$_2$—, (3-Me-pyridyl)CH$_2$—, (4-Me-pyridyl)CH$_2$—, (1-imidazolyl)CH$_2$—, (oxazolyl)CH$_2$—, (isoxazolyl)CH$_2$—, (1-benzimidazolyl)CH$_2$—, (cyclopropyl)CH$_2$—, (cyclobutyl)CH$_2$—, (cyclopentyl)CH$_2$—, (cyclohexyl)CH$_2$—, (morpholino)CH$_2$—, (N-pipridinyl)CH$_2$—, phenyl-CH$_2$CH$_2$—, (phenyl)$_2$CHCH$_2$—, (2-F-phenyl)CH$_2$CH$_2$—, (3-F-phenyl)CH$_2$CH$_2$—, (4-F-phenyl)CH$_2$CH$_2$—, (2-Cl-phenyl)CH$_2$CH$_2$—, (3-Cl-phenyl)CH$_2$CH$_2$—, (4-Cl-phenyl)CH$_2$CH$_2$—, (2,3-diF-phenyl)CH$_2$CH$_2$—, (2,4-diF-phenyl)CH$_2$CH$_2$—, (2,5-diF-phenyl)CH$_2$CH$_2$—, (2,6-diF-phenyl)CH$_2$CH$_2$—, (3,4-diF-phenyl)CH$_2$CH$_2$—, (3,5-diF-phenyl)CH$_2$CH$_2$—, (2,3-diCl-phenyl)CH$_2$CH$_2$—, (2,4-diCl-phenyl)CH$_2$CH$_2$—, (2,5-diCl-phenyl)CH$_2$CH$_2$—, (2,6-diCl-phenyl)CH$_2$CH$_2$—, (3,4-diCl-phenyl)CH$_2$CH$_2$—, (3,5-diCl-phenyl)CH$_2$CH$_2$—, (3-F-4-Cl-phenyl)CH$_2$CH$_2$—, (3-F-5-Cl-phenyl)CH$_2$CH$_2$—, (3-Cl-4-F-phenyl)CH$_2$CH$_2$—, (2-MeO-phenyl)CH$_2$CH$_2$—, (3-MeO-phenyl)CH$_2$CH$_2$—, (4-MeO-phenyl)CH$_2$CH$_2$—, (2-Me-phenyl)CH$_2$CH$_2$—, (3-Me-phenyl)CH$_2$CH$_2$—, (4-Me-phenyl)CH$_2$CH$_2$—, (2-MeS-phenyl)CH$_2$CH$_2$—, (3-MeS-phenyl)CH$_2$CH$_2$—, (4-MeS-phenyl)CH$_2$CH$_2$—, (2-CF$_3$O-phenyl)CH$_2$CH$_2$—, (3-CF$_3$O-phenyl)CH$_2$CH$_2$—, (4-CF$_3$O-phenyl)CH$_2$CH$_2$—, (furanyl)CH$_2$CH$_2$—, (thienyl)CH$_2$CH$_2$—, (pyridyl)CH$_2$CH$_2$—, (2-Me-pyridyl)CH$_2$CH$_2$—, (3-Me-pyridyl)CH$_2$CH$_2$—, (4-Me-pyridyl)CH$_2$CH$_2$—, (imidazolyl)CH$_2$CH$_2$—, (oxazolyl)CH$_2$CH$_2$—, (isoxazolyl)CH$_2$CH$_2$—, (benzimidazolyl)CH$_2$CH$_2$—,(cyclopropyl)CH$_2$CH$_2$—, (cyclobutyl)CH$_2$CH$_2$—, (cyclopentyl)CH$_2$CH$_2$—, (cyclohexyl)CH$_2$CH$_2$—, (morpholino)CH$_2$CH$_2$—, or (N-pipridinyl)CH$_2$CH$_2$—;

$R^{11}$, at each occurrence, is independently selected from H, =O, methyl, ethyl, phenyl, benzyl, phenethyl, 4-F-phenyl, (4-F-phenyl)CH$_2$—, (4-F-phenyl)CH$_2$CH$_2$—, 3-F-phenyl, (3-F-phenyl)CH$_2$—, (3-F-phenyl)CH$_2$CH$_2$—, 2-F-phenyl, (2-F-phenyl)CH$_2$—, (2-F-phenyl)CH$_2$CH$_2$—, 4-Cl-phenyl, (4-Cl-phenyl)CH$_2$—, (4-Cl-phenyl)CH$_2$CH$_2$—, 3-Cl-phenyl, (3-Cl-phenyl)CH$_2$—, (3-Cl-phenyl)CH$_2$CH$_2$—, 4-CH$_3$-phenyl, (4-CH$_3$-phenyl)CH$_2$—, (4-CH$_3$-phenyl)CH$_2$CH$_2$—, 3-CH$_3$-phenyl, (3-CH$_3$-phenyl)CH$_2$—, (3-CH$_3$-phenyl)CH$_2$CH$_2$—, 4-CF$_3$-phenyl, (4-CF$_3$-phenyl)CH$_2$—, (4-CF$_3$-phenyl)CH$_2$CH$_2$—, pyrid-2-yl, pyrid-3-yl, pyrid-4-yl, cyclohexyl, cycloheptyl, piperidinyl, or homopiperidinyl; and $R^{13}$, at each occurrence, is independently selected from H, F, Cl, OH, —CH$_3$, —CH$_2$CH$_3$, —OCH$_3$, or —CF$_3$.

[16] In another preferred embodiment the present invention provides for a compound of Formula (Ic):

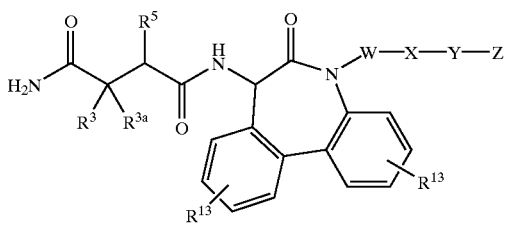

(Ic)

or a pharmaceutically acceptable salt or prodrug thereof.

[17] In another preferred embodiment the present invention provides for a compound of Formula (Id):

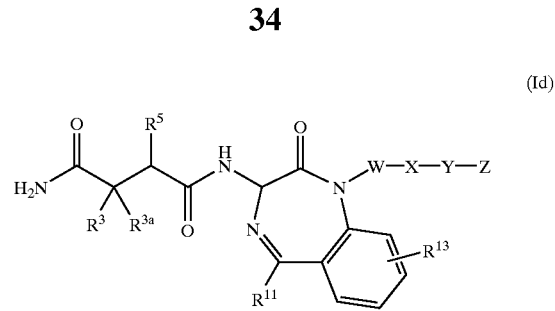

(Id)

or a pharmaceutically acceptable salt or prodrug thereof.

[18] In another preferred embodiment the present invention provides for a compound of Formula (Ie):

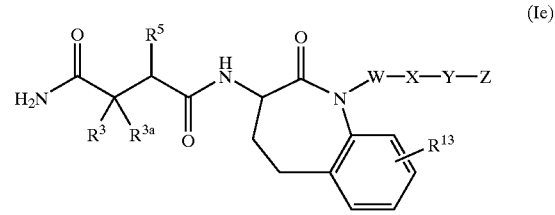

(Ie)

or a pharmaceutically acceptable salt or prodrug thereof.

[19] In another preferred embodiment the present invention provides for a compound of Formula (If):

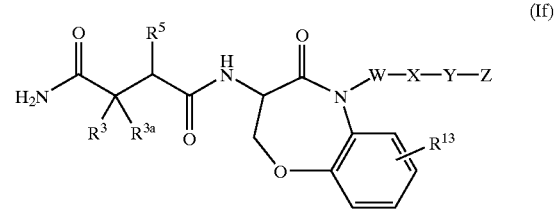

(If)

or a pharmaceutically acceptable salt or prodrug thereof.

[20] In another preferred embodiment the present invention provides for a compound of Formula (Ig):

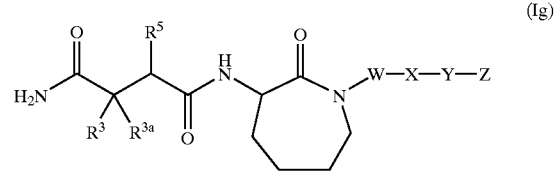

(Ig)

or a pharmaceutically acceptable salt or prodrug thereof.

[21] In another preferred embodiment the present invention provides for a compound of Formula (I) selected from:

1-[3-methyl-1-[1,3-dihydro-1-methyl-2-oxo-5-phenyl-2H-1,4-benzodiazepin-3-ylcarbamoyl]-butyl]-cyclopent-3-enecarboxylic amide;

1-[3-methyl-1-[1,3-dihydro-1-methyl-2-oxo-5-phenyl-2H-1,4-benzodiazepin-3-ylcarbamoyl]-butyl]-cyclopentanecarboxylic amide;

1-[3-methyl-1-[1,3-dihydro-1-methyl-2-oxo-5-(4-chlorophenyl)-2H-1,4-benzodiazepin-3-ylcarbamoyl]-butyl]-cyclohexanecarboxylic amide;

1-[3-methyl-1-[1,3-dihydro-1-methyl-2-oxo-5-phenyl-2H-1,4-benzodiazepin-3-ylcarbamoyl]-butyl]-cyclohexanecarboxylic amide;

1-[3-Methyl-1-(5-methyl-6-oxo-6,7-dihydro-5H-dibenzo[b,
  d]azepin-7-ylcarbamoyl)-butyl]-cyclohexanecarboxylic
  acid amide;
1-[3-Methyl-1-(5-methyl-6-oxo-6,7-dihydro-5H-dibenzo[b,
  d]azepin-7-ylcarbamoyl)-butyl]-cyclohexanecarboxylic
  acid amide;
1-(1-{1-[3-(2-Fluoro-phenoxy)-benzyl]-2-oxo-2,3,4,5-
  tetrahydro-1H-benzo[b]azepin-3-ylcarbamoyl}-3-
  methyl-butyl)-cyclopent-3-enecarboxylic acid amide;
1-{3-Methyl-1-[2-oxo-1-(3-phenylamino-benzyl)-2,3,4,5-
  tetrahydro-1H-benzo[b]azepin-3-ylcarbamoyl]-butyl}-
  cyclopent-3-enecarboxylic acid amide;
1-{3-Methyl-1-[2-oxo-1-(3-phenylamino-benzyl)-2,3,4,5-
  tetrahydro-1H-benzo[b]azepin-3-ylcarbamoyl]-butyl}-
  cyclopentanecarboxylic acid amide;
1-[2-Cyclopropyl-1-[1,3-dihydro-1-methyl-2-oxo-5-
  phenyl-2H-1,4-benzodiazepin-3-ylcarbamoyl]-ethyl]-
  cyclopent-3-enecarboxylic amide;
1-[2-Cyclopropyl-1-[1,3-dihydro-1-methyl-2-oxo-5-(2-
  trifluoromethylphenyl)-2H-1,4-benzodiazepin-3-
  ylcarbamoyl]-ethyl]-cyclopent-3-enecarboxylic amide;
1-[2-Cyclopropyl-1-(5-methyl-6-oxo-6,7-dihydro-5H-
  dibenzo[b,d]azepin-7-ylcarbamoyl)-ethyl]-cyclopent-3-
  enecarboxylic acid amide;
1-{3-Methyl-1-[2-oxo-1-(3-o-tolylamino-benzyl)-azepan-3-
  ylcarbamoyl]-butyl}-cyclopent-3-enecarboxylic acid
  amide;
1-[3-Methyl-1-(5-methyl-6-oxo-6,7-dihydro-5H-dibenzo[b,
  d]azepin-7-ylcarbamoyl)-butyl]-cyclopent-3-
  enecarboxylic acid amide;
1-[3-methyl-1-[1,3-dihydro-1-methyl-2-oxo-5-(4-
  chlorophenyl)-2H-1,4-benzodiazepin-3-ylcarbamoyl]-
  butyl]-cyclopent-3-enecarboxylic amide;
1-[3-Methyl-1-(5-methyl-6-oxo-6,7-dihydro-5H-dibenzo[b,
  d]azepin-7-ylcarbamoyl)-butyl]-cyclopentanecarboxylic
  acid amide;
1-[3-methyl-1-[1,3-dihydro-1-methyl-2-oxo-5-(4-
  chlorophenyl)-2H-1,4-benzodiazepin-3-ylcarbamoyl]-
  butyl]-cyclopentanecarboxylic amide;
1-[3-methyl-1-[1,3-dihydro-1-methyl-2-oxo-5-(4-
  trifluoromethylphenyl)-2H-1,4-benzodiazepin-3-
  ylcarbamoyl]butyl]-cyclopent-3-enecarboxylic amide;
1-[3-methyl-1-[1,3-dihydro-1-(i-propyl)-2-oxo-5-(2-
  fluorophenyl)-2H-1,4-benzodiazepin-3-ylcarbamoyl]-
  butyl]-cyclopent-3-enecarboxylic amide;
1-[3-methyl-1-[1,3-dihydro-1-methyl-2-oxo-5-(4-
  trifluoromethylphenyl)-2H-1,4-benzodiazepin-3-
  ylcarbamoyl]-butyl]-cyclopentanecarboxylic amide;
1-[3-methyl-1-[1,3-dihydro-1-(2-cyclopropylethyl)-2-oxo-
  5-(2-fluorophenyl)-2H-1,4-benzodiazepin-3-
  ylcarbamoyl]-butyl]-cyclopent-3-enecarboxylic amide;
1-[3-methyl-1-[1,3-dihydro-1-(2-methylpropyl)-2-oxo-5-
  (2-fluorophenyl)-2H-1,4-benzodiazepin-3-ylcarbamoyl]-
  butyl]-cyclopent-3-enecarboxylic amide;
1-[3-methyl-1-[1,3-dihydro-1-methyl-2-oxo-5-(4-
  chlorophenyl)-2H-1,4-benzodiazepin-3-ylcarbamoyl]-
  butyl]-cyclobutanecarboxylic amide;
1-[3-methyl-1-[1,3-dihydro-1-methyl-2-oxo-5-phenyl-2H-
  1,4-benzodiazepin-3-ylcarbamoyl]-butyl]-
  cyclobutanecarboxylic amide; and
1-[3-methyl-1-[1,3-dihydro-1-methyl-2-oxo-5-cycloheptyl-
  2H-1,4-benzodiazepin-3-ylcarbamoyl]-butyl]-cyclopent-
  3-enecarboxylic amide.

In a more preferred embodiment of the present invention,
Q is $NH_2$.

It is appreciated that certain features of the invention,
which are, for clarity, described herein in the context of
separate embodiments, may also be provided in combination
in a single embodiment. As such, it is understood that any
and all embodiments of the present invention may be taken
in conjunction with any other embodiment to describe
additional embodiments of the present invention.
Conversely, various features of the invention which are for
brevity, described herein in the context of a single
embodiment, may also be provided separately or in any
subcombination. As such, it is understood that any elements
of an embodiment are meant to be combined with any and
all other elements from any of the embodiments to describe
additional embodiments.

In a preferred embodiment Ring B is selected from:

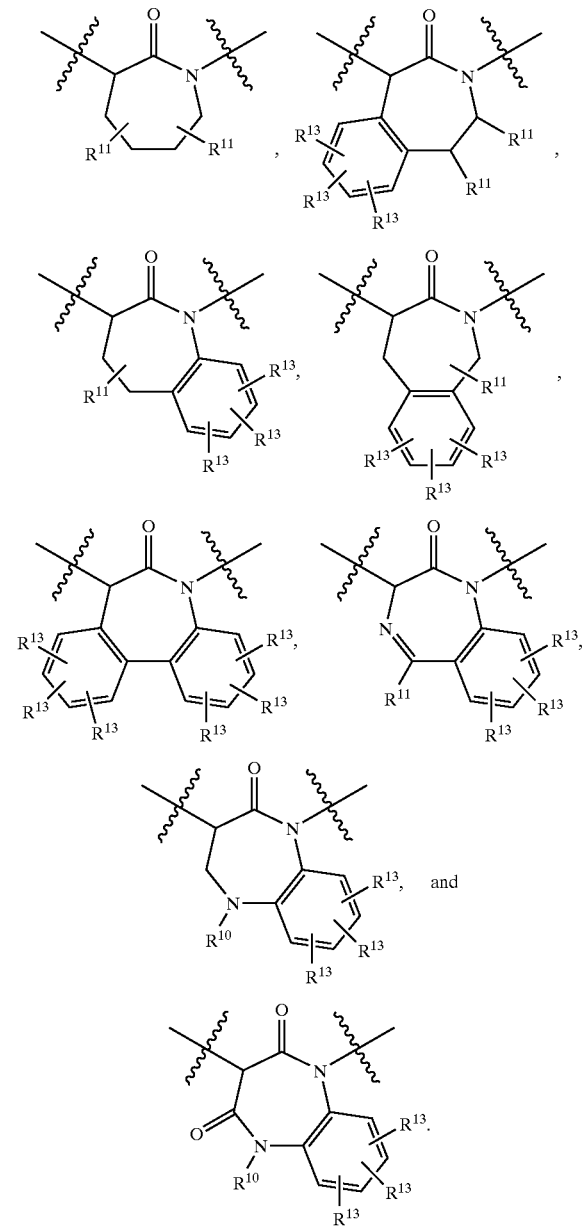

In another preferred embodiment Ring B is selected from:

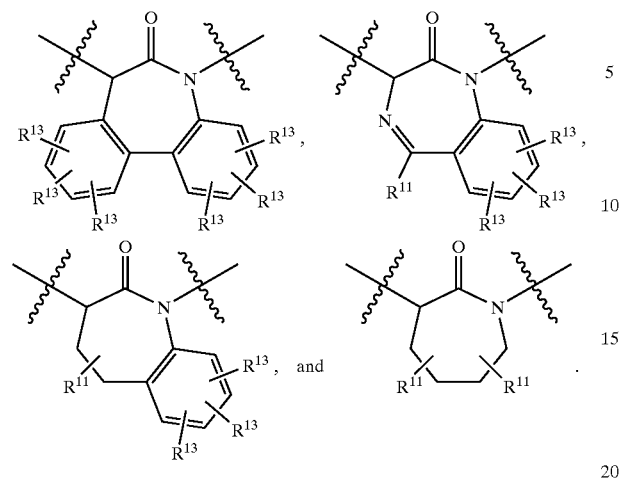

In another preferred embodiment Ring B is singly:

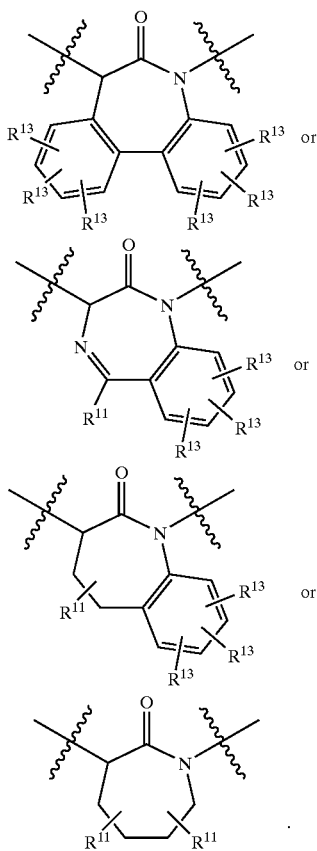

In another preferred embodiment Ring B is singly:

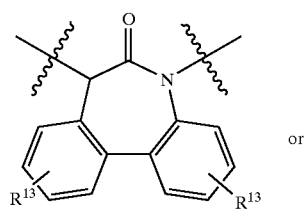

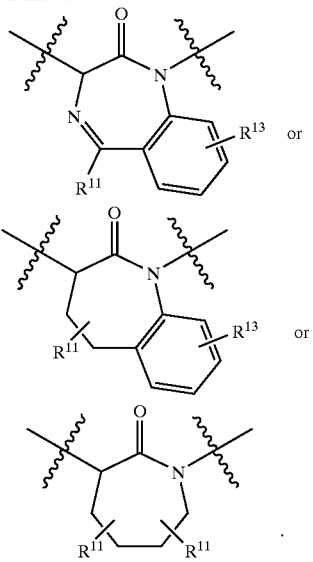

Also included in the present invention are compounds as set forth in the embodiments above wherein $R^3$ and $R^{3a}$ are combined to form a 3–8 membered carbocyclic moiety; and $R^5$ and $R^{5a}$ are not combined to form a 3–8 membered carbocyclic moiety.

Also included in the present invention are compounds as set forth in the embodiments above wherein $R^3$ and $R^{3a}$ are not combined to form a 3–8 membered carbocyclic moiety; and $R^5$ and $R^{5a}$ are combined to form a 3–8 membered carbocyclic moiety;

Also included in the present invention are compounds as set forth in the embodiments above wherein $R^3$ and $R^{3a}$ are combined to form a 3–8 membered carbocyclic moiety; and $R^5$ and $R^{5a}$ are also combined to form a 3–8 membered carbocyclic moiety.

Also included in the present invention are compounds as set forth in the embodiments above wherein $R^3$ and $R^{3a}$ are combined to form a 3–8 membered carbocyclic moiety which is saturated or partially unsaturated.

In another preferred embodiment $R^3$ and $R^{3a}$ are combined to form a 3–8 membered carbocyclic moiety selected from, cyclobutyl, cyclopentyl, cyclopentenyl, and cyclohexyl.

In another preferred embodiment $R^3$ and $R^{3a}$ are combined to form a cyclobutyl moiety.

In another preferred embodiment $R^3$ and $R^{3a}$ are combined to form a cyclopentyl moiety.

In another preferred embodiment $R^3$ and $R^{3a}$ are combined to form a cyclopentenyl moiety.

In another preferred embodiment $R^3$ and $R^{3a}$ are combined to form a cyclohexyl moiety.

Also included in the present invention are compounds as set forth in the embodiments above wherein $R^5$ and $R^{5a}$ are combined to form a 3–8 membered carbocyclic moiety which is saturated or partially unsaturated.

In another preferred embodiment $R^5$ and $R^{5a}$ are combined to form a 3–8 membered carbocyclic moiety selected from, cyclobutyl, cyclopentyl, cyclopentenyl, and cyclohexyl.

In another preferred embodiment $R^5$ and $R^{5a}$ are combined to form a cyclobutyl moiety.

In another preferred embodiment $R^5$ and $R^{5a}$ are combined to form a cyclopentyl moiety.

In another preferred embodiment $R^5$ and $R^{5a}$ are combined to form a cyclopentenyl moiety.

In another preferred embodiment $R^5$ and $R^{5a}$ are combined to form a cyclohexyl moiety.

Also included in the present invention are compounds as set forth in the embodiments above wherein $R^3$ and $R^{3a}$ are combined to form a 3–8 membered carbocyclic moiety; $R^5$ is $C_1$–$C_6$ alkyl, $C_2$–$C_6$ alkenyl, $C_2$–$C_6$ alkynyl, or $(C_3$–$C_6$ cycloalkyl)$C_1$–$C_3$ alkyl-; and $R^{5a}$ is H.

In another preferred embodiment $R^3$ and $R^{3a}$ are combined to form a 3–8 membered carbocyclic moiety; $R^5$ is $C_1$–$C_6$ alkyl, $C_2$–$C_6$ alkenyl, or $(C_3$–$C_6$ cycloalkyl)$C_1$–$C_3$ alkyl-; and $R^{5a}$ is H.

In three more preferred embodiments $R^3$ and $R^{3a}$ are combined to form a 3–8 membered carbocyclic moiety; $R^5$ is $C_1$–$C_6$ alkyl or $C_2$–$C_6$ alkenyl or $(C_3$–$C_6$ cycloalkyl)$C_1$–$C_3$ alkyl-; and $R^{5a}$ is H.

In another preferred embodiment $R^3$ and $R^{3a}$ are combined to form a 3–8 membered carbocyclic moiety; $R^5$ is $C_1$–$C_4$ alkyl, $C_2$–$C_4$ alkenyl, or $(C_3$–$C_6$ cycloalkyl)$C_1$–$C_2$ alkyl-; and $R^{5a}$ is H.

In another preferred embodiment $R^3$ and $R^{3a}$ are combined to form a 3–8 membered carbocyclic moiety; $R^5$ is methyl, ethyl, propyl, butyl, allyl, cyclopropylmethyl, cyclobutylmethyl, or cyclohexylmethyl; and $R^{5a}$ is H.

In another preferred embodiment $R^3$ and $R^{3a}$ are combined to form a 3–8 membered carbocyclic moiety; $R^5$ is ethyl, propyl, butyl, allyl, or cyclopropylmethyl; and $R^{5a}$ is H.

In another preferred embodiment $R^3$ and $R^{3a}$ are combined to form a 3–8 membered carbocyclic moiety; $R^5$ is n-propyl, i-propyl, n-butyl, i-butyl, s-butyl, allyl, or cyclopropylmethyl; and $R^{5a}$ is H.

In another preferred embodiment $R^3$ and $R^{3a}$ are combined to form a 3–8 membered carbocyclic moiety; $R^5$ is n-butyl, i-butyl, or cyclopropylmethyl; and $R^{5a}$ is H.

In more preferred embodiments $R^3$ and $R^{3a}$ are combined to form a 3–8 membered carbocyclic moiety; $R^5$ is methyl or ethyl or propyl or butyl or allyl or cyclopropylmethyl or cyclobutylmethyl or cyclohexylmethyl; and $R^{5a}$ is H.

Also included in the present invention are compounds as set forth in the embodiments above wherein $R^5$ is $C_1$–$C_8$ alkyl, $C_2$–$C_8$ alkenyl, $C_2$–$C_8$ alkynyl, or $(C_3$–$C_6$ cycloalkyl)$C_1$–$C_4$ alkyl, $(NR^{15}R^{16})C_1$–$C_4$ alkyl.

In another preferred embodiment $R^5$ is $C_2$–$C_8$ alkyl, $C_2$–$C_8$ alkenyl, or $C_2$–$C_8$ alkynyl.

In another preferred embodiment $R^5$ is $C_3$–$C_8$ alkyl, $C_3$–$C_8$ alkenyl, or $C_3$–$C_8$ alkynyl.

In another preferred embodiment $R^5$ is $C_4$–$C_8$ alkyl, $C_4$–$C_8$ alkenyl, $C_4$–$C_8$ alkynyl.

In another preferred embodiment $R^5$ is $C_2$–$C_8$ alkyl.
In another preferred embodiment $R^5$ is $C_3$–$C_8$ alkyl.
In another preferred embodiment $R^5$ is $C_4$–$C_8$ alkyl.
In another preferred embodiment $R^5$ is $(C_3$–$C_6$ cycloalkyl)$C_1$–$C_4$ alkyl.
In another preferred embodiment $R^5$ is $(NR^{15}R^{16})C_1$–$C_4$ alkyl.

In another preferred embodiment $R^5$ is —$CH_3$, —$CH_2CH_3$, —$CH_2CH_2CH_3$, —$CH_2CH(CH_3)_2$, —$CH_2CH_2CH_2CH_3$, —$CH_2CH_2CH_2CH_2CH_3$, —$CH_2CH_2CH(CH_3)_2$, —$CH_2CH_2CH_2CH_2CH_2CH_3$, —$CH_2CH_2CH_2CH(CH_3)_2$, —$CH_2CH_2CH_2CH_2CH(CH_3)_2$, —$CH_2NH_2$, —$CH_2N(CH_3)_2$, —$CH_2N(CH_2CH_3)_2$, —$CH_2CH_2NH_2$, —$CH_2CH_2N(CH_3)_2$, —$CH_2CH_2N(CH_2CH_3)_2$, —$CH_2$-cyclopropyl, —$CH_2$-cyclobutyl, —$CH_2$-cyclopentyl, or —$CH_2$-cyclohexyl.

In another preferred embodiment $R^5$ is —$CH_3$, —$CH_2CH_3$, —$CH_2CH_2CH_3$, —$CH_2CH(CH_3)_2$, —$CH_2CH_2CH_2CH_3$, —$CH_2CH_2CH_2CH_2CH_3$, —$CH_2CH_2CH(CH_3)_2$, —$CH_2CH_2CH_2CH_2CH_2CH_3$, —$CH_2CH_2CH_2CH(CH_3)_2$, or —$CH_2CH_2CH_2CH_2CH(CH_3)_2$.

In another preferred embodiment $R^5$ is —$CH_2NH_2$, —$CH_2N(CH_3)_2$, —$CH_2N(CH_2CH_3)_2$, —$CH_2CH_2NH_2$, —$CH_2CH_2N(CH_3)_2$, or —$CH_2CH_2N(CH_2CH_3)_2$.

In another preferred embodiment $R^5$ is —$CH_2$-cyclopropyl, —$CH_2$-cyclobutyl, —$CH_2$-cyclopentyl, or —$CH_2$-cyclohexyl.

Also included in the present invention are compounds as set forth in the embodiments above wherein $R^6$ is H.

Also included in the present invention are compounds as set forth in the embodiments above wherein $R^{11}$ is H, $NR^{18}R^{19}$;

$C_1$–$C_4$ alkyl optionally substituted with 0–1 $R^{11a}$;

phenyl substituted with 0–3 $R^{11b}$;

$C_3$–$C_7$ cycloalkyl substituted with 0–3 $R^{11b}$; or pyridinyl substituted with 0–3 $R^{11b}$;

wherein $R^{11a}$ is phenyl substituted with 0–3 $R^{11b}$;

wherein $R^{11b}$, at each occurrence, is independently selected from H, OH, Cl, F, $CF_3$, methyl, ethyl, propyl, butyl, methoxy, ethoxy, and propoxy.

In another preferred embodiment $R^{11}$ is independently selected from H, methyl, ethyl, cyclopentyl, cyclohexyl, cycloheptyl, phenyl, benzyl, phenethyl, 4-F-phenyl, (4-F-phenyl)$CH_2$—, (4-F-phenyl)$CH_2CH_2$—, 3-F-phenyl, (3-F-phenyl)$CH_2$—, (3-F-phenyl)$CH_2CH_2$—, 2-F-phenyl, (2-F-phenyl)$CH_2$—, (2-F-phenyl)$CH_2CH_2$—, 4-Cl-phenyl, (4-Cl-phenyl)$CH_2$—, (4-Cl-phenyl)$CH_2CH_2$—, 3-Cl-phenyl, (3-Cl-phenyl)$CH_2$—, (3-Cl-phenyl)$CH_2CH_2$—, 4-$CH_3$-phenyl, (4-$CH_3$-phenyl)$CH_2$—, (4-$CH_3$-phenyl)$CH_2CH_2$—, 3-$CH_3$-phenyl, (3-$CH_3$-phenyl)$CH_2$—, (3-$CH_3$-phenyl)$CH_2CH_2$—, 4-$CF_3$-phenyl, (4-$CF_3$-phenyl)$CH_2$—, (4-$CF_3$-phenyl)$CH_2CH_2$—, pyrid-2-yl, 4-F-pyrid-2-yl, 4-Cl-pyrid-2-yl, 4-$CH_3$-pyrid-2-yl, 4-$CF_3$-pyrid-2-yl, pyrid-3-yl, 4-F-pyrid-3-yl, 4-Cl-pyrid-3-yl, 4-$CH_3$-pyrid-3-yl, 4-$CF_3$-pyrid-3-yl, and pyrid-4-yl.

In another preferred embodiment $R^{11}$ is independently selected from H, methyl, ethyl, cyclopentyl, cyclohexyl, cycloheptyl, phenyl, 4-F-phenyl, 3-F-phenyl, 2-F-phenyl, 4-Cl-phenyl, 3-Cl-phenyl, 4-$CH_3$-phenyl, 3-$CH_3$-phenyl, 4-$CF_3$-phenyl, pyrid-2-yl, 4-F-pyrid-2-yl, 4-Cl-pyrid-2-yl, 4-$CH_3$-pyrid-2-yl, and 4-$CF_3$-pyrid-2-yl.

In another preferred embodiment $R^{11}$ is independently selected from phenyl, 4-F-phenyl, 3-F-phenyl, 2-F-phenyl, 4-Cl-phenyl, 3-Cl-phenyl, 4-$CH_3$-phenyl, 3-$CH_3$-phenyl, and 4-$CF_3$-phenyl.

In another preferred embodiment $R^{11}$ is independently selected from cyclopentyl, cyclohexyl, and cycloheptyl.

In another preferred embodiment $R^{11}$ is independently selected from pyrid-2-yl, 4-F-pyrid-2-yl, 4-Cl-pyrid-2-yl, 4-$CH_3$-pyrid-2-yl, and 4-$CF_3$-pyrid-2-yl.

Also included in the present invention are compounds as set forth in the embodiments above wherein W may be selected from a bond, —$CH_2$—, —$CH_2CH_2$—, or —$CH(CH_3)$—.

In another preferred embodiment W is a bond or —$(CH_2)p$—.

In another preferred embodiment W is a bond, —$CH_2$—, or —$CH_2CH_2$—.

In another preferred embodiment W is a bond or —$CH_2$—.
In another preferred embodiment W is —$CH_2$—.
In another preferred embodiment W is a bond.

Also included in the present invention are compounds as set forth in the embodiments above wherein the integer p may be selected from 0, 1, 2, or 3.

In another preferred embodiment the integer p is 0, 1 or 2.
In another preferred embodiment the integer p is 0 or 1.

In another preferred embodiment the integer p is 0.

Also included in the present invention are compounds as set forth in the embodiments above wherein X is a bond, $C_6$–$C_{10}$ aryl, $C_3$–$C_{10}$ carbocycle or 5 to 10 membered heterocycle.

In another preferred embodiment X is a bond, phenyl, $C_3$–$C_6$ carbocycle, or 5 to 6 membered heterocycle.

In another preferred embodiment X is a bond, phenyl, $C_3$–$C_6$ cycoalkyl, or 5 to 6 membered heterocycle.

In another preferred embodiment X is a bond;

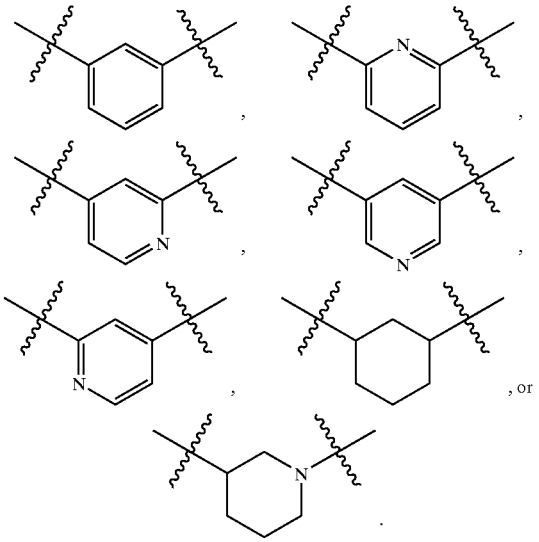

In another preferred embodiment X is a bond;

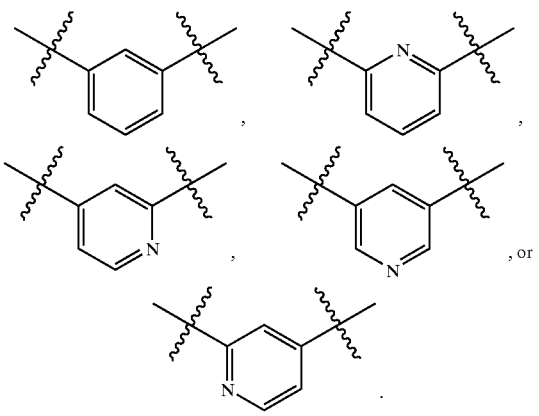

In another preferred embodiment X is a bond or phen-1,3-diyl.

In another preferred embodiment X is phen-1,3-diyl.

In another preferred embodiment X is a bond.

Also included in the present invention are compounds as set forth in the embodiments above wherein Y is a bond, —C(=O)—, —O—, —S—, —S(=O)—, —S(=O)$_2$—, —N($R^{19}$)—, —C(=O)$NR^{19b}$—, —$NR^{19b}$C(=O)—, —$NR^{19b}$S(=O)$_2$—, —S(=O)$_2$$NR^{19b}$—, —$NR^{19b}$S(=O)—, —S(=O)$NR^{19b}$—, —C(=O)O—, or —OC(=O)—.

In another preferred embodiment Y is a bond, —C(=O)—, —O—, —S—, —S(=O)—, —S(=O)$_2$—, —NH—, —N(CH$_3$)—, —C(=O)(NH—, —NHC(=O)—, —NHS(=O)$_2$—, —S(=O)$_2$NH—, —NHS(=O)—, —S(=O)NH—, —C(=O)O—, or —OC(=O)—.

In another preferred embodiment Y is a bond, —C(=O)—, —O—, —S—, —S(=O)—, —S(=O)$_2$—, —NH—, —N(CH$_3$)—, or —N (CH$_2$CH$_3$)—.

In another preferred embodiment Y is a bond, —C(=O)—, —O—, —S—, —S(=O)—, —S(=O)$_2$—, —NH—, or —N(CH$_3$)—.

In another preferred embodiment Y is a bond, —C(=O)—, —O—, —NH—, or —N(CH$_3$)—.

In another preferred embodiment Y is —O—.

In another preferred embodiment Y is —NH—.

In another preferred embodiment Y is —N(CH$_3$)—.

In another preferred embodiment Y is a bond.

Also included in the present invention are compounds as set forth in the embodiments above wherein Z is $C_1$–$C_4$ alkyl, $C_2$–$C_4$ alkenyl, $C_2$–$C_4$ alkynyl, $C_1$–$C_2$ alkyl substituted with 1–2 $R^{12a}$;

phenyl substituted with 0–4 $R^{12b}$;

$C_3$–$C_6$ carbocycle substituted with 0–3 $R^{12b}$; or 5 to 6 membered heterocycle containing 1 to 4 heteroatoms selected from nitrogen, oxygen, and sulphur, wherein said 5 to 6 membered heterocycle is substituted with 0–3 $R^{12b}$;

wherein $R^{12a}$ is phenyl substituted with 0–4 $R^{12b}$;

$C_3$–$C_6$ carbocycle substituted with 0–4 $R^{12b}$; or 5 to 6 membered heterocycle containing 1 to 4 heteroatoms selected from nitrogen, oxygen, and sulphur, wherein said 5 to 6 membered heterocycle is substituted with 0–3 $R^{12b}$; and wherein $R_{12b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, and —$OCF_3$;

In another preferred embodiment Z is $C_1$–$C_2$ alkyl substituted with 1–2 $R^{12a}$; or phenyl substituted with 0–4 $R^{12b}$;

wherein $R^{12a}$ is phenyl substituted with 0–4 $R^{12b}$;

wherein $R^{12b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, and —$OCF_3$;

In another preferred embodiment Z is $C_1$–$C_4$ alkyl, $C_2$–$C_4$ alkenyl, or $C_2$–$C_4$ alkynyl.

In another preferred embodiment Z is phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF$_3$O-phenyl, 3-CF$_3$O-phenyl, 4-CF$_3$O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, cyclopropyl, cyclobutyl, cyclopentyl, cyclohexyl, morpholino, N-piperinyl, phenyl-CH$_2$—, (2-F-phenyl)CH$_2$—, (3-F-phenyl)CH$_2$—, (4-F-phenyl)CH$_2$—, (2-Cl-phenyl)CH$_2$—, (3-Cl-phenyl)CH$_2$, (4-Cl-phenyl)CH$_2$—, (2,3-diF-phenyl)CH$_2$—, (2,4-diF-phenyl)CH$_2$—, (2,5-diF-phenyl)CH$_2$—, (2,6-diF-phenyl)CH$_2$—, (3,4-diF-phenyl)CH$_2$—, (3,5-diF-phenyl)CH$_2$—, (2,3-diCl-phenyl)CH$_2$—, (2,4-diCl-phenyl)CH$_2$—, (2,5-diCl-phenyl)CH$_2$—, (2,6-diCl-phenyl)CH$_2$—, (3,4-diCl-phenyl)CH$_2$—, (3,5-diCl-phenyl)CH$_2$—, (3-F-4-Cl-phenyl)CH$_2$—, (3-F-5-Cl-phenyl)

CH₂—, (3-Cl-4-F-phenyl)CH₂—, (2-MeO-phenyl) CH₂—, (3-MeO-phenyl)CH₂—, (4-MeO-phenyl)CH₂—, (2-Me-phenyl)CH₂—, (3-Me-phenyl)CH₂—, (4-Me-phenyl)CH₂—, (2-MeS-phenyl)CH₂—, (3-MeS-phenyl) CH₂—, 4-MeS-phenyl)CH₂—, (2-CF₃O-phenyl)CH₂—, (3-CF₃O-phenyl)CH₂—, (4-CF₃O-phenyl)CH₂—, (furanyl)CH₂—,(thienyl)CH₂—, (pyridyl)CH₂—, (2-Me-pyridyl)CH₂—, (3-Me-pyridyl)CH₂—, (4-Me-pyridyl) CH₂—, (1-imidazolyl)CH₂—, (oxazolyl)CH₂—, (isoxazolyl)CH₂—, (1-benzimidazolyl)CH₂—, (cyclopropyl)CH₂—, (cyclobutyl)CH₂—, (cyclopentyl) CH₂—, (cyclohexyl)CH₂—, (morpholino)CH₂—, (N-pipridinyl)CH₂—, or (phenyl)₂CH—.

In another preferred embodiment Z is phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF₃O-phenyl, 3-CF₃O-phenyl, 4-CF₃O-phenyl, or 4-phenyl-phenyl.

In another preferred embodiment Z is phenyl—CH₂—, (2-F-phenyl)CH₂—, (3-F-phenyl)CH₂—, (4-F-phenyl) CH₂—, (2-Cl-phenyl)CH₂—, (3-Cl-phenyl)CH₂, (4-Cl-phenyl)CH₂—, (2,3-diF-phenyl)CH₂—, (2,4-diF-phenyl) CH₂—, (2,5-diF-phenyl)CH₂—, (2,6-diF-phenyl)CH₂—, (3,4-diF-phenyl)CH₂—, (3,5-diF-phenyl)CH₂—, (2,3-diCl-phenyl)CH₂—, (2,4-diCl-phenyl)CH₂—, (2,5-diCl-phenyl)CH₂—, (2,6-diCl-phenyl)CH₂—, (3,4-diCl-phenyl)CH₂—, (3,5-diCl-phenyl)CH₂—, (3-F-4-Cl-phenyl)CH₂—, (3-F-5-Cl-phenyl)CH₂—, (3-Cl-4-F-phenyl)CH₂—, (2-MeO-phenyl)CH₂—, (3-MeO-phenyl) CH₂—, (4-MeO-phenyl)CH₂—, (2-Me-phenyl)CH₂—, (3-Me-phenyl)CH₂—, (4-Me-phenyl)CH₂—, (2-MeS-phenyl)CH₂—, (3-MeS-phenyl)CH₂—, 4-MeS-phenyl) CH₂—, (2-CF₃O-phenyl)CH₂—, (3-CF₃O-phenyl) CH₂—, (4-CF₃O-phenyl)CH₂—, or (phenyl)₂CH—.

Also included in the present invention are compounds as set forth in the embodiments above wherein $R^{13}$, at each occurrence, is independently selected from H, F, Cl, OH, —CH₃, —CH₂CH₃, —OCH₃, and —CF₃.

Also included in the present invention are compounds as set forth in the embodiments above wherein $R^{14}$ is H, phenyl, benzyl, methyl, ethyl, propyl, or butyl;

Also included in the present invention are compounds as set forth in the embodiments above wherein $R^{15}$, at each occurrence, is independently selected from H, methyl, ethyl, propyl, and butyl.

Also included in the present invention are compounds as set forth in the embodiments above wherein $R^{16}$, at each occurrence, is independently selected from H, OH, methyl, ethyl, propyl, butyl, benzyl, and phenethyl.

Also included in the present invention are compounds as set forth in the embodiments above wherein $R^{18}$, at each occurrence, is independently selected from H, methyl, ethyl, propyl, butyl, phenyl, benzyl, and phenethyl.

Also included in the present invention are compounds as set forth in the embodiments above wherein $R^{19}$, at each occurrence, is independently selected from H, methyl, ethyl, propyl, and butyl.

In a second embodiment, the present invention provides a pharmaceutical composition comprising a compound of Formula (I) and a pharmaceutically acceptable carrier.

In a third embodiment, the present invention provides a method for the treatment of neurological disorders associated with β-amyloid production comprising administering to a host in need of such treatment a therapeutically effective amount of a compound of Formula (I).

In a preferred embodiment the neurological disorder associated with β-amyloid production is Alzheimer's Disease.

In a fourth embodiment, the present invention provides a method for inhibiting γ-secretase activity for the treatment of a physiological disorder associated with inhibiting γ-secretase activity comprising administering to a host in need of such inhibition a therapeutically effective amount of a compound of Formula (I) that inhibits γ-secretase activity.

Thus, the present invention provides a method for inhibiting γ-secretase activity comprising administering to a host in need of such inhibition a therapeutically effective amount of a compound of Formula (I) that inhibits γ-secretase activity.

In a preferred embodiment the physiological disorder associated with inhibiting γ-secretase activity is Alzheimer's Disease.

In a fifth embodiment, the present invention provides a compound of Formula (I) for use in therapy.

In a preferred embodiment the present invention provides a compound of Formula (I) for use in therapy of Alzheimer's Disease.

In a sixth embodiment, the present invention provides for the use of a compound of Formula (I) for the manufacture of a medicament for the treatment of Alzheimer's Disease.

Definitions

As used herein, the term "Aβ" denotes the protein designated Aβ, β-amyloid peptide, and sometimes β/A4, in the art. Aβ is an approximately 4.2 kilodalton (kD) protein of about 39 to 43 amino acids found in amyloid plaques, the walls of meningeal and parenchymal arterioles, small arteries, capillaries, and sometimes, venules. The isolation and sequence data for the first 28 amino acids are described in U.S. Pat. No. 4,666,829. The 43 amino acid sequence is:

```
1
Asp Ala Glu Phe Arg His Asp Ser Gly Tyr

11
Glu Val His His Gln Lys Leu Val Phe Phe

21
Ala Glu Asp Val Gly Ser Asn Lys Gly Ala

31
Ile Ile Gly Leu Met Val Gly Gly Val Val

41
Ile Ala Thr
```

The term "APP", as used herein, refers to the protein known in the art as β amyloid precursor protein. This protein is the precursor for Aβ and through the activity of "secretase" enzymes, as used herein, it is processed into Aβ. Differing secretase enzymes, known in the art, have been designated β secretase, generating the N-terminus of Aβ, α secretase cleaving around the 16/17 peptide bond in Aβ, and "γ secretases", as used herein, generating C-terminal Aβ fragments ending at position 38, 39, 40, 42, and 43 or generating C-terminal extended precursors which are subsequently truncated to the above polypeptides.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e. =O), then 2 hydrogens on the atom are replaced.

When any variable (e.g. $R^{5b}$) occurs more than one time in any constituent or formula for a compound, its definition at each occurrence is independent of its definition at every other occurrence. Thus, for example, if a group is shown to be substituted with 0–2 $R^{5b}$, then said group may optionally be substituted with up to two $R^{5b}$ groups and $R^{5b}$ at each occurrence is selected independently from the definition of $R^{5b}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms; for example, "$C_1$–$C_6$ alkyl" denotes alkyl having 1, 2, 3, 4, 5, or 6 carbon atoms. Examples of alkyl include, but are not limited to, methyl, ethyl, n-propyl, i-propyl, n-butyl, i-butyl, sec-butyl, t-butyl, pentyl, and hexyl. Preferred "alkyl" group, unless otherwise specified, is "$C_1$–$C_4$ alkyl". Additionally, unless otherwise specified, "propyl" denotes n-propyl or i-propyl; "butyl" denotes n-butyl, i-butyl, sec-butyl, or t-butyl.

As used herein, "alkenyl" or "alkenylene" is intended to include hydrocarbon chains of either a straight or branched configuration and one or more unsaturated carbon-carbon bonds which may occur in any stable point along the chain. Examples of "$C_2$–$C_6$ alkenyl" include, but are not limited to, ethenyl, 1-propenyl, 2-propenyl, 1-butenyl, 2-butenyl, 3-butenyl, 3-methyl-2-butenyl, 2-pentenyl, 3-pentenyl, hexenyl, and the like.

As used herein, "alkynyl", or "alkynylene" is intended to include hydrocarbon chains of either a straight or branched configuration and one or more carbon-carbon triple bonds which may occur in any stable point along the chain, such as ethynyl, 1-propynyl, 2-propynyl, 1-butynyl, 2-butynyl, 3-butynyl, and the like.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy. Similarly, "alkylthio" or "thioalkoxy" is represents an alkyl group as defined above with the indicated number of carbon atoms attached through a sulphur bridge.

"Halo" or "halogen" as used herein refers to fluoro, chloro, bromo, and iodo. Unless otherwise specified, preferred halo is fluoro and chloro. "Counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, 2,2-difluoroethyl, heptafluoropropyl, and heptachloropropyl. "Haloalkoxy" is intended to mean a haloalkyl group as defined above with the indicated number of carbon atoms attached through an oxygen bridge; for example trifluoromethoxy, pentafluoroethoxy, 2,2,2-trifluoroethoxy, and the like. "Halothioalkoxy" is intended to mean a haloalkyl group as defined above with the indicated number of carbon atoms attached through a sulphur bridge.

"Cycloalkyl" is intended to include saturated ring groups, having the specified number of carbon atoms. For example, "$C_3$–$C_6$ cycloalkyl" denotes such as cyclopropyl, cyclobutyl, cyclopentyl, or cyclohexyl.

As used herein, "carbocycle" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred "carbocycle" are cyclopropyl, cyclobutyl, cyclopentyl, and cyclohexyl.

As used herein, "carbocyclic moiety" is intended to mean any stable 3- to 8-membered monocyclic ring of carbon atoms, any of which may be saturated or partially unsaturated. Additionally, the 3 to 8 membered monocyclic ring of carbon atoms may be contain a heteroatom selected from oxygen, sulphur, or nitrogen, wherein a carbon atom of the ring has been substituted for the heteroatom. Examples of such carbocycles include, but are not limited to, cyclopropyl, cyclobutyl, cyclopentyl, cyclohexyl, cycloheptyl, cyclooctyl, cyclopent-3-enyl, cyclohex-3-enyl, tetrahydrofurnayl, pyranyl, pyrrolidinyl, and piperidinyl. Preferred examples of a "carbocyclic moiety" are cyclopropyl, cyclobutyl, cyclopentyl, and cyclohexyl.

As used herein, the term "heterocycle" or "heterocyclic ring" is intended to mean a stable 5- to 7-membered monocyclic or bicyclic or 7- to 14-membered bicyclic heterocyclic ring which is saturated partially unsaturated or unsaturated (aromatic), and which consists of carbon atoms and 1, 2, 3 or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, but are not limited to, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, tetrazolyl; more preferred 5 to 6 membered heterocycles include, but are not limited to, pyridinyl, pyrimidinyl, triazinyl, furanyl, thienyl, thiazolyl, piperazinyl, piperidinyl, pyrazolyl, imidazolyl, and tetrazolyl. Also included are fused ring and spiro compounds containing, for example, the above heterocycles.

As used herein, the term "aryl", "$C_6$–$C_{10}$ aryl" or aromatic residue, is intended to mean an aromatic moiety containing the specified number of carbon atoms; for example phenyl, pyridinyl or naphthyl. Preferred "aryl" is phenyl. Unless otherwise specified, "aryl" may be unsubstituted or substituted with 0 to 3 groups selected from H, methyl, ethyl, propyl, butyl, methoxy, ethoxy, propoxy, butoxy, amino, hydroxy, Cl, F, Br, I, $CF_3$, $SCH_3$, $S(O)CH_3$, $SO_2CH_3$, —$N(CH_3)_2$, $N(CH_3)H$, CN, $NO_2$, $OCF_3$, C(=O)$CH_3$, $CO_2H$, $CO_2CH_3$, or $C_1$–$C_4$ haloalkyl.

As used herein, the term "heteroaryl fused radical" is intended to denote a 5 or 6 membered aromatic ring comprising carbon atoms and one or two heteroatoms selected from nitrogen, sulphur and oxygen. The 5 or 6 membered ring is fused to two adjacent atoms of a second ring wherein the second ring is a "carbocyclic moiety" or ring B as defined above. Examples of a "heteroaryl fused radical" are furanyl, imidazolyl, isoxazolyl, oxazolyl, pyrrolyl, thiophenyl, thiazolyl, isothiozalyl, pyridyl, pyridazinyl, pyrimidinyl, and pyrazinyl.

The phrase "additional lactam carbons", as used herein, is intended to denote the number of optional carbon atoms in the lactam ring B of Formula (I). Formula (I''):

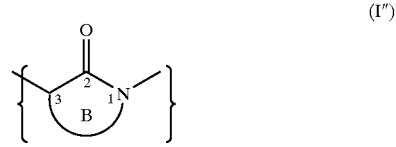

(I'')

represents the lactam ring B of Formula (I). Additional lactam carbons are carbons in lactam ring B other than the carbons numbered 2 and 3 in the backbone of the formula. The additional lactam carbons may be optionally replaced by a heteroatom selected from oxygen, nitrogen and sulfur. Lactam ring B contains 1, 2, 3, 4, 5, 6 or 7 optional carbons, wherein one optional carbon may optionally be replaced by a heteroatom, such that the total number of members of lactam ring B, including atoms numbered 1, 2 and 3 in the backbone, does not exceed 10. It is preferred that the total number of atoms of lactam ring B is 6, 7 or 8; it is more preferred that the total number of atoms of lactam ring B is seven. It is further understood that lactam ring B may optionally be unsaturated or partially unsaturated (i.e. two adjacent atoms in the ring form a double bond) wherein the backbone of lactam ring B may contain one, two or three double bonds. Examples of lactam ring B include:

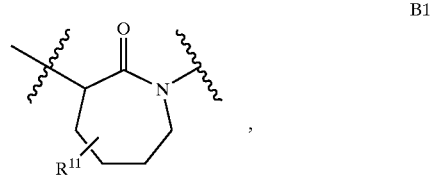

B1

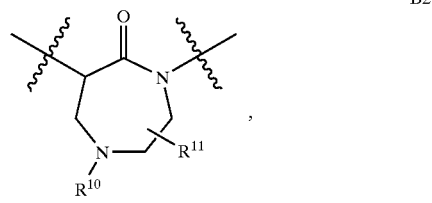

B2

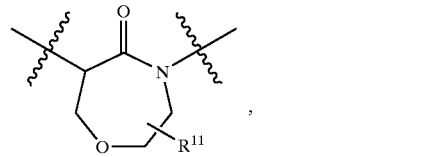

B3

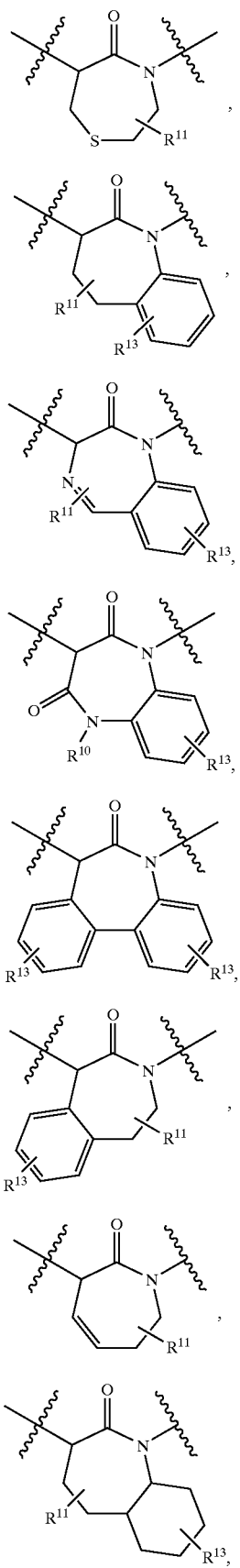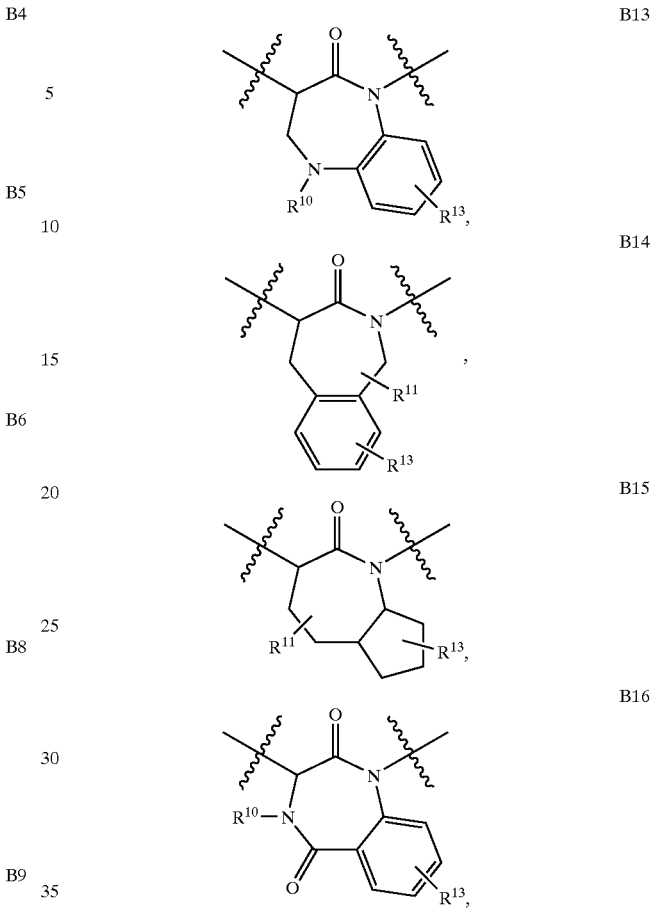

but are not intended to limit the invention. Preferred examples of lactam ring B are B1, B2, B5, B6, B8, B9, B13, and B16; more preferred examples of lactam ring B are B1, B6, B8, B9, and B13. Preferred examples of substituent $R^{10}$ or $R^{11}$ on lactam B are hydrogen, methyl, ethyl, phenyl, benzyl, phenethyl, 4-fluorophenyl, 4-chlorophenyl, 4-methylphenyl, 4-$CF_3$-phenyl, (4-fluorophenyl)methyl, (4-chlorophenyl)methyl, (4-methylphenyl)methyl, (4-$CF_3$-phenyl)methyl, (4-fluorophenyl)ethyl, (4-chlorophenyl)ethyl, (4-methylphenyl)ethyl, (4-$CF_3$-phenyl)ethyl, and 2-, 3-, and 4-pyridinyl. More preferred examples of substituent $R^{10}$ or $R^{11}$ on lactam B are methyl, ethyl, phenyl, 4-fluorophenyl, 4-chlorophenyl, 4-$CF_3$-phenyl, (4-fluorophenyl)methyl, (4-chlorophenyl)methyl, (4-$CF_3$-phenyl)methyl, and 2-, 3-, and 4-pyridinyl. Preferred examples of $R^{13}$ on lactam B are F, Cl, OH, methyl, ethyl, methoxy, and trifluoromethyl.

The compounds herein described may have asymmetric centers. One enantiomer of a compound of Formula (I) may display superior biological activity over the opposite enantiomer. For example carbon 3 of lactam ring B Formula (I″) may exist in either an S or R configuration. Thus, an R or S configuration at carbon 3 in Formula (I″) is considered part of the invention. An example of such configuration includes, the S isomer:

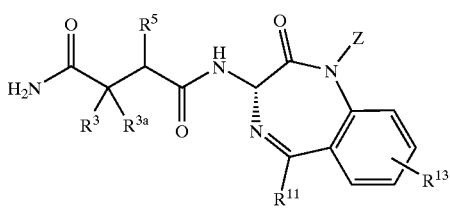

and the R isomer:

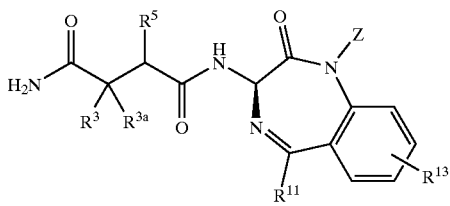

but is not intended to be limited to this example of ring B. When required, separation of the racemic material can be achieved by methods known in the art. Additionally, the carbon atoms to which $R^3$ and $R^5$ are attached may describe chiral carbons which may display superior biological activity over the opposite enantiomer. For example, where and $R^5$ is not H, then the configuration of the two centers may be described as (2R,3R), (2R,3S), (2S,3R), or (2S,3S). All configurations are considered part of the invention.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are intended to include any covalently bonded carriers which release the active parent drug according to Formula (I) in vivo when such prodrug is administered to a mammalian subject. Prodrugs of a compound of Formula (I) are prepared by modifying functional groups present in the compound in such a way that the modifications are cleaved, either in routine manipulation or in vivo, to the parent compound. Prodrugs include compounds of Formula (I) wherein a hydroxy, amino, or sulfhydryl group is bonded to any group that, when the prodrug or compound of Formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of Formula (I), and the like.

"Stable compound" and "stable structure" are meant to indicate a compound that is sufficiently robust to survive isolation to a useful degree of purity from a reaction mixture, and formulation into an efficacious therapeutic agent.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Methods for the synthesis of succinylamino lactams are known in the art and are disclosed in a number of references including PCT publication number WO 96/29313, which is hereby incorporated by reference.

Scheme 1

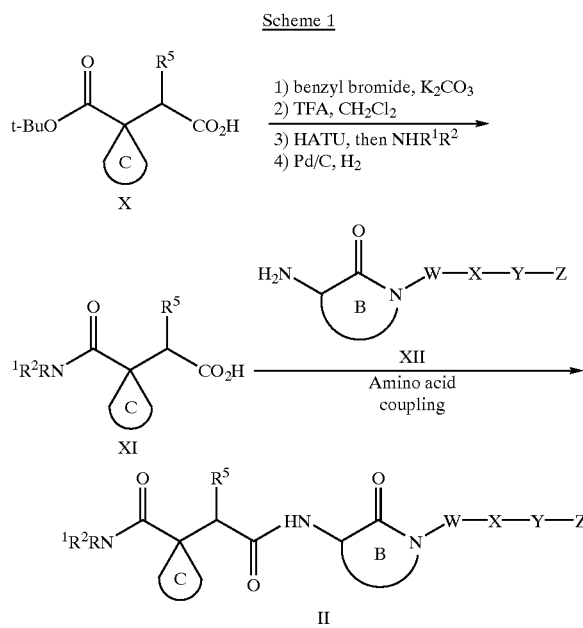

Compounds of the present invention can be prepared by an amino acid coupling procedure. An example of the synthetic method employed to prepare compounds of the present invention is illustrated in the amino acid coupling of succinate derivative XI and lactam XII to give a compound of Formula II as shown in Scheme 1. It is understood that ring C represents variables $R^3$ and $R^{3a}$ of Formula (I). The cyclic succinate derivative XI can be prepared from a mono-ester succinate derivative X which can be prepared from the corresponding diester or acid.

Examples of succinates wherein ring C is a carbocyclic or heterocyclic system are well known in the literature. For example, a dimethyl succinate having a 3-membered cyclopropyl ring C can be formed by a thermal or photolytic decomposition of a methyl 3(carbomethoxymethyl)-1-pyrazoline-3-carboxylate. See Bull. Soc. Chim. Fr. (1971), (6), 2290–5. A succinic acid derivative wherein ring C is a 4-membered cyclobutyl group can be formed by the method published in U.S. Pat. No. 3,828,025. A succinic acid derivative wherein ring C is a 5-membered cyclopentyl group can be formed using the methods described in Le Moal, H. et al., Bull. Soc. Chim. Fr., 1964, 579–584; Borenstein, M. R., et al., Heterocycles, 22, 1984, 2433–2438. Other examples of derivatives of succinate X wherein ring C is a five-membered cyclopentyl group or a 6-membered cyclohexyl group have been employed as matrix matalloproteinase inhibitors. See Bioorg. Med. Chem. Lett. (1998), 8(12), 1443–1448; Robinson, R. P., et al., Bioorg. Med. Chem. Lett. (1996), 6(14), 1719–1724. For the preparation of a succinic acid wherein ring C is an oxygen containing 3-membered oxirane see Kirshenbaum, K. S., Sharpless, K. B., J. Org. Chem. (1985), 50(11), 1979–82. For examples of succinate derivatives wherein ring C is a 5- or 6-membered heterocycle ring see Olivero, S., Dunach, E., Eur. J. Org. Chem. (1999), (8), 1885–1891; Eckardt et al. Helv. Chim. Acta, 55, 1972, 2432, 2433, 2434, 2438; Sandoz Ltd., NL 6409801 1963, Chem. Abstract., 63, 1965, 8324d; and Rice, L. M., et al., J. Med. Chem., 6, 1963, 388–402. It is understood that these references are only illustrative of the availability of some carbocyclic and heterocyclic succinates, however numerous references are known in literature which provide preparations of other substituted carbocyclic and heterocyclic succinates and their derivatives.

Scheme 2 illustrates one method for the introduction of a substitution on a carbon adjacent to the cyclic group in succinate IX via a deprotonation followed by standard alkylation procedures known to one skilled in the art. Treatment of IX with a base followed by addition of an $R^5$-LG, wherein LG is a leaving group such as a halide, mesylate, triflate or a tosylate, and subsequent deprotection of the benzyl group by hydrogenation employing, for example, $H_2$ and Pd/C, would give the desired succinate X.

Scheme 2

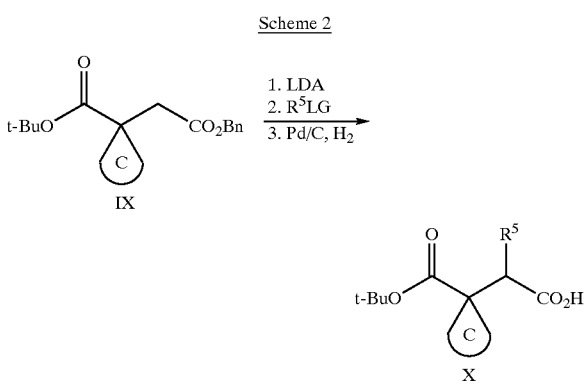

Scheme 2a

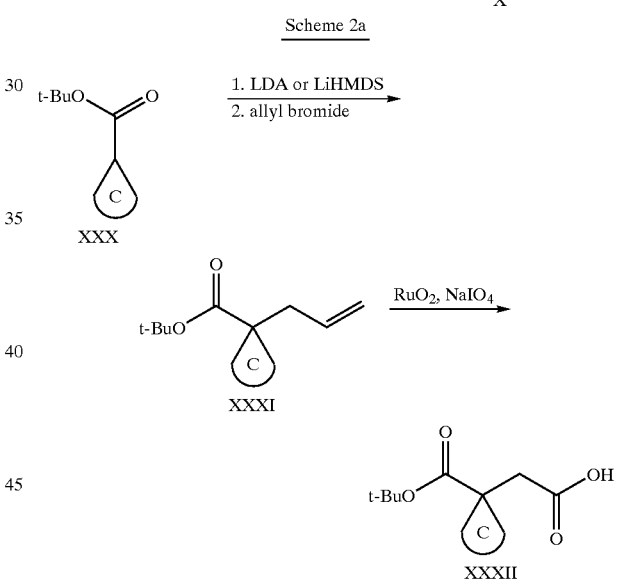

An example of a general method whereby diesters of structure IX can be obtained from cyclic esters XXX is shown in Scheme 2a. Deprotonation of such esters with, for example LDA or lithium hexamethyldisilazide, followed by reaction of the resulting ester enolate with allyl bromide provides allyl esters XXXI, which may be oxidized using ruthenium peroxide in the presence of sodium periodate to give free acids XXXII. If desired, esterification may be carried out using e.g. benzyl bromide in the presence of potassium carbonate.

Succinate acids such as XXXV with defined stereochemistry may be prepared from cyclic mono-acids XXXIII by use of a chiral auxiliary such as an oxazolidinone, as shown in Scheme 2b. Thus, acid XXXIII may be converted to the oxazolidinone XXXIV and subjected to the Evans stereospecific alkylation sequence to provide, after removal of the auxiliary, acid esters XXXV. Suitable alkylating agents include alkyl, allyl, propenyl or benzyl iodides or triflates, as is known to those skilled in the art. Use of the appropriate stereochemistry in the chiral auxiliary can provide substituted cyclic succinates of either absolute configuration.

Scheme 2b

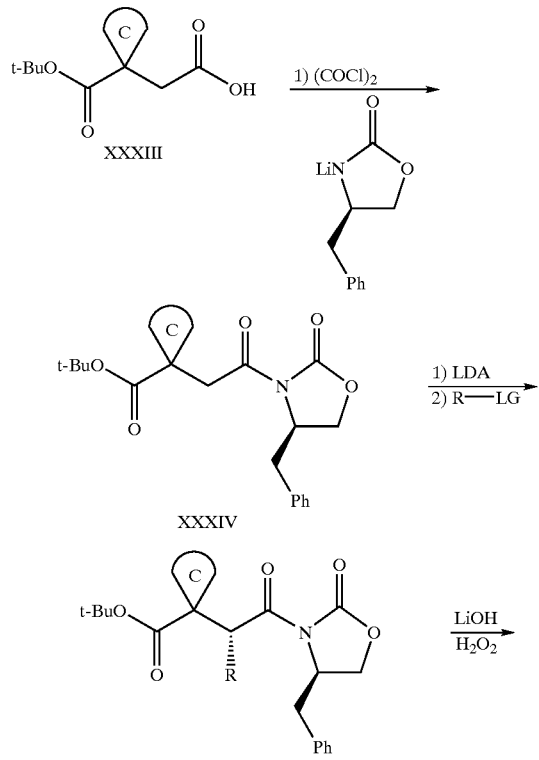

Scheme 3

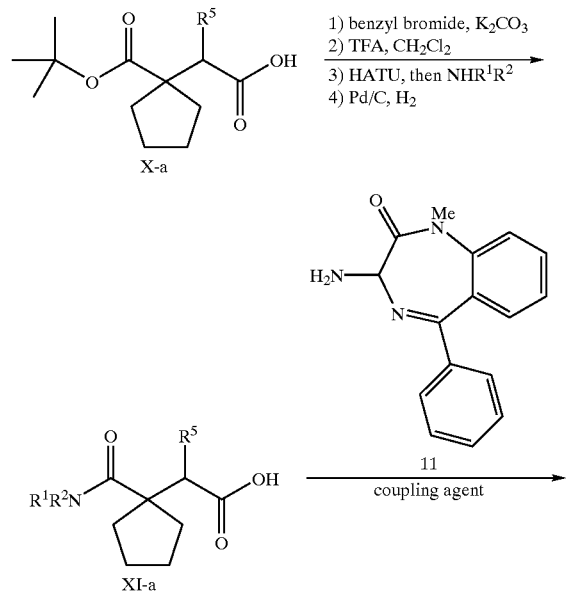

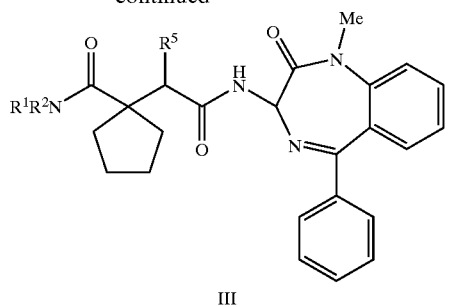

III

An example of a class of compounds compound which can be prepared according to the general methods described above is shown in Scheme 3. In step 1, cyclopentyl succinate X-a is converted to cyclopentyl succinamide XI-a. The subsequent amino acid coupling between succimamide XI-a and a benzodiazepine 11 under standard coupling conditions known to one skilled in the art would give the product III.

In the preparation of a compound of Formula I, in some cases it may be desirable to perform the coupling of an amino lactam and a succinic acid derivative prior to the amidation of the succinic acid compound. In Scheme 4 the coupling of a benzodiazepine 11 and the succinic acid derivative 10 is performed first to give the coupled product 12. Subsequent conversion of the ester function to an amide can be done by a deprotection step followed by an amino acid coupling step using standard coupling conditions to give a compound 13.

Scheme 4

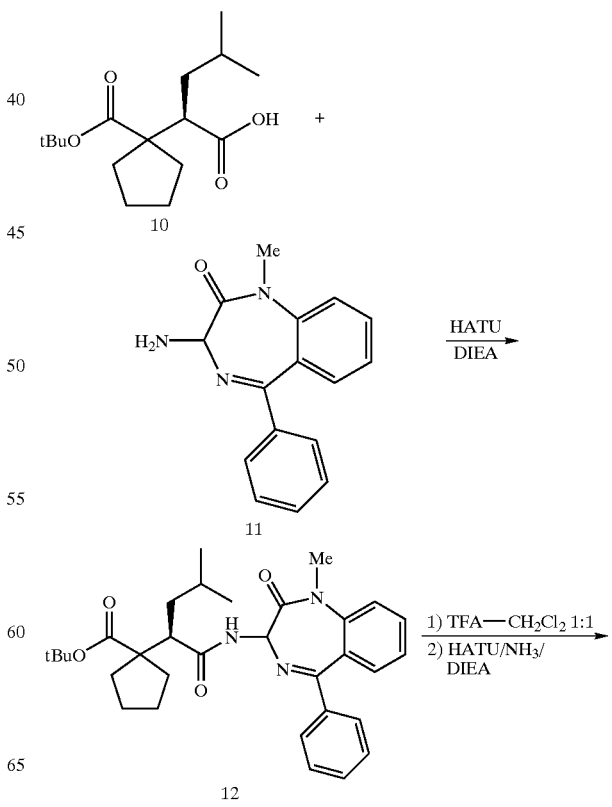

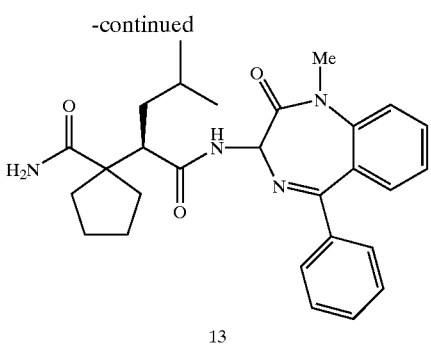

Functional Group Transformations, ed. by A. R. Katritzky, O. Meth-Cohn, C. W. Rees, Volume 5, pp 274–281 [P. D. Bailey, I. D. Collier and K. M. Morgan, Amides], Pergamon, 1995), and the skilled practitioner will adjust the methods, reagents and conditions to the example at hand.

The methods illustrated above may be modified to prepare cyclic succinoyl lactams where R5 and R5a comprise a cyclic group as shown in Scheme 4b. Thus the free acid of succinate esters prepared using the methods of Schemes 2, 2a or 2b may be suitably protected and the ester deprotected. Coupling of the free acid with an aminolactam may be carried out as described, and the remaining ester group converted to the desired amide.

Scheme 4a

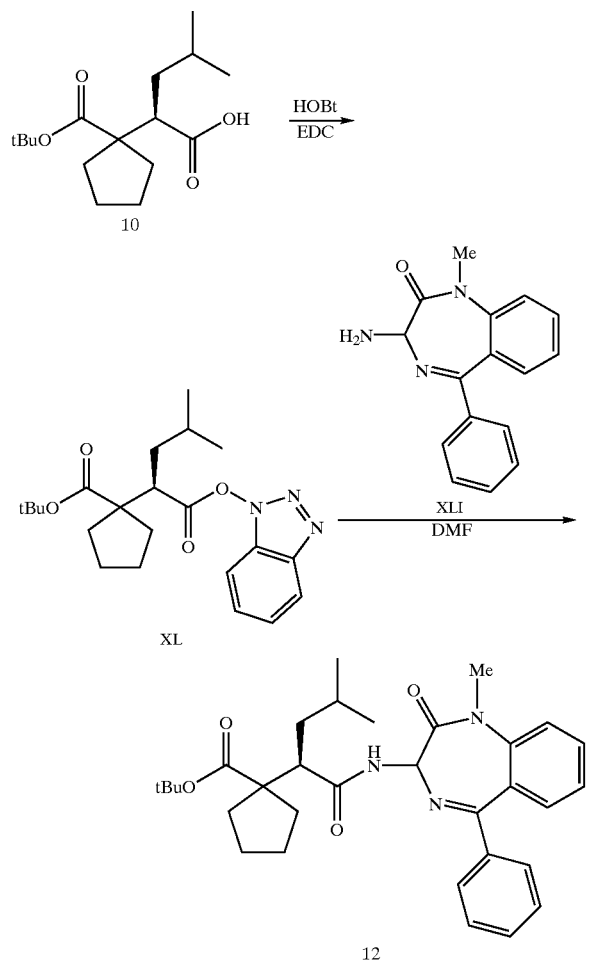

Scheme 4b

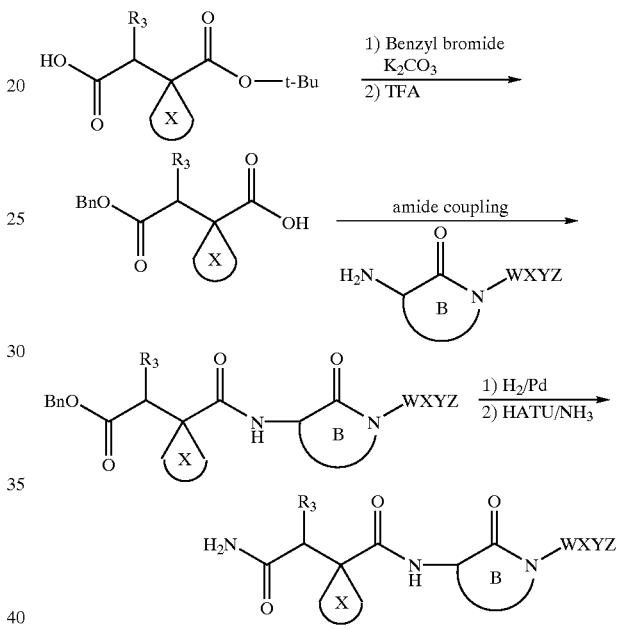

A variation of the coupling procedure of Scheme 4 useful in the synthesis of compounds of the present invention is illustrated in Scheme 4a, and involves conversion of the acid ester 10 to the corresponding HOBt ester using standard procedures, such as EDC/HOBt. In a separate step, the activated ester XL is allowed to react with a lactam amine XLI in a suitable solvent, such as DMF, preferably with warming of the reaction mixture to 40–100° C. As will be recognized by those skilled in the art, a variety of procedures for the synthesis of amides from carboxylic acids are known (see, for example, Peptide Synthesis Protocols, ed. by M. W. Pennington and B. M. Dunn, Methods in Molecular Biology, Vol. 35, Humana Press, 1994; and Comprehensive Organic Compounds of the present invention in which R3 and R3a, and R5 and R5a comprise two cyclic groups may be prepared from the corresponding cyclic succinates as shown in Scheme 4c. Bis(cyclic) succinates useful in the preparation of intermediates represented by xx are available using the methods of Overberger et al. (J. Org. Chem. 1955, 20, 1717–1720) and Belletire et al. (Tet. Lett. 1984, 25, 5969–5972).

Scheme 4c

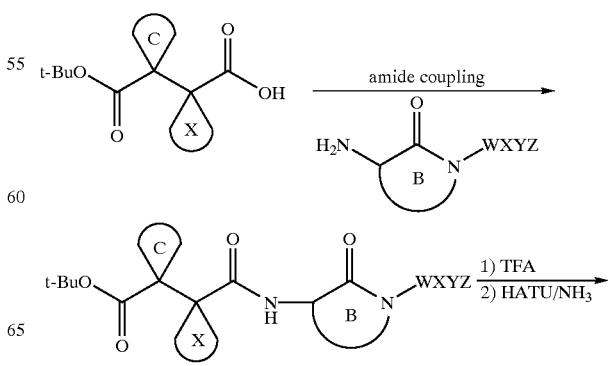

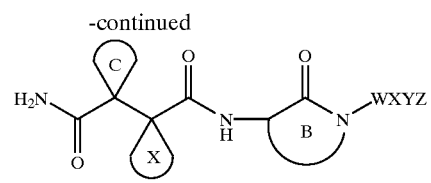

Methods for the synthesis of lactams XI of Scheme 1 as contemplated by the present invention in lactam ring B of Formula (I), including amino benzodiazepinones, dibenzo azepinones and other related heterocycles, are known in the art and are disclosed in a number of references including PCT publication number WO 98/28268, WO 99/66934, and WO 00/07995, which are hereby incorporated by reference. Additional references include Bock, et al, J. Org. Chem., 1987, 52, 3232–3239; Sherrill et al, J. Org. Chem., 1995, 60, 730–734; and Walsh, D. A., Synthesis, September 1980, p.677; and Brown, et al., Tetrahedron Letters, 1971, 8, 667–670.

An example of an L-α-amino-β-thio-ε-caprolactam, as shown in Scheme 5, where ring B is the amino lactam of XIII and J is a sulfur atom has been reported in the literature. See S. A. Ahmed et al, FEBS Letters, (1984), vol. 174, pages 76–9. One skilled in the art can extend this methodology to the synthesis of β-amino and oxygen containing rings by analogy. The sulfur-containing molecules can also be oxidized to the sulfoxide and sulfone by methods known to one skilled in the art.

Scheme 5

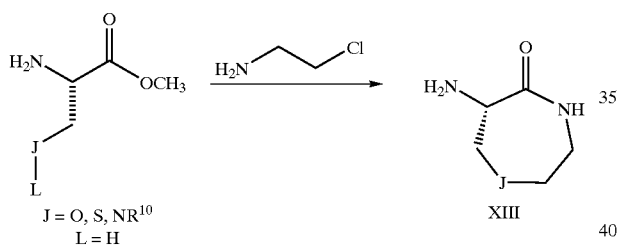

$J = O, S, NR^{10}$
$L = H$

XIII

An approach to preparing representative compounds of Formula (I) is illustrated for caprolactam 20 in Scheme 6. The lactam nitrogen of intermediate 15 can be alkylated by generating the anion with bases, such as LDA, lithium bis(trimethylsilyl)amide or sodium hydride, in solvents such as THF, with or without cosolvents such as DMPU or HMPA and reacting this with a variety of groups containing leaving groups (LG) for example, bromide, iodide, mesylate or tosylate. Alkylating agents such as alpha-bromo amides, ketones and acids, if not commercially available, can be prepared by a number of literature methods including halogenation of amino acids by diazotization. Other suitable alkylating agents such as alkyl, allylic and benzylic halides can be formed from a variety of precursors such as free-radical addition of halides or activation of alcohols, and other chemistries known to one skilled in the art. For discussion of these types of reactions, see Carey, F. A . and Sundberg, R. J., Advanced Organic Chemistry, Part A, New York: Plenum Press, 1990, pages 304–305, 342–347 and 695–698.

The N-Boc protecting group of caprolactam 16 can be removed by any number of methods well known in the literature, for example TFA in methylene chloride, to give the intermediate 17. The amine 17 can be coupled to an appropriately substituted carboxylic acid X-a, acid

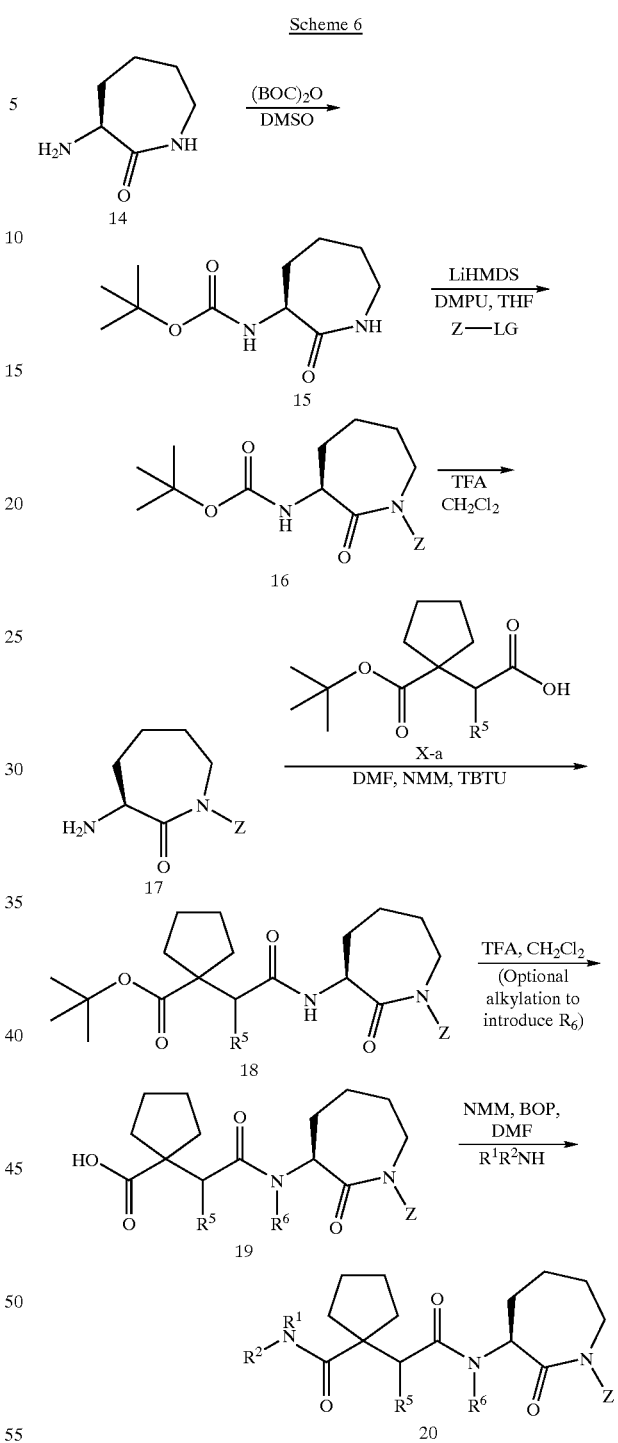

chloride or other activated acid derivative by methods well described in the literature for making amide bonds, for example, TBTU in DMF with a base such as NMM, to give the elaborated caprolactam 18. Optionally, caprolactam 18 can be alkylated using standard bases, such as LDA, NaH, or NaHMDS, to deprotonate the amide hydrogen followed by addition of an alkylating agent with an appropriate leaving group, such as halide, mesylate, or triflate in an appropriate solvent to provide an N—$R^6$ alkylated product of caprolactam 18. The t-butyl carboxyl protecting group of the N—R[6] alkylated product of caprolactam 18 can be removed, for example, by treatment with TFA in methylene chloride to give a carboxylic acid 19.

The final product 20 can be prepared by treating an activated carboxylic acid derivative of 19 with an appropriately substituted amine HNR[1]R[2]. For instance, activation of the carboxylic acid with HATU (O-(7-azabenzotriazol-1-yl)-1,1,3,3,-tetramethyluronium hexafluorophosphate) or PyBOP (benzotriazole-1-yl-oxy-tris-pyrrolidino-phosphonium hexafluorophosphate) or other coupling agents known to those skilled in the art allows condensation with ammonia to form primary amides. Similarly, condensation of the activated acid with hydroxylamine hydrochloride provides the hydroxamic acid, or reaction with a primary or secondary amine provides the substituted amine derivative. For additional acylation reactions see, for example, Carey, F. A. and Sundberg, R. J., Advanced Organic Chemistry, Part A, New York: Plenum Press, 1990, pages 475–479.

A different synthetic route to compounds of the present invention is shown in Scheme 7, step 1–5. In the method of Scheme 7, cyclization of two succinate substituents is carried out after coupling of the aminolactam and a suitable succinic acid derivative. In step 1, the amino lactam XII is coupled to an appropriately substituted succinate derivative XIV (n is 1, 2 or 3) or acid chloride by methods well described in the literature for making amide bonds, for example, TBTU in DMF with a base, for example, NMM to give the elaborated compound XV.

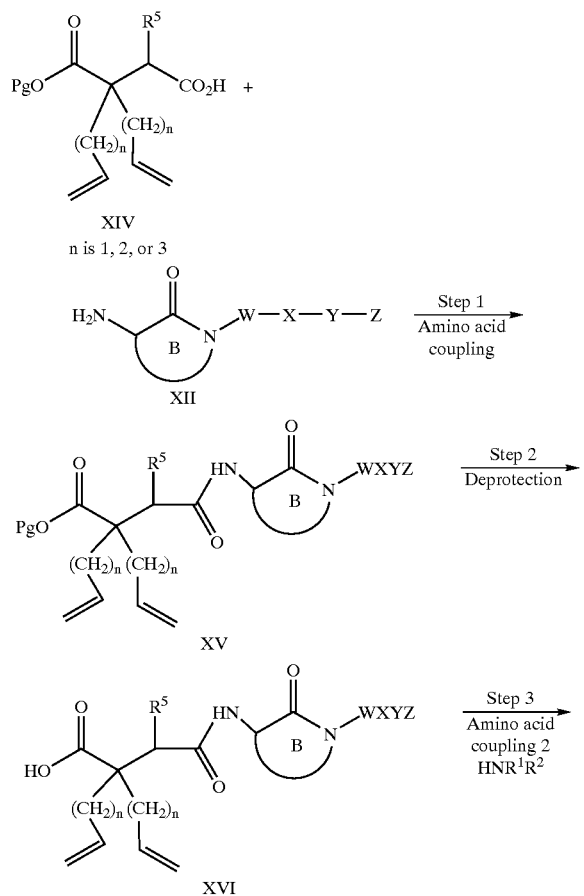

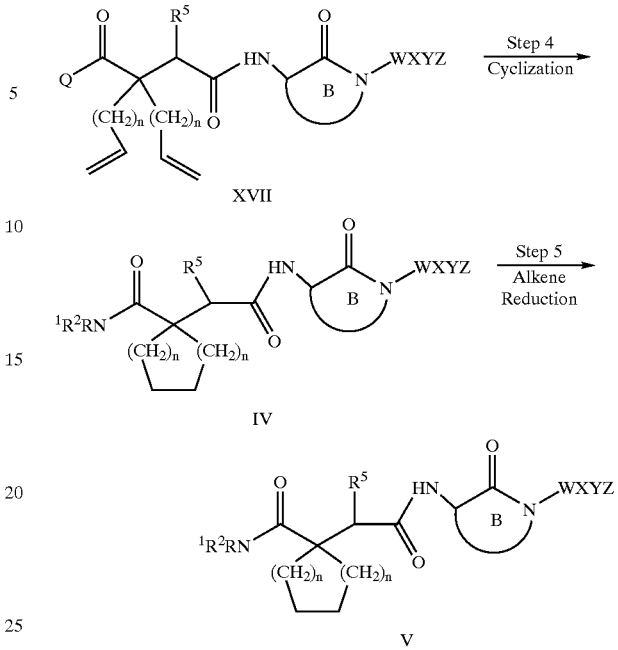

The protecting group of the carboxyl group can be removed using standard deprotection methods to provide compound XVI. A subsequent second amino acid coupling with an amine NHR[1]R[2] provides compound XVII which undergoes a ring-closing-metathesis to form a compound of formula IV in the presence of Ruthenium complexes using the method described by Grubbs and coworkers, J. Am. Chem. Soc., 114, 7324 (1992). Reduction of the cycloalkene of IV to a compound of formula V can be done using hydrogen or a hydrogen transfer reagent with Palladium as a catalyst or other reduction methods well known in the art.

The compound XIV of Scheme 7 can be prepared by a number of known procedures. See D. A. Evans et al, Org. Synth. 86, p83 (z1990) and P. Becket, M. J. Crimmin, M. H. Davis, Z. Spavold, Synlett, (1993), 137–138. The preparation of diastereomerically pure succinate XXI is outlined in Scheme 8 where acylation of an oxazolidinone with an acylating agent such as an acid chloride ClCOCH$_2$R[5] provides structure XVIII. Alkylation of XVIII with a BrCH$_2$CO$_2$t-Bu provides XIX followed by cleavage of the chiral auxiliary to give carboxylic acid XX. Subsequent alkylations of XX provides a variety of disubstituted succinate XXI which can be further alkylated to give a compound of formula XIV.

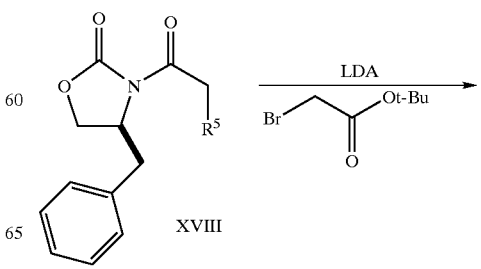

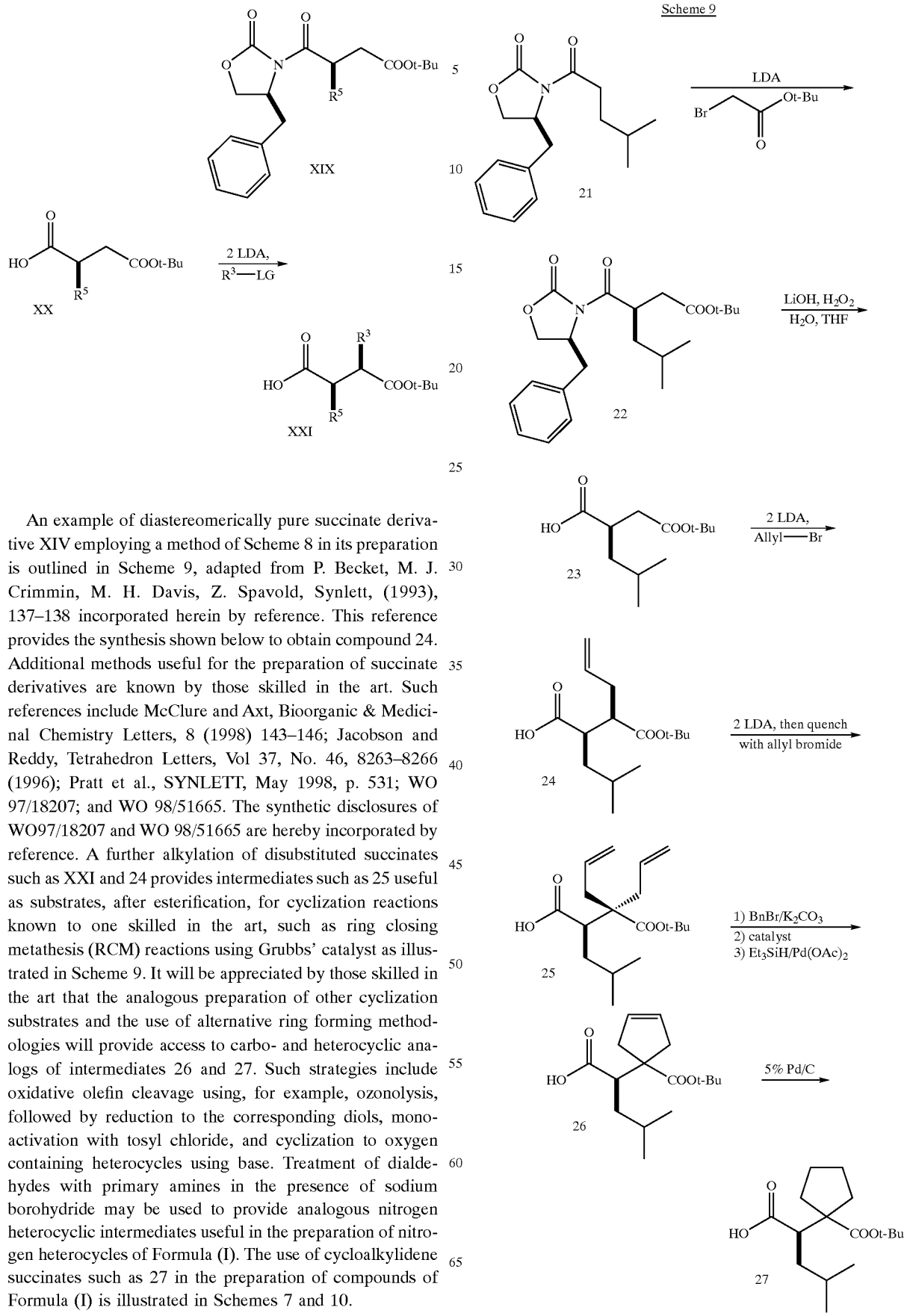

An example of diastereomerically pure succinate derivative XIV employing a method of Scheme 8 in its preparation is outlined in Scheme 9, adapted from P. Becket, M. J. Crimmin, M. H. Davis, Z. Spavold, Synlett, (1993), 137–138 incorporated herein by reference. This reference provides the synthesis shown below to obtain compound 24. Additional methods useful for the preparation of succinate derivatives are known by those skilled in the art. Such references include McClure and Axt, Bioorganic & Medicinal Chemistry Letters, 8 (1998) 143–146; Jacobson and Reddy, Tetrahedron Letters, Vol 37, No. 46, 8263–8266 (1996); Pratt et al., SYNLETT, May 1998, p. 531; WO 97/18207; and WO 98/51665. The synthetic disclosures of WO97/18207 and WO 98/51665 are hereby incorporated by reference. A further alkylation of disubstituted succinates such as XXI and 24 provides intermediates such as 25 useful as substrates, after esterification, for cyclization reactions known to one skilled in the art, such as ring closing metathesis (RCM) reactions using Grubbs' catalyst as illustrated in Scheme 9. It will be appreciated by those skilled in the art that the analogous preparation of other cyclization substrates and the use of alternative ring forming methodologies will provide access to carbo- and heterocyclic analogs of intermediates 26 and 27. Such strategies include oxidative olefin cleavage using, for example, ozonolysis, followed by reduction to the corresponding diols, monoactivation with tosyl chloride, and cyclization to oxygen containing heterocycles using base. Treatment of dialdehydes with primary amines in the presence of sodium borohydride may be used to provide analogous nitrogen heterocyclic intermediates useful in the preparation of nitrogen heterocycles of Formula (I). The use of cycloalkylidene succinates such as 27 in the preparation of compounds of Formula (I) is illustrated in Schemes 7 and 10.

The preparation of compounds 32 and 33 using the methods of Scheme 7 is shown in Scheme 10. The succinate product 29 is obtained from an amino acid coupling of a diallyl succinate 28 with a benzodiazepine 11 using a standard coupling procedure (HATU, DIEA, DMF). The carboxyl protecting group BOC is removed in TFA/$CH_2Cl_2$ to give a carboxylic acid 30. A second amino acid coupling of carboxylic acid 30 with ammonia in the presence of HATU and DIEA in DMF provides a diallyl succinate 31. A ring-closing-metathesis using a catalytic amount of $Cl_2Ru$ $(PCy3)_2(CHC_6H_6)$ as the metal carbene compound gives the cyclized product 32. Compound 33 is obtained from compound 32 by a hydrogen transfer reduction with $Pd(OH)_2/C$ and 1,4-cyclohexadiene in methanol.

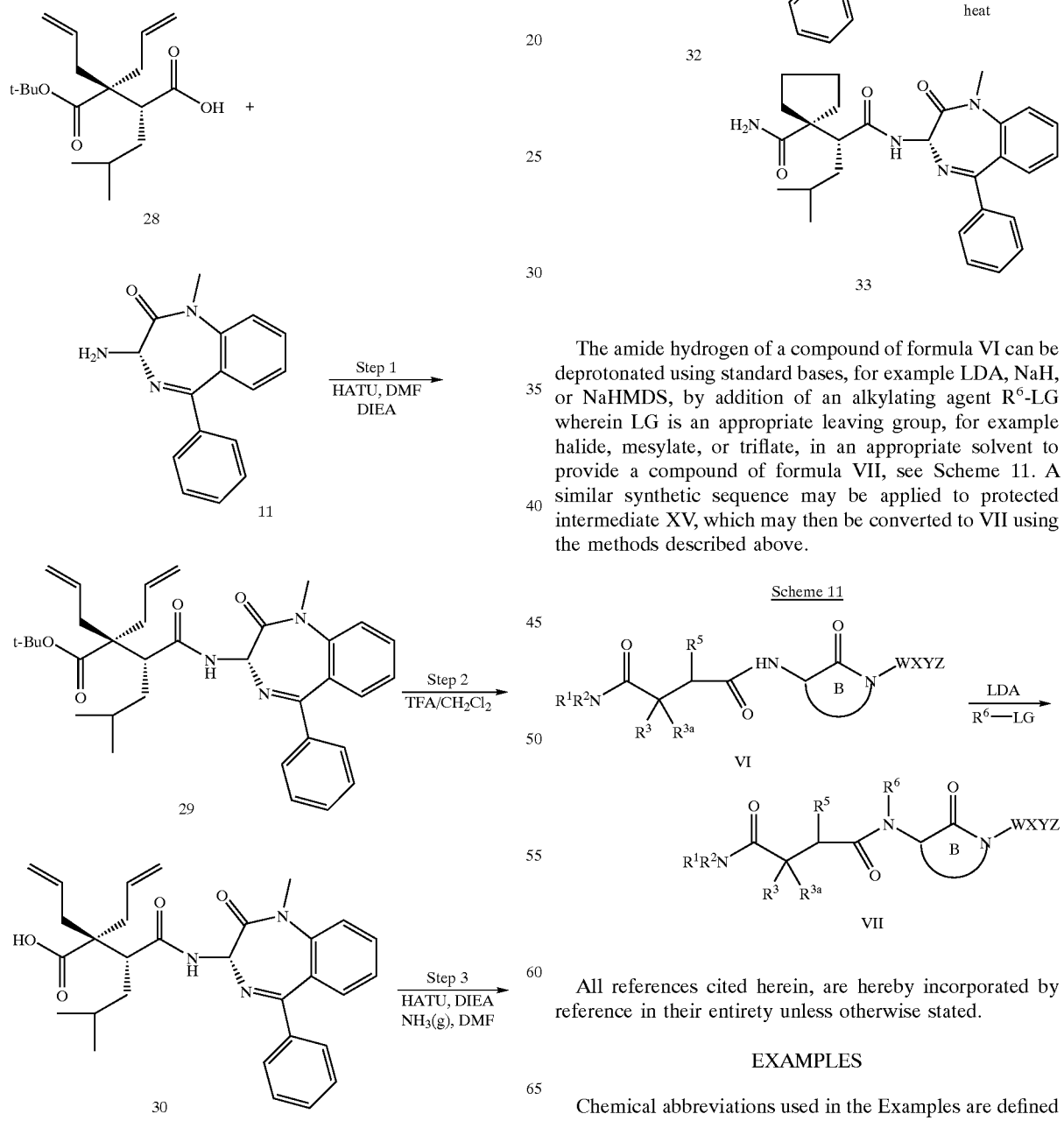

The amide hydrogen of a compound of formula VI can be deprotonated using standard bases, for example LDA, NaH, or NaHMDS, by addition of an alkylating agent $R^6$-LG wherein LG is an appropriate leaving group, for example halide, mesylate, or triflate, in an appropriate solvent to provide a compound of formula VII, see Scheme 11. A similar synthetic sequence may be applied to protected intermediate XV, which may then be converted to VII using the methods described above.

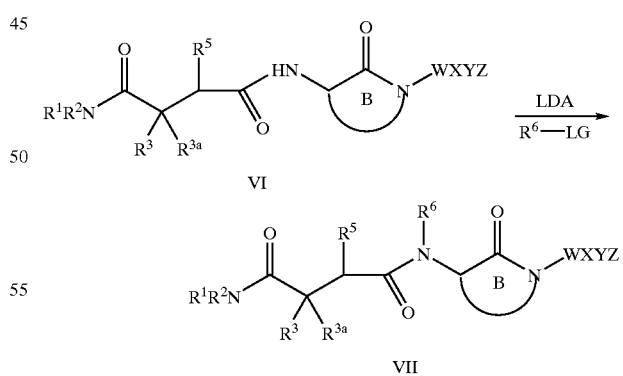

All references cited herein, are hereby incorporated by reference in their entirety unless otherwise stated.

EXAMPLES

Chemical abbreviations used in the Examples are defined as follows: "DMPU" for 1,3-dimethyl-3,4,5,6-tetrahydro-2

(1H)-pyrimidone, "TBTU" for O-(1H-benzotriazol-1-yl)-N,N,N',N'-tetramethyluronium tetrafluoroborate, "BOP" for benzotriazol-1-yloxytris-(dimethylamino)-phosphonium hexafluorophosphate, "EDC" for 1-(3-dimethylaminopropyl)-3-ethylcarbodiimide hydrochlordie, "HOBt" for 1-hydroxybenzotriazole hydrate, "TEA" for triethyl amine, "LiHMDS" for lithium bis(trimethylsilyl)amide, "HMPA" for hexamethylphosphoramide, "LDA" for lithium diisopropylamide, "DCC" for 1,3-dicyclohexylcarbodiimide, "PyBoP" for benzotriazole-1-yl-oxy-tris-pyrrolidino-phosphonium hexafluorophosphate, and "HATU" for O-(7-azabenzotriazol-1-yl)-N,N,N',N'-tetramethyluronium hexafluorophosphate. "HPLC" is an abbreviation used herein for high pressure liquid chromatography. Reverse-phase HPLC can be carried out using a Vydac C-18 column with gradient elution from 10% to 100% buffer B in buffer A (buffer A: water containing 0.1% trifluoroacetic acid, buffer B: 10% water, 90% acetonitrile containing 0.1% trifluoroacetic acid). If necessary, organic layers can be dried over sodium sulfate unless otherwise indicated. However, unless otherwise indicated, the following conditions are generally applicable.

Melting points were determined on a Mel-Temp II apparatus and are uncorrected. IR spectra were obtained on a single-beam Perkin-Elmer Spectrum 1000 FT-IR spectrometer using 4 accumulations at a resolution of 4.00 cm$^{-1}$ on samples prepared in a pressed disc of KBr or as a film on NaCl plates. Proton NMR spectra (500 MHz, referenced to tetramethylsilane) were obtained on a Bruker AMX 500 spectrometer or on a Brucler AC 300 spectrometer (300 MHz, refurned to tetramethylsilane). Mass spectra were obtained on a Shimadzu QP-5000 mass spectrometer (CI or EI), a Perkin Elmer Sciex 100 atmospheric pressure ionization (API) mass spectrometer or a Finnigan LCQ Duo LCMS ion trap electrospray ionization (ESI) mass spectrometer. HPLC analyses were obtained using a Rainin Dynamax $C_{18}$ column with UV detection at 223 nm using a standard solvent gradient program as follows:

HPLC solvent conditions: Samples were dissolved in methanol (1 mg/mL) and run using the following gradient program with a solvent flow rate of 1.0 mL/min.

| Time (min) | Acetonitrile (0.05% TFA) | H$_2$O (0.05% TFA) |
|---|---|---|
| Initial | 10 | 90 |
| 20.0 | 90 | 10 |
| 20–30 | 90 | 10 |

Elemental analyses were performed by Quantitative Technologies, Inc. (Whitehouse, N.J.).

Example 1

1-[(1R)-3-methyl-1-[1,3-dihydro-1-methyl-2-oxo-5-phenyl-2H-1,4-benzodiazepin-3-ylcarbamoyl]-butyl]-cyclopent-3-enecarboxylic amide

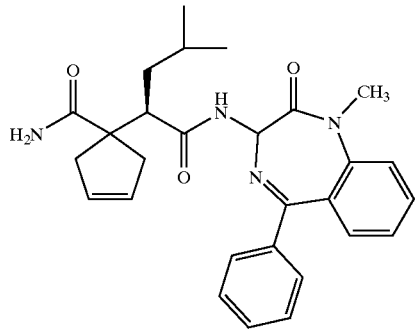

Following the disclosure of Scheme 10:
Step 1: Preparation of 2-Allyl-2-[3-methyl-1-(1-methyl-2-oxo-5-phenyl-2,3-dihydro-1H-benzo[e][1,4]diazepin-3-ylcarbamoyl)-butyl]-pent-4-enoic acid tert-butyl ester 29. Compound 28 (1.4 g, 4.5 mmol) in 50 ml DMF was added HATU (O-(7-azabenzotriazol-1-yl)-N,N,N',N'-tetramethyluronium hexafluorophosphate) (2.2 g, 5.8 mmol) followed by DIEA (N,N-diisopropylethylamine) (800 ul, 4.6 mmol). The solution was stirred at RT for one hour. A mixture of compound 11 (2.3 g, 4.6 mmol) and DIEA (920 ul, 5.2 mmol) in 50 ml DMF was added to the above solution over several minutes. The resulting solution was stirred at ambient temperature overnight, then quenched with 20 ml water. Removal of volatiles gave a yellow oil which was taken up in ethyl acetate/water (1:1). The organic layer was washed with water twice, then brine, dried over Na$_2$SO$_4$, filtered, and concentrated. The residue was purified by silica gel chromatography with hexane/ethyl acetate (8:2) to give 300 mg of product 29 (15%). $^1$H NMR (CDCl$_3$) 0.96–0.89 (dd, 6H), 1.28–1.22 (m, 1H), 1.50 (s, 9H), 1.65–1.50 (m, 1H), 2.00–1.85 (m, 1H), 3.80–2.40 (m, 5H), 3.45 (s, 3H), 5.31–5.00 (m, 5H), 5.59–5.57 (d, 1H), 6.00–5.85 (m,2H), 7.40–7.20 (m, 9H). ESI ES+=558.3 (M+1).

Preparation of 2-Diallyl-3-isobutyl-succinic acid 1-tert-butyl ester 28. To a solution of 2-allyl-3-isobutyl-succinic acid 1-tert-butyl ester (24, 3.1 g, 11.5 mmol) in 50 ml THF at −78° C. was added 0.2M LDA in THF (29 mmol, 2.5 eq). After 1 hr, a solution of allyl bromide (2.1 g, 17.4 mmol, 1.5 eq) in 30 ml THF was added slowly. The mixture was allowed to warm to ambient temperature overnight. The reaction was quenched with 30 ml of methanol, and the solvent was removed under reduced pressure to provide a yellow oil, which was taken up in ethyl acetate. The organic layer was washed twice with 1.0N citric acid and then with brine, then dried over anhydrous Na$_2$SO$_4$. Filtration and removal of solvent provided the title compound. NMR analysis indicated that the crude product contained a mixture of product 28 (>80%) and starting material 24 (<20%). The mixture was utilized in Step 1 without further purification. The $^1$H NMR signals of 28 are overlapped with those of 24. $^{13}$C NMR for 2: (CDCl$_3$) 21.2, 23.9, 26.6, 27.9, 36.4, 37.8, 37.9, 48.9, 50.6, 81.5, 118.5, 118.6, 133.3, 134.0, 173.1, 180.0. ESI ES−=619.5 (2M−1).

Step 2: Preparation of 2-Allyl-2-[3-methyl-1-(1-methyl-2-oxo-5-phenyl-2,3-dihydro-1H-benzo[e][1,4]diazepin-3-ylcarbamoyl)-butyl]-pent-4-enoic acid 30. A solution of compound 29 (300 mg, 0.54 mmol) in 50 ml TFA/CH$_2$Cl$_2$ (1:1) was stirred for 2 hr at ambient temperature, then concentrated under vacuum. Two cycles of toluene addition and removal of volatiles gave 250 mg of 30 as a white solid (92%) which was used in the next step without purification. ESI ES+=502.3 (M+1)

Step 3: Preparation of 2,2-Diallyl-3-isobutyl-N4-(1-methyl-2-oxo-5-phenyl-2,3-dihydro-1H-benzo[e][1,4]diazepin-3-yl)-succinamide 31. To a solution of 30 (250 mg, 0.5 mmol) in 30 ml DMF was added HATU (250 mg, 0.66 mmol) and DIEA (400 uL, 2.2 mmol). After stirring for 2 hrs, ammonia gas was bubbled into the solution for 5 minutes using a glass inlet tube. The mixture was then stirred at ambient temperature overnight. Water was added (10 mL) and the solvent was removed under vacuum to give a yellow oil which was taken up in ethyl acetate and water (1:1). The organic layer was washed twice with water and then brine, and dried over Na$_2$SO$_4$. After filtration and concentration, the crude product was purified using silica gel chromatography (CH$_2$Cl$_2$/methanol 10:0.5) to give compound 31 (120 mg) as a white solid (48%). $^1$H NMR (CDCl$_3$) 0.95–0.88 (dd, 6H), 1.32–1.28 (m, 1H), 1.64–1.50 (m, 1H), 1.90–1.80 (m, 1H), 2.35–2.00 (m, 1H), 2.80–2.54 (m, 4H), 3.48 (s, 3H), 5.38–5.14 (m, 5H), 5.54–5.51 (d, 1H), 5.90–5.78 (m, 2H), 7.65–7.25 (m, 9H), 8.52 (s, 1H). ESI ES+=523.2 (M+Na).

Step 4: Preparation of 1-[(1R)-3-methyl-1-[1,3-dihydro-1-methyl-2-oxo-5-phenyl-2H-1,4-benzodiazepin-3-ylcarbamoyl]-butyl]-cyclopent-3-enecarboxylic amide 32. To a solution of 31 (110 mg, 0.22 mmol) in 20ml of toluene and CH$_2$Cl$_2$ (1:1) at 100 degree was added (bis(tricyclohexylphosphine)-benzylidine ruthenium (IV) dichloride) (24 mg, 0.029 mmol). The mixture was stirred at 100 degree for 4 hrs and another 24 mg Grubbs' catalyst was added. The mixture was then stirred at 100 degree for another 4 hrs. Then the solution was cooled to RT, after which 100 mg of charcoal was added. The mixture was filtered through celite to provide a slightly yellow solution, then concentrated. The residue was purified in silica gel chromatography with CH$_2$Cl$_2$/methanol (10:0.5) to give 48 mg of 32 (46%). $^1$H NMR (CDCl$_3$) 0.97–0.90 (dd, 6H), 1.30–1.25 (m, 1H), 1.65–1.57 (m, 1H), 2.00–1.85 (m, 1H), 2.40–2.30 (d, 1H), 2.80–2.65 (m, 2H), 3.00–2.80 (d, 1H), 3.40–3.20 (m, 1H), 3.47 (s, 3H), 5.40–5.20 (s, 1H), 5.52–5.49 (d, 1H), 5.80–5.71 (m, 2H), 7.63–7.20 (m, 9H), 7.90 (s, 1H). API AP+ 473.1 (M+1).

Example 1a

Synthesis of Cyclic Succinate Intermediate 6 (Scheme 12)

Scheme 12

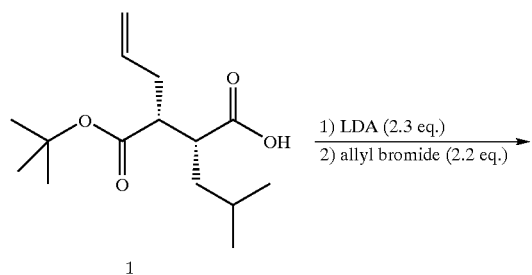

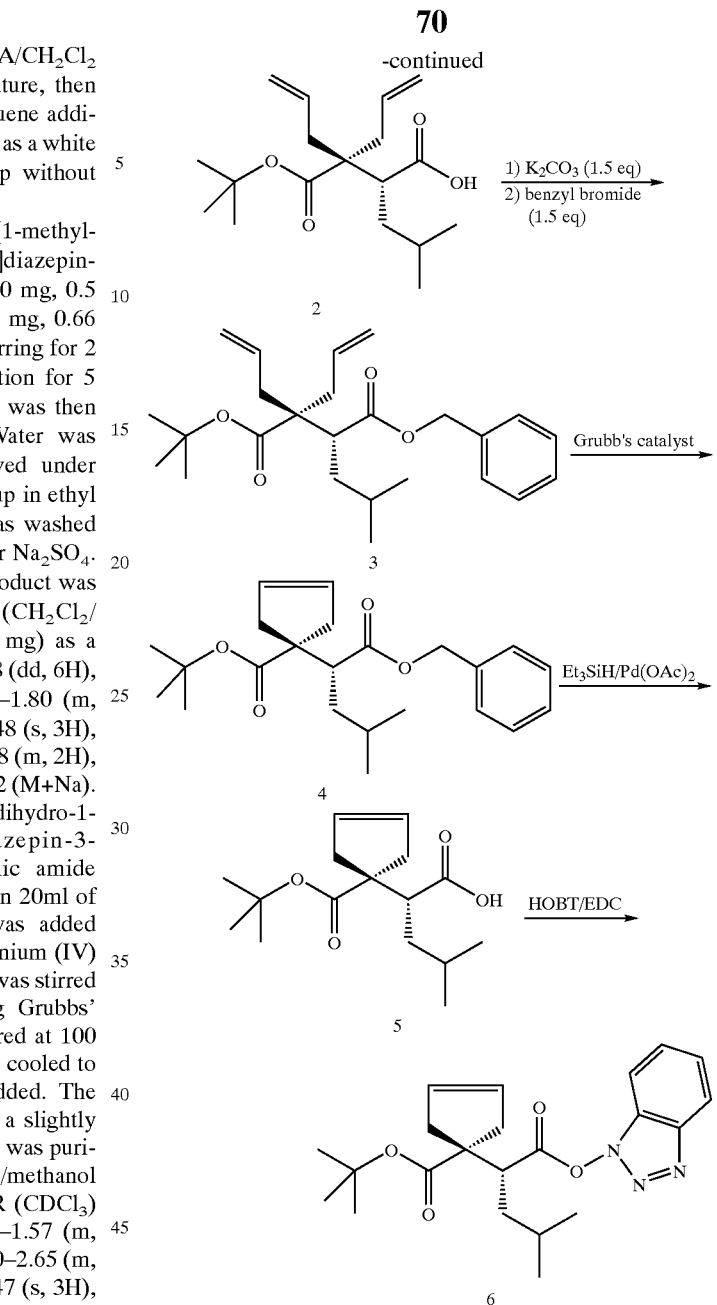

Step 1: Preparation of Diallylsuccinate Mono-acid 2

A solution 300 mmole of LDA was prepared by adding 120 mL of 2.5M n-BuLi in hexanes to 45 ml (320 mmol) DIPA in 200 ml THF at −78° C. followed by stirring in an ice bath for 30 minutes. This was added to a solution of syn-succinate 1 (34.0 g, 126 mmol) in 100 ml THF at −78° C. to give a clear yellow solution, which was stirred at that temperature for one hour. A solution of allyl bromide (21.0 g, 170 mmol) in 100 ml THF was added to the above solution over 20 minutes, and the resulting yellow solution was stirred and allowed warm to room temperature overnight. The reaction mixture was quenched with 50 ml methanol and 50 ml water. The solvents were evaporated to give a yellow viscous oil which was taken up in EtOAc (400 ml) and 200 ml 1.0N HCl. The organic layer was washed with 100 ml 1.0N HCl, and brine and dried over sodium sulfate. The solution was concentrated to give 2 as a slightly yellow oil (34.2 g, 110.3 mmol, 88%). $^{13}$C NMR (300 MHz, CDCl$_3$) 179.8, 173.0, 134.0, 133.3, 118.7, 118.4, 81.4, 50.6, 48.8, 37.8, 36.3, 27.8, 26.6, 23.8, 21.1.

Step 2: Preparation of Diallylsuccinate Diester 3

To a solution of 2 (34.2 g, 110 mmol) in 400 ml acetone was added potassium carbonate (28.0 g, 200 mmol) and benzyl bromide (28.0 g, 163 mmol). The solution was heated to reflux for 2 hours. Evaporation of the solvent gave a yellow oil which was taken up in EtOAc and water. The organic layer was washed with brine, dried over sodium sulfate and concentrated to give diester 3 (44.5 g, 100%). $^{13}$C NMR (300 MHz, CDCl$_3$) 173.7, 172.8, 134.5, 133.6, 129.0, 128.8, 128.5, 128.4, 128.3, 128.2, 118.5, 118.2, 81.0, 66.2, 50.9, 49.0, 38.5, 37.5, 37.9, 28.0, 26.7, 23.9, 21.3.

Step 3: Preparation of Cyclic Succinate Diester 4

To a solution of 3 (3.0 g, 7.5 mmol) in 700 ml solution of methylene chloride-toluene (1:1) was added 200 mg tricyclohexylphosphine[1,3-bis(2,4,6-trimethylphenyl)-4,5-dihydroimidazol-2-ylidene]benzylidine]ruthenium (IV) dichloride 200 mg (0.24 mmol). The reaction mixture was refluxed for 4 hrs at 100° C., then evaporated to give a dark oil which was purified by chromatography on silica gel with EtOAc:hexane (5:95) to give 4 as a yellow oil (1.7 g, 4.6 mmol, 62%). $^1$HNMR (300 MHz, CDCl$_3$) 0.8–0.9 (m, 6H), 0.9–1.1 (m, 1H), 1.4 (s, 9H), 1.6–1.8 (m, 2H), 2.6–3.0 (m, 4H), 5.0–5.2 (m, 2H), 5.4–5.6 (d, 2H), 7.2–7.4 (m, 5H).

Step 4: Preparation of Cyclic Succinate HOBT Ester 6

Triethylsilane was added to a solution of palladium acetate (170 mg, 0.75 mmol) in 10 ml of methylene chloride and the resulting mixture was stirred at RT for 30 minutes. Triethylamine (0.2 ml, 1.4 mmol) was added, followed by 4 (2.8 g, 7.5 mmol) in 10 ml of methylene chloride. The mixture was stirred at RT overnight, filtered through a short silica gel column, then concentrated to give 5 as a colorless oil which was used without further purification. To a solution of 5 in 100 ml methylene chloride was added triethylamine (2.0 ml, 14.3 mmol), 1-(3-dimethylaminopropyl)-3-ethylcarbodiimide HCl (EDC, 2.2 g, 11.5 mmol) and 1-hydroxybenzotriazole hydrate (HOBT, 2.2 g, 16.3 mmol). The mixture was stirred for 4 hours. The solvents were removed under reduced pressure and the resulting oil was taken up in EtOAc and water. The organic layer was washed with water and brine, then dried over sodium sulfate and concentrated. Purification by flash chromatography on silica gel with EtOAc:hexane (10:90) gave 6 (1.95 g, 4.9 mmol, 65%). $^1$HNMR (300 MHz, CDCl$_3$) 0.9–1.1(m, 6H), 1.2–1.4 (m, 1H), 1.8–2.0(m, 2H), 2.5–3.2 (m, 5H), 5.6–5.8 (m, 2H), 7.3–7.6 (m, 3H), 8.0 (d, 1H). MS: 422.1 (M+Na), 463.2 (M+Na+CH3CN), 821.4 (2M+Na).

Synthesis of Formula I Compounds 11 and Diastereomer 12 (Scheme 13)

Scheme 13

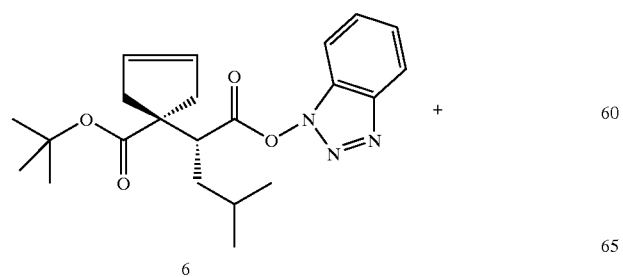

+

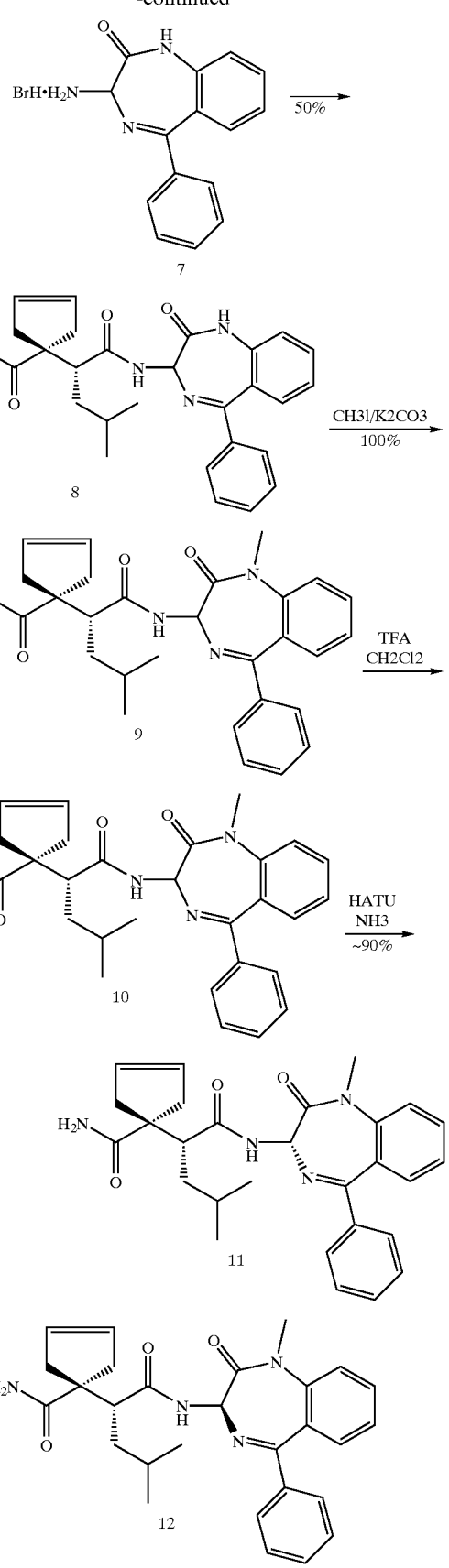

Step 1: Preparation of Benzodiazepinesuccinamide 8

A solution of racemic aminobenzodiazepine HBr salt 7 (2.6 g, 7.8 mmol), 6 (6.0 g, 15 mmol) and diisopropylethylamine (DIPEA, 1.4 ml, 8.0 mmol) in 200 ml DMF was heated at 60° C. for 3 hours. The solvents were removed under reduced pressure to give a viscous oil which was taken up in EtOAc and water. The organic layer was washed with water and brine, then dried over sodium sulfate. The solvents were evaporated under reduced pressure to give an oil which was purified by flash chromatography (30:70 EtOAc:hexane), giving 8 as a white solid (2.1 g, 4.0 mmol, 51%). ¹HNMR (300 MHz, CDCl₃) 0.8–1.2 (m, 6H), 1.2–1.4 (m, 1H), 1.4–1.6(m, 9H), 1.6–2.0 (m, 2H), 2.6–3.0 (m, 5H), 5.4–5.8 (m, 3H), 7.0–7.6 (m, 9H). MS: 516.2 (M+H), 538.2 (M+Na).

Step 2: Preparation of N-methyllactam 9

To a solution of 8 (2.1 g, 4.0 mmol) in 100 ml DMF was added iodomethane (2.0 g, 14.0 mmol) and potassium carbonate (1.0 g, 7.2 mmol). The reaction mixture was stirred at RT overnight. The solvents were evaporated under reduced pressure and the residue was taken up in EtOAc and water. The organic layer was washed with water and brine, then dried over sodium sulfate. Evaporation of solvents gave 9 as a white solid which was used without purification. ¹HNMR (300 MHz, CDCl₃) 0.8–1.2 (m, 6H), 1.2–1.4 (m, 1H), 1.4–1.6 (m, 9H), 1.6–2.0 (m, 2H), 2.6–3.0(m, 5H), 3.4 (s, 3H), 5.4–5.7 (m, 3H), 7.2–7.6 (m, 9H). MS: 530.2 (M+H), 552.2 (M+Na).

Step 3: Preparation of Succinamide Free Acid 10

A solution of 9 in 100 ml TFA-methylene chloride (1:1) was stirred for 3 hours. The solvents were removed under reduced pressure, and the resulting oil was dissolved in 50 mL of toluene and concentrated provide 10 as a yellow solid (2.0 g, 4.2 mmol). MS: 474.2 (M+H), 586.2 (M+CF3COO—).

Step 4: Synthesis of Diastereomeric Succinamides 11 and 12 (Scheme 2)

A solution of 10 (2.0 g, 4.2 mmol), O-(7-azabenzotriazol-1-yl)-N,N,N,N-tetramethyluronium hexafluorophosphate (HATU, 2.0 g, 5.3 mmol) and DIEPA (1 ml, 5.7 mmol) in 100 ml DMF was treated with ammonium gas for 5 minutes. The reaction mixture was stirred overnight, then quenched with water. The solvents were removed under reduced pressure and the resulting oil was taken up in EtOAc and water. The organic layer was washed with brine and dried over sodium sulfate. Evaporation of solvents provided the crude mixture of diastereomers which were separated by flash chromatography using EtOAc: hexane (1:1). Diastereomer 11 (900 mg) eluted first: ¹HNMR (300 MHz, CDCl₃) 0.8–1.0 (dd, 6H), 1.2–1.4 (m, 1H), 1.5–1.7 (m, 1H), 1.8–2.0 (m, 1H), 2.3–2.4 (m, 1H), 2.6–3.0(m, 3H), 3.2–3.4 (m, 1H), 3.47 (s, 3H), 5.25(s, 1H), 5.4–5.5 (d, 1H), 5.6–5.8 (m, 2H), 7.2–7.8 (m, 9H), 7.9 (s, 1H). MS: 473.2 (M+H). Diastereomer 12 (680 mg) eluted second: ¹HNMR (300 MHz, CDCl₃) 0.9–1.2 (m, 6H), 1.2–1.4 (M, 1H), 1.6–1.8 (m, 1H), 1.9–2.1 (m, 1H), 2.35–2.45 (m, 1H), 2.6–2.9 (m, 3H), 3.2 (M, 1H), 3.5 (s, 3H), 5.4 (s, 1H), 5.5 (d, 1H), 5.6–5.8 (m, 2H), 7.2–7.8 (m, 10H). MS: 473.2 (M+H), 495.1 (M+Na).

Example 2

1-[(1R)-3-methyl-1-[1,3-dihydro-1-methyl-2-oxo-5-phenyl-2H-1,4-benzodiazepin-3-ylcarbamoyl]-butyl]-cyclopentanecarboxylic amide

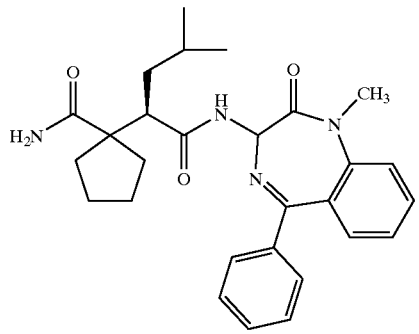

Step 5: Preparation of 1-[(1R)-3-methyl-1-[1,3-dihydro-1-methyl-2-oxo-5-phenyl-2H-1,4-benzodiazepin-3-ylcarbamoyl]-butyl]-cyclopentanecarboxylic amide 33 (Scheme 10). To a solution of compound 32(Scheme 10) (45 mg, 0.1 mmol) in 20 ml of methanol was added 400 mg of Pd(OH)2/C (20% weight, water<50%), followed by 2 ml (21 mmol) of 1,4-cyclohexadiene. The solution was heated to gentle reflux at (65 C) for 1 hr and then cooled to ambient temperature. The solution was filtered and concentrated to provide a white solid, which was purified using silica gel chromatography with CH₂Cl₂/methanol (10:0.5) to give 30 mg of 33 (Scheme 10) as a white solid, 8 (63%). ¹H NMR (CDCl₃) 0.96–0.89 (dd, 6H), 1.50–1.20 (m, 2H), 2.10–1.60 (m, 8H), 2.65–2.42 (m, 2H), 3.48 (s, 3H), 5.25 (s, 1H), 5.52–5.50 (d, 1H), 7.65–7.20 (m, 9H), 8.20 (s, 1H). ESI ES+=475.2 (M+1).

Example 2a

Synthesis of Formula I Compound 13 (Scheme 14)

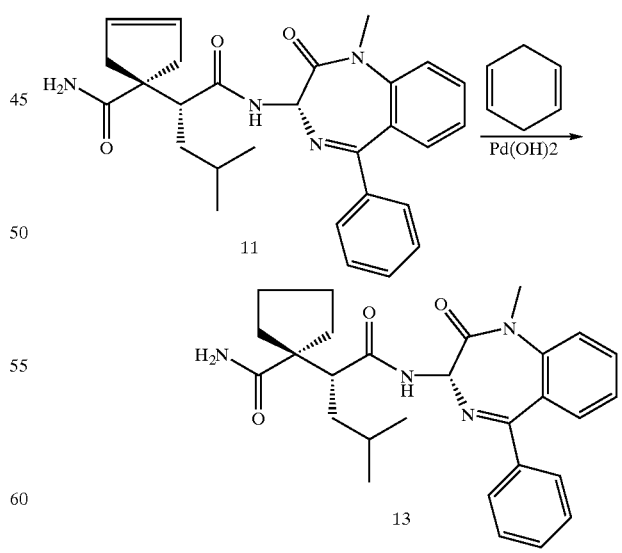

To a solution of 11 (200 mg, 0.42 mmol) in 20 mL of methanol was added 200 mg palladium hydroxide (20% on carbon, wet) and 1,4-cyclohexadiene (2 ml, 21 mmol). The reaction mixture was slowly heated to reflux (65° C.), stirred 2 hours, then filtered through celite and evaporated. Flash chromatography using methanol:methylene chloride (5:95) provided 13 as a white solid (128 mg, 0.27 mmol). ¹HNMR (300 MHz, CDCl₃) 0.8–1.0 (dd, 6H), 1.2–2.2 (m, 10H), 2.4–2.7 (m, 2H), 3.47(s, 3H), 5.3 (s, 1H), 5.5 (d, 1H), 7.2–7.6 (m, 9H), 8.2 (s, 1H). MS: 475.2(M+H), 497.2 (M+Na). The corresponding diastereomer epimeric at the benzodiazepine carbon was prepared using the same procedure beginning with 12. ¹HNMR (300 MHz, CDCl₃) 0.9–1.1 (m, 6H), 1.2–2.0 (m, 10H), 2.4–2.7 (m, 2H), 3.5 (s, 3H), 5.3 (s, 1H), 5.5 (d, 1H), 7.2–7.7 (m, 9H), 8.2 (s, 1H). MS: 475.2 (M+H), 497.2 (M+Na).

Example 3

1-[(1R)-3-methyl-1-[1,3-dihydro-1-methyl-2-oxo-5-(4-chlorophenyl)-2H-1,4-benzodiazepin-3-ylcarbamoyl]-butyl]-cyclohexanecarboxylic amide

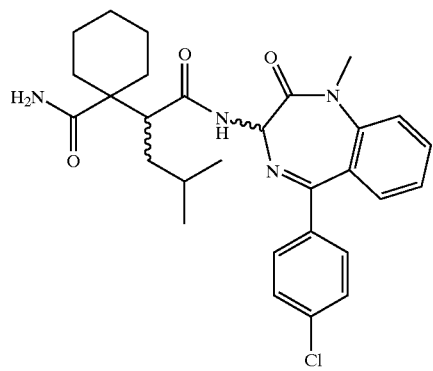

Scheme 17

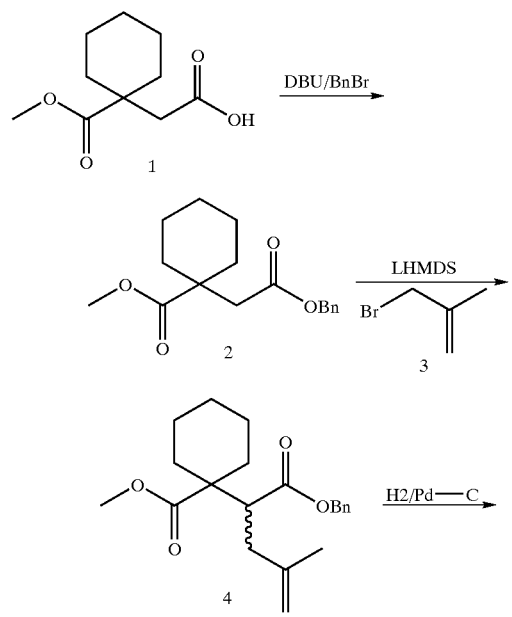

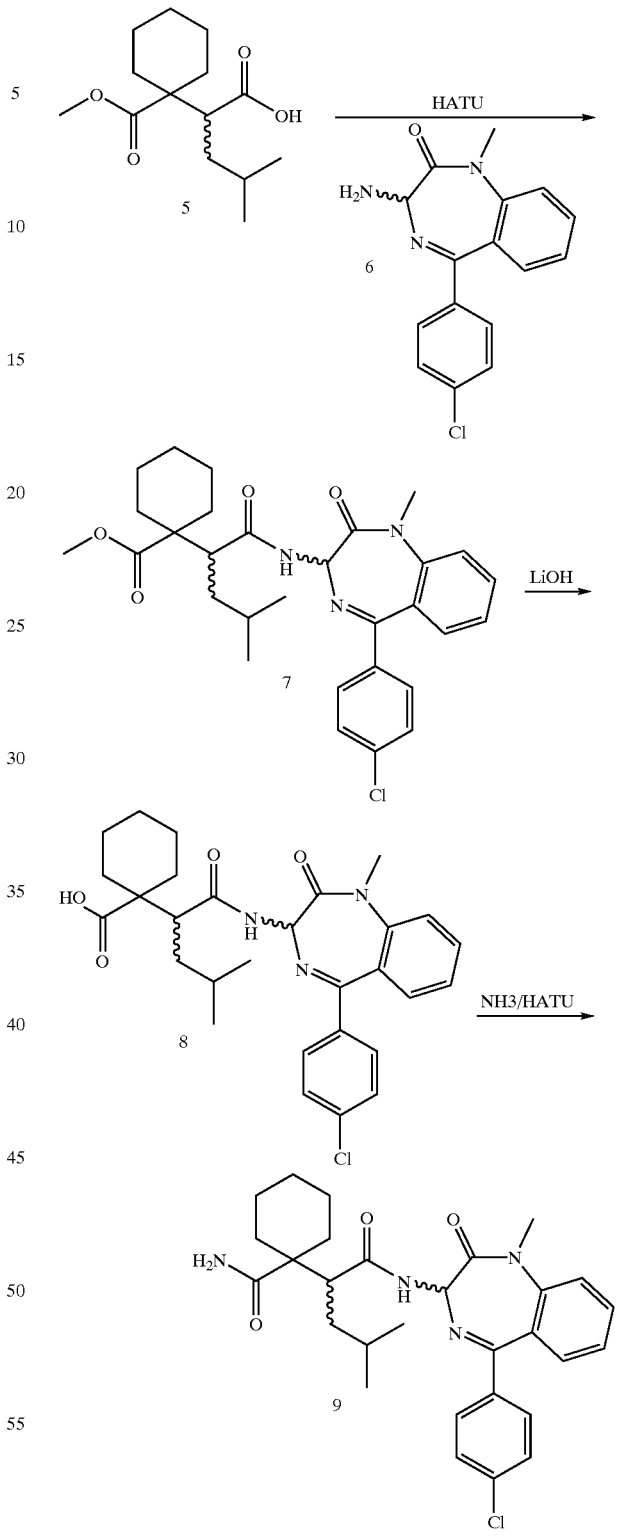

Step A: Synthesis of Intermediate 2 (Scheme 17)

The starting material 1 (prepared as the procedure described in *J. Chem. Res.* 1981, 1772–1783) (10 mmol, 2.00 g) was taken up in 50 mL of anhydrous acetonitrile and cooled to 0° C. in an ice bath. To this was added DBU (10 mmol, 1.49 mL) and the reaction was stirred for 10 minutes before adding benzyl bromide (10 mmol, 1.19 mL). The reaction was allowed to slowly warm to room temperature and stir 16 hrs. The reaction was then evaporated to an oil, taken up in methylene chloride and washed with 5% NaHSO$_4$, saturated NaHCO$_3$ and brine. The organic layer was dried over Na$_2$SO$_4$, filtered and evaporated to give the desired product (93%, 2.70 g). H$^1$-NMR (300 MHz, CDCl$_3$) δ: 1.40–1.60 (m, 10H), 2.00–2.10 (m, 2H), 2.67 (s, 2H), 3.60 (s, 3H), 5.10 (s, 2H), 7.40 (s, 5H); (M+H$^+$) 351.3.

Step B: Synthesis of Intermediate 4 (Scheme 17)

The starting material 2 (11 mmol, 3.10 g) was taken up in 50 mL anhydrous THF, cooled to −78° C. and treated with lithium bis(trimethylsilyl) amide (22 mmol, 21.2 mL of 1.0 M solution in THF) under an inert atmosphere for 1.0 hr. Bromomethylpropene (33 mmol) was added slowly at −78° C. and the reaction was allowed to gradually warm to room temperature and stir overnight. The reaction was then diluted with ethyl acetate and washed with water followed by saturated NaHCO$_3$. The organic layer was dried over Na$_2$SO$_4$, filtered and evaporated to give the desired product (96%, 3.51 g). H$^1$-NMR (300 MHz, CDCl$_3$) δ: 1.00–2.00 (m, 10H), 3.40–3.70 (m, 6H), 4.50–4.70 (m, 2H), 4.80–5.20 (m, 2H), 7.19–7.35 (m, 5H).

Step C: Synthesis of Intermediate 5 (Scheme 17)

The product obtained from the previous reaction 4 (10 mmol, 3.51 g) was taken up in 50 mL ethyl acetate and treated with 30% by weight (0.525 g) of 10% palladium on activated carbon and in a Parr shaker overnight under 50 psi H$_2$. The reaction was then purged with nitrogen, filtered through celite and evaporated in vacuo. The resulting residue was taken up in ethyl acetate and washed with saturated NaHCO$_3$. The aqueous layer was separated, acidified by the dropwise addition of concentrated HCl and extracted with ethyl acetate. The ethyl acetate extract was evaporated in vacuo to give the desired product 5 (76%, 2.01 g). H$^1$-NMR (300 MHz, CDCl$_3$) δ: 0.80–0.99 (m, 6H), 1.10–1.80 (m, 10H), 1.80–2.20 (m, 2H), 3.77 (s, 3H); (M+H$^+$) 257.3.

Step D: Synthesis of Intermediate 7 (Scheme 17)

Carboxylic acid 5 (0.27 mmol, 70 mg) was taken up in 5.0 mL of anhydrous DMF and treated with HATU (0.27 mmol, 104 mg). After 30 minutes, Hunig's base (0.54 mmol, 0.1 mL) and the benzodiazepine amine 6 (0.27 mmol, 61 mg) were added. The reaction was stirred at room temperature under a nitrogen atmosphere overnight, then diluted with ethyl acetate and washed with 5% NaHSO$_4$ followed by saturated NaHCO$_3$ and brine. The organic layer was evaporated in vacuo to give a crude yellow oil which was purified by flash chromatography using 75% hexane and 25% ethyl acetate to give the desired product (100%, 160 mg). H$^1$-NMR (300 MHz, CDCl$_3$) δ: 0.8–0.9 (m, 6H), 1.10–1.95 (m, 10H), 2.50–2.60 (m, 1H), 3.49 (s, 3H), 3.76 (d, 3H), 5.52–5.55 (m, 1H), 7.10–7.61 (m, 8H); (M+H$^+$) 538.3.

Step E: Synthesis of Intermediate 8 (Scheme 17)

The ester 7 (0.28 mmol, 150 mg) was taken up in 7.0 mL of THF and was treated with LiOH—H$_2$O (1.4 mmol, 65 mg) in 1.0 ml H$_2$O. Methanol was added to ensure homogeniety and the reaction was stirred overnight at room temperature. The reaction was then diluted with ethyl acetate and extracted with H$_2$O. The aqueous phase was separated and acidified by the dropwise addition of concentrated HCl. This was then extracted with ethyl acetate to give the desired product (46%, 67 mg). H$^1$-NMR (300 MHz, CDCl$_3$) δ: 0.8–1.00 (m, 6H), 1.10–2.00 (m, 10H), 3.50 (s, 1H), 5.50–5.60 (m, 1H), 7.30–7.65 (m, 8H); (M+H$^+$) 524.2.

Step F: Synthesis of Intermediate 9 (Scheme 17)

The acid 8 obtained from the above reaction (0.13 mmol, 67 mg) was taken up in 7.0 mL of anhydrous DMF, was added HATU (0.13 mmol, 49 mg) and stirred for 30 min. before bubbling in NH$_3$ (g) for 30 min. The reaction was then capped and allowed to stand at room temperature overnight. Afterwards, the reaction was diluted with ethyl acetate and washed with 5% NaHSO$_4$, saturated NaHCO$_3$ and brine. The organic layer was dried over Na$_2$SO$_4$, filtered and evaporated to give crude yellow oil which was purified by rotary TLC using 75% ethyl acetate and 25% hexane to give the desired product, 9 as a mixture of diastereomers (14%, 10 mg). H$^1$-NMR (300 MHz, CDCl$_3$) δ: 0.8–1.00 (m, 6H), 1.20–1.85 (m, 10H), 2.30–2.35 (d, 1H), 2.40–2.55 (m,1H), 3.50 (s, 3H), 5.52 (d, 2H), 7.10–7.90 (m, 8H); (M+H$^+$) 523.3.

Additional examples of the present invention are illustrated and prepared according to the procedures described herein using starting materials appropriate for the desired products.

Example 4

1-[(1R)-3-methyl-1-[1,3-dihydro-1-methyl-2-oxo-5-phenyl-2H-1,4-benzodiazepin-3-ylcarbamoyl]-butyl]-cyclohexanecarboxylic amide, 12

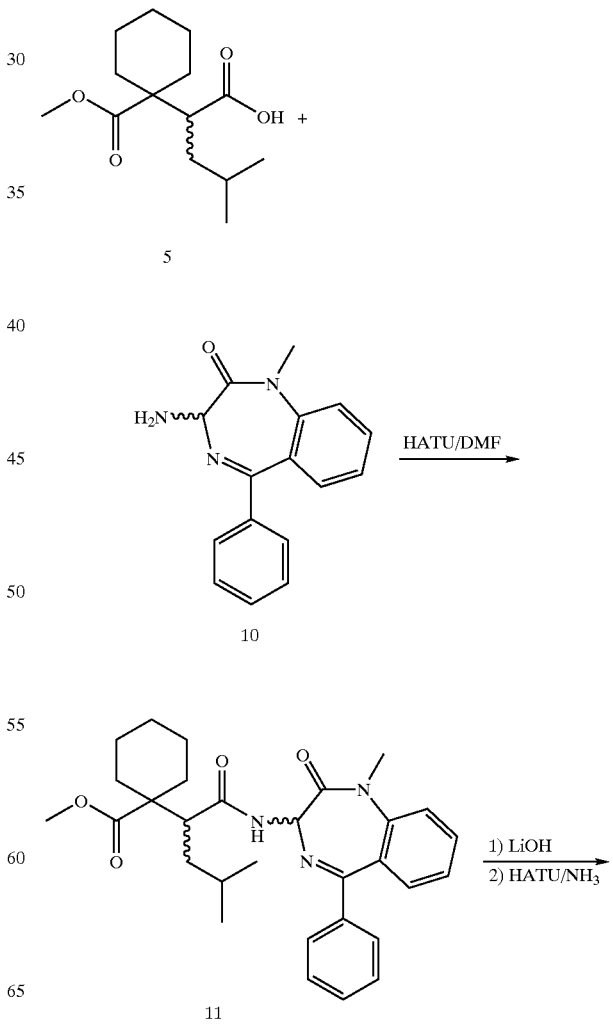

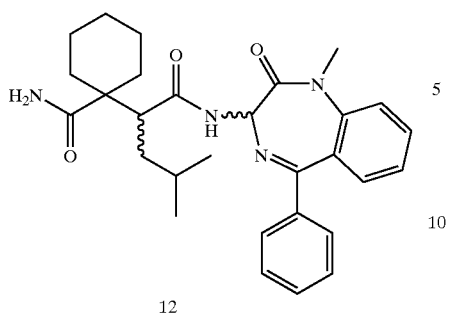

12

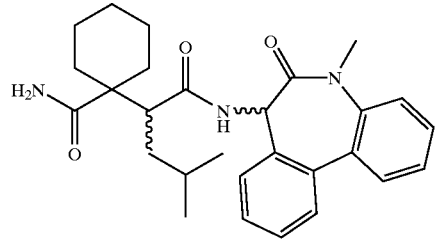

15

The title compound 12 was prepared using methods similar to those employed in Example 3. The product was obtained as an oil. $H^1$-NMR (300 MHz, $CDCl_3$) δ: 0.85–1.05 (m, 6H), 1.15–1.90 (m, 10H), 3.41–3.55 (m, 3H), 5.30–5.60 (m, 3H), 7.38–7.90 (m, 9H); (M−$H^+$) 487.2.

The title compound 15 was prepared using methods similar to those employed in Example 3. The product was obtained as an oil. $H^1$-NMR (300 MHz, $CDCl_3$) δ: 0.88 (d, 3H), 0.97 (d, 3H), 1.20–1.90 (m, 10H), 2.00 (d, 1H), 2.35 (d, 1H), 2.55 (d, 1H), 3.39 (s, 3H), 5.25–5.40 (m, 2H), 7.30–7.70 (m, 8H); (M+$H^+$) 462.3.

Example 5

1-[(1R)-3-Methyl-1-(5-methyl-6-oxo-6,7-dihydro-5H-dibenzo[b,d]-azepin-7-ylcarbamoyl)-butyl]-cyclohexanecarboxylic acid amide, 15

Examples 6 and 6a

1-[(1R)-3-Methyl-1-(2-oxo-2,3,4,5-tetrahydro-1H-benzo[b]azepin-3-ylcarbamoyl)-butyl]-cyclopent-3-enecarboxylic acid amide, 20

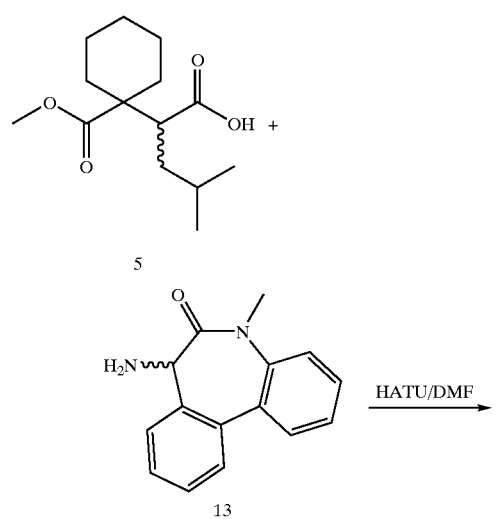

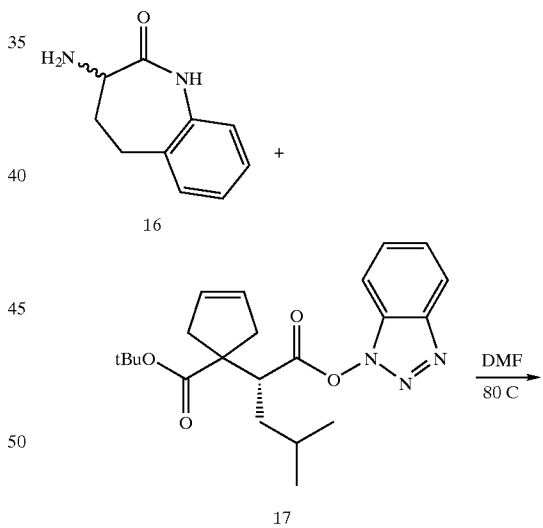

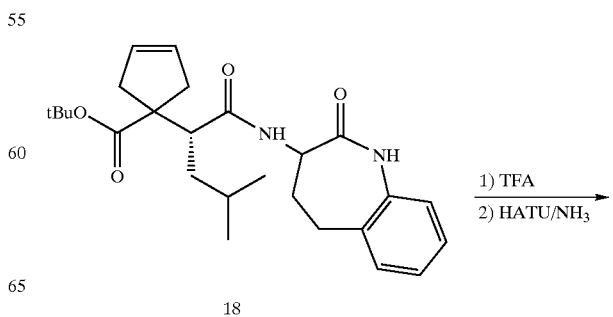

-continued

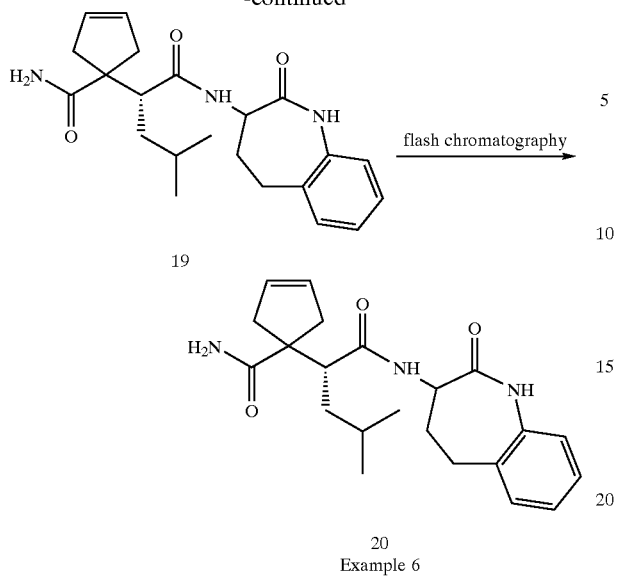

19

20
Example 6

The reaction procedures used to make compound 19 are shown in Scheme 4a and in the Equation above. Compound 16 is obtained form literature procedures (J. Med. Chem. 1999, 42, p 2621.) Compound 19, a mixture of diastereomers, was separated by flash chromatography using 100% EtOAc to give the final products Example 6 (20) and diastereomer Example 6a, respectively. Compound 20 was the first eluting isomer: $^1$H NMR (300 MHz, CDCl$_3$) 7.27–7.02 (m, 4H), 5.53 (m, 2H), 4.41–4.34 (q, 1H), 2.94–2.34 (m, 8H), 2.18–2.02 (m, 1H), 1.80–1.66 (m, 1H), 1.60–1.42 (m, 1H), 1.00 (m, 1H), 0.91–0.81 (q, 6H); MS [M+H]$^+$ 384.

Example 6a was the second eluting isomer: $^1$H NMR (300 MHz, CDCl$_3$) 7.26–7.02 (m, 4H), 5.54 (m, 2H), 4.43–4.36 (q, 1H), 2.96–2.36 (m, 8H), 2.20–2.04 (m, 1H), 1.80–1.68 (m, 1H), 1.44–1.30 (m, 1H), 1.06 (m, 1H), 0.90–0.78 (q, 6H); MS [M+H]$^+$ 384.

Example 8

1-(1-{1-[3-(2-Fluoro-phenoxy)-benzyl]-2-oxo-2,3,4, 5-tetrahydro-1H-benzo[b]azepin-3-ylcarbamoyl}-3-methyl-butyl)-cyclopent-3-enecarboxylic acid amide, 23

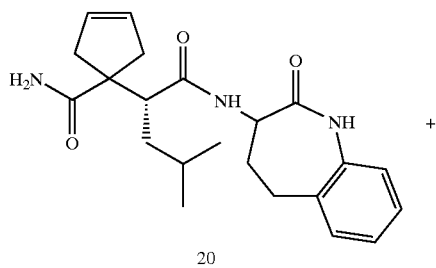

-continued

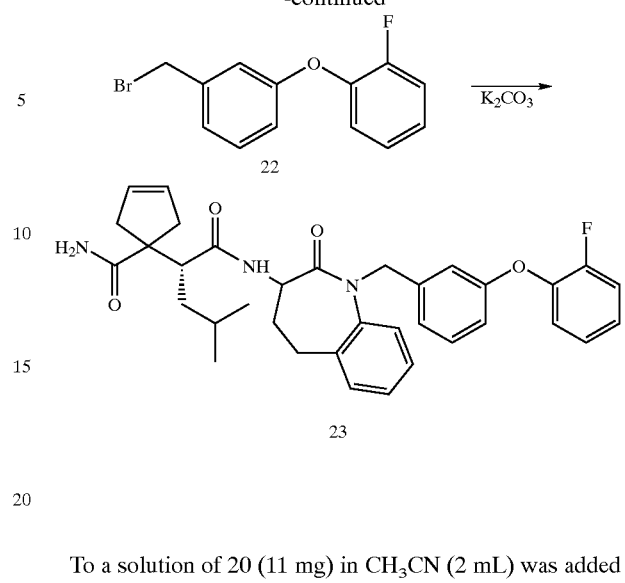

To a solution of 20 (11 mg) in CH$_3$CN (2 mL) was added K$_2$CO$_3$ (8 mg) and 3-(2-fluorophenoxy)benzyl bromide 22 (12 mg). The reaction mixture was stirred at rt for 20 hrs before the solvent was removed under pressure. The crude product was purified by flash chromatography to give compound 23 (77%, 13 mg). $^1$H NMR (300 MHz, CDCl$_3$) 7.32–6.80 (m, 12H), 5.72 (m, 1H), 5.58 (m, 1H), 5.34 (d, 1H), 4.72 (d, 1H), 4.48 (m, 1H), 3.18 (m, 1H), 2.70–2.20 (m, 8H), 1.95–1.78 (m, 2H), 1.42 (m, 1H), 1.12 (m, 1H), 0.92–0.80 (q, 6H); MS [M+H]$^+$ 584.

Example 9

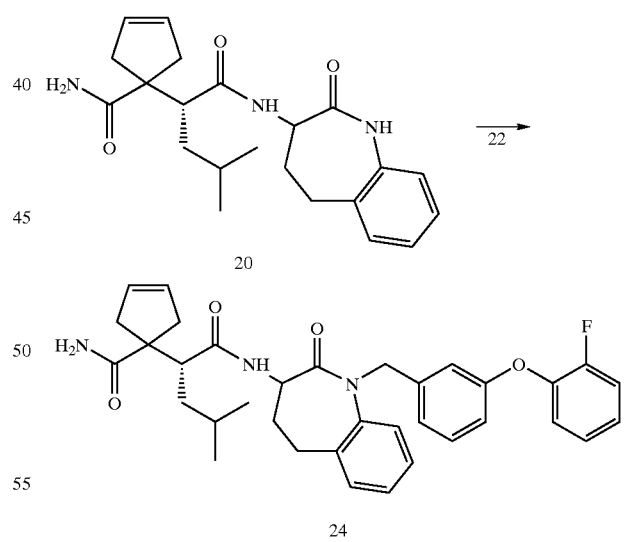

The compound of 24 was made in a similar manner as described above for Example 8. $^1$H NMR (300 MHz, CDCl$_3$) 7.30–6.78 (m, 12H), 5.68 (m, 1H), 5.60 (m, 1H), 5.3 (d, 1H), 4.76 (d, 1H), 4.50 (m, 1H), 3.15 (m, 1H), 2.66–2.20 (m, 8H), 1.96–1.80 (m, 2H), 1.44 (m, 1H), 1.15 (m, 1H), 0.94–0.84 (q, 6H); MS [M+H]$^+$ 584.

Example 10

1-{3-Methyl-1-[2-oxo-1-(3-phenylamino-benzyl)-2,3,4,5-tetrahydro-1H-benzo[b]azepin-3-ylcarbamoyl]-butyl}-cyclopent-3-enecarboxylic acid amide, 27

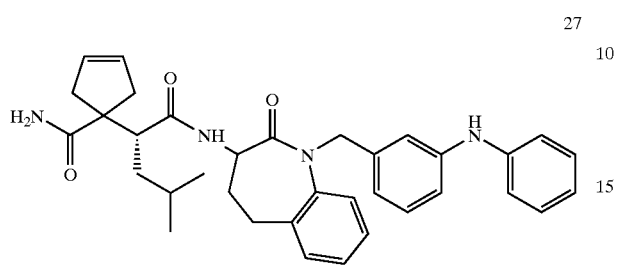

(3-Phenylamino-phenyl)-methanol (Eur. Pat. Appl. 1994, 55) was converted to the (3-Phenylamino)benzyl-bromide intermediate by mixing with $PPh_3$ and $CBr_4$ in $CH_2Cl_2$ at rt for 3 hours. The crude product was used for the synthesis of 27. The title compound 27 was prepared using methods similar to those described in Example 8. The product was obtained as an oil. $^1$H NMR (300 MHz, $CDCl_3$) 7.38–6.80 (m, 13H), 5.68 (m, 1H), 5.58 (m, 1H), 5.24 (d, 1H), 4.72 (d, 1H), 4.48 (m, 1H), 3.15 (m, 1H), 2.70–2.20 (m, 8H), 1.98–1.86 (m, 2H), 1.42 (m, 1H), 1.10 (m, 1H), 0.90–0.80 (q, 6H); MS $[M+H]^+$ 565.

Example 11

1-{3-Methyl-1-[2-oxo-1-(3-phenylamino-benzyl)-2,3,4,5-tetrahydro-1H-benzo[b]azepin-3-ylcarbamoyl]-butyl}-cyclopentanecarboxylic acid amide, 28

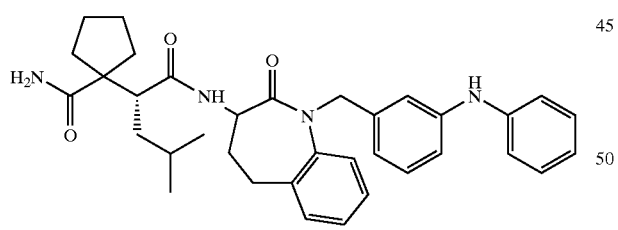

The title compound 28 was prepared by reduction of the Example 10 using 10% palladium on activated carbon in a Parr shaker overnight under 50 psi $H_2$. The product was obtained as an oil. $^1$H NMR (300 MHz, $CDCl_3$) 7.30–6.80 (m, 13H), 5.20 (d, 1H), 4.64 (d, 1H), 4.42 (m, 1H), 2.65–2.22 (m, 6H), 1.92–1.05 (m, 10H), 1.42 (m, 1H), 1.10 (m, 1H), 0.86–0.72 (q, 6H); MS $[M+H]^+$ 567.

Using the methods described herein, the following examples of a Compound of Formula (I) were prepared.

Example 12

1-[2-Cyclopropyl-1-[1,3-dihydro-1-methyl-2-oxo-5-phenyl-2H-1,4-benzodiazepin-3-ylcarbamoyl]-ethyl]-cyclopent-3-enecarboxylic amide

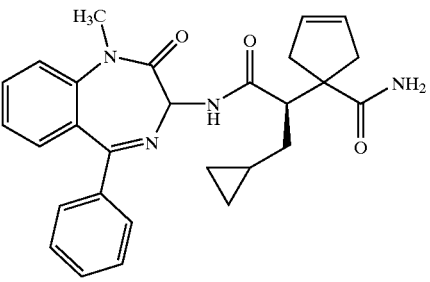

(Diastereomer A)

Optical Rotation $[\alpha]_D^{25}$ +45.3° (c 0.10, Methanol)
Melting Point 238–240° C.
Mass Ion 471 (M+H)

(Diastereomer B)

Optical Rotation $[\alpha]_D^{25}$ –18.2 (c 0.10, Methanol)
Melting Point 382–383° C.
Mass Ion 471 M+H)

Example 14

1-[2-Cyclopropyl-1-[1,3-dihydro-1-methyl-2-oxo-5-(2-trifluoromethylphenyl)-2H-1,4-benzodiazepin-3-ylcarbamoyl]-ethyl]-cyclopent-3-enecarboxylic amide

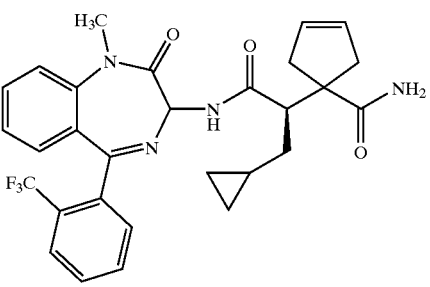

(Diastereomer B)

Optical Rotation $[\alpha]_D^{25}$ –47.3° (c 0.20, Methanol)
Melting Point 235–236° C.
Mass Ion 539(M+H)

(Diastereomer A)

Optical Rotation $[\alpha]_D^{25}$ +93.7 (c 0.05, Methanol)
Melting Point 344–345° C.
Mass Ion 539 (M+H)

Following the procedures outlined in Scheme 19 and Scheme 19a, the title compound Example 14 was prepared.

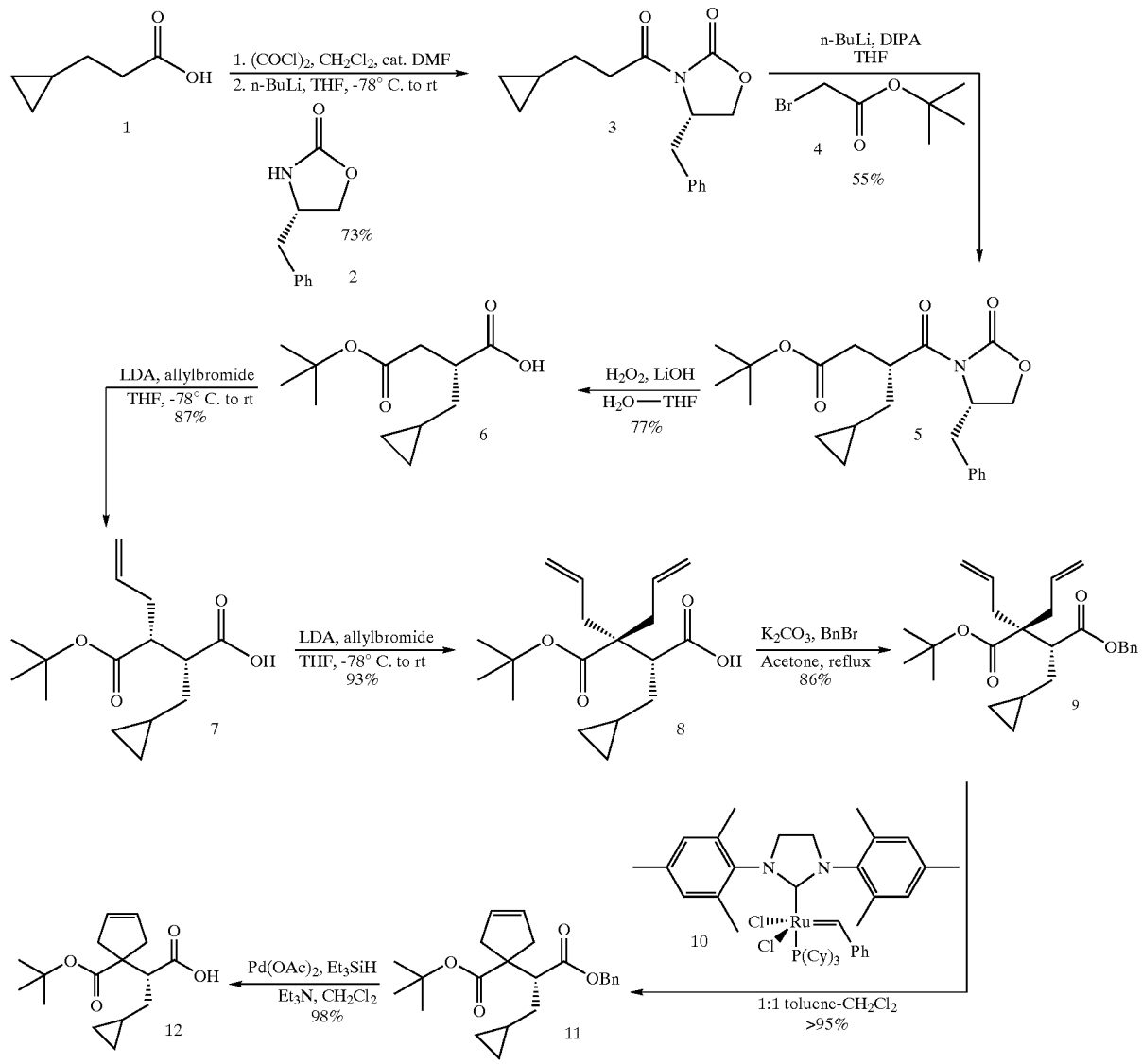

Scheme 19

Data for Compound 3; Scheme 19.
Collected 3 as a white solid: 1H NMR (CDCl$_3$) δ 7.42–7.13 (m, 5 H), 4.68 (m, 1 H), 4.18 (m, 2 H), 3.31 (dd, J=13.3, 3.3 Hz, 1 H), 4.59 (m, 2 H), 2.79 (dd, J=15.0, 3.7 Hz, 1 H), 1.60 (m, 2 H), 0.79 (m, 1 H), 0.47 (m, 2 H), 0.18–0.00 (m, 2 H).

Data for Compound 5; Scheme 19.
Collected 5 (45 g, 55%) as a white solid: $^1$H NMR (CDCl$_3$) 67 7.40–7.10 (m, 5 H), 4.65 (m, 1 H), 4.32 (m, 1 H), 4.16 (m, 2 H), 3.34 (dd, J=13.3, 3.2 Hz, 1 H), 2.96–2.53 (m, 3 H), 1.65–1.30 (m, 11 H), 0.75 (m, 1 H), 0.43 (m, 2 H), 0.02–0.00 (m, 2 H).

Data for compound 6; Scheme 19.
Collected 6 (22.5 g, 77%) as a clear viscous oil: $^1$H NMR (CDCl$_3$) δ 2.92 (m, 1 H), 2.68 (dd, J=16.6, 9.3 Hz, 1 H), 2.50 (dd, J=16.5, 5.2 Hz, 1 H), 1.67–1.38 (m, 2 H), 1.44 (s, 9 H), 0.72 (m, 1 H), 0.48 (m, 2 H), 0.08 (m, 2 H).

Data for Compound 7; Scheme 19.
Collected 7 (5.1 g, 87%) as a clear, viscous oil: $^1$H NMR (CDCl$_3$) δ 5.74 (m, 1 H), 5.07 (m, 2 H), 2.76 (m, 2 H), 2.39 (m, 2 H), 1.64 (m, 1 H), 1.47 (m, 1 H), 1.43 (s, 9 H), 0.74 (m, 1 H), 0.48 (m, 2 H), 0.08 (m, 2 H).

Data for Compound 8; Scheme 19.
Collected 8 (9.2 g, 93%) as a clear, viscous oil: $^1$H NMR (CDCl$_3$) δ 5.77 (m, 2 H), 5.10 (m, 4 H), 2.79 (dd, J=11.8, 2.9 Hz, 1 H), 2.55 (dd, J=14.5, 6.4 Hz, 1 H), 2.44 (m, 2 H), 2.28 (dd, J=14.4, 8.2 Hz, 1 H), 1.76 (ddd, J=11.9, 11.8, 6.3 Hz, 1 H), 1.40 (s, 9 H), 1.29 (m, 1 H), 0.69 (m, 1 H), 0.45 (m, 2 H), 0.02–0.00 (m, 2 H).

Data for Compound 9; Scheme 19.
Collected 9 (4.8 g, 86%) as a viscous oil: $^1$H NMR (CDCl$_3$) δ 7.43–7.29 (m, 5 H), 5.77 (m, 2 H), 5.20–4.95 (m, 6 H), 2.83 (dd, J=11.8, 2.6 Hz, 1 H), 2.49 (ddd, J=14.2, 6.3 Hz, 1 H), 2.41 (m, 2 H), 2.25 (dd, J=14.3, 7.9 Hz, 1 H), 1.81 (m, 1 H), 1.43 (s, 9 H), 1.35 (m, 1 H), 0.55 (m, 1 H), 0.35 (m, 2 H), 0.01 (m, 2 H).

Data for Compound 11; Scheme 19.
Collected 11 (4.6 g, >95%) as a viscous oil: 1H NMR (CDCl$_3$) δ 7.36 (m, 5 H), 5.51 (m, 2 H), 5.10 (m, 2 H), 3.01 (m, 1 H), 2.91–2.52 (m, 4 H), 1.78 (m, 1 H), 1.41 (s, 9 H), 1.07 (m, 1 H), 0.64 (m, 1 H), 0.38 (m, 2 H), 0.01 (m, 2 H).

Data for Compound 12; Scheme 19.

Collected 12 (1.9 g, >98%) as a clear viscous oil: ¹H NMR (CDCl₃) δ 5.60 (s, 2 H), 2.89 (m, 3 H), 2.58 (m, 2 H), 1.78 (m, 1 H), 1.44 (s, 9 H), 1.12 (m, 1 H), 0.78 (m, 1 H), 0.48 (m, 2 H), 0.20–0.00 (m, 2 H).

Scheme 19a

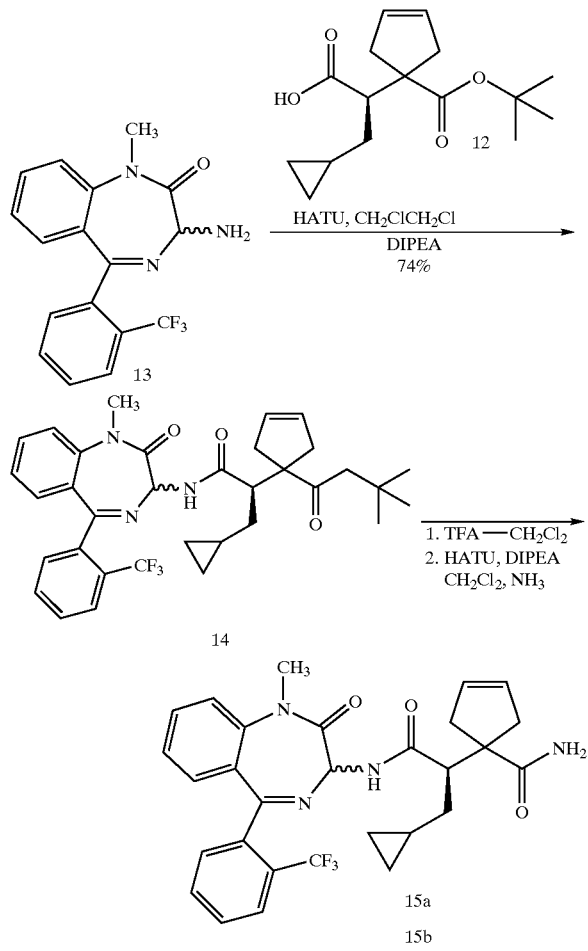

Preparation of Compound 14; Scheme 19a.

To a solution of 12 (70 mg, 0.25 mmol) and ClCH₂CH₂Cl (1.25 mL) at 0° C. was added HATU (109 mg, 0.29 mmol), DIPEA (174 µL, 1.0 mmol) and 13 (84 mg, 0.25 mmol). The reaction was warmed to rt and stirred for 18 h. The reaction was diluted with sat. NH₄Cl (70 mL). The aqueous layer was extracted with EtOAc (2×70 mL). The organic layers were combined and washed with NaHCO₃ (70 mL) and brine (70 mL). The organic layer was dried over MgSO₄ and filtered. The crude material was purified by SiO₂ chromatography (5% ethyl acetate in hexane) to afford 14 (110 mg, 74%) as a white solid: ¹H NMR (CDCl₃) δ 7.70–7.46 (m, 5 H), 7.36 (dd, J=8.3, 4.0 Hz, 1 H), 7.12 (t, J=7.7 Hz, 1 H), 7.00 (m, 1 H), 5.66–5.49 (m, 3 H), 3.49 (m, 3 H), 2.97–2.62 (m, 6 H), 1.95 (m, 2 H), 1.45 (s, 9 H), 1.02–0.70 (m, 1 H), 0.65–0.39 (m, 2 H), 0.20–0.00 (m, 2 H).

Preparation of Compounds 15a and 15b; Scheme 19a.

To a round bottom flask containing 14 (110 mg, 0.19 mmol) was added CH₂Cl₂ (1 mL) and TFA (1 mL). The solution was stirred at rt for 2 h. The solvent was removed under reduced pressure and the intermediate was dissolved in CH₂Cl₂ (5 mL). The solution was treated with HATU (76 mg, 0.2 mmol) and DIPEA (131 µM, 0.8 mmol). Ammonia gas was bubbled through the solution for 5 min. and the reaction was stirred for 18 h.

The reaction was diluted with CH₂Cl₂ (50 mL) and washed with 10% citric acid (30 mL), NaHCO₃ (30 mL) and brine (30 mL). The organic layer was dried over MgSO₄ and filtered. The solvent was removed under reduced pressure. The crude product was purified by SiO₂ chromatography (5% methanol in CH₂Cl₂) to give 15a,b (66 mg, 68%). The preparatory HPLC separation was conducted with a Waters Symmetry C18 column (5 cm×25 cm, 118 mL/min, 240 nm, 50:50 H₂O/CH₃CN; 2% TFA).

Data for Compound 15a; Scheme 19a.

Collected 15a (22 mg, 22%) as a white powder: mp 344–345° C.; ¹H NMR (CDCl₃) δ 7.98 (m, 1 H), 7.74–7.51 (m, 6 H), 7.39 (d, J=7.6 Hz, 1 H), 7.16 (t, J=7.2 Hz, 1 H), 7.05 (dd, J=7.9, 1.5 Hz, 1 H), 5.71 (m, 1 H), 5.63 (m, 1 H), 5.58 (d, J=7.8 Hz, 1 H), 5.35 (m, 1 H), 3.50 (s, 3 H), 3.24 (dt, J=16.4, 1.4 Hz, 1 H), 2.74 (m, 2 H), 2.28 (m, 1 H), 1.98 (ddd, J=13.9, 11.3, 5.9 Hz, 1 H), 1.67 (m, 1 H), 1.23 (m, 1 H), 0.85 (m, 1 H), 0.48 (m, 2 H), 0.15–0.00 (m, 2 H); IR (ATR) 3339, 2923, 1657, 1600, 1490, 1377, 1311, 1110, 1035, 912, 764, 731, 685 cm$^{-1}$; ESI MS m/z=539 [C₂₉H₂₉F₃N₄O₃+H]⁺; [α]$^{25}_D$ +93.7 (c 0.05, Methanol); HPLC>95% tr=16.20 min.

Data for Compound 15b; Scheme 19a.

Collected 15b (24 mg, 25%) as a white powder: mp 235–236° C.; ¹H NMR (CDCl₃) δ 8.16 (m, 1 H), 7.75–7.53 (m, 7 H), 7.40 (d, J=8.2 Hz, 1 H), 7.16 (t, J=7.5 Hz, 1 H), 7.04 (d, J=6.7 Hz, 1 H), 5.70 (m, 1 H), 5.64 (m, 1 H), 5.57 (d, J=8.5 Hz, 1 H), 3.51 (s, 3 H), 3.18 (d, J=16.7 Hz, 1 H), 2.78 (d, J=9.6 Hz, 1 H), 2.70 (m, 2 H), 2.35 (d, J=16.0 Hz, 1 H), 1.86 (m, 1 H), 1.34 (m, 1 H), 0.80 (m, 1 H), 0.48 (m, 2 H), 0.16 (m, 1 H), 0.03 (m, 1 H); IR (ATR) 3331, 3068, 2924, 1652, 1491, 1448, 1313, 1159, 1111, 763 cm$^{-1}$; ESI MS m/z=539 [C₂₉H₂₉F₃N₄O₃+H]⁺; [α]$^{25}_D$ -47.3 (c 0.2, Methanol); HPLC>95% tr=17.04 min.

Example 16

1-[2-Cyclopropyl-1-(5-methyl-6-oxo-6,7-dihydro-5H-dibenzo[b,d]azepin-7-ylcarbamoyl)-ethyl-]-cyclopent-3-enecarboxylic acid amide

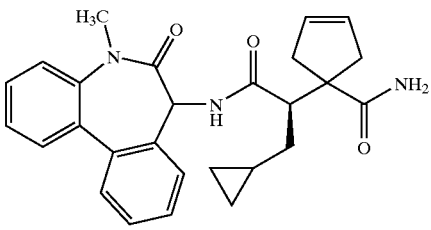

Scheme 20

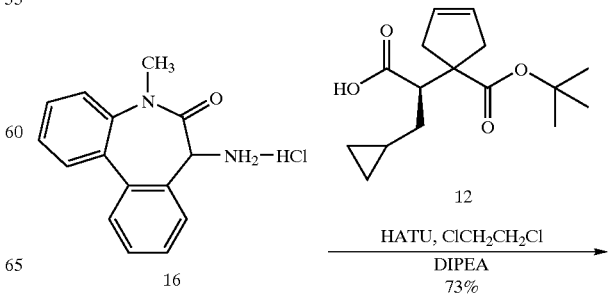

-continued

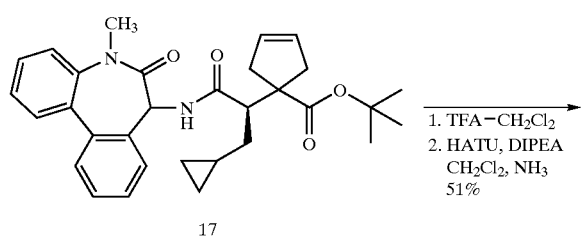

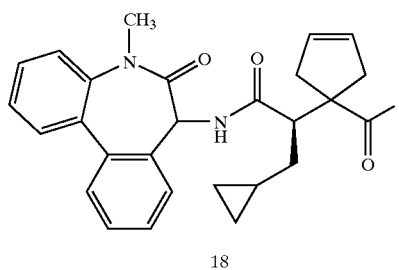

Compound 17 was prepared by the same method as compound 14 in Example 14. Collected 17 (87 mg, 73%) as a white solid: $^1$H NMR (CDCl$_3$) δ 7.63–7.30 (m, 8 H), 5.72–5.46 (m, 3 H), 5.36 (d, J=6.6 Hz, 1 H), 3.37 (s, 3 H), 3.05–2.57 (m, 5 H), 2.10–1.90 (m, 1 H), 1.46 (s, 9 H), 0.97 (m, 1 H), 0.78 (m, 1 H), 0.54 (m, 2 H), 0.12 (m, 2 H).

Compound 18 was prepared by the same method as compound 15a and 15b in Example 14. Collected 18 (32 mg, 33%) as a white powder: mp 217–222° C.; $^1$H NMR (CDCl$_3$) d 7.12–7.34 (m, 8 H), 5.72 (m, 1 H), 5.65 (m, 1 H), 5.38 (d, J=6.6 Hz, 1 H), 5.27 (m, 1 H), 3.37 (s, 3 H), 3.18 (m, 1 H), 2.93 (dd, J=11.0, 2.9 Hz, 1 H), 2.60 (m, 2 H), 2.35 (m, 1 H), 2.00 (ddd, J=14.0, 11.1, 6.3 Hz, 1 H), 1.27 (ddd, J=14.1, 8.0, 3.1 Hz, 1 H), 0.85 (m, 1 H), 0.57 (m, 2 H), 0.15 (m, 2 H); IR 3346, 3229, 1652, 1600, 1498, 1382, 1301, 917 cm$^{-1}$; ESI MS m/z=444 [C$_{27}$H$_{29}$N$_3$O$_3$+H]$^+$; [α]$^{25}_D$ 95.2 (c 0.07, Methanol); HPLC>95% tr=16.19 min. (Diastereomer A)

Example 17

1-{3-Methyl-1-[2-oxo-1-(3-o-tolylamino-benzyl)-azepan-3-ylcarbamoyl]-butyl}-cyclopent-3-enecarboxylic acid amide

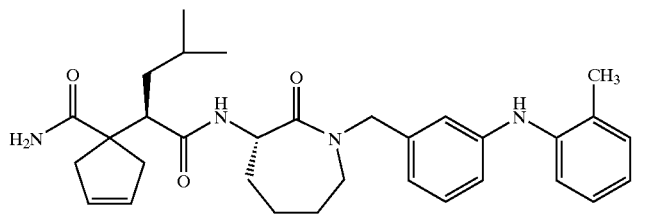

Scheme 21

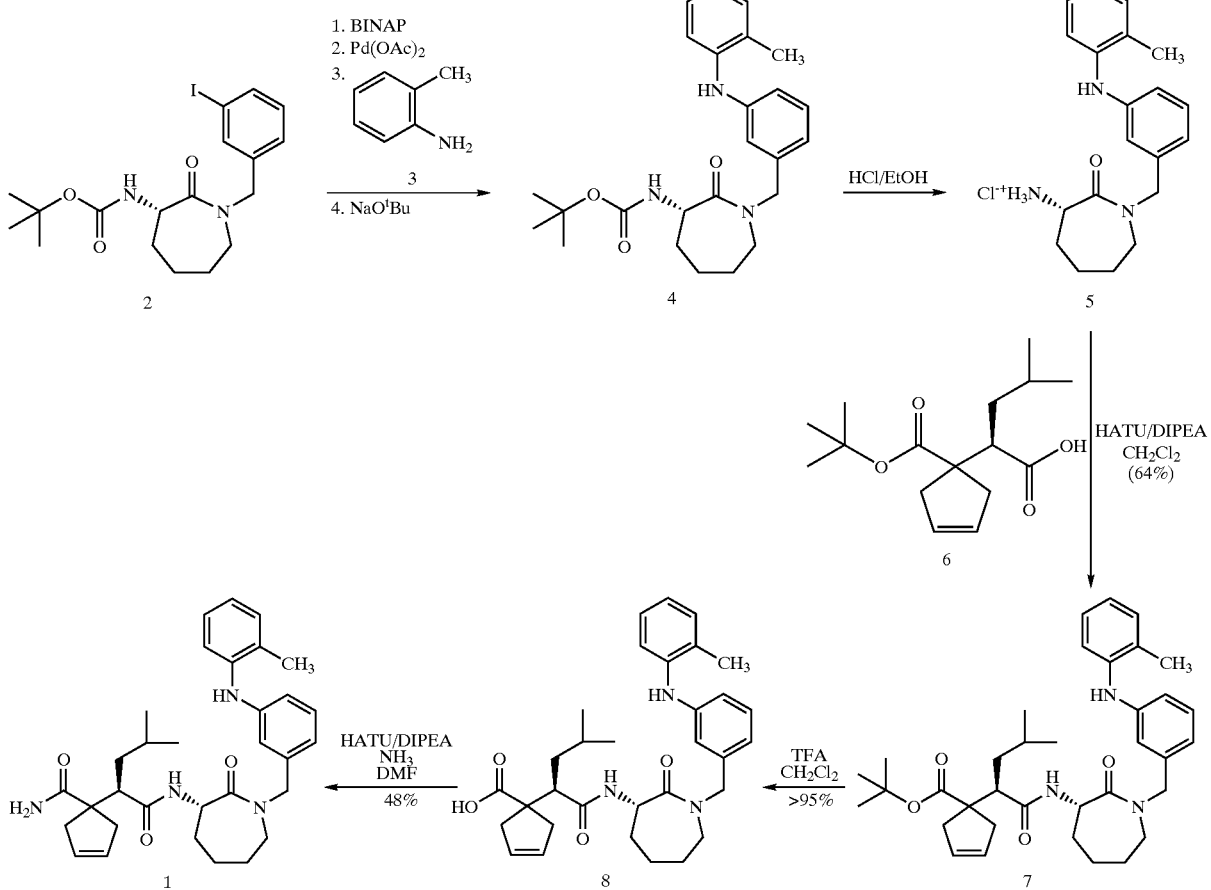

Preparation of Compound 4, Scheme 21. A solution of BINAP (0.22 g, 0.35 mmol) in toluene (12.5 mL) was degassed with Ar and refluxed at 80° C. for 1 min. After cooling the solution to room temperature, Pd(OAc)$_2$ (0.05 g, 0.23 mmol) was added and the mixture was stirred for 10 min. Next, 2 (1.03 g, 2.32 mmol) in toluene (3 mL) was added followed by p-toluidine (1.24 mL, 11.6 mmol) and NaOt-Bu (0.27 g, 2.8 mmol). The reaction was refluxed under Ar at 100° C. overnight. The reaction was diluted with H$_2$O (20 mL) and extracted with EtOAc (2×40 mL). The organic extracts were dried over MgSO$_4$, filtered through Celite, and concentrated under reduced pressure. The crude material was subjected to flash chromatography on silica (hexanes/EtOAc) to provide 4 (0.45 g, 46%) as a pink solid: $^1$H NMR (500 MHz, CDCl$_3$) d 7.25–6.71 (m, 8 H), 6.03 (m, 1 H), 5.38 (s, 1 H), 4.77 (d, J=14.68 Hz, 1 H), 4.41 (m, 1 H), 4.33 (d, J=14.67 Hz, 1 H), 3.42 (m, 1 H), 3.23 (dd, J=14.97, 4.49 Hz, 1 H), 2.24 (s, 3 H), 2.08–1.21 (m, 6 H), 1.45 (m, 9 H); APCI MS m/z=424 [C$_{25}$H$_{33}$N$_3$O$_3$]$^+$.

Preparation of Compound 5, Scheme 21. To saturated HCl/EtOH (2.6 mL) at 0° C. was added 4 (0.44 g, 1.0 mmol). The mixture was stirred overnight at room temperature and the solvent was removed under reduced pressure giving 5 (1.7 g, 94%) as an off-white solid: $^1$H NMR (500 MHz, CD$_3$OD) d 7.32–6.83 (m, 8 H), 4.67 (q, J=28.2, 14.61 Hz, 2 H), 4.40 (d, J=10.98 Hz, 1 H), 3.72–3.47 (m, 2 H), 2.33 (s, 3 H), 2.13–1.31 (m, 6 H); APCI MS m/z=324 [C$_{20}$H$_{26}$N$_3$O$_3$Cl+H]$^+$.

Preparation of Compound 7, Scheme 21. To a solution of 5 (0.2, 0.56 mmol) in CH$_2$Cl$_2$ (2.0 mL) cooled to 0° C. was added HATU (0.25 g, 0.65 mmol) and a solution of succinate 6 (0.16 g, 0.57 mmol) in CH$_2$Cl$_2$ (0.7 mL). DIPEA (0.39 mL, 2.3 mmol) was added, and the reaction was warmed to rt and stirred overnight. The reaction was concentrated, added to H$_2$O (10 mL), and extracted with EtOAc (2×20 mL). The organic extract was washed successively with H$_2$O (3×6 mL), brine (8 mL), dried over MgSO$_4$, and filtered. Solvent removal under reduced pressure afforded the crude product which was subjected to flash chromatography on silica (Hexanes/EtOAc) to provide 7 (0.21 g, 64%) as an off-white solid: $^1$H NMR (500 MHz, CDCl$_3$) d 7.27–6.74 (m, 9 H), 5.59–5.42 (m, 3 H), 4.68–4.49 (m, 3 H), 3.48–3.22 (m, 2 H), 2.86–1.00 (m, 14 H), 2.24 (s, 3 H), 1.47 (s, 9 H), 0.88 (m, 6 H); APCI MS m/z=588 [C$_{36}$H$_{49}$N$_3$O$_4$+H]$^+$.

Preparation of Compound 8, Scheme 21. A solution of 7 (0.20 g, 0.34 mmol) in 1:1 TFA/CH$_2$Cl$_2$ (12 mL) was stirred at rt overnight. The solvent was removed under reduced pressure at 60° C. to afford 8 (0.19 g, >95%) as a brown semisolid: $^1$H NMR (500 MHz, CD$_3$OD) d 7.22–6.61 (m, 8 H), 5.67–5.49 (m, 2 H), 4.62 (d, J=11.3 Hz, 1 H), 4.56–4.39 (m, 2 H), 3.47–1.02 (m, 16 H), 2.15 (s, 3 H), 0.90–0.77 (m, 6 H). APCI MS m/z=532 [C$_{32}$H$_{41}$N$_3$O$_4$+H]$^+$.

Preparation of Compound 1, Scheme 21. To a solution of DIPEA (0.75 mL, 4.3 mmol) in DMF (6.9 mL) was added 8 (0.19 g, 0.34 mmol) and HATU (0.22 g, 0.58 mmol). Ammonia gas was bubbled in the solution for 10 min, and the reaction was stirred overnight. The reaction was concentrated under reduced pressure and partitioned between EtOAc (10 mL) and H$_2$O (10 mL). The aqueous portion was extracted with EtOAc (2×10 mL). The combined organic extracts were washed successively with H$_2$O (3×4 mL) and brine (4 mL), dried over MgSO$_4$, and filtered. Solvent removal under reduced pressure afforded the crude product which was subjected to flash chromatography on silica (Hexanes/EtOAc) then (EtOAc/MeOH) to provide 1 as an off-white solid (0.086 g, 48%): mp 90–91° C.; $^1$H NMR (500 MHz, CD$_3$OD) d 7.20–6.68 (m, 8 H), 5.59 (s, 2 H), 4.65 (d, J=10.45 Hz, 1 H), 4.59 (d, J=14.68 Hz, 1 H), 4.46 (d, J=14.65 Hz, 1 H), 3.54 (m, 1 H), 3.30 (m, 1 H), 2.84 (d, J=11.8 Hz, 1 H), 2.74 (s, 2 H), 2.61 (d, J=17.2 Hz, 1 H), 2.21 (s, 3 H), 1.91–1.03 (m, 10 H), 0.90 (dd, J=13.65, 6.51 Hz, 6 H); ESI MS m/z=531 [C$_{32}$H$_{42}$N$_4$O$_3$+H]$^+$; IR (KBr) 3320 (br.), 1630 cm$^{-1}$; HPLC>95%, t$_r$=21.31 min. Optical Rotation [α]$_D^{25}$ –3.3 (c 0.10, Methanol).

Using the methods described herein, the following examples of a Compound of Formula (I) were prepared.

Example 18

1-[3-Methyl-1-(5-methyl-6-oxo-6,7-dihydro-5H-dibenzo[b,d]azepin-7-ylcarbamoyl)-butyl]-cyclopent-3-enecarboxylic acid amide

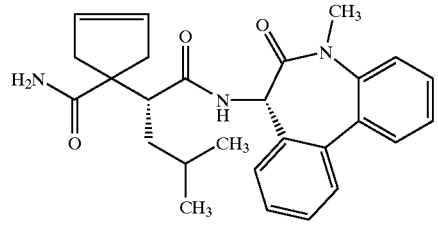

$^1$HNMR (300 MHz, CDCl$_3$) 0.8–1.0 (dd, 6H), 1.0–1.2 (m, 1H), 1.4–1.6 (m, 1H), 1.7–1.9 (m, 1H), 2.3–2.8 (m, 4H), 3.0–3.2 (m, 1H), 5.2 (s, 1H), 5.3 (s, 1H), 5.6–5.8 (m, 2H), 7.2–7.6 (m, 8H). MS: 446.4 (M+H).

Example 19

1-[3-methyl-1-[1,3-dihydro-1-methyl-2-oxo-5-(4-chlorophenyl)-2H-1,4-benzodiazepin-3-ylcarbamoyl]-butyl]-cyclopent-3-enecarboxylic amide

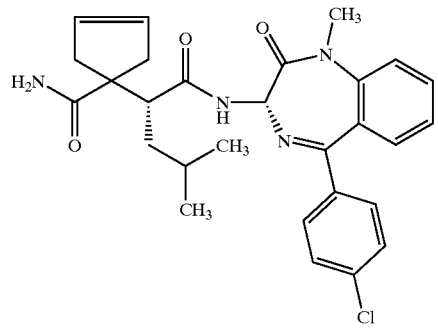

Synthesis of Formula I Compound 17 (Scheme 15)

Scheme 15

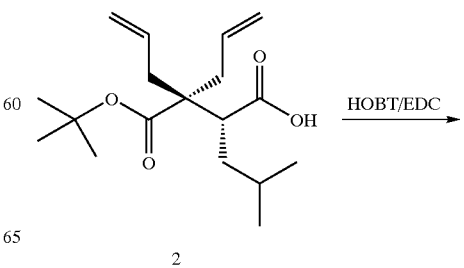

2

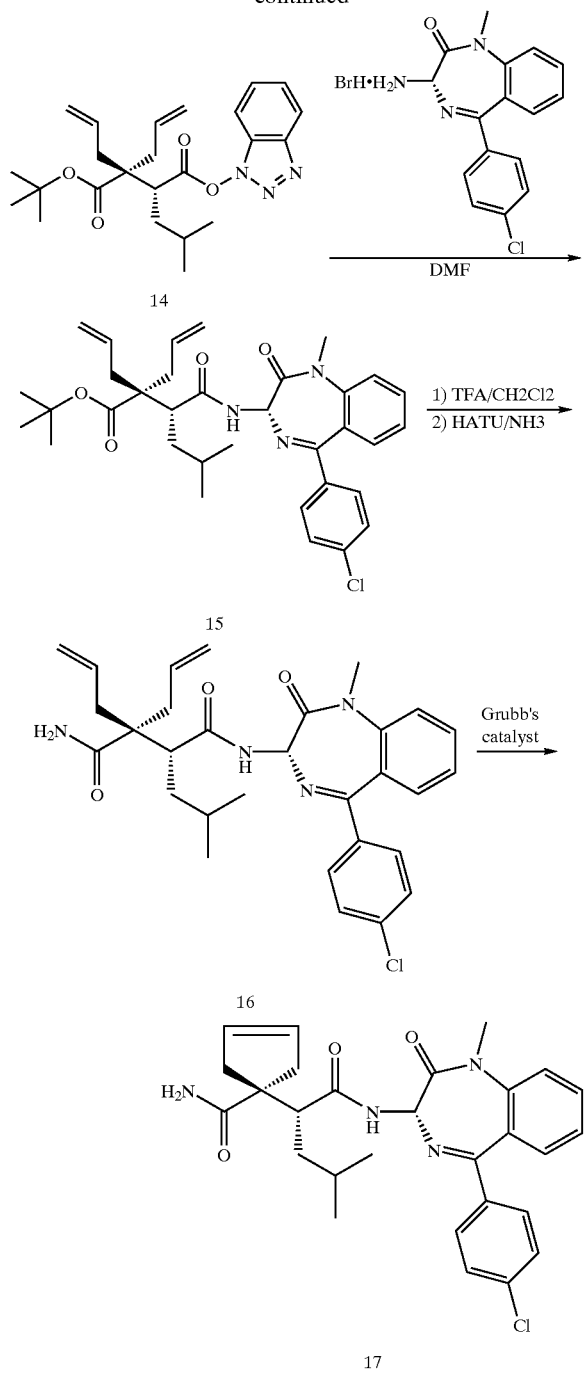

Step 1: Preparation of Diallylsuccinate HOBT Ester 14.

To a solution of 2 (30.5 g, 98.4 mmol) in 500 ml methylene chloride was added HOBT (27 g, 200 mmol), EDC (25 g, 130 mmol) and triethylamine (21 ml, 150 mmol). The solution was stirred at RT for three hours. The solvents were removed under reduced pressure, providing an oil which was taken up in EtOAc and water. The organic layer was washed with water and brine, dried over sodium sulfate, then concentrated to give the crude product as an oil. Purification by column chromatography on silica gel with EtOAc:hexane (5:95) provided 14 as a colorless oil (32.2 g, 75.4 mmol, 77%). $^1$HNMR (300 MHz, CDCl$_3$) 0.9–1.1 (m, 6H), 1.2–1.4 (m, 1H), 1.4 (s, 9H), 1.8–2.0 (m, 2H), 2.3–2.8 (m, 4H), 3.2 (m, 1H), 5.0–5.2 (m, 4H), 5.6–5.9 (m, 2H), 7.3–8.1 (m, 4H).

Step 2: Preparation of Benzodiazepinesuccinamide 16

Following the procedures described for the synthesis of 11, diallylsuccinamide intermediate 16 was prepared from 14 in reasonable yield. 14 (2.5 g, 5.9 mmol), p-chloro-BZD (2.34 g, 6.2 mmol) and DIPEA (1 ml, 5.8 mmol) in 30 ml DMF was heated to 40–50 degree overnight.

Step 3: Preparation of Formula I Compound 17

A solution of 16 (700 mg, 1.3 mmol) in 100 ml toluene and methylene chloride (1:1) and tricyclohexylphosphine[1,3-bis(2,4,6-trimethylphenyl)-4,5-dihydroimidazol-2-ylidene]benzylidine]ruthenium (IV) dichloride (100 mg, 0.1 mmol) was heated at 60° C. for two hours. The solvents were evaporated to give a dark oil which was purified by flash chromatography using EtOAc:hexane (1:1) to give 17 as a solid (390 mg, 1077 mmol, 59%). $^1$HNMR (300 MHz, CDCl$_3$) 0.8–1.0 (dd, 6H), 1.2–1.3 (m, 1H), 1.5–1.7 (m, 1H), 1.8–2.0 (m, 1H), 2.3–3.0 (m, 4H), 3.2 (m, 1H), 3.5 (s, 3H), 5.3 (s, 1H), 5.5 (d, 1H), 5.6–5.8 (m, 2H), 7.2–7.7 (m, 8H), 7.8 (s, 1H). MS: 507.4 (M+H), 529.3 (M+Na).

Example 20

1-[3-Methyl-1-(5-methyl-6-oxo-6,7-dihydro-5H-dibenzo[b,d]azepin-7-ylcarbamoyl)-butyl]-cyclopentanecarboxylic acid amide

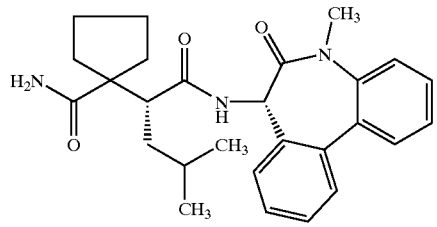

$^1$HNMR (300 MHz, CDCl$_3$) 0.8–1.0 (dd, 6H), 1.0–2.0 (m, 10H), 2.4–2.7 (m, 2H), 3.3 (s, 3H), 5.3 (d, 1H), 5.6 (s, 1H), 7.2–7.8 (m, 8H), 8.1 (s, 1H). MS: 448.4 (M+H), 470.4 (M+Na).

Example 21

1-[3-methyl-1-[1,3-dihydro-1-methyl-2-oxo-5-(4-chlorophenyl)-2H-1,4-benzodiazepin-3-ylcarbamoyl]-butyl]-cyclopentanecarboxylic amide

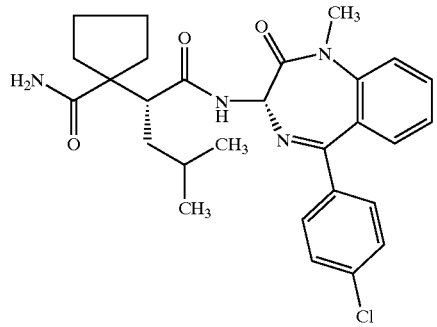

A solution of Example 19 (300 mg, 0.59 mmol) in 50 ml ethanol with 300 mg of chlorotris-(triphenylphosphine) rhodium(I), was shaken under H$_2$ (~50 psi) overnight. The solvents were removed under reduced pressure, and the resulting residue was purified by chromatography on silica gel in 5% methanol/CH2Cl2. The desired product (18) was isolated as a solid (247 mg, 0.49 mmol). ¹HNMR (300 MHz, CDCl₃) 0.8–1.0 (dd, 6H), 1.2–2.0 (m, 10H), 2.4–2.6 (m, 2H), 3.5 (s, 3H), 5.3 (s, 1H), 5.5 (d, 1H), 7.2–7.7 (m, 8H), 8.1 (s, 1H). MS: 509.4 (M+H).

Example 22

1-[3-methyl-1-[1,3-dihydro-1-methyl-2-oxo-5-(4-trifluoromethylphenyl)-2H-1,4-benzodiazepin-3-ylcarbamoyl]-butyl]-cyclopent-3-enecarboxylic amide

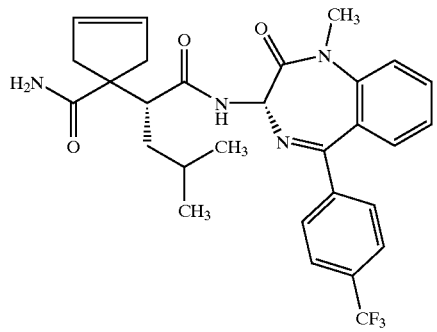

¹HNMR (300 MHz, CDCl₃) 0.8–1.0 (dd, 6H), 1.1–1.3 (m, 1H), 1.5–1.7 (m, 1H), 1.8–2.0 (m, 1H), 2.2–3.0 (m, 4H), 3.0–3.3 (m, 1H), 3.5 (s, 3H), 5.3 (s, 1H), 5.5 (d, 1H), 5.6–5.8 (m, 2H), 7.2–7.8 (m, 8H). MS: 541.5 (M+H), 563.5 (M+Na).

Example 23

Example 23a

1-[3-methyl-1-[1,3-dihydro-1-(i-propyl)-2-oxo-5-(2-fluorophenyl)-2H-1,4-benzodiazepin-3-ylcarbamoyl]-butyl]-cyclopent-3-enecarboxylic amide Example 23

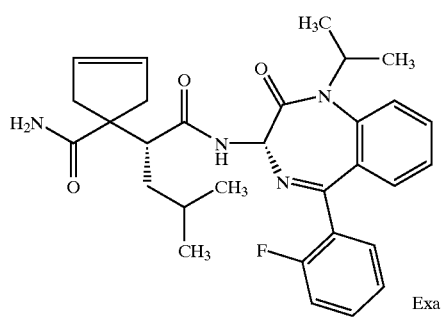

Example 23a

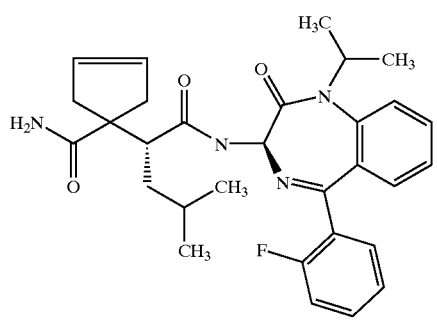

Synthesis of Formula I Compounds 21 and 22

Diastereomers 21 and 22 were prepared from diallylsuccinamide intermediate 19 according to the methods outlined in Scheme 16.

Scheme 16

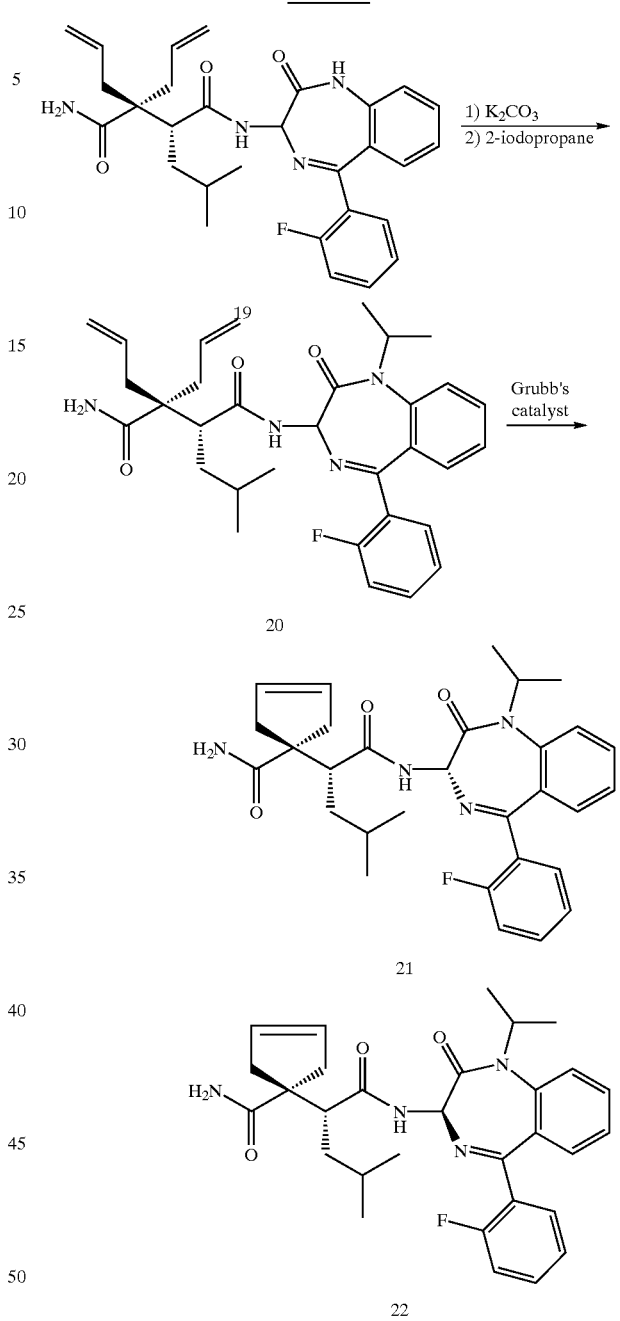

Synthesis of Diallylsuccinamde Intermediate 19

Intermediate 19 was made according to the procedures outlined in Scheme 4, using the appropriate aminobenzodiazepine. ¹HNMR (300 MHz, CDCl₃) 0.8–1.0 (m, 6H), 1.0–2.0 (m, 3H), 2.2–2.8 (m, 5H), 5.0–5.3 (m, 4H), 5.4–5.6 (d, 1H), 5.6–6.0 (m, 2H), 7.0–7.6 (m, 8H). MS: 505.3 (M+H), 527.3 (M+Na).

Synthesis of Intermediate 20 by Alkylation of 19

To a solution of 19 (150 mg, 0.3 mmol) in 20 ml DMF was added potassium carbonate (90 mg, 0.65 mmol) and 2-iodopropane (120 mg, 0.69 mmol). The reaction mixture was stirred at RT overnight. The solvents were removed under reduced pressure and the residuewas taken up in EtOAc and water. The organic layer was washed with brine, dried over sodium sulfate and concentrated, and the resulting solid was purified by column chromatography on silica gel in EtOAc:hexane (70:30) to provide 20 as a white solid (105 mg, 0.19 mmol). 20 ¹HNMR (300 MHz, CDCl₃) 0.8–1.0 (m, 6H), 1.0–1.3 (m, 3H), 1.4–1.5 (d, 3H), 1.6–2.0 (m, 2H), 2.0–2.4 (m, 3H), 2.4–2.8 (m, 2H), 4.4–4.6 (m, 1H), 5.0–5.5.2 (m, 4H), 5.3 (s, 1H), 5.4 (d, 1H), 5.6–6.0 (m, 2H), 6.8–7.6 (m, 8H), 8.4 (s, 1H). MS: 547.2 (M+H).

Synthesis of Formula I Compounds 21 and 22 by RCM Cyclization of Intermediate 20

To a solution of 20 (70 mg, 0.13 mmol) in 100 ml toluene-methylene chloride (1:1) was added tricyclohexylphosphine[1,3-bis(2,4,6-trimethylphenyl)-4,5-dihydroimidazol-2-ylidene]benzylidine]ruthenium (IV) dichloride (70 mg). The reaction mixture was refluxed for 2 hrs at 65° C., then evaporated to an oil which was purified by chromatography on silica gel with EtOAc:hexane (1:1) to collect 21 as the first eluting spot (26 mg, 0.05 mmol) ¹HNMR (300 MHz, CDCl₃) 0.7–0.9 (dd, 6H), 1.1–1.3 (m, 4H), 1.4–1.6 (m, 4H), 1.8–2.0 (m, 1H), 2.2–3.0(m, 4H), 3.2 (m, 1H), 4.4–4.6 (m, 1H), 5.2 (s, 1H), 5.4 (d, 1H), 5.6–5.8 (m, 2H), 6.9–7.6 (m, 8H), 7.8 (s, 1H). MS: 519.5 (M+H), 541.5 (M+Na). Succinamide 22 was collected as the second eluting spot (10 mg, 0.02 mmol) ¹HNMR (300 MHz, CDCl₃) 0.8–1.0 (m, 6H), 1.2–1.4 (m, 4H), 1.5 (d, 3H), 1.7 (m, 1H), 1.8–2.0 (m, 1H), 2.2–2.4 (m, 1H), 2.6–2.8 (m, 3H), 3.1–3.3 (m, 1H), 4.4–4.6 (m, 1H), 5.3 (s, 1H), 5.4 (d, 1H), 5.6–5.8 (m, 2H), 6.9–7.8 (m, 9H). MS: 519.5 (M+H), 541.5 (M+Na).

Example 24

1-[3-methyl-1-[1,3-dihydro-1-methyl-2-oxo-5-(4-trifluoromethylphenyl)-2H-1,4-benzodiazepin-3-ylcarbamoyl]-butyl]-cyclopentanecarboxylic amide

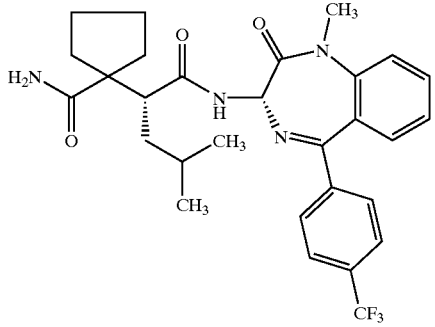

¹HNMR (300 MHz, CDCl₃) 0.8–1.0 (dd, 6H), 1.2–2.0 (m, 10H), 2.4–2.6 (m, 2H), 3.4 (s, 3H), 5.3 (s, 1H), 5.5 (d, 1H), 7.2–7.8 (m, 8H), 8.1 (s, 1H). MS: 521.5 (M+H).

Example 25

1-[3-methyl-1-[1,3-dihydro-1-(2-cyclopropylethyl)-2-oxo-5-(2-fluorophenyl)-2H-1,4-benzodiazepin-3-ylcarbamoyl]-butyl]-cyclopent-3-enecarboxylic amide

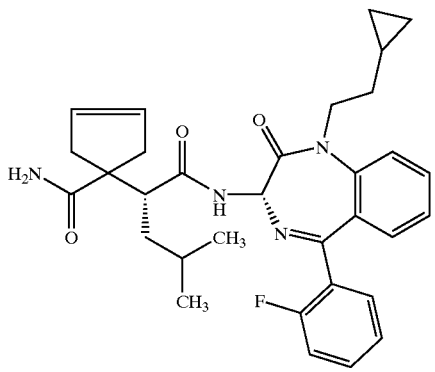

Following the procedures in Scheme 16, the following Formula I compounds were prepared. Both examples eluted as the first isomer upon chromatography on silica gel using 1:1 EtOAc:hexane.

¹HNMR (300 MHz, CDCl₃) 0.0 (m, 2H), 0.2–0.5 (m, 2H), 0.5–0.6 (m, 1H), 0.8–1.0 (dd, 6H), 1.2–1.8 (m, 4H), 1.8–2.0 (m, 1H), 2.2–3.0(m, 4H), 3.2–3.3 (m, 1H), 3.6–3.8 (m, 1H), 4.4–4.6 (m, 1H), 5.3 (s, 1H), 5.5 (s, 1H), 5.6–5.8 (m, 2H), 7.0–7.8 (m, 8H), 7.9 (s, 1H). MS: 545.5 (M+H), 567.4 (M+Na).

Example 26

1-[3-methyl-1-[1,3-dihydro-1-(2-methylpropyl)-2-oxo-5-(2-fluorophenyl)-2H-1,4-benzodiazepin-3-ylcarbamoyl]-butyl]-cyclopent-3-enecarboxylic amide

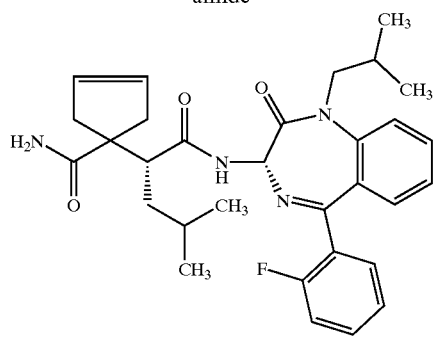

Following the procedures in Scheme 16, the following Formula I compounds were prepared. Both examples eluted as the first isomer upon chromatography on silica gel using 1:1 EtOAc:hexane.

¹HNMR (300 MHz, CDCl₃) 0.67 (d, 3H), 0.80 (d, 3H), 0.87 (d, 3H), 0.93 (d, 3H), 1.1–1.3 (m, 1H), 1.6–2.0 (m, 2H), 2.2–3.0 (m, 4H), 3.2 (d, 1H), 3.4–3.6 (m, 1H), 4.2–4.4 (m, 1H), 5.3 (s, 1H), 5.5 (d, 1H), 5.6–5.8 (m, 2H), 6.9–7.8 (m, 8H), 7.9 (s, 1H). MS: 533.3 (M+H), 555.4 (M+Na).

Example 27

1-[3-methyl-1-[1,3-dihydro-1-methyl-2-oxo-5-(4-chlorophenyl)-2H-1,4-benzodiazepin-3-ylcarbamoyl]-butyl]-cyclobutanecarboxylic amide

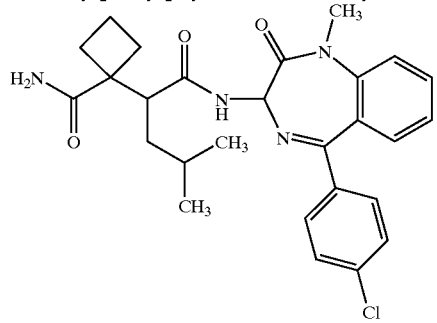

Synthesis of Formula I Compounds XVIa and XVIb (Scheme 18)

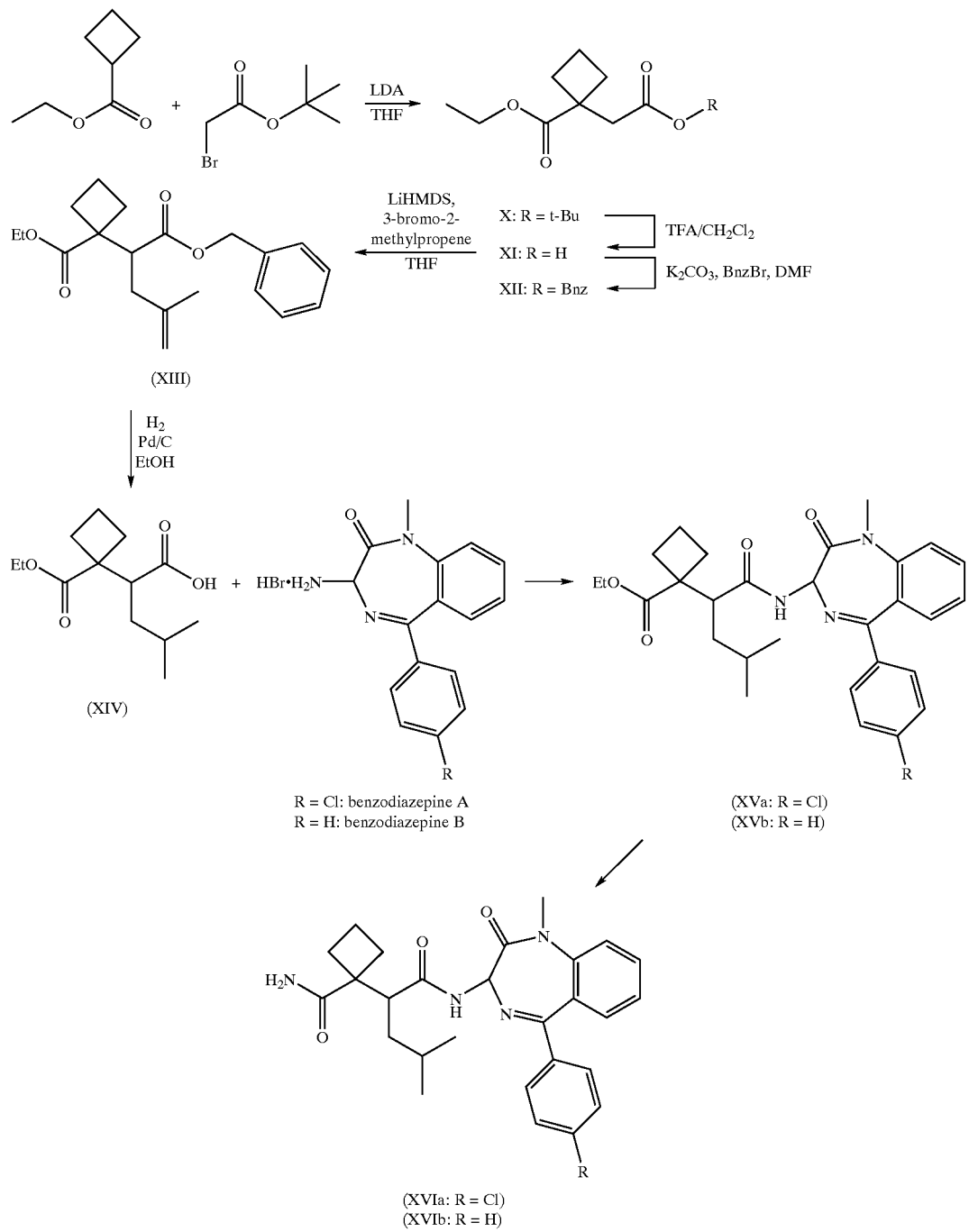

Step 1. Preparation of Diester X (Scheme 18)

A 2.5M solution of n-butyllithium in hexanes (4 mL) was added dropwise to a −78° C. solution of DIEA (10 mmol) in 40 mL dry THF under $N_2$. The mixture was stirred at 0° C. for 30 min, then cooled to −78° C. Ethyl cyclobutanecarboxylate (1.26 mL, 9.1 mmol) was added dropwise and the mixture was stirred at −78° C. for 45 min. tert-Butyl bromoacetate (1.4 mL, 9.5 mmol) was added and the mixture was stirred at RT for 4 hrs. Ethanol (0.5 mL) was added and the reaction mixture was concentrated in vacuo, then partitioned between $CH_2Cl_2$ and cold 0.5N HCl. The organic layer was dried over $MgSO_4$, filtered and evaporated in vacuo, resulting in 1.8 g of a dark amber oil (intermediate X) which was used without further purification. $^1$H-NMR(300 MHz, $CDCl_3$): δ 4.15(quart,2H), 2.77(s,2H), 2.48(m,2H), 1.94(m,4H), 1.4(s,9H), 1.26(t,3H).

Step 2. Deprotection of Diester X to Give Free Acid XI (Scheme 18)

TFA (15 mL) was added to a solution of 1.2 g (4.95 mmol) of X in 15 mL CH$_2$Cl$_2$ and the mixture stirred for 3 hrs. The mixture was concentrated in vacuo. Toluene was added and the mixture was again concentrated in vacuo. The residue was partitioned between Et$_2$O and 5% aq. NaHCO$_3$. The Et$_2$O layer was washed with 5% aq. NaHCO$_3$ and the aqueous layers were combined and carefully acidified to a pH between 3–4 using conc. HCl. This mixture was extracted twice with EtOAc. The EtOAc layers were combined, dried (MgSO$_4$) and evaporated in vacuo to give 875 mg (95% yield) of acid XI. $^1$H-NMR(300 MHz, CDCl$_3$): δ 4.18(quart,2H), 2.91(s,2H), 2.55(m,2H), 2.0(m, 4H), 1.26(t,3H).

Step 3. Synthesis of Benzyl Ester XII (Scheme 18)

K$_2$CO$_3$ (4.48 g, 32.4 mmol) was added to a solution of 2.74 g (14.71 mmol) of XI in 50 mL DMF. Benzyl bromide (1.92 mL, 16.18 mmol) was added and the reaction mixture was stirred at room temperature for 16 hrs. The mixture was partitioned between Et$_2$O and water. The water layer was washed with Et$_2$O and the organic layers were combined, dried (MgSO$_4$) and evaporated in vacuo. The residue was purified by flash chromatography on silica gel (100% Hexane to 5% EtOAc/Hex gradient) to give intermediate XII. $^1$H-NMR(300 MHz, CDCl$_3$): δ 7.33(m,5H), 5.09(s,2H), 4.1(quart,2H), 2.9(s,2H), 2.54(m,2H), 1.97(m,4H), 1.19(t, 3H).

Step 4. Alkylation of Diester XII (Scheme 18)

3.86 mL of a 1M LiHMDS in THF solution was added to a cooled (−78° C.) solution of intermediate XII (970 mg, 3.51 mmol) in 10 mL dry THF. After 15 min., 0.39 mL (3.86 mmol) of 3-bromo-2-methylpropene was added and the reaction mixture was stirred for 16 hrs at RT. The mixture was partitioned between Et$_2$O and water. The water layer was washed with Et$_2$O and the organic layers were combined, dried (MgSO$_4$) and evaporated in vacuo. 1.11 g of product XIII of suitable purity was isolated. $^1$H-NMR (300 MHz, CDCl$_3$): δ 7.28(m,5H), 5.04(ABquart,2H), 4.62 (m,2H), 4.05(m,2H), 3.0(dd,1H), 2.44–2.2(m,4H), 2.1–1.6 (m,4H), 1.65(s,3H), 1.16(t,3H).

Step 5. Preparation of Free Acid XIV (Scheme 18)

To a degassed solution of intermediate XIII in 20 mL of ethanol in a Parr bomb was added 100 mg of 5% Pd on carbon, and the mixture was agitated under 50 psi of H$_2$ for 2 hrs. The reaction mixture was filtered through celite and washed with ethanol. The alcoholic filtrate was concentrated in vacuo and the residue partitioned between CH$_2$Cl$_2$ and 1N NaOH. The layers were separated and the basic layer was acidified using conc. HCl. The acidic mixture was extracted twice with CH$_2$Cl$_2$ and these organic layers were combined, dried (MgSO$_4$) and evaporated in vacuo to give intermediate XIV. $^1$H-NMR(300 MHz, CDCl$_3$): δ 4.2(m,2H), 2.85(dd, 1H), 2.5–2.25(m,3H), 2.15–1.5(m,5H), 1.27(t,3H), 1.05(m, 1H), 0.9(m,6H).

Step 6. Coupling of Acid XIV with Aminobenzodiazepine A to Give Succinamide Xva (Scheme 18)

To a solution of XIV (218 mg, 0.9 mmol) in 5 mL of DMF were added HATU (380 mg, 1 mmol), aminobenzodiazepine hydrobromide A (362 mg, 0.95 mmol), and DIEA (0.35 mL, 2 mmol). The reaction mixture was stirred at room temperature for 4 hrs, then partitioned between EtOAc and water. The organic layer was dried (MgSO$_4$) and evaporated in vacuo. The residue was purified by flash chromatography on silica gel (EtOAc/Hexane gradient) to give 183 mg of product XVa. $^1$H-NMR(300 MHz, CDCl$_3$): δ 7.6–7.5(m, 4H), 7.4–7.3(m,4H), 7.25–7.2(m,1H), 5.53(d,1H), 4.23(m, 2H), 3.45(s,3H), 2.85(dd,1H), 2.5–2.4(m,3H), 2.38–2.27(m, 1H), 2.0–1.77(m,3H), 1.55(m,1H), 1.3(t,3H), 0.99(m,1H), 0.9(dd,6H). MS: APcI (M+H)$^+$=524.1.

Step 7. Synthesis of Formula I Compound XVIa (Scheme 18)

To a solution of intermediate XVa (183 mg, 0.35 mmol) in 5 mL of THF was added a solution of LiOH.H$_2$O (30mg, 0.7 mmol) in 2 mL of water. 1 mL of MeOH was added and the mixture was stirred at room temperature for 16 hrs. The mixture was partitioned between EtOAc and 1N HCl. The aqueous layer was washed with EtOAc and the organic layers were combined, dried (MgSO$_4$) and evaporated in vacuo. The residue was dissolved in 9 mL of DMF, and HATU (138 mg, 0.36 mmol) and DIEA (0.063 mL, 0.36 mmol) were added. NH$_3$ gas was bubbled into the mixture for 30 min., then the flask was stoppered and stirred at room temperature for 72 hrs. The mixture was partitioned between EtOAc and water. The organic layer was dried (MgSO$_4$) and evaporated in vacuo. The residue was purified by flash chromatography on silica gel (10% to 40% EtOAc/Hexane gradient) to give 28 mg of product XVIa. $^1$H-NMR: • 7.83(br s,1H), 7.65–7.51(m,4H), 7.42–7.34(m,4H), 7.26(m,1H), 5.48(d,1H), 5.33(br s,1H), 3.48(s,3H), 2.89–2.80(m,2H), 2.4–2.35(m,2H), 2.04–1.6(m,5H), 1.26(m,1H), 0.93(dd,6H). MS: APcI (M+H)$^+$=495.1.

Example 28

1-[3-methyl-1-[1,3-dihydro-1-methyl-2-oxo-5-phenyl-2H-1,4-benzodiazepin-3-ylcarbamoyl]-butyl]-cyclobutanecarboxylic amide

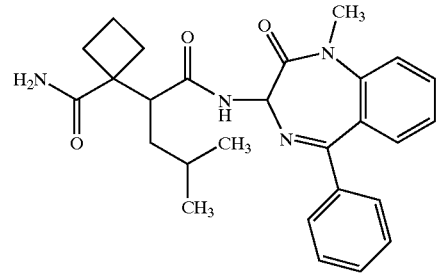

Following the procedures of Example 27 and disclosed in Scheme 18, the title compound was prepared.

Step 8. Synthesis of Succinamide Ester XVb

To a solution of intermediate XIV (250 mg, 1.03 mmol) in 5 mL of DMF was added HATU (418 mg, 1.1 mmol), aminobenzodiazepine hydrobromide B (380 mg, 1.1 mmol), and DIEA (0.38 mL, 2.2 mmol). The reaction mixture was stirred at room temperature for 16 hrs, then partitioned between EtOAc and water. The organic layer was dried (MgSO$_4$) and evaporated in vacuo. The residue was purified by flash chromatography on silica gel (EtOAc/Hexane gradient) to give 122 mg of product XVb. MS: APcI (M+H)$^+$=490.1.

Step 9. Synthesis of Formula I Compound XVIb

To a solution of intermediate XVb (122 mg, 0.25 mmol) in 3 mL of THF was added a solution of LiOH.H$_2$O (42 mg, 1 mmol) in 2 mL of water. 1 mL of MeOH was added and the mixture was stirred at room temperature for 4 hrs. The mixture was partitioned between EtOAc and 1N HCl. The aqueous layer was washed with EtOAc and the organic layers were combined, dried (MgSO$_4$) and evaporated in vacuo. The residue was dissolved in 5 mL of DMF, and HATU (103 mg, 0.27 mmol) and DIEA (0.052 mL, 0.3 mmol) were added. NH₃ gas was bubbled into the mixture for 30 min., then the flask was stoppered and stirred at room temperature for 72 hrs. The mixture was partitioned between EtOAc and water. The organic layer was dried (MgSO4) and evaporated in vacuo. The residue was purified by flash chromatography on silica gel (EtOAc/Hexane gradient) to give 8 mg of product XVIb. ¹H-NMR: δ 7.88(br s,1H), 7.61–7.34(m,9H), 7.24(m,1H), 5.48(d,1H), 5.33(br s,1H), 3.46(s,3H), 2.88–2.8(m,2H), 2.43–2.28(m,2H), 2.02–1.6(m, 5H), 1.25(m,1H), 0.92(dd,6H). MS: APcI (M+H)⁺=461.1

Example 29

1-[3-methyl-1-[1,3-dihydro-1-methyl-2-oxo-5-cycloheptyl-2H-1,4-benzodiazepin-3-ylcarbamoyl]-butyl]-cyclopent-3-enecarboxylic amide

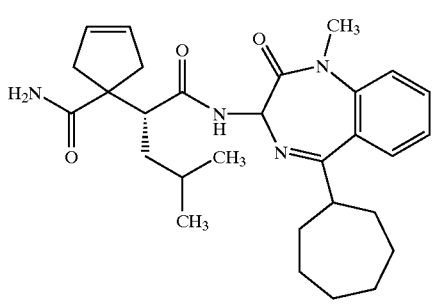

Step 1. Preparation of 2-aminophenyl Cycloheptyl Ketone 3

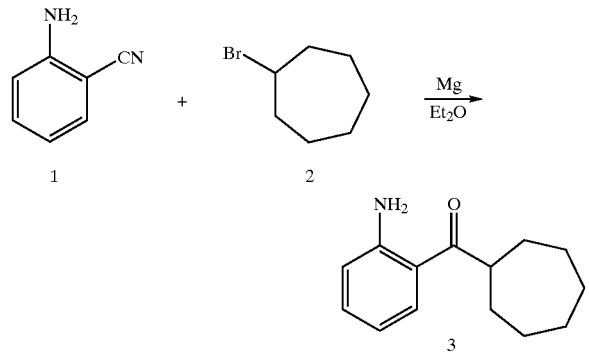

To magnesium (8.26 g, 0.34 mol) was added ether (30 mL), followed by addition of 2 (50 g, 0.28 mol) in ether (200 mL) at a rate that maintained the reflux over 2 h. The reaction mixture was then heated at reflux for 20 h. A solution of 1 (11.8 g, 0.10 mol) in ether (100 mL) was added to the reaction mixture slowly with vigorous stirring. After refluxing for 3 h, the reaction mixture was cooled to 0° C. 10% aq. HCl (300 mL) was added slowly and stirring was continued overnight. To the reaction mixture was added 30% aq. NaOH at 0° C. to pH~11. The resulting mixture was filtered through a pad of celite. The aqueous layer was extracted with ethyl acetate (3×200 mL). The extracts were combined and washed with brine, then dried over Na₂SO₄. After evaporation of the solvent, the residue was purified on silica gel, using 10% ethyl acetate-hexane, to afford 3 (16.43 g, 76%) as an orange oil. MS m/z 218.4 (MH⁺).

Step 2. Preparation of Cbz-protected Aminobenzodiazepine 6

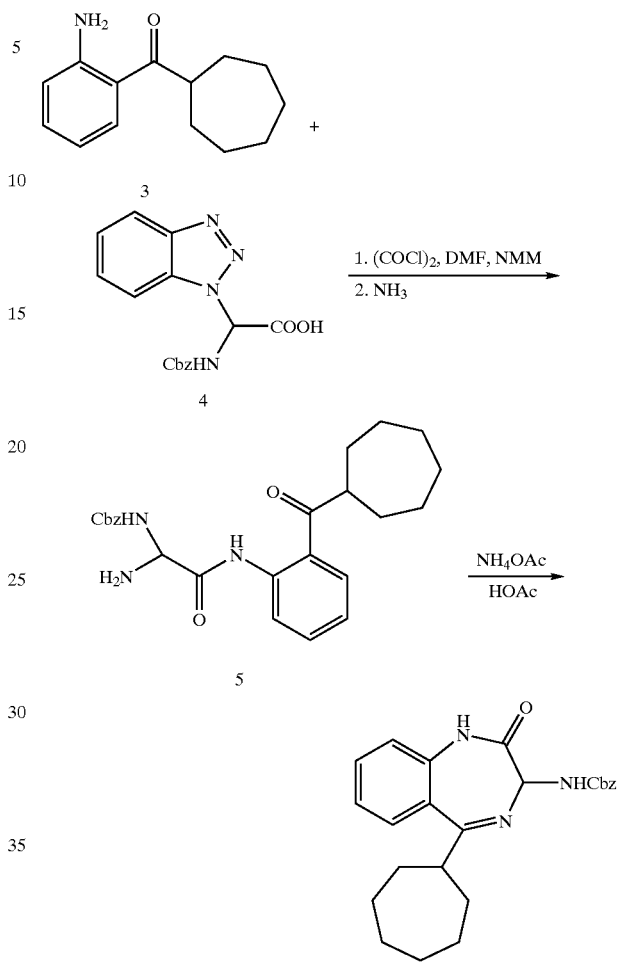

To a solution of 4 (27.09 g, 83 mmol) in THF (anhydrous, 200 mL) at 0° C. was added oxalyl chloride (7.24 mL, 83 mmol) via syringe over 5 min., followed by DMF (anhydrous, 0.24 mL). Stirring was continued for 2 h at 0° C. To the above yellow reaction mixture was added a solution of 3 (16.40 g, 75.5 mmol) and N-methylmorpholine (18.26 mL, 166 mmol) in dry THF (100 mL) over ca. 20 min. Precipitates were formed and the reaction mixture was slowly warmed to room temperature and stirred for 2 h. The precipitates were filtered and washed with THF (50 mL). Ammonia was passed through the filtrate for 30 min. with stirring at room temperature. The reaction mixture was diluted with methanol (150 mL), saturated with ammonia and stirred for 1 h. After evaporation of solvents, the residue was dissolved in ethyl acetate (1200 mL) and washed with NaOH (1N, 2×200 mL). The aqueous layer was extracted with ethyl acetate (2×200 mL). The extracts were combined and washed with water (4×100 mL), brine (150 mL), and dried (K₂CO₃). Evaporation of the solvent gave a yellow solid 5. The crude solid 5 was dissolved in acetic acid (400 mL), followed by addition of ammonium acetate (20 g). The reaction mixture was stirred at ambient temperature for 24 h, and then concentrated. To the residue was added ethyl acetate (300 mL) and aqueous NaOH (1N) until pH>8, cooled in an ice bath. The solid was filtered, washed with water and cold ether sequentially, and dried in air overnight to give a white solid 6 (12 g, 40% over three steps). MS m/z 406.5 (MH⁺).

Step 3. N-Methylation of Benzodiazepine 6

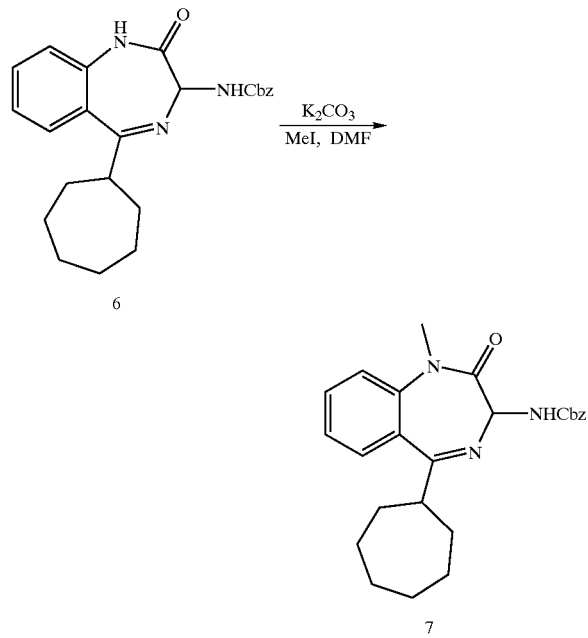

To a mixture of 6 (1.0 g, 2.47 mmol) and potassium carbonate (0.68 g, 4.93 mmol) in dry DMF (10 mL) was added iodomethane (0.46 mL, 7.41 mmol). The reaction mixture was stirred at ambient temperature for 20 h, then poured into water (200 mL). The precipitates were filtered, washed with water and dried in air to afford 7 (1.01 g, 97%) as a white solid. MS m/z 420.4 (MH⁺).

Step 4. Synthesis of Aminobenzodiazepine 8

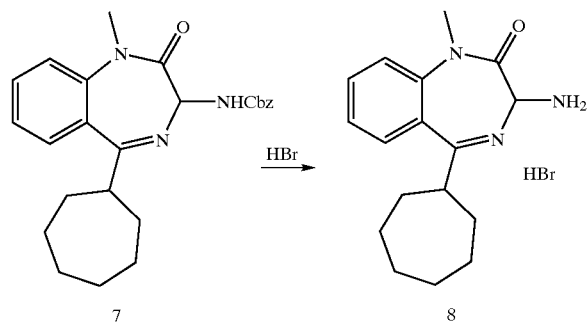

The crude product 7 (1.0 g, 2.4 mmol) from the above reaction was dissolved in methylene chloride (10 mL), treated with anhydrous HBr gas for 1 h until disappearance of 7 on TLC. The reaction mixture was diluted with ether (100 mL) and decanted. The precipitates were washed with ether and decanted (3×100 mL). The remaining ether was removed in vacuo and the residue was dried under vacuum to afford 8 (0.88 g, 100%) as a white solid. MS m/z 366.0 (MH⁺), 286.1 (MH⁺−HBr).

Step 5. Coupling of 8 with Diallylsuccinate 9

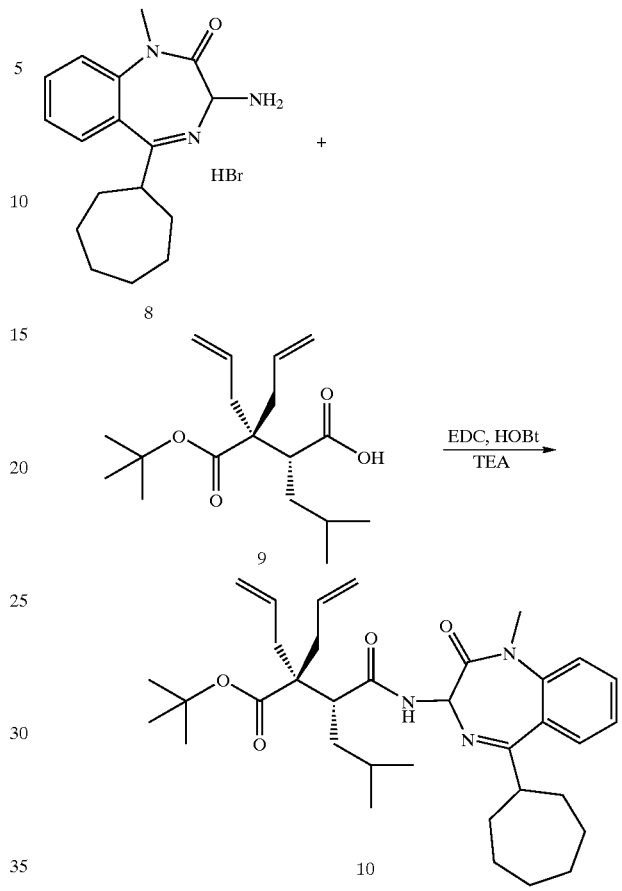

8 (230 mg, 0.63 mmol), 9 (195 mg, 0.63 mmol) and 1-hydroxybenzotriazole hydrate (HOBT, 102 mg, 0.76 mmol) were dissolved in CH₂Cl₂ and cooled to 0° C., then 1-(3-dimethylaminopropyl)-3-ethylcarbodiimide hydrochloride (EDC, 242 mg, 1.26 mmol) and triethylamine (0.22 mL, 1.58 mmol) were added. After stirring for 2 days at ambient temperature, the reaction mixture was diluted with ethyl acetate, washed with water and brine then dried (Na₂SO₄). After evaporation of the solvent, the residue was purified on silica gel (increasing gradient of 20–50% ethyl acetate/hexane) to afford product 10 (268 mg, 29%). MS m/z 578.6 (MH⁺).

Step 6. Preparation of Succinate Free Acid 11

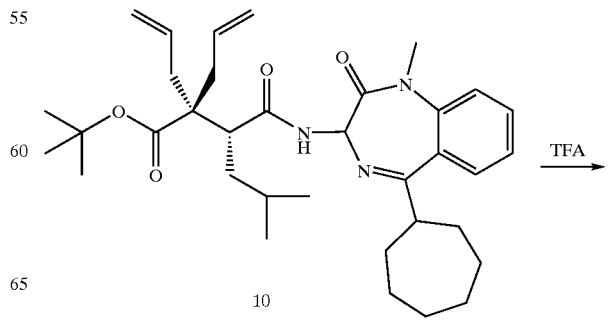

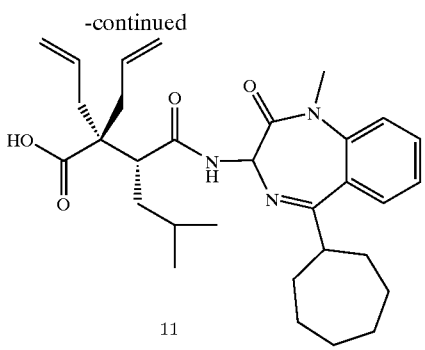

10 (268 mg, 0.46 mmol) was dissolved in CH₂Cl₂/TFA (2 mL, 1:1) and stirred for 5 h at ambient temperature. Evaporation of the solvent gave product 11 (258 mg) as a sticky oil which was used for next step without purification.

Step 7. Synthesis of Diallylsuccinate 12

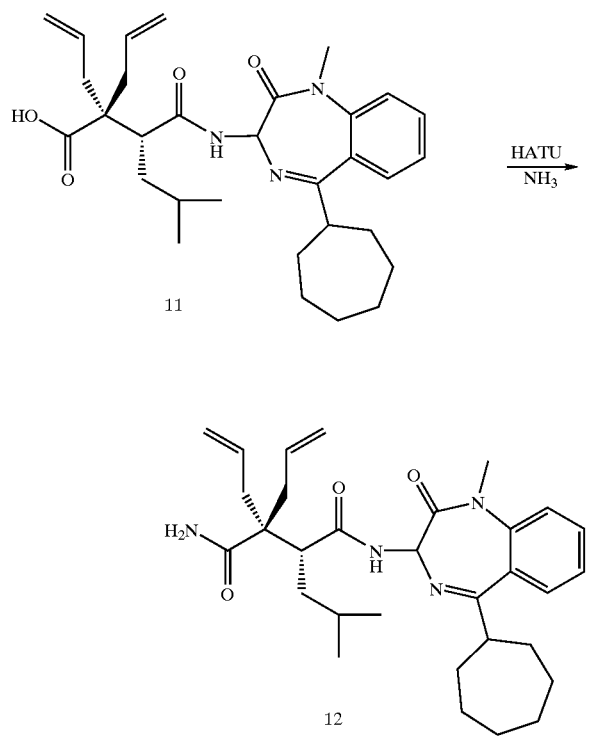

11 (240 mg, 0.46 mmol) and HATU (350 mg, 0.92 mmol) were dissolved in DMF (2 mL) and diisopropylethylamine (0.16 mL, 0.92 mmol) was added. The mixture was stirred for 15 min at ambient temperature, and then treated with anhydrous ammonia for 20 min. Stirring was continued overnight. DMF was removed in vacuo, and the residue was diluted with ethyl acetate, washed with water and brine, then dried over MgSO₄. After evaporation of the solvent, the residue was purified on silica gel (5% methanol/methylene chloride) to afford product 12 as a white solid. 12, a mixture of two diastereomers, was then separated on silica gel, using increasing gradient of 20–50% ethyl acetate-methylene chloride, to give first eluting isomer 12a (43 mg, 18%) and the second eluting isomer 12b (61 mg, 25%) both as a white solids. 12a: MS m/z 521.2 (MH⁺). 12b: MS m/z 521.2 (MH⁺).

Step 8. Synthesis of Formula I Compound 13

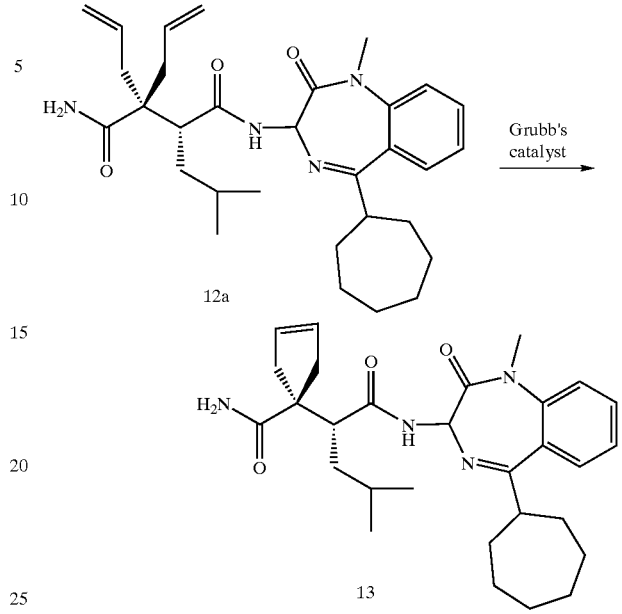

To a solution of 12a (30 mg, 0.06 mmol) in CH₂Cl₂-toluene (4 mL, 1:1) was added tricyclohexylphosphine[1,3-bis(2,4,6-trimethylphenyl)-4,5-dihydroimidazol-2-ylidene][benzylidine]ruthenium (IV) dichloride (5 mg, 0.006 mmol), and the reaction mixture was heated at 60° C. for 4 h. The reaction mixture was concentrated and the residue was purified on silica gel, using 40% ethyl acetate-methylene chloride, to afford 13 (19 mg, 63%) as a white solid. ¹H NMR (300 MHz, CDCl₃) •: 0.91 (dd, J=16.8, 6.2 Hz, 6H), 1.18–2.04 (m, br, 15H), 2.25–2.38 (m, 1H), 2.60–2.71 (m, 2H), 2.72–2.83 (m, 1H), 2.95–3.05 (m, 1H), 3.18–3.28 (m, 1H), 3.4 (s, 3H), 5.23–5.35 (m, 2H), 5.62–5.76 (m, 2H), 7.20–7.42 (m, 3H), 7.45–7.60 (m, 2H), 7.86 (s, br, 1H); MS m/z 493.5 (MH⁺).

Example 30

1-[3-methyl-1-[1,3-dihydro-1-methyl-2-oxo-5-(2-trifluoromethylphenyl)-2H-1,4-benzodiazepin-3-ylcarbamoyl]-butyl]-cyclopent-3-enecarboxylic amide

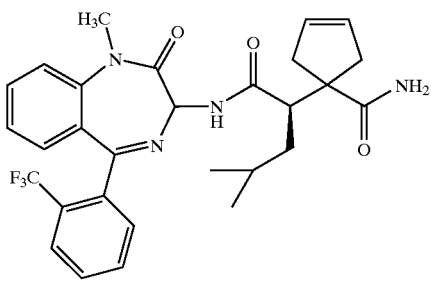

Example 30 can be prepared by the methods disclosed herein using the intermediates disclosed in Scheme 22

Scheme 22
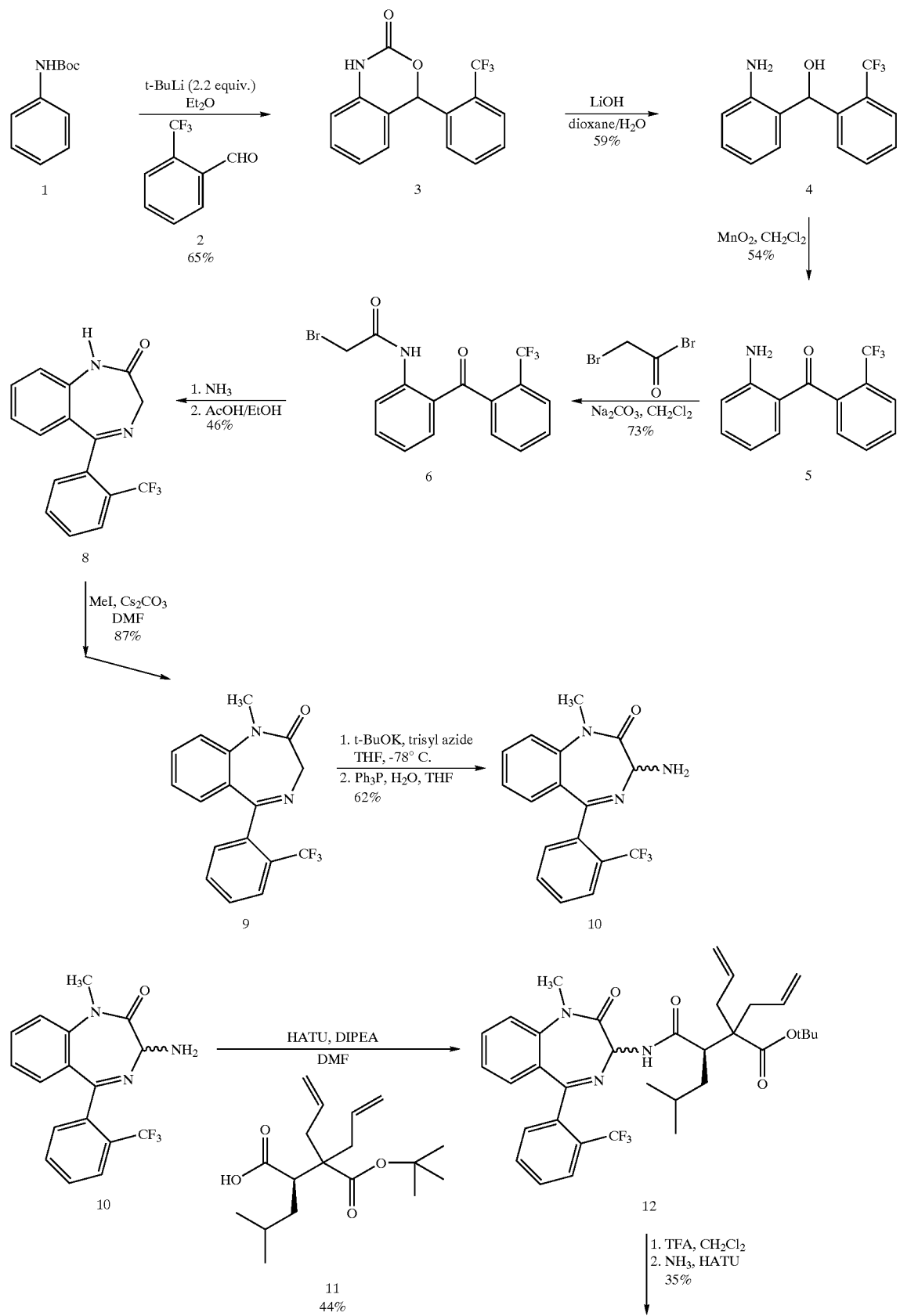

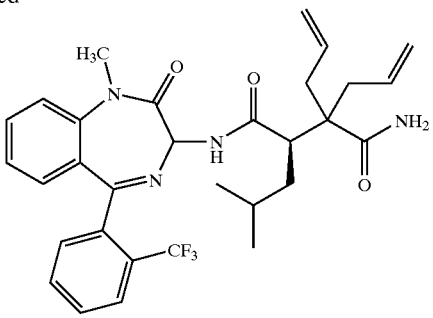

13

Preparation of Compound 3, Scheme 22. To a solution of compound 1 (87.7 g, 453 mmol) in Et$_2$O (910 mL) at −78° C. under a nitrogen atmosphere was added t-BuLi (1.7 M solution in pentane, 605 mL) while maintaining a solution temperature of −78° C. The solution was allowed to warm to −10° C. and maintained at that temperature for 3 h. A solution of 2 (79 g, 453 mmol) in Et$_2$O (100 mL) was added and the solution was stirred at −10° C. for an additional 2 h. The resulting solution was allowed to warm to room temperature while stirring for 17 h. An aqueous solution of saturated NH$_4$Cl (400 mL) was added and the layers were separated. Acid (1 N HCl) was added until a pH=1 was obtained, the aqueous layer was extracted with ethyl acetate (3×200 mL). The organic extracts were combined, washed with brine, filtered, dried over anhydrous Na$_2$SO$_4$, and concentrated to yield a orange oil. Addition of a 1/1 (v/v) solution of Et$_2$O/Hexanes resulted in precipitation of 3 (86 g 65%) as a tan solid that was used without further purification: $^1$H NMR (300 MHz, CDCl$_3$) 7.89–6.52 (m, 10 H); ESI MS m/z=294 [C$_{15}$H$_{10}$F$_3$NO$_2$+H]$^+$.

Preparation of Compound 4, Scheme 22. A solution of compound 3 (23.2 g, 79.2 mmol) and LiOH (16.5 g, 0.4 mole) in a 1/1 (V/V) of dioxane/H$_2$O (250 mL each) was refluxed for 18 h. Methylene chloride was added to the solution and the layers were separated. The aqueous layer was extracted with additional CH$_2$Cl$_2$ (2×100 mL). The organic layers were combined, dried over anhydrous Na$_2$SO$_4$, filtered, and concentrated to yield 4 (12.5 g, 59%) as a yellow oil that was used without further purification: $^1$H NMR (300 MHz, CDCl$_3$) 9.42 (s, 2 H), 7.89–6.52 (m, 9 H); ESI MS m/z=268 [C$_{14}$H$_{12}$F$_3$NO+H]$^+$.

Preparation of Compound 5, Scheme 22. To a solution of compound 4 (12.4 g, 46.4 mmol), in CH$_2$Cl$_2$ (300 mL) was added MnO$_2$ (21.1 g, 0.232 mole) and the resulting heterogenous solution was stirred for 14 h at room temperature, filtered through celite, and concentrated to yield an dark orange oil. This residue was further purified by column chromatography (silica gel, 80:20Hexanes/EtOAc) to yield 5 (6.68 g, 54%) as a yellow solid: $^1$H NMR (300 MHz, CDCl$_3$) 7.82–6.35 (m, 10 H); ESI MS m/z=266 [C$_{14}$H$_{10}$F$_3$NO+H]$^+$.

Preparation of compound 6, Scheme 22. To a solution of 5 (32.8 g, 0.12 mole) at 0° C. in CH$_2$Cl$_2$ was added bromoacetyl bromide (27.5 g, 0.14 mole). A 10% aqueous solution of Na$_2$CO$_3$ (150 mL) was added slowly with stirred for 30 min. The organic layer was separated, washed with water, dried over anhydrous Na$_2$SO$_4$, filtered, and concentrated to yield 6 (35.1 g, 73%) as a cream colored solid: $^1$H NMR (300 MHz, CDCl$_3$) 8.88 (d, J=7.1 Hz, 1 H), 7.83–7.04 (m, 8 H), 4.04 (s, 2 H); ESI MS m/z=386 [C$_{16}$H$_{11}$BrF$_3$NO+H]$^+$.

Preparation of Compound 8, Scheme 22. Ammonia (500 mL) was condensed with a dry ice condensor and maintained at −78° C. To this was added a solution of 6 (35 g, 91 mmol) in CH$_2$Cl$_2$ (600 mL). After 8 h, the dry ice condensor was removed and the reaction was warmed to room temperature allowing the ammonia to evaporate. The remaining solution was washed with brine, dried over anhydrous Na$_2$SO$_4$, filtered and concentrated to yield a white solid. This solid was dissolved in EtOH (500 mL) and AcOH (15 mL), and the resulting solution was refluxed for 24 h, and concentrated to yield a yellow-red oil. Addition of Et$_2$O (300 mL) to this oil resulted in the precipitation of 8 (13 g, 47%) as a white powder: $^1$H NMR (300 MHz, CDCl$_3$) δ 9.32 (s, 1 H), 7.83–7.05 (m, 8 H), 4.39 (s, 2 H); ESI MS m/z=305 [C$_{15}$H$_{11}$F$_3$N$_2$O+H]$^+$.

Preparation of Compound 9, Scheme 22. To a solution of 8 (3.4 g, 11.2 mmol) and Cs$_2$CO$_3$ (5.46 g, 16.6 mmol) in DMF (30 mL) was added MeI (1.0 mL, 16.6 mmol) and the solution was stirred at room temperature for 4 h. At this time, the solution was diluted with ethyl acetate, (200 mL) washed with aqueous 5% LiCl (3×100 mL), brine, dried over Na$_2$SO$_4$, filtered, and concentrated to yield 9 (3.1 g, 87%) as a pale blue solid: $^1$H NMR (300 MHz, CDCl$_3$) δ 7.82–6.97 (m, 8 H), 4.42 (q$_{ab}$, J=6.5 Hz, 2 H), 3.42 (s, 3 H); ESI MS m/z=319 [C$_{17}$H$_{13}$F$_3$N$_2$O+H]$^+$.

Preparation of Compound 10, Scheme 22. To a solution of 9 (2.4 g, 7.8 mmol) in THF (56 mL) at −78° C. was added KO-t-Bu (15.8 mL, 1 M solution in THF) and the solution was stirred for 5 min. To this solution was added a solution of trisyl azide (3.1 g, 8.7 mmol) in THF (27 mL) at −78° C. After stirring for 5 min at −78° C., AcOH (2.1 g , 34.7 mmol) was added and the solution was allowed to warm to room temperature while stirring for 18 h. This solution was diluted with CH$_2$Cl$_2$ (200 mL), washed with sat. NaHCO$_3$ (2×100 mL), brine, dried over anhydrous Na$_2$SO$_4$, filtered, and concentrated to yield a yellow powder. This powder was triturated with hexanes/EtOAc 5/1 (V/V) to yield 2.1 g of a white powder. This solid was dissolved in THF (50 mL) and H$_2$O (5 mL). Triphenylphosphine 4.6 g, 17.5 mmol) was added and the solution was stirred at room temperature for 24 h. The solution was concentrated under reduced pressure. The residue was dissolved in Et$_2$O (100 mL) and extracted with 1 N HCl (2×100 mL). The acidic extracts were adjusted to pH 14 with 1 N NaOH and extracted with CH$_2$Cl$_2$ (3×75 mL). The CH$_2$Cl$_2$ extracts were washed with brine (1×100 mL), dried over anhydrous Na$_2$SO$_4$, filtered, and concentrated to yield 10 (1.6 g, 62%) as pale yellow solid: $^1$H NMR (300 MHz, CDCl$_3$) δ 7.79–6.93(m, 8 H), 4.52 (s, 1 H), 3.47 (s, 3 H), 2.46 (br. s, 2 H); ESI MS m/z=334 [C$_{17}$H$_{14}$F$_3$N$_3$O+H]$^+$.

Preparation of 12, Scheme 22. To a solution of 10 (380 mg, 1.1 mmol), DIPEA (1 mL, 5.7 mmol), and 11 (0.37 g, 1.2 mmol) in DMF (30 mL) was added HATU (0.43 g, 1.1 mmol) and the solution was allowed to stir for 24 h at room temperature. The solution was diluted with EtOAc (150 mL) and washed with 5% aqueous solution of LiCl (3×100 mL), 1 N HCl (1×100 mL), saturated aqueous NaHCO$_3$ (2×100 mL), brine, dried over anhydrous Na$_2$SO$_4$, filtered, and concentrated to yield an pale yellow oil. This residue was further purified by column chromatography (silica gel, 3:1 Hexanes/EtOAc) to yield 12 (0.31 g, 44%) as a white foam: $^1$H NMR (300 MHz, CDCl$_3$) δ 7.86–6.91 (m, 9 H), 5.82 (m, 2 H), 5.67 (m, 1 H), 5.09 (m, 4 H), 3.48 (s, 3 H), 2.73–2.28 (m, 5 H), 1.92 (m, 1 H), 1.61 (m, 1 H), 1.42 (s, 9 H), 1.27 (m, 1 H), 0.93 (m, 6 H); ESI MS m/z=626 [C$_{35}$H$_{42}$F$_3$N$_3$O$_4$+H]$^+$.

Preparation of 13, Scheme 22. To a solution of 12 (300 mg, 0.5 mmol) in CH$_2$Cl$_2$ (4 mL) was added TFA (10 mL) and the solution was allowed to stir for 24 h at room temperature. The solution was concentrated under reduced pressure, the residue was redissolved in toluene and concentrated (3×10 mL). Ammonia gas was bubbled through a solution of the residue, DIPEA (0.4 mL, 2.5 mmol), HATU (180 mg, 0.5 mmol) in DMF (5 mL) for 30 min and the solution was allowed to stir for 24 h at room temperature. The contents of the flask were partitioned between EtOAc and a 5% LiCl solution (50 mL each), the organic phase washed with 5% LiCl (3×50 mL), and dried over anhydrous Na$_2$SO$_4$, filtered, and concentrated to yield a white solid. The diastereomers were separated by column chromatography (silica gel, 2:1 EtOAc/Hexanes) to yield Diastereomer A and Diastereomer B (99 mg, 35%) as white powders:

Diastereomer A: mp 218–219° C.; $^1$H NMR (300 MHz, CDCl$_3$) δ 8.48 (s, 1 H), 7.67–7.01 (m, 8 H), 5.79 (m, 2 H), 5.53 (d, J=7.9 Hz, 2 H), 5.33 (s, 1 H), 5.18–5.04 (m, 4 H), 3.47 (s, 3 H), 2.57–2.38 (m, 5 H), 1.79 (m, 1 H), 1.28 (m, 2 H), 0.89 (d, J=6.5 Hz, 3 H), 0.85 (d, J=6.5 Hz, 3 H); IR (ATR) 3142, 2956, 1706, 1647, 1599, 1538, 1312, 1142 cm$^{-1}$; ESI MS m/z=569 [C$_{31}$H$_{35}$F$_3$N$_4$O$_3$+H]$^+$; HPLC 96.9%, t$_r$=21.6 min; Optical Rotation [α]$^{25}_D$+2.5° (c 0.01, Methanol).

Diastereomer B: mp 200–202° C.; $^1$H NMR (300 MHz, CDCl$_3$) δ 8.42 (s, 1 H), 7.67–7.05 (m, 8 H), 5.73 (m, 2 H), 5.59 (d, J=8.1 Hz, 2 H), 5.33 (s, 1 H) 5.16–5.02 (m, 4 H), 3.49 (s, 3 H), 2.56–2.41 (m, 5 H), 1.73 (m, 1 H), 1.21 (m, 2 H), 0.91 (d, J=6.8 Hz, 3 H), 0.87 (d, J=6.8 Hz, 3 H); IR (ATR) 3308, 3150, 2928, 1712, 1650, 1603, 1310 cm$^{-1}$; ESI MS m/z=569 [C$_{31}$H$_{35}$F$_3$N$_4$O$_3$+H]$^+$; HPLC 98.8%, t$_r$=21.2 min; [α]$^{25}_D$−7.4° (c 0.01, Methanol).

Compound 13 may be converted to the title compound, Example 30, by using the RCM method according to the step 4 of Example 1.

Example 500

Preparation of 3-amino-8-bromo-1,5-dimethyl-1,3-dihydro-2H-1,4-benzodiazepin-2-one

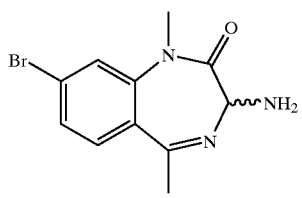

Step 1: Preparation of 1-(2-amino-4-bromophenyl)ethanone Under an argon atmosphere a solution of 3-bromoaniline (31.3 g, 181.8 mmol) and acetonitrile (75 g, 1.818 mol) in anhydrous toluene (120 ml) was added dropwise over 2.5 hours to a stirred solution of boron trichloride (23.4 g, 200 mmol) in (200 ml) hexanes cooled in an ice bath. After the addition was completed, aluminum chloride (26.6 g, 200 mmol) was added portion wise over 30 minutes. The mixture was allowed to warm to ambient temperature and then heated at reflux for 16 hours with stirring. The reaction mixture was then cooled to 10° C. and 100 mL of a 3N HCl solution was added dropwise with continued stirring. After the addition was complete, the mixture was heated at reflux for 3.5 hours, then cooled to room temperature, and the layers separated. The aqueous layer was extracted with chloroform (3×250 ml). Organic layers were combined, dried over magnesium sulfate, filtered, and concentrated to give the title compound (9.58 g, 25%). $^1$H NMR (CDCl$_3$, 300 MHz): δ 7.54 (d, 1H, J=8.8 Hz), 6.83 (d, 1H, J=1.9 Hz), 6.75 (dd, 1H, J=8.4, 1.8 Hz), 2.54 (s, 3H) ppm.

Step 2: Preparation of benzyl 8-bromo -5-methyl-2-oxo-2,3-dihydro-1H-1,4-benzodiazepin-3-ylcarbamate

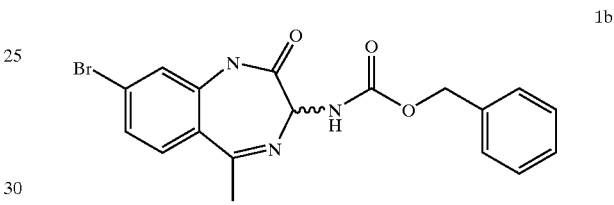

1b

Under an argon atmosphere 1H-1,2,3-benzotriazol-1-yl{[(benzyloxy)carbonyl]amino}acetic acid (6.71 g, 20.6 mmol) was suspended in anhydrous methylene chloride (92 ml) and cooled to 0° C. in an ice bath. Oxalyl chloride (2.61 g, 20.6 mmol), then N,N-dimethylformamide (38 ml) were added dropwise to the suspension. The reaction mixture was stirred at 0° C. in an ice bath for 30 minutes, at which point no further gas evolution was noted. Then a solution of 1-(2-amino-4-bromophenyl)ethanone (4.0 g, 18.7 mmol) and 4-methylmorpholine (2.84 g, 28.0 mmol) in anhydrous methylene chloride (60 ml) was added dropwise. The reaction mixture was allowed to warm to room temperature over 12 hours, then quenched with water (200 ml), and extracted with ethyl acetate (3×250 ml). The organic layers were combined, dried over magnesium sulfate, filtered and concentrated to give a semi-solid which was dissolved in tetrahydrofuran (120 ml) and methyl alcohol (35 ml). Ammonia gas was bubbled through this solution for 2.5 hours. The reaction was then concentrated to a viscous light brown oil. The oil was dissolved in acetic acid (120 ml) and ammonium acetate (4.3 g, 56.1 mmol) was added in one portion and stirred for 12 hours. The reaction mixture was diluted with water (100 ml) and then made basic (pH=10) with 25% sodium hydroxide, while stirring in an ice bath. The aqueous solution was then extracted with ethyl acetate (3×500 ml) and the organic layers combined, dried over magnesium sulfate, filtered and concentrated. The resulting residue was purified on silica gel, eluting with 40% ethyl acetate in hexanes to give the title compound (4 g, 53%). $^1$H NMR (CDCl$_3$, 300 MHz): δ 9.90 (s-br, 1H), 7.42–7.31 (m, 6H), 7.12 (d, 1H, 1.5 Hz), 7.06–7.03 (m, 1H), 5.18–5.08 (m, 3H), 2.50 (s, 3H) ppm.

Step 3: Preparation of benzyl 8-bromo-1,5-dimethyl-2-oxo-2,3-dihydro-1H-1,4-benzodiazepin-3-ylcarbamate

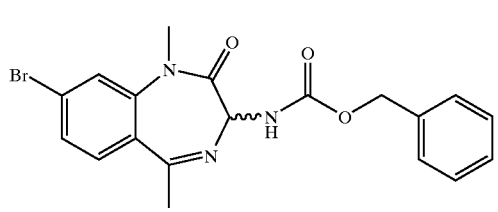

1c

The product of Step 2 (2.0 g, 4.98 mmol) was dissolved in anhydrous N,N-dimethylformamide (10 ml). To this solution was added potassium carbonate (1.72 g, 12.44 mmol) and iodomethane (0.847 g, 5.97 mmol), and the reaction mixture was sealed in a pressure flask and stirred for 12 hours at room temperature, then diluted with water and ethyl acetate (20/70 ml). The aqueous solution was then extracted with ethyl acetate (3×20 ml). The organic layers were combined, washed with water (1×100 ml), dried over magnesium sulfate, filtered and concentrated to give the title compound (1.58 g, 77.5%). $^1$H NMR (CDCl$_3$, 300 MHz): δ 7.43–7.28 (m, 7H), 6.68 (d, 1H, J=8.1 Hz), 5.15–5.05 (m, 3H), 3.38 (s, 3H), 2.45 (d, 3H, 1.5 Hz) ppm.

Step 4: Preparation of 3-amino-8-bromo-1,5-dimethyl-1,3-dihydro-2H-1,4-benzodiazepin-2-one

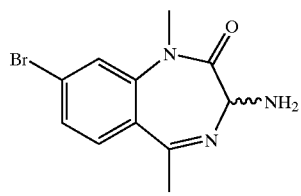

1d

The product of Step 3 (0.831 g, 2.00 mmol) was dissolved in anhydrous anisole (16 ml) and then methanesulfonic acid (3.84 g, 40 mmol) was added in one portion. The reaction mixture was heated to 40° C. for 30 minutes with stirring, then cooled to 0° C. in an ice bath and made basic (pH=10) with concentrated ammonium hydroxide. The aqueous solution was then extracted with chloroform (3×50 ml) and the organic layers combined, dried over magnesium sulfate, filtered and concentrated to give the crude product. Purification on silica gel, eluting with 10% methyl alcohol in chloroform, providing the title compound as an XXXX (0.463 g, 82%). $^1$H NMR (CDCl$_3$, 300 MHz): δ 7.32–7.23 (m, 3H), 4.12 (d, 1H, J=1.1 Hz), 3.27 (s, 3H), 2.30 (d, 3H, J=1.5 Hz) ppm.

Example 501

Scheme 23

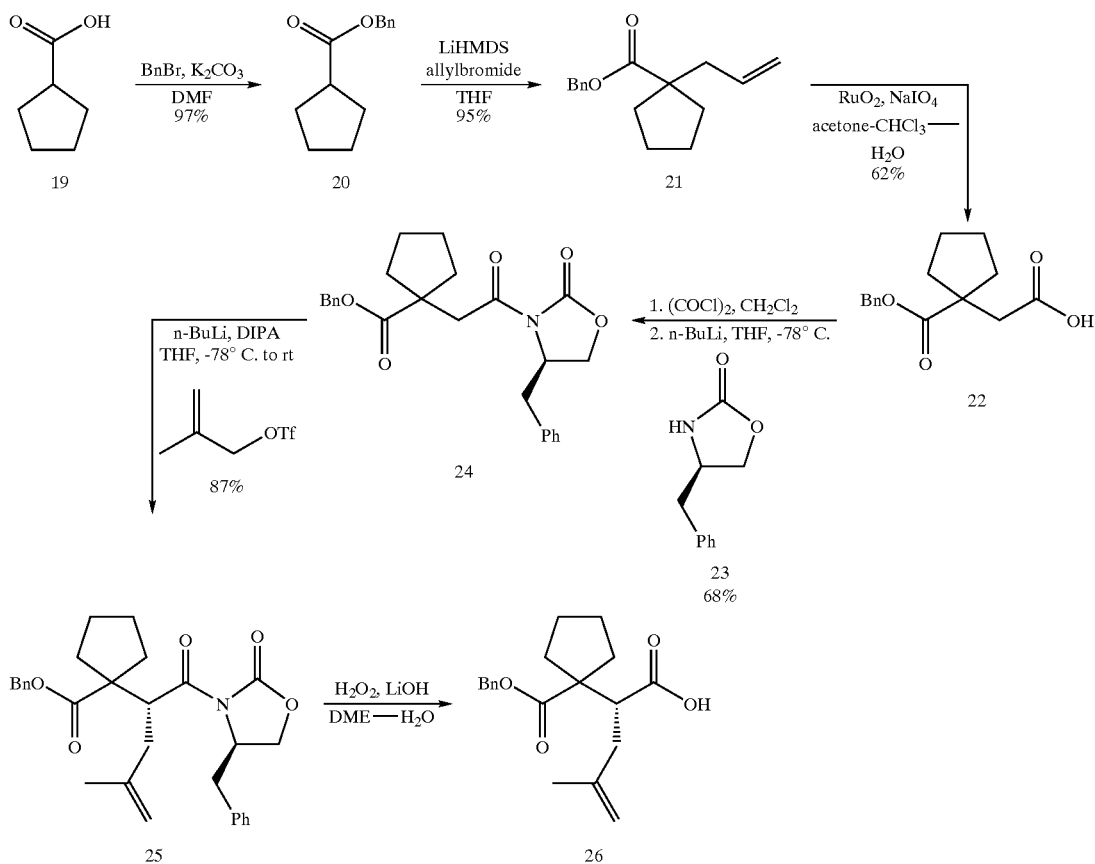

Preparation of Compound 20, Scheme 23

A three neck 3 L round bottom flask was charged with 19 (100 g, 876 mmol), benzylbromide (104 mL, 876 mmol) and DMF (876 mL). The reaction was cooled to 0° C. and to the reaction was added solid $K_2CO_3$ (170 g, 1.2 mol) in portions. The ice bath was removed and the reaction was stirred vigorously for 2 h. To the reaction was added $H_2O$ (1800 mL). The aqueous layer was extracted with Hexanes (3×1000 mL). The organic layers were combined and dried over $MgSO_4$. The solution was filtered and the solvent was removed under reduced pressure to afford 20 (174 g, 97%) as a clear oil: $^1$H NMR (CDCl$_3$) δ 7.34 (m, 5 H), 5.12 (s, 2 H), 2.79 (m, 1 H), 1.92–1.57 (m, 8 H).

Preparation of Compound 21, Scheme 23

A 2 L round bottom flask equipped with a mechanical stirring apparatus was charged with 1 M LiHMDS in hexanes (860 mL, 860 mmol) and anhydrous THF (302 mL). The solution was cooled to −78° C. and treated with 20 in THF (100 mL) added slowly through an addition funnel. After 1 h, allylbromide (90 mL, 1.0 mol) was added slowly to the reaction. The reaction was warmed slowly to rt and then stirred for 12 h. The reaction was poured into 1 N HCl (1000 mL) and stirred for 10 min. The layers were separated. The organic layer was washed with 1 N HCl (100 mL), aq. NaHCO$_3$ (500 mL) and brine (500 mL). The solution was dried over MgSO$_4$ and filtered. The solvent was removed under reduced pressure to afford 21 (189 g, 95%) as a pale yellow oil: $^1$H NMR (CDCl$_3$) δ 7.35 (m, 5 H), 5.77–5.63 (m, 1 H), 5.11 (s, 2 H), 5.02 (m, 1 H), 4.97 (m, 1 H), 2.38 (m, 2 H), 2.11 (m, 2 H), 1.68–1.51 (m, 6 H).

Preparation of Compound 22, Scheme 23

A solution of RuO$_2$.H$_2$O (2.9 g, 22 mmol) and NaIO$_4$ (44 g, 205 mmol) in 1:1 CHCl$_3$—H$_2$O (820 mL) was shaken in a separatory funnel. The layers were separated. The organic layer was poured into a 5 L 3N round bottom flask equipped with a mechanical stirring apparatus. To the reaction was added a solution of 21 (100 g, 410 mmol) in acetone (410 mL). A separate solution of NaIO$_4$ (569 g, 2.67 mol) was added in portions to a stirred solution of the reactant components. The resulting slurry was stirred vigorously for 24 h.

The reaction was filtered through a 1 L Buchner funnel to remove the excess NaIO$_4$ remaining in the reaction. The filtrate was diluted with Et$_2$O (400 mL) and 1 N NaHSO$_4$ (400 mL). The organic layer was separated and washed with 1 N NaHSO$_4$ (1×400 mL). The organic layer was diluted with Et$_2$O (1100 mL) and filtered through a Buchner funnel to afford 22 (66 g, 62%) as a light purple oil: $^1$H NMR (CDCl$_3$) δ 7.34 (m, 5 H), 5.14 (s, 2 H), 3.30 (s, 2 H), 2.31–2.16 (m, 2 H), 1.81–1.50 (m, 6 H).

Preparation of Compound 24, Scheme 23

To 22 (62 g, 238 mmol) in CH$_2$Cl$_2$ (238 mL) at rt was added oxalyl chloride (28 mL, 310 mmol). The reaction was stirred for 2 h until gas evolution subsided. The solvent was removed under reduced pressure to provide the intermediate acid chloride.

A 3 L 3N round bottom flask equipped with a mechanical stirring apparatus was charged with 23 (41 g, 230 mmol) and anhydrous THF (700 mL). The solution was cooled to −78° C. and treated with 2.5 M n-BuLi in hexanes (92 mL, 230 mmol) added through an addition funnel. After 20 min, the acid chloride intermediate in THF (67 mL) was added slowly to the solution. After addition was complete, the reaction was warmed to rt and stirred for 2 h.

The reaction was poured into sat. NH$_4$Cl (500 mL). The layers were separated. The aqueous layer was extracted with Et$_2$O (1000 mL). The organic layers were combined and washed with NaHCO$_3$ (500 mL) and brine (500 mL). The solution was dried over MgSO$_4$ and filtered. The solvents were removed under reduced pressure. The crude material was purified by SiO$_2$ chromatography (CH$_2$Cl$_2$) to afford 24 (68 g, 68%) as an off-white solid: 1H NMR (CDCl$_3$) δ 7.40–7.12 (m, 10 H), 5.15 (s, 2 H), 4.49 (m, 1 H), 4.13 (m, 2H), 3.34 (m, 2 H), 3.15 (dd, J=13.4, 3.2 Hz, 1 H), 2.65 (dd, J=13.4, 9.6 Hz, 1 H), 2.29 (m, 2 H), 1.85–1.50 (m, 6 H).

Preparation of Compound 25, Scheme 23

A 3 L 3N round bottom flask equipped with a mechanical stirring apparatus was charged with 24 (32 g, 78 mmol) and anhydrous THF (155 mL). The reaction was cooled to −60° C. and treated with 1 M LiHMDS in hexanes (78 mL, 78 mmol). The reaction was warmed to −20° C. and stirred for an 4 h.

To a 1 L 3N round bottom flask was added hexane (516 mL), 2,6-lutidine (38 mL, 326 mmol) and methallyl alcohol (26 mL, 311 mmol). The solution was stirred vigorously using a mechanical stirring apparatus. The solution was cooled to −20° C. and treated with Tf$_2$O (52 mL, 311 mmol). During the addition of Tf$_2$O, a white solid precipitated from the solution. After 1 h, the contents of the flask were poured into a Buchner funnel and transferred to a pre-cooled (−40° C.) 1000 mL round bottom flask. The solution was carefully transferred to the main reaction via cannula. Stirring was continued for 18 h at −20° C.

The reaction was poured into a stirred solution of NH$_4$Cl (1000 mL). The layers were separated. The aqueous layer was extracted with EtOAc. The organic layers were combined, washed with 10% aq. citric acid (400 mL) and brine (400 mL). The organic layer was dried over MgSO$_4$ and filtered. The solvents were removed under reduced pressure to afford 25 (28 g, 87%) as viscous oil: $^1$H NMR (CDCl$_3$) δ 7.41–7.15 (m, 10 H), 5.15 (s, 2 H), 4.72 (m, 2 H), 4.58 (m, 1 H), 4.10–3.95 (m, 2 H), 3.27 (dd, J=13.4, 3.1 Hz, 1 H), 2.67 (dd, J=13.5, 11.9 Hz, 1 H), 2.54 (dd, J=13.3, 10.2 Hz, 1 H), 2.25 (m, 2 H), 1.80–1.49 (m, 11 H).

Preparation of Compound 26, Scheme 23

To 24 (80 mg, 0.17 mmol) in 2:1 DME-H$_2$O (3 mL) was added 30% wt H$_2$O$_2$ (104 μL) and then LiOH.H$_2$O (14 mg, 0.34 mmol) in H$_2$O (0.3 mL). The reaction was stirred for 72 h at rt. To the solution was added 30% NaHSO$_3$ (0.5 mL). The reaction was diluted with NH$_4$Cl (20 mL) and extracted with EtOAc (50 mL). The organic layer was dried over MgSO$_4$ and filtered. The solvent was removed under reduced pressure. The crude material was purified by column chromatography (50% ethyl acetate in hexanes) to provide 26 (22 mg, 41%) as a clear, viscous oil: $^1$H NMR (CDCl$_3$) δ 7.35 (m, 5 H), 5.14 (m, 2 H), 4.72 (d, J=12.0 Hz, 1 H), 4.71 (s, 1 H), 3.07 (dd, J=11.6, 2.9 Hz, 1 H), 2.43 (dd, J=14.5, 11.9 Hz, 1 H), 2.19 (m, 2 H), 2.05 (m, 1 H), 1.90–1.50 (m, 9 H).

Table 2 demonstrates representative compounds envisaged within the scope of the present invention. Each formulae at the start of Table 2 are intended to be paired with each entry in the table which follows.

For example the compound 1-[(1R)-3,3-dimethyl-1-[6,7-dihydro-5-methyl-6-oxo-5H-dibenz[b,d]azepin-7-ylcarbamoyl]-butyl]-cyclopentanecarboxylic amide is represented by Example #500-B-y, which comprises the core B, succinate y, and entry #500.

For example the compound 1-[(1R)-3-methyl-1-[(3S)-1,3-dihydro-1-ethyl-2-oxo-5-phenyl-7-chloro-2H-1,4-benzodiazepin-3-yl]-butyl]-cyclohexanecarboxylic amide is represented by Example #510-D-ab, which comprises the core D, succinate ab, and entry #510.

TABLE 2
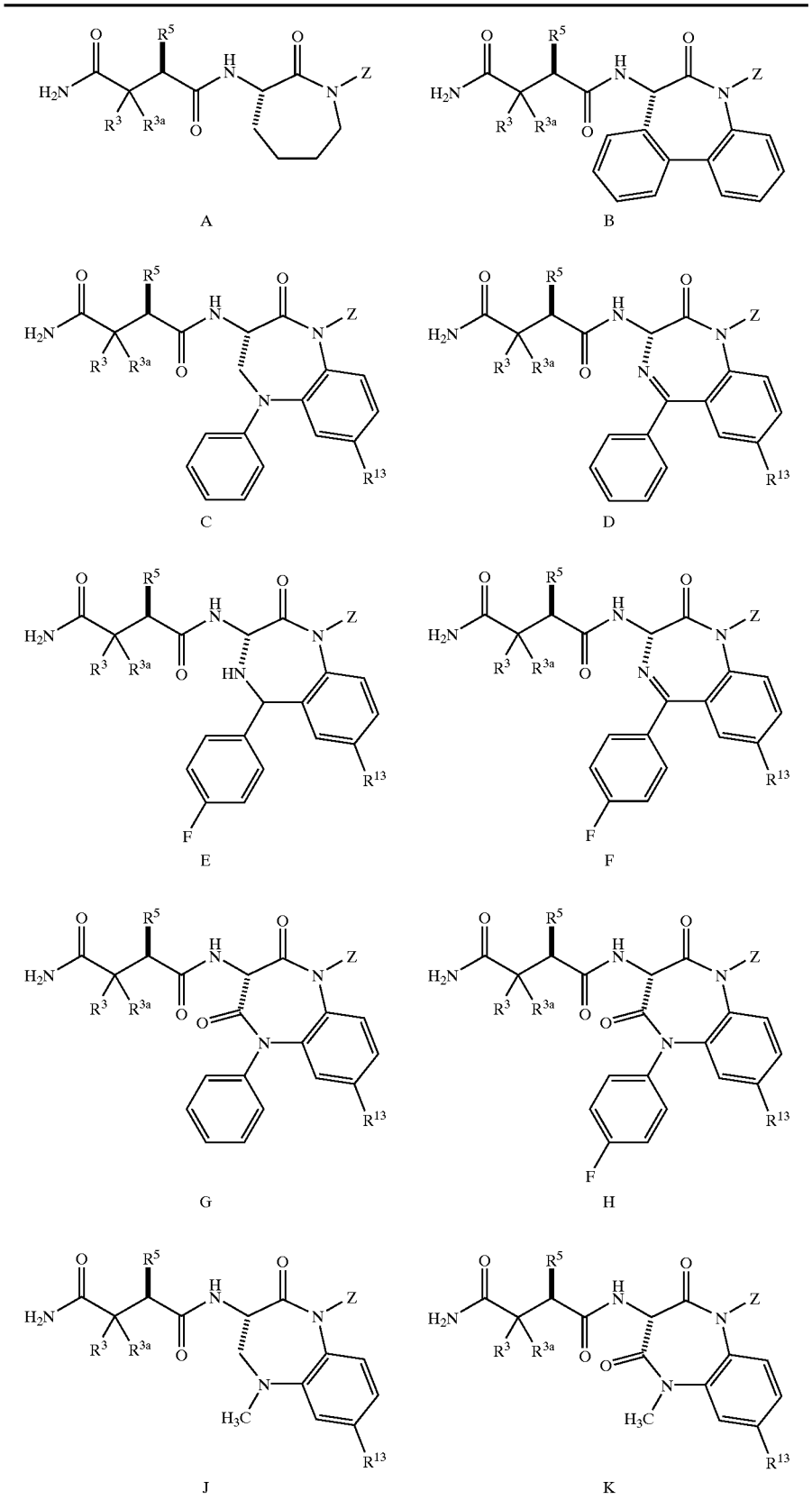

TABLE 2-continued
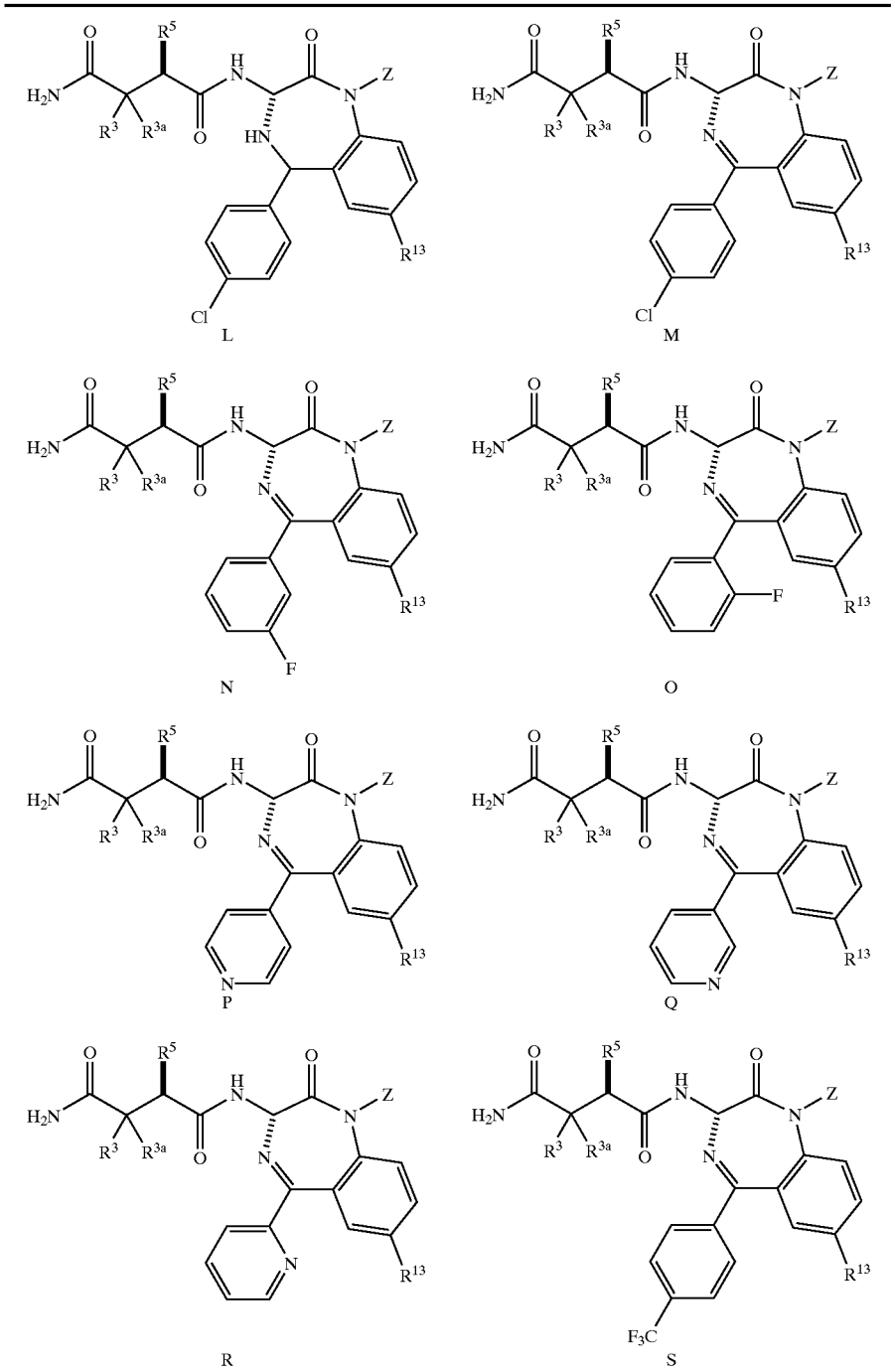
wherein $R^3$, $R^{3a}$ and $R^5$ are described, respectively, in the following moieties:
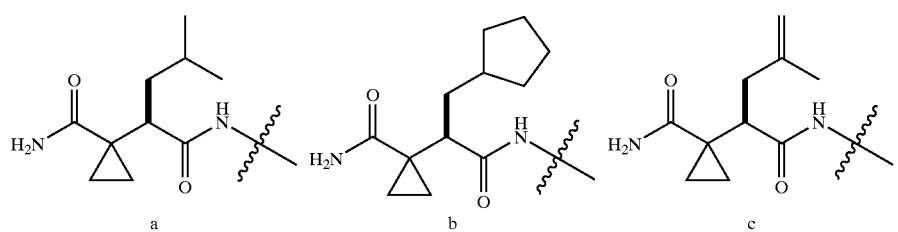

TABLE 2-continued
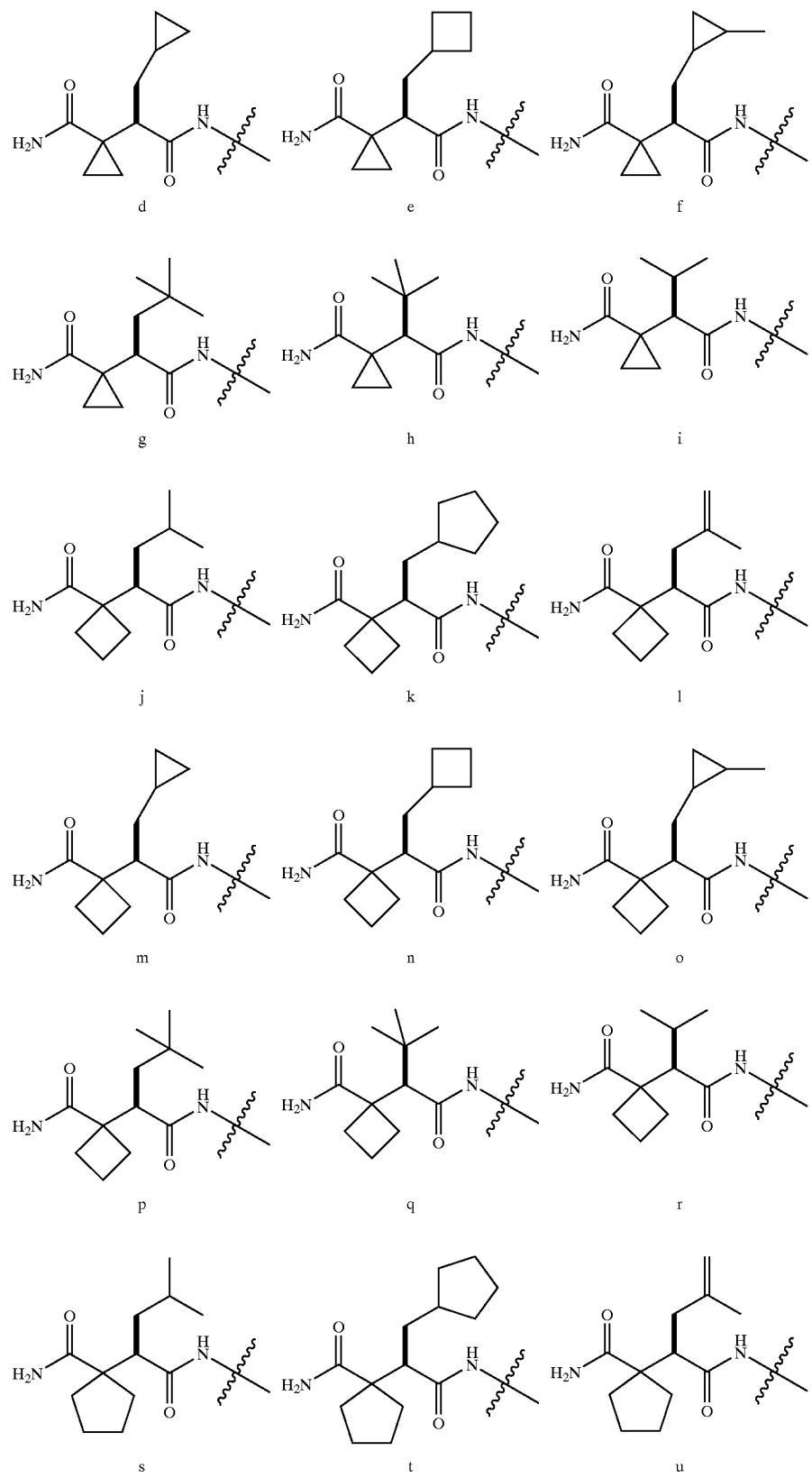

TABLE 2-continued
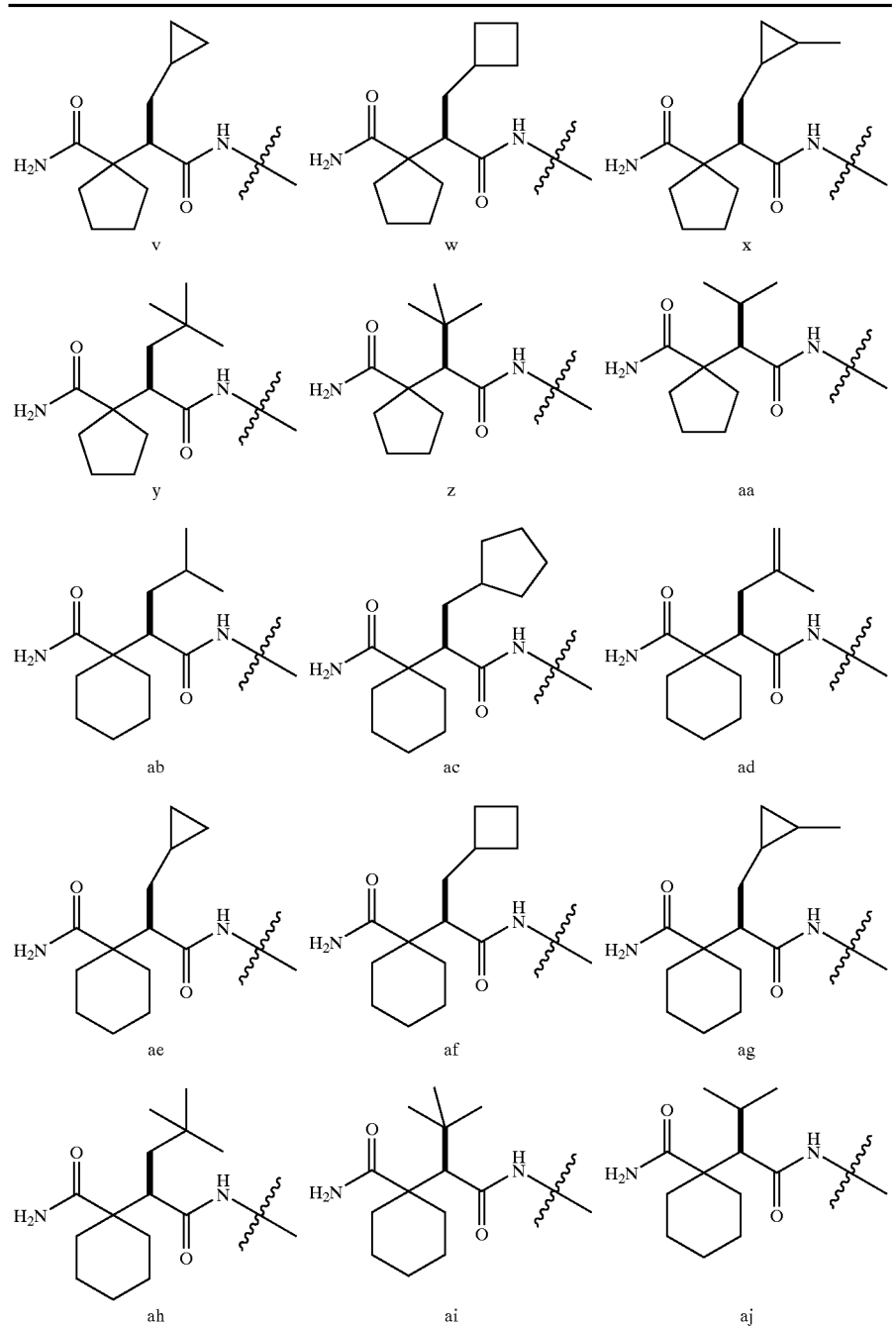
| Ex # | core | R3/R5 | R13 | Z |
|---|---|---|---|---|
| 500 | A - S | a - aj | H | methyl |
| 501 | C - S | a - aj | F | methyl |
| 502 | C - S | a - aj | Cl | methyl |
| 503 | C - S | a - aj | OH | methyl |
| 504 | C - S | a - aj | —CH₃ | methyl |
| 505 | C - S | a - aj | —CH₂CH₃ | methyl |
| 506 | C - S | a - aj | —OCH₃ | methyl |
| 507 | C - S | a - aj | —CF₃ | methyl |
| 508 | A - S | a - aj | H | ethyl |
| 509 | C - S | a - aj | F | ethyl |
| 510 | C - S | a - aj | Cl | ethyl |
| 511 | C - S | a - aj | OH | ethyl |
| 512 | C - S | a - aj | —CH₃ | ethyl |

TABLE 2-continued

| | | | | |
|---|---|---|---|---|
| 513 | C - S | a - aj | —CH$_2$CH$_3$ | ethyl |
| 514 | C - S | a - aj | —OCH$_3$ | ethyl |
| 515 | C - S | a - aj | —CF$_3$ | ethyl |
| 516 | A - S | a - aj | H | i-propyl |
| 517 | C - S | a - aj | F | i-propyl |
| 518 | C - S | a - aj | Cl | i-propyl |
| 519 | C - S | a - aj | OH | i-propyl |
| 520 | C - S | a - aj | —CH$_3$ | i-propyl |
| 521 | C - S | a - aj | —CH$_2$CH$_3$ | i-propyl |
| 522 | C - S | a - aj | —OCH$_3$ | i-propyl |
| 523 | C - S | a - aj | —CF$_3$ | i-propyl |
| 524 | A - S | a - aj | H | n-propyl |
| 525 | C - S | a - aj | F | n-propyl |
| 526 | C - S | a - aj | Cl | n-propyl |
| 527 | C - S | a - aj | OH | n-propyl |
| 528 | C - S | a - aj | —CH$_3$ | n-propyl |
| 529 | C - S | a - aj | —CH$_2$CH$_3$ | n-propyl |
| 530 | C - S | a - aj | OCH$_3$ | n-propyl |
| 531 | C - S | a - aj | —CF$_3$ | n-propyl |
| 532 | A - S | a - aj | H | n-butyl |
| 533 | C - S | a - aj | F | n-butyl |
| 534 | C - S | a - aj | Cl | n-butyl |
| 535 | C - S | a - aj | OH | n-butyl |
| 536 | C - S | a - aj | —CH$_3$ | n-butyl |
| 537 | C - S | a - aj | CH$_2$CH$_3$ | n-butyl |
| 538 | C - S | a - aj | —OCH$_3$ | n-butyl |
| 539 | C - S | a - aj | —CF$_3$ | n-butyl |
| 540 | A - S | a - aj | H | i-butyl |
| 541 | C - S | a - aj | F | i-butyl |
| 542 | C - S | a - aj | Cl | i-butyl |
| 543 | C - S | a - aj | OH | i-butyl |
| 544 | C - S | a - aj | —CH$_3$ | i-butyl |
| 545 | C - S | a - aj | —CH$_2$CH$_3$ | i-butyl |
| 546 | C - S | a - aj | —OCH$_3$ | i-butyl |
| 547 | C - S | a - aj | —CF$_3$ | i-butyl |
| 548 | A - S | a - aj | H | s-butyl |
| 549 | C - S | a - aj | F | s-butyl |
| 550 | C - S | a - aj | Cl | s-butyl |
| 551 | C - S | a - aj | OH | s-butyl |
| 552 | C - S | a - aj | —CH$_3$ | s-butyl |
| 553 | C - S | a - aj | —CH$_2$CH$_3$ | s-butyl |
| 554 | C - S | a - aj | —OCH$_3$ | s-butyl |
| 555 | C - S | a - aj | —CF$_3$ | s-butyl |
| 556 | A - S | a - aj | H | t-butyl |
| 557 | C - S | a - aj | F | t-butyl |
| 558 | C - S | a - aj | Cl | t-butyl |
| 559 | C - S | a - aj | OH | t-butyl |
| 560 | C - S | a - aj | —CH$_3$ | t-butyl |
| 561 | C - S | a - aj | —CH$_2$CH$_3$ | t-butyl |
| 562 | C - S | a - aj | —OCH$_3$ | t-butyl |
| 563 | C - S | a - aj | —CF$_3$ | t-butyl |
| 564 | A - S | a - aj | H | allyl |
| 565 | C - S | a - aj | F | allyl |
| 566 | C - S | a - aj | Cl | allyl |
| 567 | C - S | a - aj | OH | allyl |
| 568 | C - S | a - aj | —CH$_3$ | allyl |
| 569 | C - S | a - aj | —CH$_2$CH$_3$ | allyl |
| 570 | C - S | a - aj | —OCH$_3$ | allyl |
| 571 | C - S | a - aj | —CF$_3$ | allyl |
| 572 | A - S | a - aj | H | cyclopropyl |
| 573 | C - S | a - aj | F | cyclopropyl |
| 574 | C - S | a - aj | Cl | cyclopropyl |
| 575 | C - S | a - aj | OH | cyclopropyl |
| 576 | C - S | a - aj | —CH$_3$ | cyclopropyl |
| 577 | C - S | a - aj | —CH$_2$CH$_3$ | cyclopropyl |
| 578 | C - S | a - aj | —OCH$_3$ | cyclopropyl |
| 579 | C - S | a - aj | —CF$_3$ | cyclopropyl |
| 580 | A - S | a - aj | H | cyclopropyl-CH$_2$— |
| 581 | C - S | a - aj | F | cyclopropyl-CH$_2$— |
| 582 | C - S | a - aj | Cl | cyclopropyl-CH$_2$— |
| 583 | C - S | a - aj | OH | cyclopropyl-CH$_2$— |
| 584 | C - S | a - aj | —CH$_3$ | cyclopropyl-CH$_2$— |
| 585 | C - S | a - aj | —CH$_2$CH$_3$ | cyclopropyl-CH$_2$— |
| 586 | C - S | a - aj | —OCH$_3$ | cyclopropyl-CH$_2$— |
| 587 | C - S | a - aj | —CF$_3$ | cyclopropyl-CH$_2$— |
| 588 | A - S | a - aj | H | cyclobutyl |
| 589 | C - S | a - aj | F | cyclobutyl |
| 590 | C - S | a - aj | Cl | cyclobutyl |
| 591 | C - S | a - aj | OH | cyclobutyl |

TABLE 2-continued

| | | | | |
|---|---|---|---|---|
| 592 | C - S | a - aj | —CH$_3$ | cyclobutyl |
| 593 | C - S | a - aj | —CH$_2$CH$_3$ | cyclobutyl |
| 594 | C - S | a - aj | —OCH$_3$ | cyclobutyl |
| 595 | C - S | a - aj | —CF$_3$ | cyclobutyl |
| 596 | A - S | a - aj | H | cyclobutyl-CH$_2$— |
| 597 | C - S | a - aj | F | cyclobutyl-CH$_2$— |
| 598 | C - S | a - aj | Cl | cyclobutyl-CH$_2$— |
| 599 | C - S | a - aj | OH | cyclobutyl-CH$_2$— |
| 600 | C - S | a - aj | —CH$_3$ | cyclobutyl-CH$_2$— |
| 601 | C - S | a - aj | —CH$_2$CH$_3$ | cyclobutyl-CH$_2$— |
| 602 | C - S | a - aj | —OCH$_3$ | cyclobutyl-CH$_2$— |
| 603 | C - S | a - aj | —CF$_3$ | cyclobutyl-CH$_2$— |
| 604 | A - S | a - aj | H | cyclopentyl |
| 605 | C - S | a - aj | F | cyclopentyl |
| 606 | C - S | a - aj | Cl | cyclopentyl |
| 607 | C - S | a - aj | OH | cyclopentyl |
| 608 | C - S | a - aj | —CH$_3$ | cyclopentyl |
| 609 | C - S | a - aj | —CH$_2$CH$_3$ | cyclopentyl |
| 610 | C - S | a - aj | —OCH$_3$ | cyclopentyl |
| 611 | C - S | a - aj | —CF$_3$ | cyclopentyl |
| 612 | A - S | a - aj | H | cyclopentyl-CH$_2$— |
| 613 | C - S | a - aj | F | cyclopentyl-CH$_2$— |
| 614 | C - S | a - aj | Cl | cyclopentyl-CH$_2$— |
| 615 | C - S | a - aj | OH | cyclopentyl-CH$_2$— |
| 616 | C - S | a - aj | —CH$_3$ | cyclopentyl-CH$_2$— |
| 617 | C - S | a - aj | —CH$_2$CH$_3$ | cyclopentyl-CH$_2$— |
| 618 | C - S | a - aj | —OCH$_3$ | cyclopentyl-CH$_2$— |
| 619 | C - S | a - aj | —CF$_3$ | cyclopentyl-CH$_2$— |
| 620 | A - S | a - aj | H | cyclohexyl |
| 621 | C - S | a - aj | F | cyclohexyl |
| 622 | C - S | a - aj | Cl | cyclohexyl |
| 623 | C - S | a - aj | OH | cyclohexyl |
| 624 | C - S | a - aj | —CH$_3$ | cyclohexyl |
| 625 | C - S | a - aj | —CH$_2$CH$_3$ | cyclohexyl |
| 626 | C - S | a - aj | —OCH$_3$ | cyclohexyl |
| 627 | C - S | a - aj | —CF$_3$ | cyclohexyl |
| 628 | A - S | a - aj | H | cyclohexyl-CH$_2$— |
| 629 | C - S | a - aj | F | cyclohexyl-CH$_2$— |
| 630 | C - S | a - aj | Cl | cyclohexyl-CH$_2$— |
| 631 | C - S | a - aj | OH | cyclohexyl-CH$_2$— |
| 632 | C - S | a - aj | —CH$_3$ | cyclohexyl-CH$_2$— |
| 633 | C - S | a - aj | —CH$_2$CH$_3$ | cyclohexyl-CH$_2$— |
| 634 | C - S | a - aj | —OCH$_3$ | cyclohexyl-CH$_2$— |
| 635 | C - S | a - aj | —CF$_3$ | cyclohexyl-CH$_2$— |
| 636 | A - S | a - aj | H | phenyl |
| 637 | C - S | a - aj | F | phenyl |
| 638 | C - S | a - aj | Cl | phenyl |
| 639 | C - S | a - aj | OH | phenyl |
| 640 | C - S | a - aj | —CH$_3$ | phenyl |
| 641 | C - S | a - aj | —CH$_2$CH$_3$ | phenyl |
| 642 | C - S | a - aj | —OCH$_3$ | phenyl |
| 643 | C - S | a - aj | —CF$_3$ | phenyl |
| 644 | A - S | a - aj | H | 2-F-phenyl |
| 645 | C - S | a - aj | F | 2-F-phenyl |
| 646 | C - S | a - aj | Cl | 2-F-phenyl |
| 647 | C - S | a - aj | OH | 2-F-phenyl |
| 648 | C - S | a - aj | —CH$_3$ | 2-F-phenyl |
| 649 | C - S | a - aj | —CH$_2$CH$_3$ | 2-F-phenyl |
| 650 | C - S | a - aj | —OCH$_3$ | 2-F-phenyl |
| 651 | C - S | a - aj | —CF$_3$ | 2-F-phenyl |
| 652 | A - S | a - aj | H | 3-F-phenyl |
| 653 | C - S | a - aj | F | 3-F-phenyl |
| 654 | C - S | a - aj | Cl | 3-F-phenyl |
| 655 | C - S | a - aj | OH | 3-F-phenyl |
| 656 | C - S | a - aj | —CH$_3$ | 3-F-phenyl |
| 657 | C - S | a - aj | —CH$_2$CH$_3$ | 3-F-phenyl |
| 658 | C - S | a - aj | —OCH$_3$ | 3-F-phenyl |
| 659 | C - S | a - aj | —CF$_3$ | 3-F-phenyl |
| 660 | A - S | a - aj | H | 4-F-phenyl |
| 661 | C - S | a - aj | F | 4-F-phenyl |
| 662 | C - S | a - aj | Cl | 4-F-phenyl |
| 663 | C - S | a - aj | OH | 4-F-phenyl |
| 664 | C - S | a - aj | —CH$_3$ | 4-F-phenyl |
| 665 | C - S | a - aj | —CH$_2$CH$_3$ | 4-F-phenyl |
| 666 | C - S | a - aj | —OCH$_3$ | 4-F-phenyl |
| 667 | C - S | a - aj | —CF$_3$ | 4-F-phenyl |
| 668 | A - S | a - aj | H | 3-Cl-phenyl |
| 669 | C - S | a - aj | F | 3-Cl-phenyl |
| 670 | C - S | a - aj | Cl | 3-Cl-phenyl |

TABLE 2-continued

| | | | | |
|---|---|---|---|---|
| 671 | C - S | a - aj | OH | 3-Cl-phenyl |
| 672 | C - S | a - aj | —CH$_3$ | 3-Cl-phenyl |
| 673 | C - S | a - aj | —CH$_2$CH$_3$ | 3-Cl-phenyl |
| 674 | C - S | a - aj | —OCH$_3$ | 3-Cl-phenyl |
| 675 | C - S | a - aj | —CF$_3$ | 3-Cl-phenyl |
| 676 | A - S | a - aj | H | 4-Cl-phenyl |
| 677 | C - S | a - aj | F | 4-Cl-phenyl |
| 678 | C - S | a - aj | Cl | 4-Cl-phenyl |
| 679 | C - S | a - aj | OH | 4-Cl-phenyl |
| 680 | C - S | a - aj | —CH$_3$ | 4-Cl-phenyl |
| 681 | C - S | a - aj | —CH$_2$CH$_3$ | 4-Cl-phenyl |
| 682 | C - S | a - aj | —OCH$_3$ | 4-Cl-phenyl |
| 683 | C - S | a - aj | —CF$_3$ | 4-Cl-phenyl |
| 684 | A - S | a - aj | H | 3-Me-phenyl |
| 685 | C - S | a - aj | F | 3-Me-phenyl |
| 686 | C - S | a - aj | Cl | 3-Me-phenyl |
| 687 | C - S | a - aj | OH | 3-Me-phenyl |
| 688 | C - S | a - aj | —CH$_3$ | 3-Me-phenyl |
| 689 | C - S | a - aj | —CH$_2$CH$_3$ | 3-Me-phenyl |
| 690 | C - S | a - aj | —OCH$_3$ | 3-Me-phenyl |
| 691 | C - S | a - aj | —CF$_3$ | 3-Me-phenyl |
| 692 | A - S | a - aj | H | 4-Me-phenyl |
| 693 | C - S | a - aj | F | 4-Me-phenyl |
| 694 | C - S | a - aj | Cl | 4-Me-phenyl |
| 695 | C - S | a - aj | OH | 4-Me-phenyl |
| 696 | C - S | a - aj | —CH$_3$ | 4-Me-phenyl |
| 697 | C - S | a - aj | —CH$_2$CH$_3$ | 4-Me-phenyl |
| 698 | C - S | a - aj | —OCH$_3$ | 4-Me-phenyl |
| 699 | C - S | a - aj | —CF$_3$ | 4-Me-phenyl |
| 700 | A - S | a - aj | H | 3-MeO-phenyl |
| 701 | C - S | a - aj | F | 3-MeO-phenyl |
| 702 | C - S | a - aj | Cl | 3-MeO-phenyl |
| 703 | C - S | a - aj | OH | 3-MeO-phenyl |
| 704 | C - S | a - aj | —CH$_3$ | 3-MeO-phenyl |
| 705 | C - S | a - aj | —CH$_2$CH$_3$ | 3-MeO-phenyl |
| 706 | C - S | a - aj | —OCH$_3$ | 3-MeO-phenyl |
| 707 | C - S | a - aj | —CF$_3$ | 3-MeO-phenyl |
| 708 | A - S | a - aj | H | 4-MeO-phenyl |
| 709 | C - S | a - aj | F | 4-MeO-phenyl |
| 710 | C - S | a - aj | Cl | 4-MeO-phenyl |
| 711 | C - S | a - aj | OH | 4-MeO-phenyl |
| 712 | C - S | a - aj | —CH$_3$ | 4-MeO-phenyl |
| 713 | C - S | a - aj | —CH$_2$CH$_3$ | 4-MeO-phenyl |
| 714 | C - S | a - aj | —OCH$_3$ | 4-MeO-phenyl |
| 715 | C - S | a - aj | —CF$_3$ | 4-MeO-phenyl |
| 716 | A - S | a - aj | H | 3-F$_3$C-phenyl |
| 717 | C - S | a - aj | F | 3-F$_3$C-phenyl |
| 718 | C - S | a - aj | Cl | 3-F$_3$C-phenyl |
| 719 | C - S | a - aj | OH | 3-F$_3$C-phenyl |
| 720 | C - S | a - aj | —CH$_3$ | 3-F$_3$C-phenyl |
| 721 | C - S | a - aj | —CH$_2$CH$_3$ | 3-F$_3$C-phenyl |
| 722 | C - S | a - aj | —OCH$_3$ | 3-F$_3$C-phenyl |
| 723 | C - S | a - aj | —CF$_3$ | 3-F$_3$C-phenyl |
| 724 | A - S | a - aj | H | 4-F$_3$C-phenyl |
| 725 | C - S | a - aj | F | 4-F$_3$C-phenyl |
| 726 | C - S | a - aj | Cl | 4-F$_3$C-phenyl |
| 727 | C - S | a - aj | OH | 4-F$_3$C-phenyl |
| 728 | C - S | a - aj | —CH$_3$ | 4-F$_3$C-phenyl |
| 729 | C - S | a - aj | —CH$_2$CH$_3$ | 4-F$_3$C-phenyl |
| 730 | C - S | a - aj | —OCH$_3$ | 4-F$_3$C-phenyl |
| 731 | C - S | a - aj | —CF$_3$ | 4-F$_3$C-phenyl |

Utility

Aβ production has been implicated in the pathology of Alzheimer's Disease (AD). The compounds of the present invention have utility for the prevention and treatment of AD by inhibiting Aβ production. Methods of treatment target formation of Aβ production through the enzymes involved in the proteolytic processing of β amyloid precursor protein. Compounds that inhibit β or γ secretase activity, either directly or indirectly, control the production of Aβ. Such inhibition of β or γ secretases reduces production of Aβ, and is expected to reduce or prevent the neurological disorders associated with Aβ protein, such as Alzheimer's Disease.

Cellular screening methods for inhibitors of Aβ production, testing methods for the in vivo suppression of Aβ production, and assays for the detection of secretase activity are known in the art and have been disclosed in numerous publications, including J.Med.Chem. 1999, 42, 3889–3898, PCT publication number WO 98/22493, EPO publication number 0652009, U.S. Pat. Nos. 5,703,129 and 5,593,846; all hereby incorporated by reference.

The compounds of the present invention have utility for the prevention and treatment of disorders involving Aβ production, such as cerebrovascular disorders.

Compounds of Formula (I) are expected to possess γ-secretase inhibitory activity. The γ-secretase inhibitory activity of the compounds of the present invention is demonstrated using assays for such activity, for example, using the assay described below. Compounds of the present invention have been shown to inhibit the activity of γ-secretase, as determined by the Aβ immunoprecipitation assay.

Compounds provided by this invention should also be useful as standards and reagents in determining the ability of a potential pharmaceutical to inhibit Aβ production. These would be provided in commercial kits comprising a compound of this invention.

As used herein "$\mu$g" denotes microgram, "mg" denotes milligram, "g" denotes gram, "$\mu$L" denotes microliter, "mL" denotes milliliter, "L" denotes liter, "nM" denotes nanomolar, "$\mu$M" denotes micromolar, "mM" denotes millimolar, "M" denotes molar, "nm" denotes nanometer, "SDS" denotes sodium dodecyl sulfate, and "DMSO" denotes dimethyl sulfoxide, and "EDTA" denotes ethylenediaminetetraacetato.

A compound is considered to be active if it has an $IC_{50}$ or $K_i$ value of less than about 100 $\mu$M for the inhibition of Aβ production. Preferrably the $IC_{50}$ or $K_i$ value is less than about 10 $\mu$M; more preferrably the $IC_{50}$ or $K_i$ value is less than about 0.1 $\mu$M. Compounds of the present invention have been shown to inhibit Aβ protein production with an $IC_{50}$ or $K_i$ value of less than 100 $\mu$M.

β Amyloid Precursor Protein Accumulation Assay

A novel assay to evaluate the accumulation of Aβ protein was developed to detect potential inhibitors of secretase. The assay uses the N 9 cell line, characterized for expression of exogenous APP by immunoblotting and immunoprecipitation.

The effect of test compounds on the accumulation of Aβ in the conditioned medium is tested by immunoprecipitation. Briefly, N 9 cells are grown to confluency in 6-well plates and washed twice with 1×Hank's buffered salt solution. The cells are starved in methionine/cysteine deficient media for 30 min, followed by replacement with fresh deficient media containing 150 uCi S35 Translabel (Amersham). Test compounds dissolved in DMSO (final concentration 1%) are added together with the addition of radiolabel. The cells are incubated for 4 h at 37° C. in a tissue culture incubator.

At the end of the incubation period, the conditioned medium is harvested and pre-cleared by the addition of 5 $\mu$l normal mouse serum and 50 ul of protein A Sepharose (Pharmacia), mixed by end-over-end rotation for 30 minutes at 4° C., followed by a brief centrifugation in a microfuge. The supernatant is then harvested and transferred to fresh tubes containing 5 ug of a monoclonal antibody (clone 1101.1; directed against an internal peptide sequence in Aβ) and 50 $\mu$l protein A Sepharose. After incubation overnight at 4° C., the samples are washed three times with high salt washing buffer (50 mM Tris, pH 7.5, 500 mM NaCl, 5 mM EDTA, 0.5% Nonidet P-40), three times with low salt wash buffer (50 mM Tris, pH 7.5, 150 mM NaCl, 5 mM EDTA, 0.5% Nonidet P-40), and three times with 10 mM Tris, pH 7.5. The pellet after the last wash is resuspended in SDS sample buffer (Laemmli, 1970) and boiled for 3 minutes. The supernatant is then fractionated on either 10–20% Tris/Tricine SDS gels or on 16.5% Tris/Tricine SDS gels. The gels are dried and exposed to X-ray film or analyzed by phosphorimaging. The resulting image is analyzed for the presence of Aβ polypeptides. The steady-state level of Aβ in the presence of a test compound is compared to wells treated with DMSO (1%) alone. A typical test compound blocks Aβ accumulation in the conditioned medium, and is therefore considered active, with an $IC_{50}$ less than 100 $\mu$M.

C-Terminus β Amyloid Precursor Protein Accumulation Assay

The effect of test compounds on the accumulation of C-terminal fragments is determined by immunoprecipitation of APP and fragments thereof from cell lysates. N 9 cells are metabolically labeled as above in the presence or absence of test compounds. At the end of the incubation period, the conditioned medium are harvested and cells lysed in RIPA buffer (10 mM Tris, pH 8.0 containing 1% Triton X-100, 1% deoxycholate, 0.1% SDS, 150 mM NaCl, 0.125% $NaN_3$). Again, lysates are precleared with 5 ul normal rabbit serum/50 ul protein A Sepharose, followed by the addition of BC-1 antiserum (15 $\mu$l;) and 50 $\mu$l protein A Sepharose for 16 hours at 4° C. The immunoprecipitates are washed as above, bound proteins eluted by boiling in SDS sample buffer and fractionated by Tris/Tricine SDS-PAGE. After exposure to X-ray film or phosphorimager, the resulting images are analyzed for the presence of C-terminal APP fragments. The steady-state level of C-terminal APP fragments is compared to wells treated with DMSO (1%) alone. A typical test compound stimulates C-terminal fragment accumulation in the cell lysates, and is therefore considered active, with an $IC_{50}$ less than 100 $\mu$M.

Aβ Immunoprecipitation Assay

This immunoprecipitation assay is specific for γ secretase (i.e., proteolytic activity required to generate the C-terminal end of Aβ either by direct cleavage or generating a C-terminal extended species which is subsequently further proteolyzed). N 9 cells are pulse labeled in the presence of a reported γ secretase inhibitor (MDL 28170) for 1 h, followed by washing to remove radiolabel and MDL 28170. The media is replaced and test compounds are added. The cells are chased for increasing periods of times and A β is isolated from the conditioned medium and C-terminal fragments from cell lysates (see above). The test compounds are characterized whether a stabilization of C-terminal fragments is observed and whether Aβ is generated from these accumulated precursor. A typical test compound prevents the generation of Aβ out of accumulated C-terminal fragments and is considered active with an $IC_{50}$ less than 100 $\mu$M.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to prevent or treat neurological disorders related to β-amyloid production or accumulation, such as Alzheimer's disease and Down's Syndrome.

The compounds of this invention can be administered by any means that produces contact of the active agent with the agent's site of action in the body of a host, such as a human or a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient,and the effect desired. An ordinarily skilled physician or veterinarian can readily determine and prescribe the effective amount of the drug required to prevent, counter, or arrest the progress of the condition.

Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid. and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

What is claimed is:

1. A compound of Formula (I):

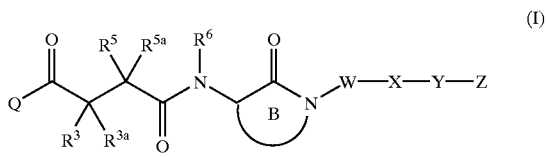

or a pharmaceutically acceptable salt thereof, wherein:
Q is —NR$^1$R$^2$;
R$^1$ is H, C$_1$–C$_4$ alkyl, phenyl, benzyl, C$_3$–C$_6$ cycloalkyl, or (C$_3$–C$_6$ cycloalkyl)methyl-;
R$^2$ is H, C$_1$–C$_4$ alkyl, OH, C$_1$–C$_4$ alkoxy, phenyl, benzyl, C$_3$–C$_6$ cycloalkyl, or (C$_3$–C$_6$ cycloalkyl)methyl-;
R$^3$ and R$^{3a}$ may be combined to form a 3–8 membered carbocyclic moiety;
   wherein said 3–8 membered carbocyclic moiety is saturated or partially unsaturated;
   wherein said 3–8 membered carbocyclic moiety may optionally contain a heteroatom selected from —O—, —S—, —S(=O)—, —S(=O)$_2$—, —N=, —NH—, and —N(R$^{20}$)—, and
   wherein said 3–8 membered carbocyclic moiety is substituted with 0–4 R$^4$;
additionally, two R$^4$ substituents on adjacent atoms may be combined to form a benzo fused radical; wherein said benzo fused radical is substituted with 0–4 R$^{23}$;

additionally, two R⁴ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{23}$;

additionally, two $R^4$ substituents on the same or adjacent carbon atoms may be combined to form a $C_3$–$C_6$ carbocycle substituted with 0–3 $R^{23}$;

alternatively, $R^3$ is H; $C_1$–$C_6$ alkyl substituted with 0–3 $R^4$;

$C_2$–$C_6$ alkenyl substituted with 0–3 $R^4$; or $C_2$–$C_6$ alkynyl substituted with 0–3 $R^4$; and $R^{3a}$ is H, $C_1$–$C_6$ alkyl, or $C_2$–$C_6$ alkenyl;

$R^4$, at each occurrence, is independently selected from H, OH, Cl, F, Br, I, CN, $NO_2$, $CF_3$, acetyl, $SCH_3$, $S(=O)CH_3$, $S(=O)_2CH_3$, $NR^{15}R^{16}$, $OR^{14a}$, $C_1$–$C_4$ alkyl, $C_2$–$C_6$ alkenyl, alkynyl, $C_1$–$C_4$ alkoxy, $C_1$–$C_4$ haloalkyl, $C_1$–$C_4$ haloalkoxy, and $C_1$–$C_4$ haloalkyl-S—, $C_3$–$C_6$ carbocycle, aryl, and a 5 to 6 membered heterocycle containing 1 to 4 heteroatoms selected from nitrogen, oxygen, and sulphur;

$R^5$ is H, $C_1$–$C_6$ alkoxy;
$C_1$–$C_6$ alkyl substituted with 0–3 $R^{5b}$;
$C_2$–$C_6$ alkenyl substituted with 0–3 $R^{5b}$;
$C_2$–$C_6$ alkynl substituted with 0–3 $R^{5b}$;
$C_3$–$C_{10}$ carbocycle substituted with 0–3 $R^{5c}$;
aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5a}$ is H, $C_1$–$C_4$ alkyl, or $C_2$–$C_4$ alkenyl;
$R^{5b}$, at each occurrence, is independently selected from: H, $C_1$–$C_6$ alkyl, $CF_3$, $OR^{14}$, Cl, F, Br, I, =O, CN, $NO_2$, $NR^{15}R^{16}$;
$C_3$–$C_{10}$ carbocycle substituted with 0–3 $R^{5c}$;
aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

alternatively, $R^5$ and $R^{5a}$ may be combined to form a 3–8 membered carbocyclic moiety;
wherein said 3–8 membered carbocyclic moiety is saturated or partially unsaturated;
wherein said 3–8 membered carbocyclic moiety may optionally contain a heteroatom selected from —O—, —S—, —S(=O)—, —S(=O)$_2$—, —N=, —NH—, and —N($R^{20}$)—, and
wherein said 3–8 membered carbocyclic moiety is substituted with 0–4 $R^{5c}$;

provided at least:
1) $R^3$ and $R^{3a}$ are combined to form a 3–8 membered carbocyclic moiety; or
2) $R^5$ and $R^{5a}$ are combined to form a 3–8 membered carbocyclic moiety; or
3) $R^3$ and $R^{3a}$ are combined to form a 3–8 membered carbocyclic moiety and $R^5$ and $R^{5a}$ are combined to form a 3–8 membered carbocyclic moiety;

$R^6$ is H;
$C_1$–$C_6$ alkyl substituted with 0–3 $R^{6a}$;
$C_3$–$C_{10}$ carbocycle substituted with 0–3 $R^{6b}$; or
$C_6$–$C_{10}$ aryl substituted with 0–3 $R^{6b}$;

$R^{6a}$, at each occurrence, is independently selected from H, $C_1$–$C_6$ alkyl, $OR^{14}$, Cl, F, Br, I, =O, CN, $NO_2$, $NR^{15}R^{16}$, aryl or $CF_3$;

$R^{6b}$, at each occurrence, is independently selected from H, OH, Cl, F, Br, I, CN, $NO_2$, $NR^{15}R^{16}$, $CF_3$, $C_1$–$C_6$ alkyl, $C_1$–$C_4$ alkoxy, $C_1$–$C_4$ haloalkyl, and $C_1$–$C_4$ haloalkoxy;

Ring B is selected from:

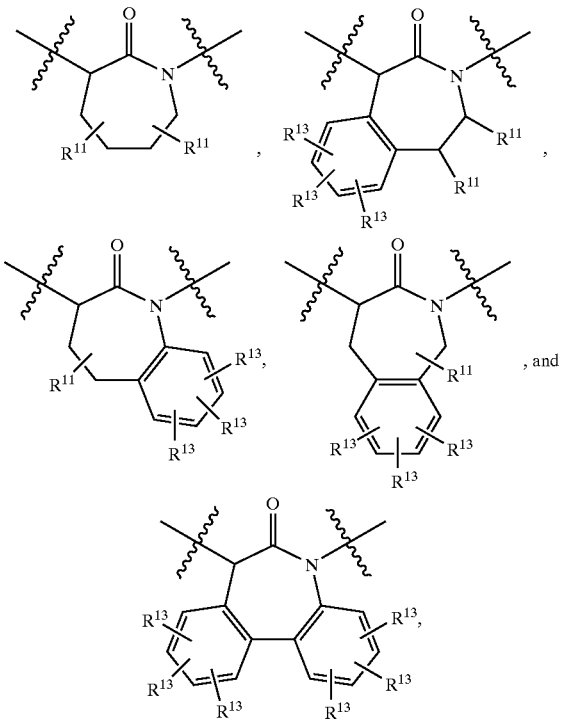

$R^{11}$, at each occurrence, is independently selected from H, $C_1$–$C_4$ alkoxy, Cl, F, Br, I, =O, CN, $NO_2$, $NR^{18}R^{19}$, $C(=O)R^{17}$, $C(=O)OR^{17}$, $C(=O)NR^{18}R^{19}$, $S(=O)_2NR^{18}R^{19}$, $CF_3$;
$C_1$–$C_6$ alkyl optionally substituted with 0–3 $R^{11a}$;
$C_6$–$C_{10}$ aryl substituted with 0–3 $R^{11b}$;
$C_3$–$C_{10}$ carbocycle substituted with 0–3 $R^{11b}$; or
5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$;
phenyl substituted with 0–3 $R^{11b}$;
$C_3$–$C_6$ cycloalkyl substituted with 0–3 $R^{11b}$; and
5 to 6 membered heterocycle containing 1 to 4 heteroatoms selected from nitrogen, oxygen, and sulphur, wherein said 5 to 6 membered heterocycle is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

W is a bond or —(CR$^8$R$^{8a}$)$_p$—;

p is 0, 1, 2, 3, or 4;

R$^8$ and R$^{8a}$, at each occurrence, are independently selected from H, F, C$_1$–C$_4$ alkyl, C$_2$–C$_4$ alkenyl, C$_2$–C$_4$ alkynyl and C$_3$–C$_8$ cycloalkyl;

X is a bond;
 aryl substituted with 0–3 R$^{Xb}$;
 C$_3$–C$_{10}$ carbocycle substituted with 0–3 R$^{Xb}$; or
 5 to 10 membered heterocycle substituted with 0–2 R$^{Xb}$;

R$^{Xb}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, and C$_1$–C$_4$ halothioalkoxy;

Y is a bond or —(CR$^9$R$^{9a}$)$_t$—V—(CR$^9$R$^{9a}$)$_u$—;

t is 0, 1, or 2;

u is 0, 1, or 2;

R$^9$ and R$^{9a}$, at each occurrence, are independently selected from H, F, C$_1$–C$_6$ alkyl or C$_3$–C$_8$ cycloalkyl;

V is a bond, —C(=O)—, —O—, —S—, —S(=O)—, —S(=O)$_2$—, —N(R$^{19}$)—, —C(=O)NR$^{19b}$—, —NR$^{19b}$C(=O)—, —NR$^{19b}$S(=O)$_2$—, —S(=O)$_2$NR$^{19b}$—, —NR$^{19b}$S(=O)—, —S(=O)NR$^{19b}$—, —C(=O)O—, or —OC(=O)—;

Z is H;
 C$_1$–C$_8$ alkyl substituted with 0–3 R$^{12a}$;
 C$_2$–C$_6$ alkenyl substituted with 0–3 R$^{12a}$;
 C$_2$–C$_6$ alkynyl substituted with 0–3 R$^{12a}$;
 C$_6$–C$_{10}$ aryl substituted with 0–4 R$^{12b}$;
 C$_3$–C$_{10}$ carbocycle substituted with 0–4 R$^{12b}$; or
 5 to 10 membered heterocycle containing 1 to 4 heteroatoms selected from nitrogen, oxygen, and sulphur, wherein said 5 to 10 membered heterocycle is substituted with 0–3 R$^{12b}$;

R$^{12a}$, at each occurrence, is independently selected from H, OH, Cl, F, Br, I, CN, NO$_2$, NR$^{15}$R$^{16}$, —C(=O)NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, C$_1$–C$_4$ haloalkyl-S—, aryl substituted with 0–4 R$^{12b}$;
 C$_3$–C$_{10}$ carbocycle substituted with 0–4 R$^{12b}$; or
 5 to 10 membered heterocycle containing 1 to 4 heteroatoms selected from nitrogen, oxygen, and sulphur, wherein said 5 to 10 membered heterocycle is substituted with 0–3 R$^{12b}$;

R$^{12b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_3$–C$_6$ cycloalkyl, C$_1$–C$_6$ alkyl, C$_1$–C$_4$ alkoxy, C$_1$–C$_4$ haloalkyl, C$_1$–C$_4$ haloalkoxy, C$_1$–C$_4$ haloalkyl-S, and aryl substituted with 0–3 R$^{12c}$;

R$^{12c}$, at each occurrence, is independently selected from H, methyl, ethyl, propyl, methoxy, ethoxy, amino, hydroxy, Cl, F, Br, I, CF$_3$, SCH$_3$, S(O)CH$_3$, SO$_2$CH$_3$, —N(CH$_3$)$_2$, N(CH$_3$)H, CN, NO$_2$, OCF$_3$, C(=O)CH$_3$, CO$_2$H, CO$_2$CH$_3$, and C$_1$–C$_3$ haloalkyl;

R$^{13}$, at each occurrence, is independently selected from H, OH, C$_1$–C$_6$ alkyl, C$_1$–C$_4$ alkoxy, Cl, F, Br, I, CN, NO$_2$, NR$^{15}$R$^{16}$, and CF$_3$;

R$^{14}$ is H, phenyl, benzyl, C$_1$–C$_6$ alkyl, C$_2$–C$_6$ alkoxyalkyl, or C$_3$–C$_6$ cycloalkyl;

R$^{14a}$ is H, phenyl, benzyl, or C$_1$–C$_4$ alkyl;

R$^{15}$, at each occurrence, is independently selected from H, C$_1$–C$_6$ alkyl, benzyl, phenethyl, (C$_1$–C$_6$ alkyl)-C(=O)—, and (C$_1$–C$_6$ alkyl)-S(=O)$_2$—;

R$^{16}$, at each occurrence, is independently selected from H, C$_1$–C$_6$ alkyl, benzyl, phenethyl, (C$_1$–C$_6$ alkyl)-C(=O)—, and (C$_1$–C$_6$ alkyl)-S(=O)$_2$—;

R$^{17}$ is H, C$_1$–C$_6$ alkyl, C$_2$–C$_6$ alkoxyalkyl, aryl substituted by 0–4 R$^{17a}$, or —CH$_2$-aryl substituted by 0–4 R$^{17a}$;

R$^{17a}$ is H, methyl, ethyl, propyl, butyl, methoxy, ethoxy, propoxy, butoxy, —OH, F, Cl, Br, I, CF$_3$, OCF$_3$, SCH$_3$, S(O)CH$_3$, SO$_2$CH$_3$, —NH$_2$, —N(CH$_3$)$_2$, or C$_1$–C$_4$ haloalkyl;

R$^{18}$, at each occurrence, is independently selected from H, C$_1$–C$_6$ alkyl, phenyl, benzyl, phenethyl, (C$_1$–C$_6$ alkyl)-C(=O)—, and (C$_1$–C$_6$ alkyl)-S(=O)$_2$—;

R$^{19}$, at each occurrence, is independently selected from H, OH, C$_1$–C$_6$ alkyl, phenyl, benzyl, phenethyl, (C$_1$–C$_6$ alkyl)-C(=O)—, and (C$_1$–C$_6$ alkyl)-S(=O)$_2$—;

additionally, R$^{18}$ and R$^{19}$, when substituents on the same atom, may be combined to form a 3 to 6 membered heterocyclic ring;

R$^{19b}$, at each occurrence, is independently is H or C$_1$–C$_4$ alkyl;

R$^{20}$ is H, C(=O)R$^{17}$, C(=O)OR$^{17}$, C(=O)NR$^{18}$R$^{19}$, S(=O)$_2$NR$^{18}$R$^{19}$, S(=O)$_2$R$^{17}$;
 C$_1$–C$_6$ alkyl optionally substituted with 0–3 R$^{20a}$; or
 C$_6$–C$_{10}$ aryl substituted with 0–4 R$^{20b}$;

R$^{20a}$, at each occurrence, is independently selected from H, C$_1$–C$_4$ alkyl, OR$^{14}$, Cl, F, Br, I, =O, CN, NO$_2$, NR$^{15}$R$^{16}$, CF$_3$, or aryl substituted with 0–4 R$^{20b}$;

R$^{20b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_4$ alkyl, C$_1$–C$_4$ alkoxy, C$_1$–C$_4$ haloalkyl, C$_1$–C$_4$ haloalkoxy, and C$_1$–C$_4$ haloalkyl-S—;

R$^{23}$, at each occurrence, is independently selected from H, OH, C$_1$–C$_6$ alkyl, C$_1$–C$_4$ alkoxy, Cl, F, Br, I, CN, NO$_2$, NR$^{15}$R$^{16}$, and CF$_3$.

2. A compound of claim 1 of Formula (II):

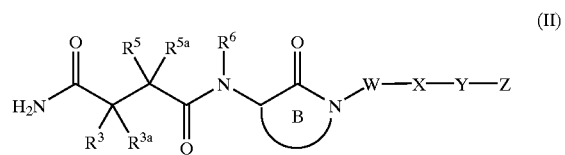

(II)

or a pharmaceutically acceptable salt thereof, wherein:

R$^3$ and R$^{3a}$ may be combined to form a 3–8 membered carbocyclic moiety selected from cyclopropyl, cyclobutyl, cyclopentyl, cyclopentenyl, cyclohexyl, and cyclohexenyl;

alternatively, R$^3$ and R$^{3a}$ are independently selected from the group H, C$_1$–C$_6$ alkyl, C$_2$–C$_6$ alkenyl, and C$_2$–C$_6$ alkynyl;

R$^5$ is H;
 C$_1$–C$_4$ alkyl substituted with 0–1 R$^{5b}$;
 C$_2$–C$_4$ alkenyl substituted with 0–1 R$^{5b}$;
 C$_2$–C$_4$ alkynyl substituted with 0–1 R$^{5b}$;

R$^{5a}$ is H, C$_1$–C$_4$ alkyl, or C$_2$–C$_4$ alkenyl;

R$^{5b}$ is selected from:
 H, methyl, ethyl, propyl, butyl, CF$_3$, Cl, F, NR$^{15}$R$^{16}$, cyclopropyl, cyclobutyl, cyclopentyl, and cyclohexyl;

alternatively, R$^5$ and R$^{5a}$ may be combined to form a 3–8 membered carbocyclic moiety selected from cyclopropyl, cyclobutyl, cyclopentyl, cyclopentenyl, cyclohexyl and cyclohexenyl;
provided at least:
1) $R^3$ and $R^{3a}$ are combined to form a 3–8 membered carbocyclic moiety; or
2) $R^5$ and $R^{5a}$ are combined to form a 3–8 membered carbocyclic moiety; or
3) $R^3$ and $R^{3a}$ are combined to form a 3–8 membered carbocyclic moiety and $R^5$ and $R^{5a}$ are combined to form a 3–8 membered carbocyclic moiety;
Ring B is selected from:

3. A compound, according to claim 1, of Formula (I):

(I)

or a pharmaceutically acceptable salt thereof, wherein:
Q is —$NR^1R^2$;
$R^1$ is H, methyl, ethyl, propyl, butyl, phenyl, benzyl, cyclopropyl, cyclobutyl, cyclopentyl, cyolohexyl, cyclopropylmethyl, cyclobutylmethyl, cyclopentylmethyl, or cyclohexylmethyl;
$R^2$ is H, methyl, ethyl, propyl, butyl, OH, methoxy, ethoxy, propoxy, phenyl, benzyl, cyclopropyl, cyclobutyl, cyclopentyl, cyclohexyl, cyclopropylmethyl, cyclobutylmethyl, cyclopentylmethyl, or cyclohexylmethyl;
$R^3$ and $R^{3a}$ are may be combined to form a 3–8 membered carbocyclic moiety seleted from cyclopropyl, cyclobutyl, cyclopentyl, cyclopentenyl, cyclohexyl, and cyclohexenyl
wherein said 3–8 membered carbocyclic moiety is saturated or partially unsaturated;

wherein said 3–8 membered carbocyclic moiety may optionally contain a heteroatom selected from —O—, —S—, —S(=O)—, —S(=O)$_2$—, —N=, —NH—, and —N($R^{20}$)—, and
wherein said 3–8 membered carbocyclic moiety is substituted with 0–4 $R^4$;
alternatively, $R^3$ and $R^{3a}$ are independently selected from the group H, $C_1$–$C_6$ alkyl, $C_2$–$C_6$ alkenyl, and $C_2$–$C_6$ alkynyl;
additionally, two $R^4$ substituents on adjacent atoms may be combined to form a benzo fused radical; wherein said benzo fused radical is substituted with 0–4 $R^{23}$;
additionally, two $R^4$ substituents on adjacent atoms may be combined to form a 5 to 6 membered heteroaryl fused radical, wherein said 5 to 6 membered heteroaryl fused radical comprises 1 or 2 heteroatains selected from N, O, and S; wherein said 5 to 6 membered hetetoaryl fused radical is substituted with 0–3 $R^{23}$;
additionally, two $R^4$ substituents on the same or adjacent carbon atoms may be combined to form a $C_3$–$C_6$ carbocycle substituted with 0–3 $R^{23}$;
$R^4$, at each occurrence, is independently selected from H, OH, Cl, F, Br, I, CN, $NO_2$, $CF_3$, acetyl, $SCH_3$, S(=O)$CH_3$, S(=O)$_2$$CH_3$, $NR^{15}R^{16}$, $OR^{14a}$, $C_1$–$C_4$ alkyl, $C_2$–$C_6$ alkenyl, alkynyl, $C_1$–$C_4$ alkoxy, $C_1$–$C_4$ haloalkyl, $C_1$–$C_4$ haloalkoxy, and $C_1$–$C_4$ haloalkyl-S—, $C_3$–$C_6$ carbocycle, aryl, and a
5 to 6 membered heterocycle containing 1 to 4 heteroatoms selected from nitrogen, oxygen, and sulphur;
$R^5$ is H, $C_1$–$C_6$ alkoxy;
$C_1$–$C_6$ alkyl substituted with 0–3 $R^{5b}$;
$C_2$–$C_6$ alkenyl substituted with 0–3 $R^{5b}$;
$C_2$–$C_6$ alkynyl substituted with 0–3 $R^{5b}$;
$C_3$–$C_{10}$ carbocycle substituted with 0–3 $R^{5c}$;
aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5a}$ is H, $C_1$–$C_4$ alkyl, or $C_2$–$C_4$ alkenyl;
$R^{5b}$, at each occurrence, is independently selected from: H, $C_1$–$C_6$ alkyl, $CF_3$, $OR^{14}$, Cl, F, Br, I, =O, CN, $NO_2$, $NR^{15}R^{16}$;
$C_3$–$C_{10}$ carbocycle substituted with 0–3 $R^{5c}$;
aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5c}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2$$CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;
$R^6$ is H;
$C_1$–$C_6$ alkyl substituted with 0–3 $R^{6a}$;
$C_3$–$C_{10}$ carbocycle substituted with 0–3 $R^{6b}$; or
$C_6$–$C_{10}$ aryl substituted with 0–3 $R^{6b}$;
$R^{6a}$, at each occurrence, is independently selected from H, $C_1$–$C_6$ alkyl, $OR^{14}$, Cl, F, Br, I, =O, CN, $NO_2$, $NR^{15}R^{16}$, aryl or $CF_3$;
$R^{6b}$, at each occurrence, is independently selected from H, OH, Cl, F, Br, I, CN, $NO_2$, $NR^{15}R^{16}$, $CF_3$, $C_1$–$C_6$ alkyl, $C_1$–$C_4$ alkoxy, $C_1$–$C_4$ haloalkyl, and $C_1$–$C_4$ haloalkoxy;

Ring B is selected from:

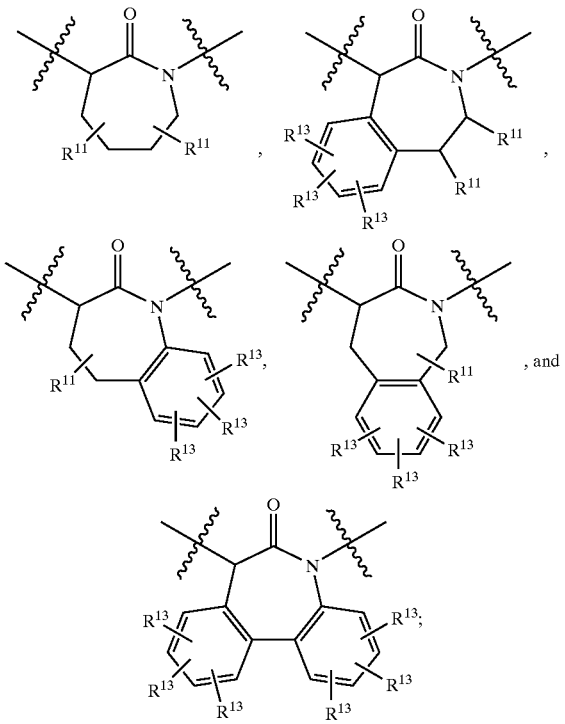

R[11], at each occurrence, is independently selected from H, $C_1$–$C_4$ alkoxy, Cl, F, Br, I, =O, CN, $NO_2$, $NR^{18}R^{19}$, $C(=O)R^{17}$, $C(=O)OR^{17}$, $C(=O)NR^{18}R^{19}$, $S(=O)_2NR^{18}R^{19}$, $CF_3$;
  $C_1$–$C_6$ alkyl optionally substituted with 0–3 $R^{11a}$;
  aryl substituted with 0–3 $R^{11b}$;
  $C_3$–$C_{10}$ carbocycle substituted with 0–3 $R^{11b}$; or
  5 to 10 membered heterocycle containing 1 to 4 heteroatoms selected from nitrogen, oxygen, and sulphur, wherein said 5 to 10 membered heterocycle is substituted with 0–3 $R^{11b}$;

R[11a], at each occurrence, is independently selected from H, $C_1$–$C_6$ alkyl, $OR^{14}$, Cl, F, Br, I, =O, CN, $NO_2$, $NR^{15}R^{16}$, $CF_3$;
  phenyl substituted with 0–3 $R^{11b}$;
  $C_3$–$C_6$ cycloalkyl substituted with 0–3 $R^{11b}$; and
  5 to 6 membered heterocycle containing 1 to 4 heteroatoms selected from nitrogen, oxygen, and sulphur, wherein said 5 to 6 membered heterocycle is substituted with 0–3 $R^{11b}$;

R[11b], at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

W is a bond or —$(CR^8R^{8a})_p$—;
p is 0, 1, 2, 3, or 4;
$R^8$ and $R^{8a}$, at each occurrence, are independently selected from H, F, $C_1$–$C_4$ alkyl, $C_2$–$C_4$ alkenyl, $C_2$–$C_4$ alkynyl and $C_3$–$C_8$ cycloalkyl;
X is a bond;
  aryl substituted with 0–3 $R^{Xb}$;
  $C_3$–$C_{10}$ carbocycle substituted with 0–3 $R^{Xb}$; or
  5 to 10 membered heterocycle substituted with 0–2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ halothioalkoxy;
Y is a bond or —$(CR^9R^{9a})_t$—V—$(CR^9R^{9a})_u$—;
t is 0, 1, or 2;
u is 0, 1, or 2;
$R^9$ and $R^{9a}$, at each occurrence, are independently selected from H, F, $C_1$–$C_6$ alkyl or $C_3$–$C_8$ cycloalkyl;
V is a bond, —C(=O)—, —O—, —S—, —S(=O)—, —$S(=O)_2$—, —$N(R^{19})$—, —$C(=O)NR^{19b}$—, —$NR^{19b}C(=O)$—, —$NR^{19b}S(=O)_2$—, —$S(=O)_2NR^{19b}$—, —$NR^{19b}S(=O)$—, —$S(=O)NR^{19b}$—, —C(=O)O—, or —OC(=O)—;
Z is H;
  $C_1$–$C_8$ alkyl substituted with 0–3 $R^{12a}$;
  $C_2$–$C_6$ alkenyl substituted with 0–3 $R^{12a}$;
  $C_2$–$C_6$ alkynyl substituted with 0–3 $R^{12a}$;
  aryl substituted with 0–4 $R^{12b}$;
  $C_3$–$C_{10}$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from H, OH, Cl, F, Br, I, CN, $NO_2$, $NR^{15}R^{16}$, —$C(=O)NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, aryl substituted with 0–4 $R^{12b}$;
  $C_3$–$C_{10}$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_3$–$C_6$ cycloalkyl, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S, and aryl substituted with 0–3 $R^{12c}$;

$R^{12c}$, at each occurrence, is independently selected from H, methyl, ethyl, propyl, methoxy, ethoxy, amino, hydroxy, Cl, F, Br, I, $CF_3$, $SCH_3$, $S(O)CH_3$, $SO_2CH_3$, —$N(CH_3)_2$, $N(CH_3)H$, CN, $NO_2$, $OCF_3$, $C(=O)CH_3$, $CO_2H$, $CO_2CH_3$, and $C_1$–$C_3$ haloalkyl;
$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;
$R^{14}$ is H, phenyl, benzyl, $C_1$–$C_6$ alkyl, $C_2$–$C_6$ alkoxyalkyl, or $C_3$–$C_6$ cycloalkyl;
$R^{14a}$ is H, phenyl, benzyl, or $C_1$–$C_4$ alkyl;
$R^{15}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-$S(=O)_2$—;
$R^{16}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-$S(=O)_2$—;
$R^{17}$ is H, $C_1$–$C_6$ alkyl, $C_2$–$C_6$ alkoxyalkyl, aryl substituted by 0–4 $R^{17a}$, or —$CH_2$-aryl substituted by 0–4 $R^{17a}$;
$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(CH_3)_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

$R^{19}$, at each occurrence, is independently selected from H, OH, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

additionally, $R^{18}$ and $R^{19}$, when substituents on the same atom, may be combined to form a 3 to 6 membered heterocyclic ring;

$R^{19b}$, at each occurrence, is independently is H or $C_1$–$C_4$ alkyl;

$R^{20}$ is H, C(=O)$R^{17}$, C(=O)O$R^{17}$, C(=O)N$R^{18}R^{19}$, S(=O)$_2$N$R^{18}R^{19}$, S(=O)$_2R^{17}$;
$C_1$–$C_6$ alkyl optionally substituted with 0–3 $R^{20a}$; or aryl substituted with 0–4 $R^{20b}$;

$R^{20a}$, at each occurrence, is independently selected from H, $C_1$–$C_4$ alkyl, O$R^{14}$, Cl, F, Br, I, =O, CN, NO$_2$, N$R^{15}R^{16}$, CF$_3$, or aryl substituted with 0–4 $R^{20b}$;

$R^{20b}$, at each occurrence, is independently selected from H, OH, Cl, F, Br, I, CN, NO$_2$, N$R^{15}R^{16}$, CF$_3$, acetyl, SCH$_3$, S(=O)CH$_3$, S(=O)$_2$CH$_3$, $C_1$–$C_4$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{23}$, at each occurrence, is independently selected from H, OH, $C_1$–$C_6$ alkyl, $C_1$–$C_4$ alkoxy, Cl, F, Br, I, CN, NO$_2$, N$R^{15}R^{16}$, and CF$_3$.

4. A compound, according to claim 1, of Formula (Ia):

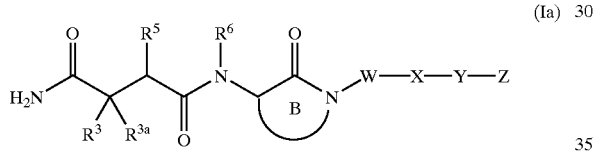

(Ia)

or a pharmaceutically acceptable salt thereof, wherein:
$R^3$ and $R^{3a}$ are combined to form a 3–8 membered carbocyclic moiety;
wherein said 3–8 membered carbocyclic moiety is saturated or partially unsaturated;
wherein said 3–8 membered carbocyclic moiety is substituted with 0–4 $R^4$;
additionally, two $R^4$ substituents on adjacent atoms may be combined to form a benzo fused radical; wherein said benzo fused radical is substituted with 0–4 $R^{23}$;
additionally, two $R^4$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{23}$;
additionally, two $R^4$ substituents on the same or adjacent carbon atoms may be combined to form a $C_3$–$C_6$ carbocycle substituted with 0–3 $R^{23}$;

$R^4$, at each occurrence, is independently selected from H, OH, Cl, F, Br, I, CN, NO$_2$, CF$_3$, acetyl, SCH$_3$, S(=O)CH$_3$, S(=O)$_2$CH$_3$, N$R^{15}R^{16}$, O$R^{14a}$, $C_1$–$C_4$ alkyl, $C_2$–$C_6$ alkenyl, alkynyl, $C_1$–$C_4$ alkoxy, $C_1$–$C_4$ haloalkyl, $C_1$–$C_4$ haloalkoxy, and $C_1$–$C_4$ haloalkyl-S—, $C_3$–$C_6$ carbocycle, aryl, and a
5 to 6 membered heterocycle containing 1 to 4 heteroatoms selected from nitrogen, oxygen, and sulphur; and $R^5$ is H, $C_1$–$C_4$ alkoxy;
$C_1$–$C_6$ alkyl substituted with 0–3 $R^{5b}$;
$C_2$–$C_6$ alkenyl substituted with 0–3 $R^{5b}$;
$C_2$–$C_6$ alkynyl substituted with 0–3 $R^{5b}$;
$C_3$–$C_{10}$ carbocycle substituted with 0–3 $R^{5c}$;
$C_6$–$C_{10}$ aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5b}$, at each occurrence, is independently selected from: H, $C_1$–$C_6$ alkyl, CF$_3$, O$R^{14}$, Cl, F, Br, I, =O, CN, NO$_2$, N$R^{15}R^{16}$;
$C_3$–$C_{10}$ carbocycle substituted with 0–3 $R^{5c}$;
aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, NO$_2$, N$R^{15}R^{16}$, CF$_3$, acetyl, SCH$_3$, S(=O)CH$_3$, S(=O)$_2$CH$_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^6$ is H, methyl, or ethyl;
Ring B is selected from:

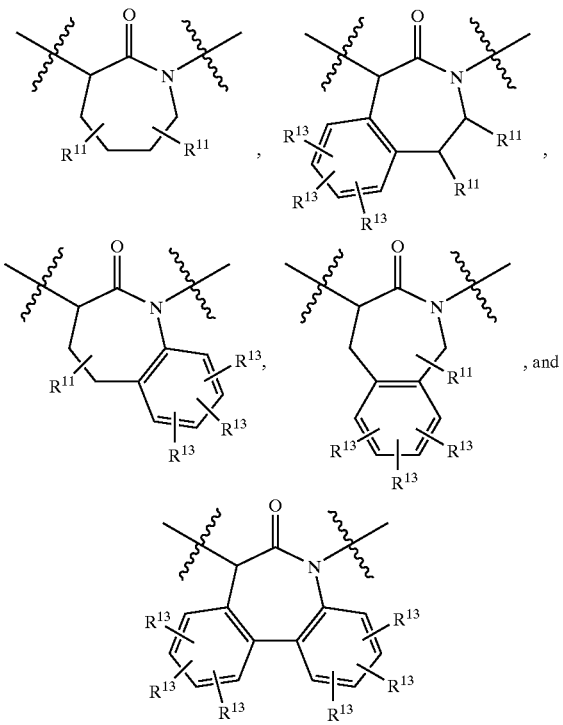

$R^{11}$, at each occurrence, is independently selected from H, $C_1$–$C_4$ alkoxy, Cl, F, Br, I, =O, CN, NO$_2$, N$R^{18}R^{19}$, C(=O)$R^{17}$, C(=O)O$R^{17}$, C(=O)N$R^{18}R^{19}$, S(=O)$_2$N$R^{18}R^{19}$, CF$_3$;
$C_1$–$C_6$ alkyl optionally substituted with 0–3 $R^{11a}$;
aryl substituted with 0–3 $R^{11b}$;
$C_3$–$C_{10}$ carbocycle substituted with 0–3 $R^{11b}$; or
5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11a}$, at each occurrence, is independently selected from H, $C_1$–$C_6$ alkyl, O$R^{14}$, Cl, F, Br, I, =O, CN, NO$_2$, N$R^{15}R^{16}$, CF$_3$;

phenyl substituted with 0–3 $R^{11b}$;

$C_3$–$C_6$ cycloalkyl substituted with 0–3 $R^{11b}$; and 5 to 6 membered heterocycle containing 1 to 4 heteroatoms selected from nitrogen, oxygen, and sulphur, wherein said 5 to 6 membered heterocycle is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

W is a bond or —$(CH_2)_p$—;

p is 1 or 2;

X is a bond;

phenyl substituted with 0–2 $R^{Xb}$;

$C_3$–$C_6$ carbocycle substituted with 0–2 $R^{Xb}$; or 5 to 6 membered heterocycle substituted with 0–2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_3$ haloalkyl, $C_1$–$C_3$ haloalkoxy, and $C_1$–$C_3$ halothioalkoxy;

Y is a bond, —C(=O)—, —O—, —S—, —S(=O)—, —S(=O)$_2$—, —N($R^{19}$)—, —C(=O)$NR^{19b}$—, —$NR^{19b}$C(=O)—, —$NR^{19b}$S(=O)$_2$—, —S(=O)$_2$$NR^{19b}$—, —$NR^{19b}$S(=O)—, —S(=O)$NR^{19b}$—, —C(=O)O—, or —OC(=O)—;

Z is H;

$C_1$–$C_8$ alkyl substituted with 0–3 $R^{12a}$;

$C_2$–$C_6$ alkenyl substituted with 0–3 $R^{12a}$;

$C_2$–$C_6$ alkynyl substituted with 0–3 $R^{12a}$;

aryl substituted with 0–4 $R^{12b}$;

$C_3$–$C_{10}$ carbocycle substituted with 0–4 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R_{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, aryl substituted with 0–4 $R^{12b}$;

$C_3$–$C_{10}$ carbocycle substituted with 0–4 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_3$–$C_6$ cycloalkyl, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S, and aryl substituted with 0–3 $R^{12c}$;

$R^{12c}$, at each occurrence, is independently selected from H, methyl, ethyl, propyl, methoxy, ethoxy, amino, hydroxy, Cl, F, Br, I, $CF_3$, $SCH_3$, $S(O)CH_3$, $SO_2CH_3$, —$N(CH_3)_2$, $N(CH_3)H$, CN, $NO_2$, $OCF_3$, C(=O)$CH_3$, $CO_2H$, $CO_2CH_3$, and $C_1$–$C_3$ haloalkyl;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{16}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{17}$ is H, $C_1$–$C_6$ alkyl, $C_2$–$C_6$ alkoxyalkyl, aryl substituted by 0–4 $R^{17a}$, or —$CH_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(CH_3)_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

$R^{19}$, at each occurrence, is independently selected from H, OH, methyl, ethyl, propyl, butyl, phenyl, benzyl, phenethyl;

additionally, $R^{18}$ and $R^{19}$, when substituents on the same atom, may be combined to form a 3 to 6 membered heterocyclic ring selected from pyrrolyl, imidazolyl, imidazolidinyl, pyrrolidinyl, piperidinyl, piperazinyl, and morpholinyl;

$R^{19b}$, at each occurrence, is independently is H or $C_1$–$C_4$ alkyl; and $R^{23}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$.

5. A compound, according to claim 1, of Formula (Ib):

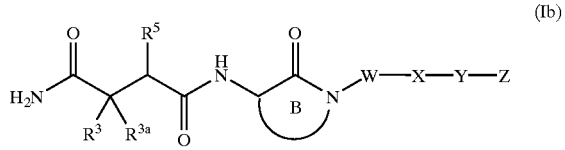

(Ib)

or a pharmaceutically acceptable salt thereof, wherein:

$R^3$ and $R^{3a}$ may be combined to form a 3–8 membered carbocyclic moiety;

wherein said 3–8 membered carbocyclic moiety is saturated or partially unsaturated;

wherein said 3–8 membered carbocyclic moiety is substituted with 0–4 $R^4$;

additionally, two $R^4$ substituents on adjacent atoms may be combined to form a benzo fused radical; wherein said benzo fused radical is substituted with 0–4 $R^{23}$;

additionally, two $R^4$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{23}$;

additionally, two $R^4$ substituents on the same or adjacent carbon atoms may be combined to form a $C_3$–$C_6$ carbocycle substituted with 0–3 $R^{23}$;

$R^4$, at each occurrence, is independently selected from H, OH, Cl, F, Br, I, CN, $NO_2$, $CF_3$, acetyl, $SCH_3$, $S(=O)CH_3$, $S(=O)_2CH_3$, $NR^{15}R^{16}$, $OR^{14a}$, $C_1$–$C_4$ alkyl, $C_2$–$C_6$ alkenyl, alkynyl, $C_1$–$C_4$ alkoxy, $C_1$–$C_4$ haloalkyl, $C_1$–$C_4$ haloalkoxy, and $C_1$–$C_4$ haloalkyl-S—, $C_3$–$C_6$ carbocycle, aryl, and a 5 to 6 membered heterocycle containing 1 to 4 heteroatoms selected from nitrogen, oxygen, and sulphur; and R⁵ is H;
  C₁–C₆ alkyl substituted with 0–3 R⁵ᵇ;
  C₂–C₆ alkenyl substituted with 0–3 R⁵ᵇ;
  C₂–C₆ alkynyl substituted with 0–3 R⁵ᵇ;
  C₃–C₁₀ carbocycle substituted with 0–3 R⁵ᶜ;
  aryl substituted with 0–3 R⁵ᶜ; or
  5 to 10 membered heterocycle containing 1 to 4 heteroatoms selected from nitrogen, oxygen, and sulphur, wherein said 5 to 10 membered heterocycle is substituted with 0–3 R⁵ᶜ;

R⁵ᵇ, at each occurrence, is independently selected from:
  H, C₁–C₆ alkyl, CF₃, OR¹⁴, Cl, F, Br, I, =O, CN, NO₂, NR¹⁵R¹⁶;
  C₃–C₁₀ carbocycle substituted with 0–3 R⁵ᶜ;
  aryl substituted with 0–3 R⁵ᶜ; or
  5 to 10 membered heterocycle containing 1 to 4 heteroatoms selected from nitrogen, oxygen, and sulphur, wherein said 5 to 10 membered heterocycle is substituted with 0–3 R⁵ᶜ;

R⁵ᶜ, at each occurrence, is independently selected from H, OH, Cl, F, Br, I, CN, NO₂, NR¹⁵R¹⁶, CF₃, acetyl, SCH₃, S(=O)CH₃, S(=O)₂CH₃, C₁–C₆ alkyl, C₁–C₄ alkoxy, C₁–C₄ haloalkyl, C₁–C₄ haloalkoxy, and C₁–C₄ haloalkyl-S—;

Ring B is selected from:

[chemical structures]

R¹¹, at each occurrence, is independently selected from H, C₁–C₄ alkoxy, Cl, F, Br, I, =O, CN, NO₂, NR¹⁸R¹⁹, C(=O)R¹⁷, C(=O)OR¹⁷, C(=O)NR¹⁸R¹⁹, S(=O)₂NR¹⁸R¹⁹, CF₃;
  C₁–C₆ alkyl optionally substituted with 0–3 R¹¹ᵃ;
  aryl substituted with 0–3 R¹¹ᵇ;
  C₃–C₁₀ carbocycle substituted with 0–3 R¹¹ᵇ; or
  5 to 10 membered heterocycle containing 1 to 4 heteroatoms selected from nitrogen, oxygen, and sulphur, wherein said 5 to 10 membered heterocycle is substituted with 0–3 R¹¹ᵇ;

R¹¹ᵃ, at each occurrence, is independently selected from H, C₁–C₆ alkyl, OR¹⁴, Cl, F, Br, I, =O, CN, NO₂, NR¹⁵R¹⁶, CF₃;
  phenyl substituted with 0–3 R¹¹ᵇ;
  C₃–C₆ cycloalkyl substituted with 0–3 R¹¹ᵇ; and
  5 to 6 membered heterocycle containing 1 to 4 heteroatoms selected from nitrogen, oxygen, and sulphur, wherein said 5 to 6 membered heterocycle is substituted with 0–3 R¹¹ᵇ;

R¹¹ᵇ, at each occurrence, is independently selected from H, OH, Cl, F, Br, I, CN, NO₂, NR¹⁵R¹⁶, CF₃, acetyl, SCH₃, S(=O)CH₃, S(=O)₂CH₃, C₁–C₆ alkyl, C₁–C₄ alkoxy, C₁–C₄ haloalkyl, C₁–C₄ haloalkoxy, and C₁–C₄ haloalkyl-S—;

W is a bond;
X is a bond;
Y is a bond;
Z is H;
  C₁–C₈ alkyl substituted with 0–3 R¹²ᵃ;
  C₂–C₆ alkenyl substituted with 0–3 R¹²ᵃ;
  C₂–C₆ alkynyl substituted with 0–3 R¹²ᵃ;
  aryl substituted with 0–4 R¹²ᵇ;
  C₃–C₁₀ carbocycle substituted with 0–4 R¹²ᵇ; or
  5 to 10 membered heterocycle containing 1 to 4 heteroatoms selected from nitrogen, oxygen, and sulphur, wherein said 5 to 10 membered heterocycle is substituted with 0–3 R¹²ᵇ;

R¹²ᵃ, at each occurrence, is independently selected from H, OH, Cl, F, Br, I, CN, NO₂, NR¹⁵R¹⁶, —C(=O)NR¹⁵R¹⁶, CF₃, acetyl, SCH₃, S(=O)CH₃, S(=O)₂CH₃, C₁–C₆ alkyl, C₁–C₄ alkoxy, C₁–C₄ haloalkyl, C₁–C₄ haloalkoxy, C₁–C₄ haloalkyl-S—, aryl substituted with 0–4 R¹²ᵇ;
  C₃–C₁₀ carbocycle substituted with 0–4 R¹²ᵇ; or
  5 to 10 membered heterocycle containing 1 to 4 heteroatoms selected from nitrogen, oxygen, and sulphur, wherein said 5 to 10 membered heterocycle is substituted with 0–3 R¹²ᵇ;

R¹²ᵇ, at each occurrence, is independently selected from H, OH, Cl, F, Br, I, CN, NO₂, NR¹⁵R¹⁶, CF₃, acetyl, SCH₃, S(=O)CH₃, S(=O)₂CH₃, C₁–C₆ alkyl, C₁–C₄ alkoxy, C₁–C₄ haloalkyl, C₁–C₄ haloalkoxy, and C₁–C₄ haloalkyl-S—;

R¹³, at each occurrence, is independently selected from H, OH, C₁–C₆ alkyl, C₁–C₄ alkoxy, Cl, F, Br, I, CN, NO₂, NR¹⁵R¹⁶, and CF₃;

R¹⁴ is H, phenyl, benzyl, C₁–C₆ alkyl, C₂–C₆ alkoxyalkyl, or C₃–C₆ cycloalkyl;

R¹⁴ᵃ is H, phenyl, benzyl, or C₁–C₄ alkyl;

R¹⁵, at each occurrence, is independently selected from H, C₁–C₆ alkyl, benzyl, phenethyl, (C₁–C₆ alkyl)-C(=O)—, and (C₁–C₆ alkyl)-S(=O)₂—;

R¹⁶, at each occurrence, is independently selected from H, C₁–C₆ alkyl, benzyl, phenethyl, (C₁–C₆ alkyl)-C(=O)—, and (C₁–C₆ alkyl)-S(=O)₂—;

R¹⁷ is H, C₁–C₆ alkyl, C₂–C₆ alkoxyalkyl, aryl substituted by 0–4 R¹⁷ᵃ, or —CH₂-aryl substituted by 0–4 R¹⁷ᵃ;

R¹⁷ᵃ is H, methyl, ethyl, propyl, butyl, methoxy, ethoxy, propoxy, butoxy, —OH, F, Cl, Br, I, CF₃, OCF₃, SCH₃, S(O)CH₃, SO₂CH₃, —NH₂, —N(CH₃)₂, or C₁–C₄ haloalkyl;

R¹⁸, at each occurrence, is independently selected from H, C₁–C₆ alkyl, phenyl, benzyl, phenethyl, (C₁–C₆ alkyl)-C(=O)—, and (C₁–C₆ alkyl)-S(=O)₂—;

R¹⁹, at each occurrence, is independently selected from H, OH, methyl, ethyl, propyl, butyl, phenyl, benzyl, phenethyl; and $R^{23}$, at each occurrence, is independently selected from H, OH, $C_1-C_6$ alkyl, $C_1-C_4$ alkoxy, Cl, F, Br, I, CN, $NO_2$, $NR^{15}R^{16}$, and $CF_3$.

6. A compound of Formula (Ib) according to claim 5, or a pharmaceutically acceptable salt thereof, wherein:

$R^3$ and $R^{3a}$ may be combined to form a 3–8 membered carbocyclic moiety;
wherein said 3–8 membered carbocyclic moiety is saturated or partially unsaturated;
wherein said 3–8 membered carbocyclic moiety is substituted with 0–3 $R^4$;

$R^4$, at each occurrence, is independently selected from H, OH, Cl, F, Br, I, CN, $NO_2$, $CF_3$, acetyl, $SCH_3$, $S(=O)CH_3$, $S(=O)_2CH_3$, $NR^{15}R^{16}$, $OR^{14a}$, $C_1-C_4$ alkyl, $C_2-C_4$ alkenyl, $C_2-C_4$ alkynyl, $C_1-C_4$ alkoxy, $C_1-C_4$ haloalkyl, $C_1-C_4$ haloalkoxy, and $C_1-C_4$ haloalkyl-S—;

$R^5$ is H;
  $C_1-C_6$ alkyl substituted with 0–3 $R^{5b}$;
  $C_2-C_6$ alkenyl substituted with 0–3 $R^{5b}$;
  $C_2-C_6$ alkynyl substituted with 0–3 $R^{5b}$;
  $C_3-C_{10}$ carbocycle substituted with 0–3 $R^{5c}$;
  aryl substituted with 0–3 $R^{5c}$; or
  5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5b}$, at each occurrence, is independently selected from: H, $C_1-C_6$ alkyl, $CF_3$, $OR^{14}$, Cl, F, Br, I, =O, CN, $NO_2$, $NR^{15}R^{16}$;
  $C_3-C_{10}$ carbocycle substituted with 0–3 $R^{5c}$;
  aryl substituted with 0–3 $R^{5c}$; or
  5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1-C_6$ alkyl, $C_1-C_4$ alkoxy, $C_1-C_4$ haloalkyl, and $C_1-C_4$ haloalkoxy;

Ring B is selected from:

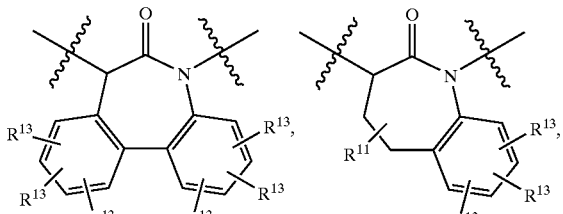

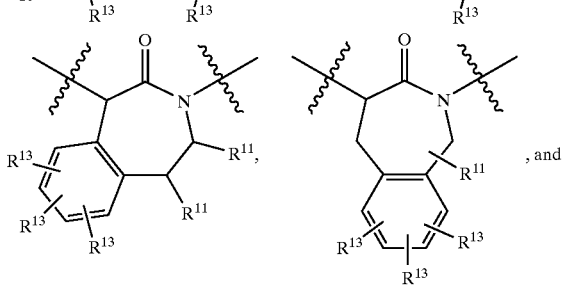

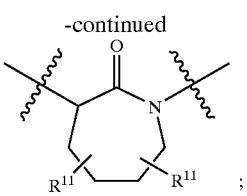

$R^{11}$, at each occurrence, is independently selected from H, =O, $NR^{18}R^{19}$, $CF_3$;
  $C_1-C_4$ alkyl optionally substituted with 0–1 $R^{11a}$;
  phenyl substituted with 0–3 $R^{11b}$;
  $C_3-C_7$ carbocycle substituted with 0–3 $R^{11b}$; and
  5 to 7 membered heterocycle containing 1 to 4 heteroatoms selected from nitrogen, oxygen, and sulphur, wherein said 5 to 7 membered heterocycle is substituted with 0–3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11a}$, at each occurrence, is independently selected from H, $C_1-C_4$ alkyl, $OR^{14}$, F, Cl, =O, $NR^{15}R^{16}$, $CF_3$, or phenyl substituted with 0–3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1-C_2$ haloalkyl, and $C_1-C_2$ haloalkoxy;

W is a bond;
X is a bond;
Y is a bond;
Z is H;
  $C_1-C_8$ alkyl substituted with 0–3 $R^{12a}$;
  $C_2-C_6$ alkenyl substituted with 0–3 $R^{12a}$; or
  $C_2-C_6$ alkynyl substituted with 0–3 $R^{12a}$;

$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$, $C_1-C_6$ alkyl, $C_1-C_4$ alkoxy, $C_1-C_4$ haloalkyl, $C_1-C_4$ haloalkoxy, $C_1-C_4$ haloalkyl-S—, aryl substituted with 0–4 $R^{12b}$;
  $C_3-C_{10}$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$; and wherein said 5 to 10 membered heterocycle is selected from pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1-C_6$ alkyl, $C_1-C_4$ alkoxy, $C_1-C_4$ haloalkyl, $C_1-C_4$ haloalkoxy, and $C_1-C_4$ haloalkyl-S—;

$R^{13}$, at each occurrence, is independently selected from H, OH, $C_1-C_6$ alkyl, $C_1-C_4$ alkoxy, Cl, F, Br, I, CN, $NO_2$, $NR^{15}R^{16}$, and $CF_3$;

$R^{14}$ is H, phenyl, benzyl, $C_1-C_6$ alkyl, $C_2-C_6$ alkoxyalkyl, or $C_3-C_6$ cycloalkyl;

$R^{14a}$ is H, phenyl, benzyl, or $C_1$-$C_4$ alkyl;

$R^{15}$, at each occurrence, is independently selected from H, $C_1$-$C_6$ alkyl, benzyl, phenethyl, ($C_1$-$C_4$ alkyl)-C(=O)—, and ($C_1$-$C_4$ alkyl)-S(=O)$_2$—;

$R^{16}$, at each occurrence, is independently selected from H, $C_1$-$C_6$ alkyl, benzyl, phenethyl, ($C_1$-$C_4$ alkyl)-C(=O)—, and ($C_1$-$C_4$ alkyl)-S(=O)$_2$—;

$R^{18}$, at each occurrence, is independently selected from H, $C_1$-$C_6$ alkyl, phenyl, benzyl, phenethyl, ($C_1$-$C_6$ alkyl)-C(=O)—, and ($C_1$-$C_6$ alkyl)-S(=O)$_2$—; and $R^{19}$, at each occurrence, is independently selected from H, OH, methyl, ethyl, propyl, butyl, phenyl, benzyl, and phenethyl.

7. A compound of Formula (Ib) according to claim 6 or a pharmaceutically acceptable salt thereof wherein:

$R^3$ and $R^{3a}$ may be combined to form a 3–6 membered carbocyclic moiety;
  wherein said 3–6 membered carbocyclic moiety is saturated or partially unsaturated;
  wherein said 3–6 membered carbocyclic moiety is substituted with 0–2 $R^4$;

$R^4$, at each occurrence, is independently selected from H, OH, Cl, F, Br, I, CN, NO$_2$, CF$_3$, acetyl, SCH$_3$, methyl, ethyl, methoxy, ethoxy, allyl, —OCF$_3$, and —SCF$_3$;

$R^5$ is H;
  $C_1$-$C_4$ alkyl substituted with 0–3 $R^{5b}$;
  $C_2$-$C_4$ alkenyl substituted with 0–3 $R^{5b}$; or
  $C_2$-$C_4$ alkynyl substituted with 0–3 $R^{5b}$;

$R^{5b}$, at each occurrence, is independently selected from:
  H, methyl, ethyl, propyl, butyl, CF$_3$, OR$^{14}$, Cl, F, Br, I, =O;
  $C_3$-$C_6$ carbocycle substituted with 0–3 $R^{5c}$;
  phenyl substituted with 0–3 $R^{5c}$; or
  5 to 6 membered heterocycle containing 1 to 4 heteroatoms selected from nitrogen, oxygen, and sulphur, wherein said 5 to 6 membered heterocycle is substituted with 0–3 $R^{5c}$;

$R^{5c}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, $C_1$-$C_4$ alkyl, $C_1$-$C_3$ alkoxy, $C_1$-$C_2$ haloalkyl, and $C_1$-$C_2$ haloalkoxy;

Ring B is selected from:

$R^{11}$, at each occurrence, is independently selected from H, =O, NR$^{18}$R$^{19}$, CF$_3$;
  $C_1$-$C_4$ alkyl optionally substituted with 0–1 $R^{11a}$;
  phenyl substituted with 0–3 $R^{11b}$;
  $C_3$-$C_7$ carbocycle substituted with 0–3 $R^{11b}$; and
  5 to 7 membered heterocycle containing 1 to 4 heteroatoms selected from nitrogen, oxygen, and sulphur, wherein said 5 to 7 membered heterocycle is substituted with 0–3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11a}$, at each occurrence, is independently selected from H, methyl, ethyl, propyl, butyl, methoxy, ethoxy, propoxy, phenoxy, F, Cl, =O, NR$^{15}$R$^{16}$, CF$_3$, or phenyl substituted with 0–3 $R^{11b}$;

$R^{11b}$, at each occurrence, is independently selected from H, OH, Cl, F, NR$^{15}$R$^{16}$, CF$_3$, methyl, ethyl, propyl, butyl, methoxy, ethoxy, propoxy, $C_1$-$C_2$ haloalkyl, and $C_1$-$C_2$ haloalkoxy;

W is a bond;
X is a bond;
Y is a bond;
Z is H;
  $C_1$-$C_4$ alkyl substituted with 0–3 $R^{12a}$;
  $C_2$-$C_4$ alkenyl substituted with 0–3 $R^{12a}$; or
  $C_2$-$C_4$ alkynyl substituted with 0–3 $R^{12a}$;

$R^{12a}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, $C_1$-$C_4$ alkyl, $C_1$-$C_3$ alkoxy, $C_1$-$C_2$ haloalkyl, and $C_1$-$C_2$ haloalkoxy;

$R^{13}$, at each occurrence, is independently selected from H, OH, $C_1$-$C_6$ alkyl, $C_1$-$C_4$ alkoxy, Cl, F, Br, I, CN, NO$_2$, NR$^{15}$R$^{16}$, and CF$_3$;

$R^{14}$ is H, phenyl, benzyl, $C_1$-$C_4$ alkyl, or $C_2$-$C_4$ alkoxyalkyl;

$R^{15}$, at each occurrence, is independently selected from H, $C_1$-$C_4$ alkyl, and benzyl;

$R^{16}$, at each occurrence, is independently selected from H, methyl, ethyl, propyl, butyl, benzyl, phenethyl, methyl-C(=O)—, ethyl-C(=O)—, methyl-S(=O)$_2$—, and ethyl-S(=O)$_2$—;

$R^{18}$, at each occurrence, is independently selected from H, methyl, ethyl, propyl, butyl, phenyl, benzyl, and phenethyl; and $R^{19}$, at each occurrence, is independently selected from H, methyl, ethyl, propyl, and butyl.

8. A compound of Formula (Ib) according to claim 7 or a pharmaceutically acceptable salt thereof wherein:

$R^3$ and $R^{3a}$ may be combined to form a 3–6 membered carbocyclic moiety selected from cyclopropyl, cyclobutyl, cyclopentyl, cyclopentenyl, cyclohexyl, and cyclohexenyl; wherein said 3–6 membered carbocyclic moiety is substituted with 0–1 $R^4$;

R⁴ is selected from H, OH, Cl, F, CN, CF₃, methyl, ethyl, methoxy, ethoxy, allyl, and —OCF₃;

R⁵ is C₁–C₄ alkyl substituted with 0–1 R⁵ᵇ;
C₂–C₄ alkenyl substituted with 0–1 R⁵ᵇ;
C₂–C₄ alkynyl substituted with 0–1 R⁵ᵇ;

R⁵ᵇ, at each occurrence, is independently selected from:
H, methyl, ethyl, propyl, butyl, CF₃, OR¹⁴, =O;
C₃–C₆ carbocycle substituted with 0–2 R⁵ᶜ;
phenyl substituted with 0–3 R⁵ᶜ; or
5 to 6 membered heterocycle containing 1 to 4 heteroatoms selected from nitrogen, oxygen, and sulphur, wherein said 5 to 6 membered heterocycle is substituted with 0–3 R⁵ᶜ; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

R⁵ᶜ, at each occurrence, is independently selected from H, OH, Cl, F, NR¹⁵R¹⁶, CF₃, acetyl, SCH₃, S(=O)CH₃, S(=O)₂CH₃, methyl, ethyl, propyl, butyl, methoxy, ethoxy, propoxy, C₁–C₂ haloalkyl, and C₁–C₂ haloalkoxy;

Ring B is selected from:

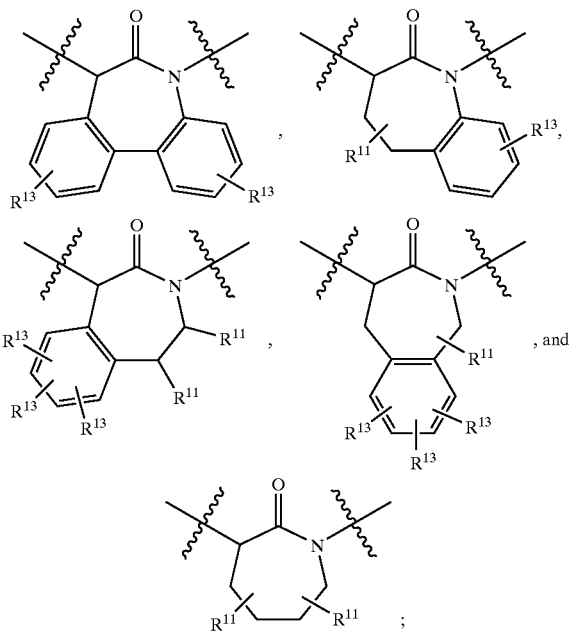

R¹¹, at each occurrence, is independently selected from H, =O, NR¹⁸R¹⁹;
C₁–C₄ alkyl optionally substituted with 0–1 R¹¹ᵃ;
phenyl substituted with 0–3 R¹¹ᵇ;
cyclohexyl substituted with 0–3 R¹¹ᵇ;
cycloheptyl substituted with 0–3 R¹¹ᵇ;
5 to 7 membered heterocycle containing 1 to 4 heteroatoms selected from nitrogen, oxygen, and sulphur, wherein said 5 to 7 membered heterocycle is substituted with 0–3 R¹¹ᵇ; wherein said 5 to-7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

R¹¹ᵃ, at each occurrence, is independently selected from H, methyl, ethyl, propyl, methoxy, ethoxy, propoxy, phenoxy, F, Cl, =O, NR¹⁵R¹⁶, CF₃, or phenyl substituted with 0–3 R¹¹ᵇ;

R¹¹ᵇ, at each occurrence, is independently selected from H, OH, Cl, F, NR¹⁵R¹⁶, CF₃, methyl, ethyl, propyl, butyl, methoxy, ethoxy, propoxy, C₁–C₂ haloalkyl, and C₁–C₂ haloalkoxy;

W is a bond;
X is a bond;
Y is a bond;
Z is H;
C₁–C₄ alkyl substituted with 0–1 R¹²ᵃ;
C₂–C₄ alkenyl substituted with 0–1 R¹²ᵃ; or
C₂–C₄ alkynyl substituted with 0–1 R¹²ᵃ;

R¹²ᵃ, at each occurrence, is independently selected from H, OH, Cl, F, NR¹⁵R¹⁶, CF₃, acetyl, SCH₃, S(=O)CH₃, S(=O)₂CH₃, methyl, ethyl, propyl, butyl, methoxy, ethoxy, propoxy, C₁–C₂ haloalkyl, and C₁–C₂ haloalkoxy;

R¹³, at each occurrence, is independently selected from H, OH, methyl, ethyl, propyl, butyl, methoxy, ethoxy, Cl, F, Br, CN, NR¹⁵R¹⁶, and CF₃;

R¹⁴ is H, phenyl, benzyl, methyl, ethyl, propyl, or butyl;

R¹⁵, at each occurrence, is independently selected from H, methyl, ethyl, propyl, and butyl;

R¹⁶, at each occurrence, is independently selected from H, methyl, ethyl, propyl, butyl, benzyl, and phenethyl;

R¹⁸, at each occurrence, is independently selected from H, methyl, ethyl, propyl, butyl, phenyl, benzyl, and phenethyl; and R¹⁹, at each occurrence, is independently selected from H, methyl, ethyl, propyl, and butyl.

9. A compound of Formula (Ib) according to claim 8 wherein:

R³ and R³ᵃ may be combined to form cyclobutyl, cyclopentyl, cyclopentenyl, or cyclohexyl;

R⁵ is —CH₃, —CH₂CH₃, —CH₂CH₂CH₃, —CH(CH₃)₂, —CH₂CH₂CH₂CH₃, —CH(CH₃)CH₂CH₃, —CH₂CH(CH₃)₂, —CH₂C(CH₃)₃, —CH₂CH₂CH₂CH₂CH₃, —CH(CH₃)CH₂CH₂CH₃, —CH₂CH(CH₃)CH₂CH₃, —CH₂CH₂CH(CH₃)₂, —CH(CH₂CH₃)₂, —CF₃, —CH₂CF₃, —CH₂CH₂CF₃, —CH₂CH₂CH₂CF₃, —CH₂CH₂CH₂CH₂CF₃, —CH=CH₂, —CH₂CH=CH₂, —CH=CHCH₃, cis-CH₂CH=CH(CH₃), trans-CH₂CH=CH(CH₃), trans-CH₂CH=CH(C₆H₅), —CH₂CH=C(CH₃)₂, cis-CH₂CH=CHCH₂CH₃, trans-CH₂CH=CHCH₂CH₃, cis-CH₂CH₂CH=CH(CH₃), trans-CH₂CH₂CH=CH(CH₃), trans-CH₂CH=CHCH₂(C₆H₅), —C≡CH, —CH₂C≡CH, —CH₂C≡C(CH₃), —CH₂C≡C(C₆H₅)—CH₂CH₂C≡CH, —CH₂CH₂C≡C(CH₃), —CH₂CH₂C≡C(C₆H₅)—CH₂CH₂CH₂C≡CH, —CH₂CH₂CH₂C≡C(CH₃), —CH₂CH₂CH₂C≡C(C₆H₅)cyclopropyl-CH₂—, cyclobutyl-CH₂—, cyclopentyl-CH₂—, cyclohexyl-CH₂—, (2-CH₃-cyclopropyl)CH₂—, (3-CH₃-cyclobutyl)CH₂—, cyclopropyl-CH₂CH₂—, cyclobutyl-CH₂CH₂—, cyclopentyl-CH₂CH₂—, cyclohexyl-CH₂CH₂—, (2-CH₃-cyclopropyl)CH₂CH₂—, (3-CH₃-cyclobutyl)CH₂CH₂—, phenyl-CH₂—, (2-F-phenyl)CH₂—, (3-F-phenyl)CH₂—, (4-F-phenyl)CH₂—, furanyl-CH₂—, thienyl-CH₂—, pyridyl-CH₂—, 1-imidazolyl-CH₂—, oxazolyl-CH₂—, isoxazolyl-CH₂—, phenyl-CH₂CH₂—, (2-F-phenyl)CH₂CH₂—, (3-F-phenyl)CH₂CH₂—, (4-F-phenyl)CH₂CH₂—, furanyl-CH₂CH₂—, thienyl-CH₂CH₂—, pyridyl-CH₂CH₂—, 1-imidazolyl-CH₂CH₂—, oxazolyl-CH₂CH₂—, isoxazolyl-CH₂CH₂—,
W is a bond;
X is a bond;
Y is a bond;
Z is methyl, ethyl, i-propyl, n-propyl, n-butyl, i-butyl, s-butyl, t-butyl, or allyl;
Ring B is selected from:

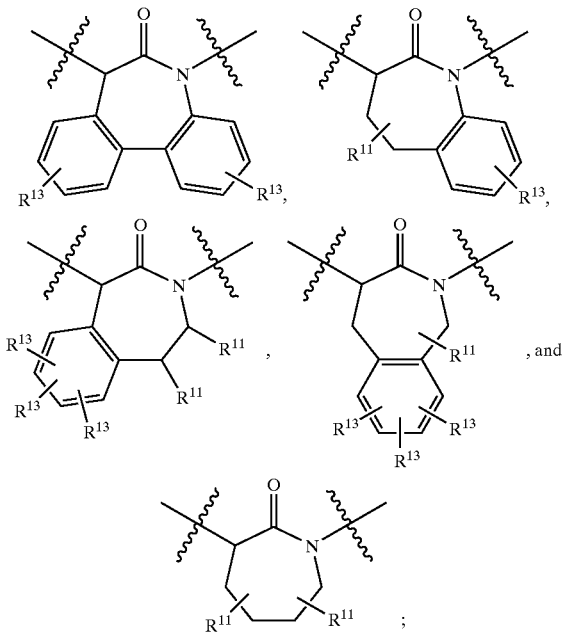

$R^{11}$, at each occurrence, is independently selected from H, =O, methyl, ethyl, phenyl, benzyl, phenethyl, 4-F-phenyl, (4-F-phenyl)CH₂—, (4-F-phenyl)CH₂CH₂—, 3-F-phenyl, (3-F-phenyl)CH₂—, (3-F-phenyl)CH₂CH₂—, 2-F-phenyl, (2-F-phenyl)CH₂—, (2-F-phenyl)CH₂CH₂—, 4-Cl-phenyl, (4-Cl-phenyl)CH₂—, (4-Cl-phenyl)CH₂CH₂—, 3-Cl-phenyl, (3-Cl-phenyl)CH₂—, (3-Cl-phenyl)CH₂CH₂—, 4-CH₃-phenyl, (4-CH₃-phenyl)CH₂—, (4-CH₃-phenyl)CH₂CH₂—, 3-CH₃-phenyl, (3-CH₃-phenyl)CH₂—, (3-CH₃-phenyl)CH₂CH₂—, 4-CF₃-phenyl, (4-CF₃-phenyl)CH₂—, (4-CF₃-phenyl)CH₂CH₂—, pyrid-2-yl, pyrid-3-yl, pyrid-4-yl, cyclohexyl, cycloheptyl, piperidinyl, or homopiperidinyl; and $R^{13}$, at each occurrence, is independently selected from H, F, Cl, OH, —CH₃, —CH₂CH₃, —OCH₃, or —CF₃.

10. A compound of Formula (Ib) according to claim 8 wherein:
$R^3$ and $R^{3a}$ are combined to form cyclobutyl, cyclopentyl, cyclopentenyl, or cyclohexyl;
$R^5$ is —CH₃, —CH₂CH₃, —CH₂CH₂CH₃, —CH(CH₃)₂, —CH₂CH₂CH₂CH₃, —CH(CH₃)CH₂CH₃, —CH₂CH(CH₃)₂, —CH₂C(CH₃)₃, —CH₂CH₂CH₂CH₂CH₃, —CH(CH₃)CH₂CH₂CH₃, —CH₂CH(CH₃)CH₂CH₃, —CH₂CH₂CH(CH₃)₂, —CH(CH₂CH₃)₂, cyclopropyl-CH₂—, cyclobutyl-CH₂—, (2-CH₃-cyclopropyl)CH₂—, or (3-CH₃-cyclobutyl)CH₂—;
W is a bond;
X is a bond;
Y is a bond;
Z is methyl, ethyl, i-propyl, n-propyl, n-butyl, i-butyl, s-butyl, t-butyl, or allyl;

Ring B is selected from:

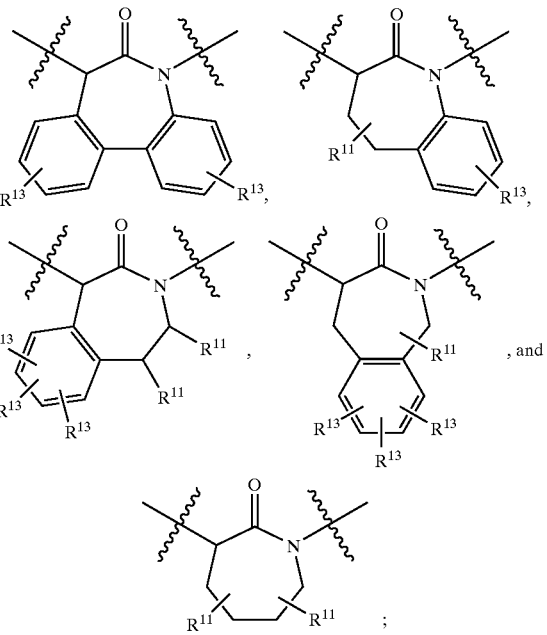

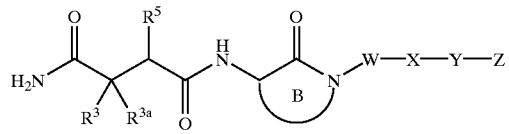

$R^{11}$, at each occurrence, is independently selected from H, =O, methyl, ethyl, phenyl, benzyl, phenethyl, 4-F-phenyl, (4-F-phenyl)CH₂—, (4-F-phenyl)CH₂CH₂—, 3-F-phenyl, (3-F-phenyl)CH₂—, (3-F-phenyl)CH₂CH₂—, 2-F-phenyl, (2-F-phenyl)CH₂—, (2-F-phenyl)CH₂CH₂—, 4-Cl-phenyl, (4-Cl-phenyl)CH₂—, (4-Cl-phenyl)CH₂CH₂—, 3-Cl-phenyl, (3-Cl-phenyl)CH₂—, (3-Cl-phenyl)CH₂CH₂—, 4-CH₃-phenyl, (4-CH₃-phenyl)CH₂—, (4-CH₃-phenyl)CH₂CH₂—, 3-CH₃-phenyl, (3-CH₃-phenyl)CH₂—, (3-CH₃-phenyl)CH₂CH₂—, 4-CF₃-phenyl, (4-CF₃-phenyl)CH₂—, (4-CF₃-phenyl)CH₂CH₂—, pyrid-2-yl, pyrid-3-yl, pyrid-4-yl, cyclohexyl, cycloheptyl, piperidinyl, or homopiperidinyl; and $R^{13}$, at each occurrence, is independently selected from H, F, Cl, OH, —CH₃, —CH₂CH₃, —OCH₃, or —CF₃.

11. A compound according to claim 1 of Formula (Ib):

(Ib)

or a pharmaceutically acceptable salt thereof, wherein:
$R^3$ and $R^{3a}$ may be combined to form a 3–8 membered carbocyclic moiety;
 wherein said 3–8 membered carbocyclic moiety is saturated or partially unsaturated;
 wherein said 3–8 membered carbocyclic moiety is substituted with 0–3 $R^4$;
$R^4$, at each occurrence, is independently selected from H, OH, Cl, F, Br, I, CN, NO₂, CF₃, acetyl, SCH₃, S(=O)CH₃, S(=O)₂CH₃, NR¹⁵R¹⁶, OR¹⁴ᵃ, C₁-C₄ alkyl, C₂-C₄ alkenyl, C₂-C₄ alkynyl, C₁-C₄ alkoxy, C₁-C₄ haloalkyl, C₁-C₄ haloalkoxy, and C₁-C₄ haloalkyl-S—;

R$^5$ is H;
C$_1$–C$_6$ alkyl substituted with 0–3 R$^{5b}$;
C$_2$–C$_6$ alkenyl substituted with 0–3 R$^{5b}$;
C$_2$–C$_6$ alkynyl substituted with 0–3 R$^{5b}$;
C$_3$–C$_{10}$ carbocycle substituted with 0–3 R$^{5c}$;
C$_6$–C$_{10}$ aryl substituted with 0–3 R$^{5c}$; or
5 to 10 membered heterocycle containing 1 to 4 heteroatoms selected from nitrogen, oxygen, and sulphur, wherein said 5 to 10 membered heterocycle is substituted with 0–3 R$^{5c}$;

R$^{5b}$, at each occurrence, is independently selected from:
H, C$_1$–C$_6$ alkyl, CF$_3$, OR$^{14}$, Cl, F, Br, I, =O, CN, NO$_2$, NR$^{15}$R$^{16}$;
C$_3$–C$_{10}$ carbocycle substituted with 0–3 R$^{5c}$;
C$_6$–C$_{10}$ aryl substituted with 0–3 R$^{5c}$; or
5 to 10 membered heterocycle containing 1 to 4 heteroatoms selected from nitrogen, oxygen, and sulphur, wherein said 5 to 10 membered heterocycle is substituted with 0–3 R$^{5c}$;

R$^{5c}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, and C$_1$–C$_4$ haloalkoxy;

Ring B is selected from:

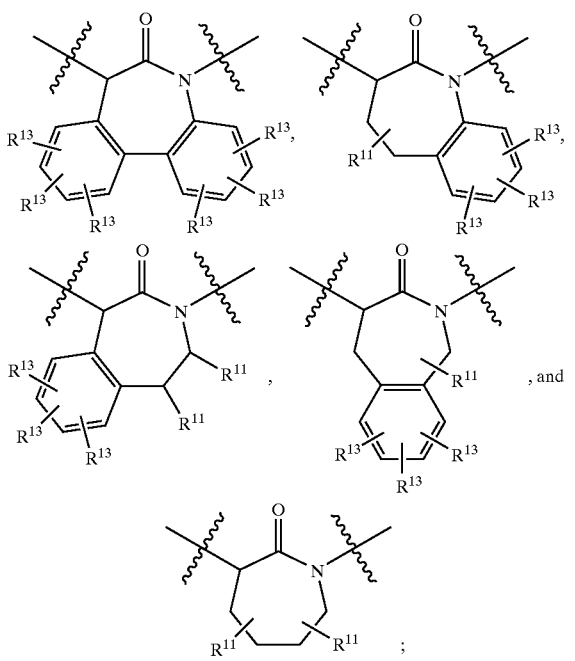

R$^{11}$, at each occurrence, is independently selected from H, =O, NR$^{18}$R$^{19}$, CF$_3$;
C$_1$–C$_4$ alkyl optionally substituted with 0–1 R$^{11a}$;
phenyl substituted with 0–3 R$^{11b}$;
C$_3$–C$_7$ carbocycle substituted with 0–3 R$^{11b}$; and
5 to 7 membered heterocycle containing 1 to 4 heteroatoms selected from nitrogen, oxygen, and sulphur, wherein said 5 to 7 membered heterocycle is substituted with 0–3 R$^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

R$^{11a}$, at each occurrence, is independently selected from H, C$_1$–C$_4$ alkyl, OR$^{14}$, F, Cl, =O, NR$^{15}$R$^{16}$, CF$_3$, or phenyl substituted with 0–3 R$^{11b}$;

R$^{11b}$, at each occurrence, is independently selected from H, OH, Cl, F, NR$^{15}$R$^{16}$, CF$_3$, methyl, ethyl, propyl, butyl, methoxy, ethoxy, propoxy, C$_1$–C$_2$ haloalkyl, and C$_1$–C$_2$ haloalkoxy;

W is a bond, —CH$_2$—, —CH$_2$CH$_2$—;

X is a bond;
phenyl substituted with 0–2 R$^{Xb}$;
C$_3$–C$_6$ cycloalkyl substituted with 0–2 R$^{Xb}$; or
5 to 6 membered heterocycle substituted with 0–2 R$^{Xb}$;

R$^{Xb}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, C$_1$–C$_4$ alkyl, C$_1$–C$_3$ alkoxy, C$_1$–C$_2$ haloalkyl, and C$_1$–C$_2$ haloalkoxy;

Y is a bond, —C(=O)—, —O—, —S—, —S(=O)—, —S(=O)$_2$—, —N(R$^{19}$)—, —C(=O)NR$^{19b}$—, —NR$^{19b}$C(=O)—, —NR$^{19b}$S(=O)$_2$—, —S(=O)$_2$NR$^{19b}$—, —NR$^{19b}$S(=O)—, —S(=O)NR$^{19b}$—, —C(=O)O—, or —OC(=O)—;

Z is C$_1$–C$_3$ alkyl substituted with 1–2 R$^{12a}$;
aryl substituted with 0–4 R$^{12b}$;
C$_3$–C$_{10}$ carbocycle substituted with 0–3 R$^{12b}$; or
5 to 10 membered heterocycle containing 1 to 4 heteroatoms selected from nitrogen, oxygen, and sulphur, wherein said 5 to 10 membered heterocycle is substituted with 0–3 R$^{12b}$;

R$^{12a}$, at each occurrence, is independently selected from aryl substituted with 0–4 R$^{12b}$;
C$_3$–C$_{10}$ carbocycle substituted with 0–4 R$^{12b}$; and
5 to 10 membered heterocycle containing 1 to 4 heteroatoms selected from nitrogen, oxygen, and sulphur, wherein said 5 to 10 membered heterocycle is substituted with 0–3 R$^{12b}$;

R$^{12b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, and C$_1$–C$_4$ haloalkyl-S—;

R$^{13}$, at each occurrence, is independently selected from H, OH, C$_1$–C$_6$ alkyl, C$_1$–C$_4$ alkoxy, Cl, F, Br, I, CN, NO$_2$, NR$^{15}$R$^{16}$, and CF$_3$;

R$^{14}$ is H, phenyl, benzyl, C$_1$–C$_6$ alkyl, C$_2$–C$_6$ alkoxyalkyl, or C$_3$–C$_6$ cycloalkyl;

R$^{14a}$ is H, phenyl, benzyl, or C$_1$–C$_4$ alkyl;

R$^{15}$, at each occurrence, is independently selected from H, C$_1$–C$_6$ alkyl, benzyl, phenethyl, (C$_1$–C$_4$ alkyl)-C(=O)—, and (C$_1$–C$_4$ alkyl)-S(=O)$_2$—;

R$^{16}$, at each occurrence, is independently selected from H, OH, C$_1$–C$_6$ alkyl, benzyl, phenethyl, (C$_1$–C$_4$ alkyl)-C(=O)—, and (C$_1$–C$_4$ alkyl)-S(=O)$_2$—;

R$^{18}$, at each occurrence, is independently selected from H, C$_1$–C$_6$ alkyl, phenyl, benzyl, phenethyl, (C$_1$–C$_6$ alkyl)-C(=O)—, and (C$_1$–C$_6$ alkyl)-S(=O)$_2$—;

R$^{19}$, at each occurrence, is independently selected from H, OH, methyl, ethyl, propyl, butyl, phenyl, benzyl, and phenethyl; and R$^{19b}$, at each occurrence, is independently selected from H, methyl, ethyl, propyl, butyl, phenyl, benzyl, and phenethyl.

12. A compound of Formula (Ib) according to claim 11 or a pharmaceutically acceptable salt thereof wherein:
R$^3$ and R$^{3a}$ may be combined to form a 3–6 membered carbocyclic moiety;
wherein said 3–6 membered carbocyclic moiety is saturated or partially unsaturated;

wherein said 3–6 membered carbocyclic moiety is substituted with 0–2 $R^4$;

$R^4$, at each occurrence, is independently selected from H, OH, Cl, F, Br, I, CN, $NO_2$, $CF_3$, acetyl, $SCH_3$, methyl, ethyl, methoxy, ethoxy, allyl, —$OCF_3$, and —$SCF_3$;

$R^5$ is H;
  $C_1$–$C_4$ alkyl substituted with 0–3 $R^{5b}$;
  $C_2$–$C_4$ alkenyl substituted with 0–3 $R^{5b}$; or
  $C_2$–$C_4$ alkynyl substituted with 0–3 $R^{5b}$;

$R^{5b}$, at each occurrence, is independently selected from: H, methyl, ethyl, propyl, butyl, $CF_3$, $OR^{14}$, Cl, F, Br, I, =O;
  $C_3$–$C_6$ carbocycle substituted with 0–3 $R^{5c}$;
  phenyl substituted with 0–3 $R^{5c}$; or
  5 to 6 membered heterocycle containing 1 to 4 heteroatoms selected from nitrogen, oxygen, and sulphur, wherein said 5 to 6 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

Ring B is selected from:

[chemical structures]

$R^{11}$, at each occurrence, is independently selected from H, =O, $NR^{18}R^{19}$, $CF_3$;
  $C_1$–$C_4$ alkyl optionally substituted with 0–1 $R^{11a}$;
  phenyl substituted with 0–3 $R^{11b}$;
  $C_3$–$C_7$ carbocycle substituted with 0–3 $R^{11b}$; and
  5 to 7 membered heterocycle containing 1 to 4 heteroatoms selected from nitrogen, oxygen, and sulphur, wherein said 5 to 7 membered heterocycle is substituted with 0–3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11a}$, at each occurrence, is independently selected from H, methyl, ethyl, propyl, butyl, methoxy, ethoxy, propoxy, phenoxy, F, Cl, =O, $NR^{15}R^{16}$, $CF_3$, or phenyl substituted with 0–3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;

W is a bond, —$CH_2$—, —$CH_2CH_2$—;

X is a bond;
  phenyl substituted with 0–1 $R^{Xb}$;
  $C_3$–$C_6$ cycloalkyl substituted with 0–1 $R^{Xb}$; or
  5 to 6 membered heterocycle substituted with 0–1 $R^{Xb}$;

$R^{Xb}$ is selected from H, OH, Cl, F, $NR^{15}R^{16}$, $CF_3$, acetyl, $SCH_3$, $S(=O)CH_3$, $S(=O)_2CH_3$, methyl, ethyl, propyl, methoxy, ethoxy, propoxy, and —$OCF_3$;

Y is a bond, —C(=O)—, —O—, —S—, —S(=O)—, —S(=O)$_2$—, —NH—, —N($CH_3$)—, or —N($CH_2CH_3$)—;

Z is $C_1$–$C_2$ alkyl substituted with 1–2 $R^{12a}$;
  aryl substituted with 0–4 $R^{12b}$;
  $C_3$–$C_{10}$ carbocycle substituted with 0–3 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from aryl substituted with 0–4 $R^{12b}$;
  $C_3$–$C_{10}$ carbocycle substituted with 0–4 $R^{12b}$; and
  5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_4$ alkyl, or $C_2$–$C_4$ alkoxyalkyl;

$R^{15}$, at each occurrence, is independently selected from H, $C_1$–$C_4$ alkyl, and benzyl;

$R^{16}$, at each occurrence, is independently selected from H, OH, methyl, ethyl, propyl, butyl, benzyl, phenethyl, methyl-S(=O)—, ethyl-S(=O)—, methyl-S(=O)$_2$—, and ethyl-S(=O)$_2$—;

$R^{18}$, at each occurrence, is independently selected from H, methyl, ethyl, propyl, butyl, phenyl, benzyl, and phenethyl; and $R^{19}$, at each occurrence, is independently selected from H, methyl, ethyl, propyl, and butyl.

13. A compound of Formula (Ib) according to claim 12 or a pharmaceutically acceptable salt thereof wherein:

$R^3$ and $R^{3a}$ may be combined to form a 3–6 membered carbocyclic moiety selected from cyclopropyl, cyclobutyl, cyclopentyl, cyclopentenyl, cyclohexyl, and cyclohexenyl; wherein said 3–6 membered carbocyclic moiety is substituted with 0–1 $R^4$;

$R^4$ is selected from H, OH, Cl, F, CN, $CF_3$, methyl, ethyl, methoxy, ethoxy, allyl, and —$OCF_3$;

$R^5$ is $C_1$–$C_4$ alkyl substituted with 0–1 $R^{5b}$;
  $C_2$–$C_4$ alkenyl substituted with 0–1 $R^{5b}$;
  $C_2$–$C_4$ alkynyl substituted with 0–1 $R^{5b}$;

$R^{5b}$, at each occurrence, is independently selected from: H, methyl, ethyl, propyl, butyl, $CF_3$, $OR^{14}$, =O;

$C_3$–$C_6$ carbocycle substituted with 0–2 $R^{5c}$;
phenyl substituted with 0–3 $R^{5c}$; or
5 to 6 membered heterocycle containing 1 to 4 heteroatoms selected from nitrogen, oxygen, and sulphur, wherein said 5 to 6 membered heterocycle is substituted with 0–3 $R^{5c}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{5c}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy;

Ring B is selected from:

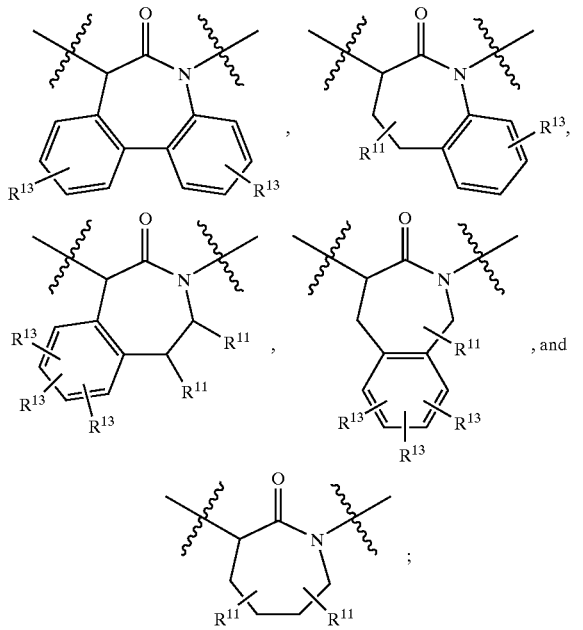

;

$R^{11}$, at each occurrence, is independently selected from H, =O, $NR^{18}R^{19}$;
$C_1$–$C_4$ alkyl optionally substituted with 0–1 $R^{11a}$;
phenyl substituted with 0–3 $R^{11b}$;
cyclohexyl substituted with 0–3 $R^{11b}$;
cycloheptyl substituted with 0–3 $R^{11b}$;
5 to 7 membered heterocycle containing 1 to 4 heteroatoms selected from nitrogen, oxygen, and sulphur, wherein said 5 to 7 membered heterocycle is substituted with 0–3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11a}$, at each occurrence, is independently selected from H, methyl, ethyl, propyl, methoxy, ethoxy, propoxy, phenoxy, F, Cl, =O, $NR^{15}R^{16}$, $CF_3$, or phenyl substituted with 0–3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;

W is a bond or —$CH_2$—;

X is a bond;
phenyl substituted with 0–1 $R^{Xb}$;
$C_3$–$C_6$ cycloalkyl substituted with 0–1 $R^{Xb}$; or
5 to 6 membered heterocycle substituted with 0–1 $R^{Xb}$;

$R^{Xb}$ is selected from H, OH, Cl, F, $NR^{15}R^{16}$, $CF_3$, acetyl, methyl, ethyl, methoxy, ethoxy, and —$OCF_3$;

Y is a bond, —C(=O)—, —O—, —S—, —S(=O)—, —S(=O)$_2$—, —NH—, —N(CH$_3$)—, or —N(CH$_2$CH$_3$)—;

Z is $C_1$–$C_2$ alkyl substituted with 1–2 $R^{12a}$;
aryl substituted with 0–4 $R^{12b}$;
$C_3$–$C_{10}$ carbocycle substituted with 0–3 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from aryl substituted with 0–4 $R^{12b}$;
$C_3$–$C_{10}$ carbocycle substituted with 0–4 $R^{12b}$; and
5 to 10 membered heterocycle containing 1 to 4 heteroatoms selected from nitrogen, oxygen, and sulphur, wherein said 5 to 10 membered heterocycle is substituted with 0–3 $R^{12b}$; and wherein said 5 to 10 membered heterocycle is selected from pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl;

$R^{12b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, and —$OCF_3$;

$R^{13}$, at each occurrence, is independently selected from H, OH, methyl, ethyl, propyl, butyl, methoxy, ethoxy, Cl, F, Br, CN, $NR^{15}R^{16}$, and $CF_3$;

$R^{14}$ is H, phenyl, benzyl, methyl, ethyl, propyl, or butyl;

$R^{15}$, at each occurrence, is independently selected from H, methyl, ethyl, propyl, and butyl;

$R^{16}$, at each occurrence, is independently selected from H, OH, methyl, ethyl, propyl, butyl, benzyl, and phenethyl;

$R^{18}$, at each occurrence, is independently selected from H, methyl, ethyl, propyl, butyl, phenyl, benzyl, and phenethyl; and $R^{19}$, at each occurrence, is independently selected from H, methyl, ethyl, propyl, and butyl.

14. A compound of Formula (Ib) according to claim 13 wherein:

$R^3$ and $R^{3a}$ may be combined to form cyclobutyl, cyclopentyl, cyclopentenyl, or cyclohexyl;

$R^5$ is —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$CH_2C(CH_3)_3$, —$CH_2CH_2CH_2CH_2CH_3$, —$CH(CH_3)CH_2CH_2CH_3$, —$CH_2CH(CH_3)CH_2CH_3$, —$CH_2CH_2CH(CH_3)_2$, —$CH(CH_2CH_3)_2$, cyclopropyl-$CH_2$—, cyclobutyl-$CH_2$—, (2-$CH_3$-cyclopropyl)$CH_2$—, or (3-$CH_3$-cyclobutyl)$CH_2$—;

W is a bond or —$CH_2$—;

X is a bond;

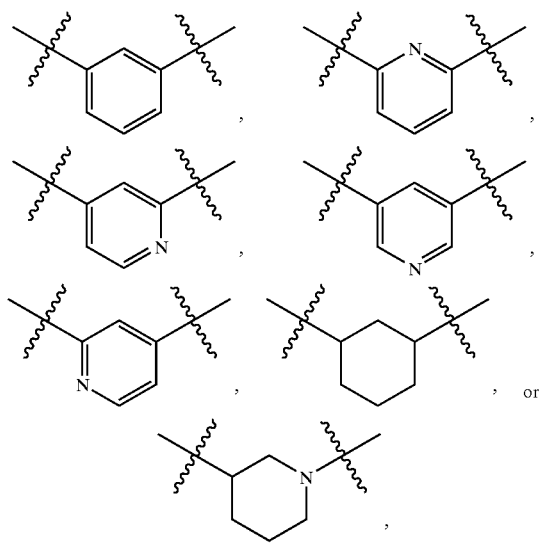

, or

Y is a bond, —C(=O)—, —O—, —S—, —S(=O)—, —S(=O)₂—, —NH—, or —N(CH₃)—,

Z is phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF₃O-phenyl, 3-CF₃O-phenyl, 4-CF₃O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, cyclopropyl, cyclobutyl, cyclopentyl, cyclohexyl, morpholino, N-piperinyl, phenyl-CH₂—, (2-F-phenyl)CH₂—, (3-F-phenyl)CH₂—, (4-F-phenyl)CH₂—, (2-Cl-phenyl)CH₂—, (3-Cl-phenyl)CH₂, (4-Cl-phenyl)CH₂—, (2,3-diF-phenyl)CH₂—, (2,4-diF-phenyl)CH₂—, (2,5-diF-phenyl)CH₂—, (2,6-diF-phenyl)CH₂—, (3,4-diF-phenyl)CH₂—, (3,5-diF-phenyl)CH₂—, (2,3-diCl-phenyl)CH₂—, (2,4-diCl-phenyl)CH₂—, (2,5-diCl-phenyl)CH₂—, (2,6-diCl-phenyl)CH₂—, (3,4-diCl-phenyl)CH₂—, (3,5-diCl-phenyl)CH₂—, (3-F-4-Cl-phenyl)CH₂—, (3-F-5-Cl-phenyl)CH₂—, (3-Cl-4-F-phenyl)CH₂—, (2-MeO-phenyl)CH₂—, (3-MeO-phenyl)CH₂—, (4-MeO-phenyl)CH₂—, (2-Me-phenyl)CH₂—, (3-Me-phenyl)CH₂—, (4-Me-phenyl)CH₂—, (2-MeS-phenyl)CH₂—, (3-MeS-phenyl)CH₂—, 4-MeS-phenyl)CH₂—, (2-CF₃O-phenyl)CH₂—, (3-CF₃O-phenyl)CH₂—, (4-CF₃O-phenyl)CH₂—, (furanyl)CH₂—, (thienyl)CH₂—, (pyridyl)CH₂—, (2-Me-pyridyl)CH₂—, (3-Me-pyridyl)CH₂—, (4-Me-pyridyl)CH₂—, (1-imidazolyl)CH₂—, (oxazolyl)CH₂—, (isoxazolyl)CH₂—, (1-benzimidazolyl)CH₂—, (cyclopropyl)CH₂—, (cyclobutyl)CH₂—, (cyclopentyl)CH₂—, (cyclohexyl)CH₂—, (morpholino)CH₂—, (N-piperidinyl)CH₂—, phenyl-CH₂CH₂—, (phenyl)₂CHCH₂—, (2-F-phenyl)CH₂CH₂—, (3-F-phenyl)CH₂CH₂—, (4-F-phenyl)CH₂CH₂—, (2-Cl-phenyl)CH₂CH₂—, (3-Cl-phenyl)CH₂CH₂—, (4-Cl-phenyl)CH₂CH₂—, (2,3-diF-phenyl)CH₂CH₂—, (2,4-diF-phenyl)CH₂CH₂—, (2,5-diF-phenyl)CH₂CH₂—, (2,6-diF-phenyl)CH₂CH₂—, (3,4-diF-phenyl)CH₂CH₂—, (3,5-diF-phenyl)CH₂CH₂—, (2,3-diCl-phenyl)CH₂CH₂—, (2,4-diCl-phenyl)CH₂CH₂—, (2,5-diCl-phenyl)CH₂CH₂—, (2,6-diCl-phenyl)CH₂CH₂—, (3,4-diCl-phenyl)CH₂CH₂—, (3,5-diCl-phenyl)CH₂CH₂—, (3-F-4-Cl-phenyl)CH₂CH₂—, (3-F-5-Cl-phenyl)CH₂CH₂—, (3-Cl-4-F-phenyl)CH₂CH₂—, (2-MeO-phenyl)CH₂CH₂—, (3-MeO-phenyl)CH₂CH₂—, (4-MeO-phenyl)CH₂CH₂—, (2-Me-phenyl)CH₂CH₂—, (3-Me-phenyl)CH₂CH₂—, (4-Me-phenyl)CH₂CH₂—, (2-MeS-phenyl)CH₂CH₂—, (3-MeS-phenyl)CH₂CH₂—, (4-MeS-phenyl)CH₂CH₂—, (2-CF₃O-phenyl)CH₂CH₂—, (3-CF₃O-phenyl)CH₂CH₂—, (4-CF₃O-phenyl)CH₂CH₂—, (furanyl)CH₂CH₂—, (thienyl)CH₂CH₂—, (pyridyl)CH₂CH₂—, (2-Me-pyridyl)CH₂CH₂—, (3-Me-pyridyl)CH₂CH₂—, (4-Me-pyridyl)CH₂CH₂—, (imidazolyl)CH₂CH₂—, (oxazolyl)CH₂CH₂—, (isoxazolyl)CH₂CH₂—, (benzimidazolyl)CH₂CH₂—, (cyclopropyl)CH₂CH₂—, (cyclobutyl)CH₂CH₂—, (cyclopentyl)CH₂CH₂—, (cyclohexyl)CH₂CH₂—, (morpholino)CH₂CH₂—, or (N-piperidinyl)CH₂CH₂—;

$R^{11}$, at each occurrence, is independently selected from H, =O, methyl, ethyl, phenyl, benzyl, phenethyl, 4-F-phenyl, (4-F-phenyl)CH₂—, (4-F-phenyl)CH₂CH₂—, 3-F-phenyl, (3-F-phenyl)CH₂—, (3-F-phenyl)CH₂CH₂—, 2-F-phenyl, (2-F-phenyl)CH₂—, (2-F-phenyl)CH₂CH₂—, 4-Cl-phenyl, (4-Cl-phenyl)CH₂—, (4-Cl-phenyl)CH₂CH₂—, 3-Cl-phenyl, (3-Cl-phenyl)CH₂—, (3-Cl-phenyl)CH₂CH₂—, 4-CH₃-phenyl, (4-CH₃-phenyl)CH₂—, (4-CH₃-phenyl)CH₂CH₂—, 3-CH₃-phenyl, (3-CH₃-phenyl)CH₂—, (3-CH₃-phenyl)CH₂CH₂—, 4-CF₃-phenyl, (4-CF₃-phenyl)CH₂—, (4-CF₃-phenyl)CH₂CH₂—, pyrid-2-yl, pyrid-3-yl, pyrid-4-yl, cyclohexyl, cycloheptyl, piperidinyl, or homopiperidinyl; and $R^{13}$, at each occurrence, is independently selected from H, F, Cl, OH, —CH₃, —CH₂CH₃, —OCH₃, or —CF₃.

15. A compound according to claim 5 of Formula (Ic):

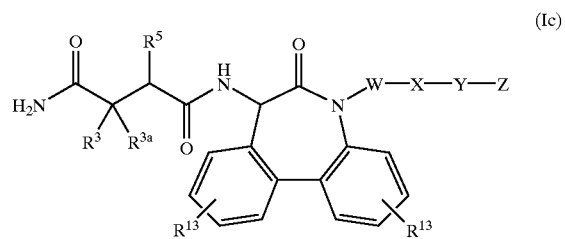

(Ic)

or a pharmaceutically acceptable salt thereof.

16. A compound according to claim 5 of Formula (Ie):

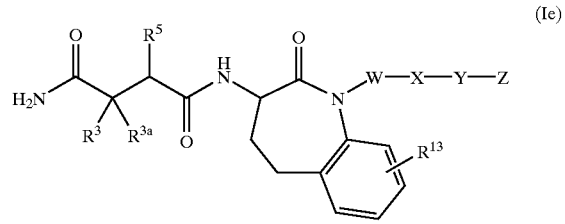

(Ie)

or a pharmaceutically acceptable salt thereof.

17. A compound according to claim 5 of Formula (Ig):

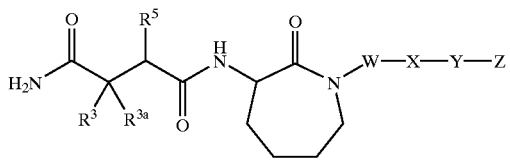

(Ig)

or a pharmaceutically acceptable salt thereof.

18. A compound according to claim 1 selected from:
1-[3-Methyl-1-(5-methyl-6-oxo-6,7-dihydro-5H-dibenzo[b,d]-azepin-7-ylcarbamoyl)-butyl]-cyclohexanecarboxylic acid amide;
1-[3-Methyl-1-(5-methyl-6-oxo-6,7-dihydro-5H-dibenzo[b,d]-azepin-7-ylcarbamoyl)-butyl]-cyclohexanecarboxylic acid amide;
1-(1-{1-[3-(2-Fluoro-phenoxy)-benzyl]-2-oxo-2,3,4,5-tetrahydro-1H-benzo[b]azepin-3-ylcarbamoyl}-3-methyl-butyl)-cyclopent-3-enecarboxylic acid amide;
1-{3-Methyl-1-[2-oxo-1-(3-phenylamino-benzyl)-2,3,4,5-tetrahydro-1H-benzo[b]azepin-3-ylcarbamoyl]-butyl}-cyclopent-3-enecarboxylic acid amide;
1-{3-Methyl-1-[2-oxo-1-(3-phenylamino-benzyl)-2,3,4,5-tetrahydro-1H-benzo[b]azepin-3-ylcarbamoyl]-butyl}-cyclopentanecarboxylic acid amide;
1-[2-Cyclopropyl-1-(5-methyl-6-oxo-6,7-dihydro-5H-dibenzo[b,d]azepin-7-ylcarbamoyl)-ethyl]-cyclopent-3-enecarboxylic acid amide;
1-{3-Methyl-1-[2-oxo-1-(3-o-tolylamino-benzyl)-azepan-3-ylcarbamoyl]-butyl}-cyclopent-3-enecarboxylic acid amide;
1-[3-Methyl-1-(5-methyl-6-oxo-6,7-dihydro-5H-dibenzo[b,d]azepin-7-ylcarbamoyl)-butyl]-cyclopent-3-enecarboxylic acid amide; and
1-[3-Methyl-1-(5-methyl-6-oxo-6,7-dihydro-5H-dibenzo[b,d]azepin-7-ylcarbamoyl)-butyl]-cyclopentanecarboxylic acid amide.

19. A pharmaceutical composition comprising a compound according to claim 1 and a pharmaceutically acceptable carrier.

20. A compound according to claim 5 of formula (Ib):

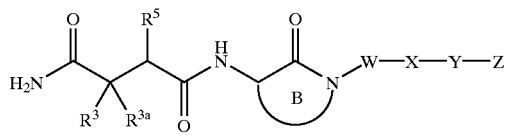

(Ib)

or a pharmaceutically acceptable salt thereof, wherein:
$R^3$ and $R^{3a}$ may be combined to form a 3–8 membered carbocyclic moiety;
wherein said 3–8 membered carbocyclic moiety is saturated or partially unsaturated;
wherein said 3–8 membered carbocyclic moiety is substituted with 0–4 $R^4$;
additionally, two $R^4$ substituents on adjacent atoms may be combined to form a benzo fused radical; wherein said benzo fused radical is substituted with 0–4 $R^{23}$;
additionally, two $R^4$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{23}$;
additionally, two $R^4$ substituents on the same or adjacent carbon atoms may be combined to form a $C_3$–$C_6$ carbocycle substituted with 0–3 $R^{23}$;
$R^4$, at each occurrence, is independently selected from H, OH, Cl, F, Br, I, CN, $NO_2$, $CF_3$, acetyl, $SCH_3$, $S(=O)CH_3$, $S(=O)_2CH_3$, $NR^{15}R^{16}$, $OR^{14a}$, $C_1$–$C_4$ alkyl, $C_2$–$C_6$ alkenyl, alkynyl, $C_1$–$C_4$ alkoxy, $C_1$–$C_4$ haloalkyl, $C_1$–$C_4$ haloalkoxy, and $C_1$–$C_4$ haloalkyl-S—, $C_3$–$C_6$ carbocycle, aryl, and a
5 to 6 membered heterocycle containing 1 to 4 heteroatoms selected from nitrogen, oxygen, and sulphur; and
$R^5$ is H;
$C_1$–$C_6$ alkyl substituted with 0–3 $R^{5b}$;
$C_2$–$C_6$ alkenyl substituted with 0–3 $R^{5b}$;
$C_2$–$C_6$ alkynyl substituted with 0–3 $R^{5b}$;
$C_3$–$C_{10}$ carbocycle substituted with 0–3 $R^{5c}$;
aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5b}$, at each occurrence, is independently selected from:
H, $C_1$–$C_6$ alkyl, $CF_3$, $OR^{14}$, Cl, F, Br, I, =O, CN, $NO_2$, $NR^{15}R^{16}$;
$C_3$–$C_{10}$ carbocycle substituted with 0–3 $R^{5c}$;
aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;
Ring B is

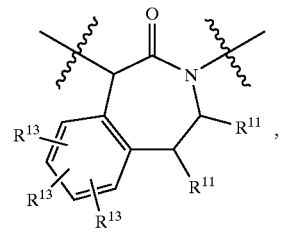

$R^{11}$, at each occurrence, is independently selected from H, $C_1$–$C_4$ alkoxy, Cl, F, Br, I, =O, CN, $NO_2$, $NR^{18}R^{19}$, $C(=O)R^{17}$, $C(=O)OR^{17}$, $C(=O)NR^{18}R^{19}$, $S(=O)_2NR^{18}R^{19}$, $CF_3$;
$C_1$–$C_6$ alkyl optionally substituted with 0–3 $R^{11a}$;
aryl substituted with 0–3 $R^{11b}$;
$C_3$–$C_{10}$ carbocycle substituted with 0–3 $R^{11b}$; or
5 to 10 membered heterocycle containing 1 to 4 heteroatoms selected from nitrogen, oxygen, and sulphur, wherein said 5 to 10 membered heterocycle is substituted with 0–3 $R^{11b}$;
$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$;
phenyl substituted with 0–3 $R^{11b}$;
$C_3$–$C_6$ cycloalkyl substituted with 0–3 $R^{11b}$; and 5 to 6 membered heterocycle containing 1 to 4 heteroatoms selected from nitrogen, oxygen, and sulphur, wherein said 5 to 6 membered heterocycle is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

W is a bond;
X is a bond;
Y is a bond;
Z is H;
  $C_1$–$C_8$ alkyl substituted with 0–3 $R^{12a}$;
  $C_2$–$C_6$ alkenyl substituted with 0–3 $R^{12a}$;
  $C_2$–$C_6$ alkynyl substituted with 0–3 $R^{12a}$;
  aryl substituted with 0–4 $R^{12b}$;
  $C_3$–$C_{10}$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;

$R_{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, aryl substituted with 0–4 $R^{12b}$;
  $C_3$–$C_{10}$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{16}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{17}$ is H, $C_1$–$C_6$ alkyl, $C_2$–$C_6$ alkoxyalkyl, aryl substituted by 0–4 $R^{17a}$, or —$CH_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(CH_3)_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

$R^{19}$, at each occurrence, is independently selected from H, OH, methyl, ethyl, propyl, butyl, phenyl, benzyl, phenethyl; and $R^{23}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$.

21. A compound, according to claim 5, of Formula (Ib):

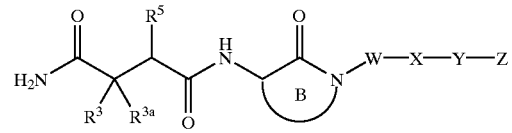

(Ib)

or a pharmaceutically acceptable salt thereof, wherein:

$R^3$ and $R^{3a}$ may be combined to form a 3–8 membered carbocyclic moiety;
  wherein said 3–8 membered carbocyclic moiety is saturated or partially unsaturated;
  wherein said 3–8 membered carbocyclic moiety is substituted with 0–4 $R^4$;

additionally, two $R^4$ substituents on adjacent atoms may be combined to form a benzo fused radical; wherein said benzo fused radical is substituted with 0–4 $R^{23}$;

additionally, two $R^4$ substituents on adjacent atoms may be combined to form a 5 to 6 membered hetoroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{23}$;

additionally, two $R^4$ substituents on the same or adjacent carbon atoms may be combined to form a $C_3$–$C_6$ carbocycle substituted with 0–3 $R^{23}$;

$R^4$, at each occurrence, is independently selected from H, OH, Cl, F, Br, I, CN, $NO_2$, $CF_3$, acetyl, $SCH_3$, $S(=)CH_3$, $S(=O)_2CH_3$, $NR^{15}R^{16}$, $OR^{14a}$, $C_1$–$C_4$ alkyl, $C_2$–$C_6$ alkenyl, alkynyl, $C_1$–$C_4$ alkoxy, $C_1$–$C_4$ haloalkyl, $C_1$–$C_4$ haloalkoxy, and $C_1$–$C_4$ haloalkyl-S—, $C_3$–$C_6$ carbocycle, aryl, and a
  5 to 6 membered heterocycle containing 1 to 4 heteroatoms selected from nitrogen, oxygen, and sulphur; and $R^5$ is H;
  $C_1$–$C_6$ alkyl substituted with 0–3 $R^{5b}$;
  $C_2$–$C_6$ alkenyl substituted with 0–3 $R^{5b}$;
  $C_2$–$C_6$ alkynyl substituted with 0–3 $R^{5b}$;
  $C_3$–$C_{10}$ carbocycle substituted with 0–3 $R^{5c}$;
  aryl substituted with 0–3 $R^{5c}$; or
  5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5b}$, at each occurrence, is independently selected from:
  H, $C_1$–$C_6$ alkyl, $CF_3$, $OR^{14}$, Cl, F, Br, I, =O, CN, $NO_2$, $NR^{15}R^{16}$;
  $C_3$–$C_{10}$ carbocycle substituted with 0–3 $R^{5c}$;
  aryl substituted with 0–3 $R^{5c}$; or
  5 to $^{10}$ membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

Ring B is selected from:

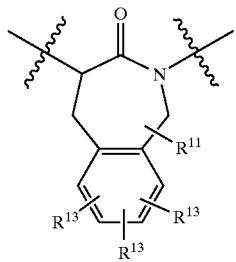

$R^{11}$, at each occurrence, is independently selected from H, $C_1$–$C_4$ alkoxy, Cl, F, Br, I, =O, CN, $NO_2$, $NR^{18}R^{19}$, $C(=O)R^{17}$, $C(=O)OR^{17}$, $C(=O)NR^{18}R^{19}$, $S(=O)_2NR^{18}R^{19}$, $CF_3$;
$C_1$–$C_6$ alkyl optionally substituted with 0–3 $R^{11a}$;
aryl substituted with 0–3 $R^{11b}$;
$C_3$–$C_{10}$ carbocycle substituted with 0–3 $R^{11b}$; or
5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$;
phenyl substituted with 0–3 $R^{11b}$;
$C_3$–$C_6$ cycloalkyl substituted with 0–3 $R^{11b}$; and
5 to 6 membered heterocycle containing 1 to 4 heteroatoms selected from nitrogen, oxygen, and sulphur, wherein said 5 to 6 membered heterocycle is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

W is a bond;
X is a bond;
Y is a bond;
Z is H;
$C_1$–$C_8$ alkyl substituted with 0–3 $R^{12a}$;
$C_2$–$C_6$ alkenyl substituted with 0–3 $R^{12a}$;
$C_2$–$C_6$ alkynyl substituted with 0–3 $R^{12a}$;
aryl substituted with 0–4 $R^{12b}$;
$C_3$–$C_{10}$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, aryl substituted with 0–4 $R^{12b}$;
$C_3$–$C_{10}$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{16}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{17}$ is H, $C_1$–$C_6$ alkyl, $C_2$–$C_6$ alkoxyalkyl, aryl substituted by 0–4 $R^{17a}$, or —$CH_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(CH_3)_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

$R^{19}$, at each occurrence, is independently selected from H, OH, methyl, ethyl, propyl, butyl, phenyl, benzyl, phenethyl; and $R^{23}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$.

22. A compound, according to claim 1 of Formula (Ib):

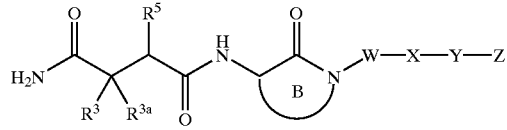

(Ib)

or a pharmaceutically acceptable salt thereof, wherein:
$R^3$ and $R^{3a}$ are combined to form a 3–8 membered carbocyclic moiety;
wherein said 3–8 membered carbocyclic moiety is saturated or partially unsaturated;
wherein said 3–8 membered carbocyclic moiety is substituted with 0–4 $R^4$;
additionally, two $R^4$ substituents on adjacent atoms may be combined to form a benzo fused radical; wherein said benzo fused radical is substituted with 0–4 $R^{23}$;
additionally, two $R^4$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{23}$;
additionally, two $R^4$ substituents on the same or adjacent carbon atoms may be combined to form a $C_3$–$C_6$ carbocycle substituted with 0–3 $R^{23}$;
$R^4$, at each occurrence, is independently selected from H, OH, Cl, F, Br, I, CN, $NO_2$, $CF_3$, acetyl, $SCH_3$, $S(=O)CH_3$, $S(=O)_2CH_3$, $NR^{15}R^{16}$, $OR^{14a}$, $C_1$–$C_4$ alkyl, $C_2$–$C_6$ alkenyl, alkynyl, $C_1$–$C_4$ alkoxy, $C_1$–$C_4$ haloalkyl, $C_1$–$C_4$ haloalkoxy, and $C_1$–$C_4$ haloalkyl-S—, $C_3$–$C_6$ carbocycle, aryl, and a 5 to 6 membered heterocycle containing 1 to 4 heteroatoms selected from nitrogen, oxygen, and sulphur; and $R^5$ is H, $C_1$–$C_4$ alkoxy;
$C_1$–$C_6$ alkyl substituted with 0–3 $R^{5b}$;
$C_2$–$C_6$ alkenyl substituted with 0–3 $R^{5b}$;
$C_2$–$C_6$ alkynyl substituted with 0–3 $R^{5b}$;
$C_3$–$C_{10}$ carbocycle substituted with 0–3 $R^{5c}$;
aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5b}$, at each occurrence, is independently selected from:
H, $C_1$–$C_6$ alkyl, $CF_3$, $OR^{14}$, Cl, F, Br, I, =O, CN, $NO_2$, $NR^{15}R^{16}$;
$C_3$–$C_{10}$ carbocycle substituted with 0–3 $R^{5c}$;
aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

Ring B is

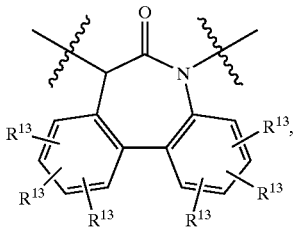

$R^{11}$, at each occurrence, is independently selected from H, $C_1$–$C_4$ alkoxy, Cl, F, Br, I, =O, CN, $NO_2$, $NR^{18}R^{19}$, $C(=O)R^{17}$, $C(=O)OR^{17}$, $C(=O)NR^{18}R^{19}$, $S(=O)_2NR^{18}R^{19}$, $CF_3$;
$C_1$–$C_6$ alkyl optionally substituted with 0–3 $R^{11a}$;
aryl substituted with 0–3 $R^{11b}$;
$C_3$–$C_{10}$ carbocycle substituted with 0–3 $R^{11b}$; or
5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$;
phenyl substituted with 0–3 $R^{11b}$;
$C_3$–$C_6$ cycloalkyl substituted with 0–3 $R^{11b}$; and
5 to 6 membered heterocycle containing 1 to 4 heteroatoms selected from nitrogen, oxygen, and sulphur, wherein said 5 to 6 membered heterocycle is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

W is a bond;
X is a bond;
Y is a bond;
Z is H;
$C_1$–$C_8$ alkyl substituted with 0–3 $R^{12a}$;
$C_2$–$C_6$ alkenyl substituted with 0–3 $R^{12a}$;
$C_2$–$C_6$ alkynyl substituted with 0–3 $R^{12a}$;
aryl substituted with 0–4 $R^{12b}$;
$C_3$–$C_{10}$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, aryl substituted with 0–4 $R^{12b}$;
$C_3$–$C_{10}$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{16}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{17}$ is H, $C_1$–$C_6$ alkyl, $C_2$–$C_6$ alkoxyalkyl, aryl substituted by 0–4 $R^{17a}$, or —$CH_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(CH_3)_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

$R^{19}$, at each occurrence, is independently selected from H, OH, methyl, ethyl, propyl, butyl, phenyl, benzyl, phenethyl; and $R^{23}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$.

23. A compound, according to claim 5, of Formula (Ib):

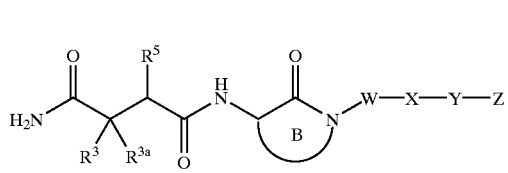
(Ib)

or a pharmaceutically salt thereof, wherein:

$R^3$ and $R^{3a}$ are combined to form a 3–8 membered carbocyclic moiety;
  wherein said 3–8 membered carbocyclic moiety is saturated or partially unsaturated;
  wherein said 3–8 membered carbocyclic moiety is substituted with 0–4 $R^4$;

additionally, two $R^4$ substituents on adjacent atoms may be combined to form a benzo fused radical; wherein said benzo fused radical is substituted with 0–4 $R^{23}$;

additionally, two $R^4$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{23}$;

additionally, two $R^4$ substituents on the same or adjacent carbon atoms may be combined to form a $C_3$–$C_6$ carbocycle substituted with 0–3 $R^{23}$;

$R^4$, at each occurrence, is independently selected from H, OH, Cl, F, Br, I, CN, $NO_2$, $CF_3$, acetyl, $SCH_3$, $S(=O)CH_3$, $S(=O)_2CH_3$, $NR^{15}R^{16}$, $OR^{14a}$, $C_1$–$C_4$ alkyl, $C_2$–$C_6$ alkenyl, alkynyl, $C_1$–$C_4$ alkoxy, $C_1$–$C_4$ haloalkyl, $C_1$–$C_4$ haloalkoxy, and $C_1$–$C_4$ haloalkyl-S—, $C_3$–$C_6$ carbocycle, aryl, and a
  5 to 6 membered heterocycle containing 1 to 4 heteroatoms selected from nitrogen, oxygen, and sulphur; and $R^5$ is H;
  $C_1$–$C_6$ alkyl substituted with 0–3 $R^{5b}$;
  $C_2$–$C_6$ alkenyl substituted with 0–3 $R^{5b}$;
  $C_2$–$C_6$ alkynyl substituted with 0–3 $R^{5b}$;
  $C_3$–$C_{10}$ carbocycle substituted with 0–3 $R^{5c}$;
  aryl substituted with 0–3 $R^{5c}$; or
  5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5b}$, at each occurrence, is independently selected from: H, $C_1$–$C_6$ alkyl, $CF_3$, $OR^{14}$, Cl, F, Br, I, =O, CN, $NO_2$, $NR^{15}R^{16}$;
  $C_3$–$C_{10}$ carbocycle substituted with 0–3 $R^{5c}$;
  aryl substituted with 0–3 $R^{5c}$; or
  5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

Ring B is

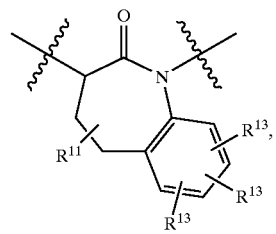

$R^{11}$, at each occurrence, is independently selected from H, $C_1$–$C_4$ alkoxy, Cl, F, Br, I, =O, CN, $NO_2$, $NR^{18}R^{19}$, $C(=O)R^{17}$, $C(=O)OR^{17}$, $C(=O)NR^{18}R^{19}$, $S(=O)_2NR^{18}R^{19}$, $CF_3$;
  $C_1$–$C_6$ alkyl optionally substituted with 0–3 $R^{11a}$;
  aryl substituted with 0–3 $R^{11b}$;
  $C_3$–$C_{10}$ carbocycle substituted with 0–3 $R^{11b}$; or
  5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$;
  phenyl substituted with 0–3 $R^{11b}$;
  $C_3$–$C_6$ cycloalkyl substituted with 0–3 $R^{11b}$; and
  5 to 6 membered heterocycle containing 1 to 4 heteroatoms selected from nitrogen, oxygen, and sulphur, wherein said 5 to 6 membered heterocycle is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

W is a bond;
X is a bond;
Y is a bond;
Z is H;
  $C_1$–$C_8$ alkyl substituted with 0–3 $R^{12a}$;
  $C_2$–$C_6$ alkenyl substituted with 0–3 $R^{12a}$;
  $C_2$–$C_6$ alkynyl substituted with 0–3 $R^{12a}$;
  aryl substituted with 0–4 $R^{12b}$;
  $C_3$–$C_{10}$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, aryl substituted with 0–4 $R^{12b}$;
  $C_3$–$C_{10}$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{16}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{17}$ is H, $C_1$–$C_6$ alkyl, $C_2$–$C_6$ alkoxyalkyl, aryl substituted by 0–4 $R^{17a}$, or —$CH_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(CH_3)_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

$R^{19}$, at each occurrence, is independently selected from H, OH, methyl, ethyl, propyl, butyl, phenyl, benzyl, phenethyl; and $R^{23}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$.

24. A compound, according to claim 5, of Formula (Ib):

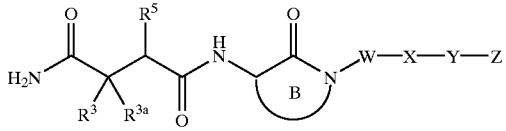

(Ib)

or a pharmaceutically acceptable salt thereof, wherein:
$R^3$ and $R^{3a}$ are combined to form a 3–8 membered carbocyclic moiety;
wherein said 3–8 membered carbocyclic moiety is saturated or partially unsaturated;
wherein said 3–8 membered carbocyclic moiety is substituted with 0–4 $R^4$;
additionally, two $R^4$ substituents on adjacent atoms may be combined to form a benzo fused radical; wherein said benzo fused radical is substituted with 0–4 $R^{23}$;
additionally, two $R^4$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{23}$;
additionally, two $R^4$ substituents on the same or adjacent carbon atoms may be combined to form a $C_3$–$C_6$ carbocycle substituted with 0–3 $R^{23}$;
$R^4$, at each occurrence, is independently selected from H, OH, Cl, F, Br, I, CN, $NO_2$, $CF_3$, acetyl, $SCH_3$, S(=O)$CH_3$, S(=O)$_2CH_3$, $NR^{15}R^{16}$, $OR^{14a}$, $C_1$–$C_4$ alkyl, $C_2$–$C_6$ alkenyl, alkynyl, $C_1$–$C_4$ alkoxy, $C_1$–$C_4$ haloalkyl, $C_1$–$C_4$ haloalkoxy, and $C_1$–$C_4$ haloalkyl-S—, $C_3$–$C_6$ carbocycle, aryl, and a
5 to 6 membered heterocycle containing 1 to 4 heteroatoms selected from nitrogen, oxygen, and sulphur; and $R^5$ is H;
$C_1$–$C_6$ alkyl substituted with 0–3 $R^{5b}$;
$C_2$–$C_6$ alkenyl substituted with 0–3 $R^{5b}$;
$C_2$–$C_6$ alkynyl substituted with 0–3 $R^{5b}$;
$C_3$–$C_{10}$ carbocycle substituted with 0–3 $R^{5c}$;
aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5b}$, at each occurrence, is independently selected from: H, $C_1$–$C_6$ alkyl, $CF_3$, $OR^{14}$, Cl, F, Br, I, =O, CN, $NO_2$, $NR^{15}R^{16}$;
$C_3$–$C_{10}$ carbocycle substituted with 0–3 $R^{5c}$;
aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

Ring B is

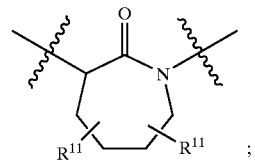

;

$R^{11}$, at each occurrence, is independently selected from H, $C_1$–$C_4$ alkoxy, Cl, F, Br, I, =O, CN, $NO_2$, $NR^{18}R^{19}$, C(=O)$R^{17}$, C(=O)$OR^{17}$, C(=O)$NR^{18}R^{19}$, S(=O)$_2NR^{18}R^{19}$, $CF_3$;
$C_1$–$C_6$ alkyl optionally substituted with 0–3 $R^{11a}$;
aryl substituted with 0–3 $R^{11b}$;
$C_3$–$C_{10}$ carbocycle substituted with 0–3 $R^{11b}$; or
5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$;
phenyl substituted with 0–3 $R^{11b}$;
$C_3$–$C_6$ cycloalkyl substituted with 0–3 $R^{11b}$; and
5 to 6 membered heterocycle containing 1 to 4 heteroatoms selected from nitrogen, oxygen, and sulphur, wherein said 5 to 6 membered heterocycle is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

W is a bond;
X is a bond;
Y is a bond;
Z is H;
$C_1$–$C_8$ alkyl substituted with 0–3 $R^{12a}$;
$C_2$–$C_6$ alkenyl substituted with 0–3 $R^{12a}$;
$C_2$–$C_6$ alkynyl substituted with 0–3 $R^{12a}$;

aryl substituted with 0–4 $R^{12b}$;

$C_3$–$C_{10}$ carbocycle substituted with 0–4 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, S(=O)$CH_3$, S(=O)$_2$$CH_3$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, aryl substituted with 0–4 $R^{12b}$;

$C_3$–$C_{10}$ carbocycle substituted with 0–4 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2$$CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{16}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{17}$ is H, $C_1$–$C_6$ alkyl, $C_2$–$C_6$ alkoxyalkyl, aryl substituted by 0–4 $R^{17a}$, or —$CH_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, S(O)$CH_3$, $SO_2CH_3$, —$NH_2$, —N($CH_3$)$_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

$R^{19}$, at each occurrence, is independently selected from H, OH, methyl, ethyl, propyl, butyl, phenyl, benzyl, phenethyl; and $R^{23}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$.

25. A pharmaceutical composition comprising a compound according to claim 2 and a pharmaceutically acceptable carrier.

26. A pharmaceutical composition comprising a compound according to claim 3 and a pharmaceutically acceptable carrier.

27. A pharmaceutical composition comprising a compound according to claim 4 and a pharmaceutically acceptable carrier.

28. A pharmaceutical composition comprising a compound according to claim 5 and a pharmaceutically acceptable carrier.

29. A pharmaceutical composition comprising a compound according to claim 6 and a pharmaceutically acceptable carrier.

30. A pharmaceutical composition comprising a compound according to claim 7 and a pharmaceutically acceptable carrier.

31. A pharmaceutical composition comprising a compound according to claim 8 and a pharmaceutically acceptable carrier.

32. A pharmaceutical composition comprising a compound according to claim 9 and a pharmaceutically acceptable carrier.

33. A pharmaceutical composition comprising a compound according to claim 10 and a pharmaceutically acceptable carrier.

34. A pharmaceutical composition comprising a compound according to claim 11 and a pharmaceutically acceptable carrier.

35. A pharmaceutical composition comprising a compound according to claim 12 and a pharmaceutically acceptable carrier.

36. A pharmaceutical composition comprising a compound according to claim 13 and a pharmaceutically acceptable carrier.

37. A pharmaceutical composition comprising a compound according to claim 14 and a pharmaceutically acceptable carrier.

38. A pharmaceutical composition comprising a compound according to claim 15 and a pharmaceutically acceptable carrier.

39. A pharmaceutical composition comprising a compound according to claim 16 and a pharmaceutically acceptable carrier.

40. A pharmaceutical composition comprising a compound according to claim 17 and a pharmaceutically acceptable carrier.

41. A pharmaceutical composition comprising a compound according to claim 18 and a pharmaceutically acceptable carrier.

42. A pharmaceutical composition comprising a compound according to claim 19 and a pharmaceutically acceptable carrier.

43. A pharmaceutical composition comprising a compound according to claim 20 and a pharmaceutically acceptable carrier.

44. A pharmaceutical composition comprising a compound according to claim 21 and a pharmaceutically acceptable carrier.

45. A pharmaceutical composition comprising a compound according to claim 22 and a pharmaceutically acceptable carrier.

46. A pharmaceutical composition comprising a compound according to claim 23 and a pharmaceutically acceptable carrier.

47. A pharmaceutical composition comprising a compound according to claim 24 and a pharmaceutically acceptable carrier.

48. A method for the treatment of Alzheimer's Disease comprising administering to a host in need of such treatment a therapeutically effective amount of a compound of claim 1.

49. A method for the treatment of Alzheimer's Disease comprising administering to a host in need of such treatment a therapeutically effective amount of a compound of claim 2.

50. A method for the treatment of Alzheimer's Disease comprising administering to a host in need of such treatment a therapeutically effective amount of a compound of claim 2.

51. A method for the treatment of Alzheimer's Disease comprising administering to a host in need of such treatment a therapeutically effective amount of a compound of claim 3.

52. A method for the treatment of Alzheimer's Disease comprising administering to a host in need of such treatment a therapeutically effective amount of a compound of claim 4.

53. A method for the treatment of Alzheimer's Disease comprising administering to a host in need of such treatment a therapeutically effective amount of a compound of claim 5.

54. A method for the treatment of Alzheimer's Disease comprising administering to a host in need of such treatment a therapeutically effective amount of a compound of claim 6.

55. A method for the treatment of Alzheimer's Disease comprising administering to a host in need of such treatment a therapeutically effective amount of a compound of claim 7.

56. A method for the treatment of Alzheimer's Disease comprising administering to a host in need of such treatment a therapeutically effective amount of a compound of claim 8.

57. A method for the treatment of Alzheimer's Disease comprising administering to a host in need of such treatment a therapeutically effective amount of a compound of claim 9.

58. A method for the treatment of Alzheimer's Disease comprising administering to a host in need of such treatment a therapeutically effective amount of a compound of claim 10.

59. A method for the treatment of Alzheimer's Disease comprising administering to a host in need of such treatment a therapeutically effective amount of a compound of claim 11.

60. A method for the treatment of Alzheimer's Disease comprising administering to a host in need of such treatment a therapeutically effective amount of a compound of claim 12.

61. A method for the treatment of Alzheimer's Disease comprising administering to a host in need of such treatment a therapeutically effective amount of a compound of claim 13.

62. A method for the treatment of Alzheimer's Disease comprising administering to a host in need of such treatment a therapeutically effective amount of a compound of claim 14.

63. A method for the treatment of Alzheimer's Disease comprising administering to a host in need of such treatment a therapeutically effective amount of a compound of claim 15.

64. A method for the treatment of Alzheimer's Disease comprising administering to a host in need of such treatment a therapeutically effective amount of a compound of claim 16.

65. A method for the treatment of Alzheimer's Disease comprising administering to a host in need of such treatment a therapeutically effective amount of a compound of claim 17.

66. A method for the treatment of Alzheimer's Disease comprising administering to a host in need of such treatment a therapeutically effective amount of a compound of claim 18.

67. A method for the treatment of Alzheimer's Disease comprising administering to a host in need of such treatment a therapeutically effective amount of a compound of claim 19.

68. A method for the treatment of Alzheimer's Disease comprising administering to a host in need of such treatment a therapeutically effective amount of a compound of claim 20.

69. A method for the treatment of Alzheimer's Disease comprising administering to a host in need of such treatment a therapeutically effective amount of a compound of claim 21.

70. A method for the treatment of Alzheimer's Disease comprising administering to a host in need of such treatment a therapeutically effective amount of a compound of claim 22.

71. A method for the treatment of Alzheimer's Disease comprising administering to a host in need of such treatment a therapeutically effective amount of a compound of claim 23.

72. A method for the treatment of Alzheimer's Disease comprising administering to a host in need of such treatment a therapeutically effective amount of a compound of claim 24.

* * * * *